(12) United States Patent
Sim et al.

(10) Patent No.: US 11,588,111 B2
(45) Date of Patent: Feb. 21, 2023

(54) CONDENSED-CYCLIC COMPOUND AND ORGANIC LIGHT-EMITTING DEVICE INCLUDING THE SAME

(71) Applicant: SAMSUNG DISPLAY CO., LTD., Yongin-si (KR)

(72) Inventors: Munki Sim, Yongin-si (KR); Junha Park, Yongin-si (KR); Hyoyoung Lee, Yongin-si (KR); Youngkook Kim, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 151 days.

(21) Appl. No.: 15/866,885

(22) Filed: Jan. 10, 2018

(65) Prior Publication Data

US 2019/0044072 A1 Feb. 7, 2019

(30) Foreign Application Priority Data

Aug. 4, 2017 (KR) .................. 10-2017-0099082

(51) Int. Cl.
*H01L 51/50* (2006.01)
*H01L 51/00* (2006.01)
(Continued)

(52) U.S. Cl.
CPC ........ *H01L 51/0072* (2013.01); *C07D 471/04* (2013.01); *C07D 519/00* (2013.01);
(Continued)

(58) Field of Classification Search
None
See application file for complete search history.

(56) References Cited

U.S. PATENT DOCUMENTS 5,645,948 A 7/1997 Shi et al.
6,465,115 B2 10/2002 Shi et al.
(Continued)

FOREIGN PATENT DOCUMENTS

CN 105315219 A 2/2016
CN 105315265 A 2/2016
(Continued)

OTHER PUBLICATIONS

Tong et al; Light-Driven Proton Reduction in Aqueous Medium Catalyzed by a Family of Cobalt Complexes with Tetradentate Polyoyridine-Type Ligands, 2015, Inorganic Chemistry, 54, 7873-7884. (Year: 2015).*

(Continued)

*Primary Examiner* — Gregory D Clark
(74) *Attorney, Agent, or Firm* — Lewis Roca Rothgerber Christie LLP

(57) ABSTRACT

A condensed cyclic compound and an organic light-emitting device, the compound being represented by Formula 1:

<Formula 1>

17 Claims, 4 Drawing Sheets

(51) Int. Cl.
- *H01L 51/52* (2006.01)
- *C07D 471/04* (2006.01)
- *C07F 9/53* (2006.01)
- *C07F 9/6561* (2006.01)
- *C07F 9/6568* (2006.01)
- *C07D 519/00* (2006.01)

(52) U.S. Cl.
CPC .......... *C07F 9/5325* (2013.01); *C07F 9/6561* (2013.01); *C07F 9/65685* (2013.01); *H01L 51/0067* (2013.01); *H01L 51/506* (2013.01); *H01L 51/5262* (2013.01); *H01L 51/5012* (2013.01); *H01L 51/5016* (2013.01); *H01L 51/5056* (2013.01); *H01L 51/5064* (2013.01); *H01L 51/5072* (2013.01); *H01L 51/5088* (2013.01); *H01L 51/5092* (2013.01); *H01L 2251/552* (2013.01)

(56) References Cited

U.S. PATENT DOCUMENTS

| | | | |
|---|---|---|---|
| 6,596,415 | B2 | 7/2003 | Shi et al. |
| 6,818,919 | B2 | 11/2004 | Robeson et al. |
| 7,189,989 | B2 | 3/2007 | Ise |
| 7,982,213 | B2 | 7/2011 | Okajima et al. |
| 8,436,344 | B2 | 5/2013 | Seo et al. |
| 8,455,272 | B2 | 6/2013 | Sato |
| 8,999,525 | B2 | 4/2015 | Lee et al. |
| 9,178,001 | B2 | 11/2015 | Kwak et al. |
| 9,252,368 | B2 | 2/2016 | Aihara et al. |
| 9,391,281 | B2 | 7/2016 | Lee et al. |
| 9,425,407 | B2 | 8/2016 | Hwang et al. |
| 9,705,088 | B2 | 7/2017 | Park et al. |
| 9,718,764 | B2 | 8/2017 | Stoessel et al. |
| 9,997,716 | B2 | 6/2018 | Zeng et al. |
| 10,023,599 | B2 | 7/2018 | Bierbach et al. |
| 10,236,452 | B2 | 3/2019 | Jeong et al. |
| 10,249,824 | B2 | 4/2019 | Park et al. |
| 10,297,762 | B2 | 5/2019 | Zeng et al. |
| 10,361,375 | B2 | 7/2019 | Zeng et al. |
| 10,367,147 | B2 | 7/2019 | Kim et al. |
| 11,152,576 | B2 | 10/2021 | Heo et al. |
| 11,228,001 | B2 | 1/2022 | Heo et al. |
| 2002/0132134 | A1 | 9/2002 | Hu et al. |
| 2003/0165715 | A1 | 9/2003 | Yoon et al. |
| 2004/0036077 | A1 | 2/2004 | Ise |
| 2004/0053069 | A1 | 3/2004 | Sotoyama et al. |
| 2004/0137270 | A1 | 7/2004 | Seo et al. |
| 2005/0002857 | A1 | 1/2005 | Pez et al. |
| 2005/0221124 | A1 | 10/2005 | Hwang et al. |
| 2005/0274961 | A1* | 12/2005 | Lou ............... H01L 51/5088 257/82 |
| 2006/0252857 | A1 | 11/2006 | Schafer et al. |
| 2007/0200490 | A1 | 8/2007 | Kawamura et al. |
| 2009/0019768 | A1 | 1/2009 | Toseland et al. |
| 2009/0134784 | A1 | 5/2009 | Lin et al. |
| 2010/0039026 | A1 | 2/2010 | Yang et al. |
| 2010/0155714 | A1 | 6/2010 | Seo et al. |
| 2010/0200883 | A1 | 8/2010 | Sato |
| 2010/0320451 | A1 | 12/2010 | Kawamura |
| 2011/0121268 | A1 | 5/2011 | Nagao et al. |
| 2011/0121274 | A1 | 5/2011 | Parham et al. |
| 2011/0156013 | A1 | 6/2011 | Kim et al. |
| 2011/0198629 | A1 | 8/2011 | Lee et al. |
| 2011/0227053 | A1 | 9/2011 | Bae et al. |
| 2012/0056165 | A1 | 3/2012 | Kawamura et al. |
| 2012/0126692 | A1 | 5/2012 | Ise et al. |
| 2012/0223276 | A1 | 9/2012 | Parham et al. |
| 2012/0256172 | A1 | 10/2012 | Ito et al. |
| 2012/0267620 | A1 | 10/2012 | Min et al. |
| 2012/0286249 | A1 | 11/2012 | Lee et al. |
| 2013/0001526 | A1 | 1/2013 | Kwak et al. |
| 2013/0306959 | A1 | 11/2013 | Ikeda et al. |
| 2014/0027754 | A1 | 1/2014 | Ueoka et al. |
| 2014/0138659 | A1 | 5/2014 | Shin et al. |
| 2014/0299192 | A1 | 10/2014 | Lee et al. |
| 2014/0323723 | A1 | 10/2014 | Ahn et al. |
| 2014/0330013 | A1 | 11/2014 | Aihara et al. |
| 2015/0014656 | A1 | 1/2015 | Lim et al. |
| 2015/0041773 | A1 | 2/2015 | Park et al. |
| 2015/0060787 | A1 | 3/2015 | Park et al. |
| 2015/0069342 | A1 | 3/2015 | Lee et al. |
| 2015/0069347 | A1 | 3/2015 | Kim et al. |
| 2015/0069355 | A1 | 3/2015 | Hwang et al. |
| 2015/0171336 | A1 | 6/2015 | Park et al. |
| 2015/0303380 | A1 | 10/2015 | Kambe et al. |
| 2015/0318510 | A1 | 11/2015 | Ito et al. |
| 2015/0349268 | A1 | 12/2015 | Zeng et al. |
| 2016/0028021 | A1 | 1/2016 | Zeng et al. |
| 2016/0043327 | A1 | 2/2016 | Yoo et al. |
| 2016/0046563 | A1 | 2/2016 | Stoessel et al. |
| 2016/0164004 | A1 | 6/2016 | Seo et al. |
| 2016/0197289 | A1 | 7/2016 | Sado et al. |
| 2016/0218298 | A1 | 7/2016 | Lee et al. |
| 2016/0315268 | A1 | 10/2016 | Stoessel |
| 2016/0351817 | A1 | 12/2016 | Kim |
| 2017/0098779 | A1 | 4/2017 | Lee et al. |
| 2017/0200902 | A1 | 7/2017 | Lee et al. |
| 2017/0271596 | A1 | 9/2017 | Lee |
| 2017/0317294 | A1 | 11/2017 | Kim et al. |
| 2018/0051003 | A1 | 2/2018 | Koo et al. |
| 2018/0102484 | A1 | 4/2018 | Mizutani et al. |
| 2019/0233398 | A1* | 8/2019 | Oh ................. C07D 401/10 |
| 2019/0245149 | A1 | 8/2019 | Heo |
| 2019/0263834 | A1 | 8/2019 | Jeong et al. |
| 2019/0341558 | A1 | 11/2019 | Yang et al. |
| 2020/0048232 | A1 | 2/2020 | Cha et al. |
| 2020/0131138 | A1 | 4/2020 | Han |
| 2021/0020848 | A1 | 1/2021 | Yang et al. |
| 2021/0119137 | A1 | 4/2021 | Cha et al. |

FOREIGN PATENT DOCUMENTS

| | | | |
|---|---|---|---|
| EP | 3072943 | A1 | 9/2016 |
| EP | 3246963 | A2 | 11/2017 |
| JP | 10-017860 | A | 1/1998 |
| JP | 10-338871 | A | 12/1998 |
| JP | 11-087067 | A | 3/1999 |
| JP | 2003045662 | A | 2/2003 |
| JP | 2003-123983 | A | 4/2003 |
| JP | 2004-022334 | | 1/2004 |
| JP | 2004-103576 | A | 4/2004 |
| JP | 2004-107263 | A | 4/2004 |
| JP | 2004-281390 | A | 10/2004 |
| JP | 2007-508275 | A | 4/2007 |
| JP | 4060669 | B2 | 12/2007 |
| JP | 2008-120688 | A | 5/2008 |
| JP | 2009-021336 | A | 1/2009 |
| JP | 2010-141353 | A | 6/2010 |
| JP | 2010-182637 | A | 8/2010 |
| JP | 2010-195708 | A | 9/2010 |
| JP | 2011-012190 | A | 1/2011 |
| JP | 2011-49512 | A | 3/2011 |
| JP | 2013-100239 | A | 5/2013 |
| JP | 2015-504600 | A | 2/2015 |
| JP | 2015-524797 | A | 8/2015 |
| JP | 2016-6039 | A | 1/2016 |
| JP | 2016-19002 | A | 2/2016 |
| JP | 2016-516084 | A | 6/2016 |
| JP | 2017-31131 | A | 2/2017 |
| JP | 2017-509635 | A | 4/2017 |
| JP | 2017-107992 | A | 6/2017 |
| KR | 10-2003-0067773 | A | 8/2003 |
| KR | 10-0525408 | B1 | 10/2005 |
| KR | 10-0691543 | B1 | 3/2007 |
| KR | 10-2010-0056398 | A | 5/2010 |
| KR | 10-0958641 | | 5/2010 |
| KR | 10-2010-0088612 | A | 8/2010 |
| KR | 10-2010-0099327 | A | 9/2010 |
| KR | 10-2011-0040874 | A | 4/2011 |
| KR | 10-2011-0075690 | A | 7/2011 |
| KR | 10-2011-0094271 | A | 8/2011 |
| KR | 10-2012-0020901 | A | 3/2012 |

(56) References Cited

FOREIGN PATENT DOCUMENTS

| KR | 10-2012-0051598 A | 5/2012 |
|---|---|---|
| KR | 10-2012-0057198 A | 5/2012 |
| KR | 10-2012-0065214 A | 6/2012 |
| KR | 10-2012-0101558 A | 9/2012 |
| KR | 10-2012-0104087 A | 9/2012 |
| KR | 10-2012-0104246 A | 9/2012 |
| KR | 10-2012-0116838 A | 10/2012 |
| KR | 10-2012-0127683 A | 11/2012 |
| KR | 10-2012-0138671 A | 12/2012 |
| KR | 10-2013-0116041 A | 10/2013 |
| KR | 10-2013-0127567 A | 11/2013 |
| KR | 10-2013-0135181 A | 12/2013 |
| KR | 10-2013-0142969 A | 12/2013 |
| KR | 10-2014-0009918 A | 1/2014 |
| KR | 10-2014-0009919 A | 1/2014 |
| KR | 10-2014-0076520 A | 6/2014 |
| KR | 10-2014-0079306 A | 6/2014 |
| KR | 10-2014-0082351 A | 7/2014 |
| KR | 10-2014-0091049 A | 7/2014 |
| KR | 20140132244 A | 11/2014 |
| KR | 10-2015-0018229 A | 2/2015 |
| KR | 10-2015-0025259 A | 3/2015 |
| KR | 10-2015-0027897 A | 3/2015 |
| KR | 10-2015-0028860 A | 3/2015 |
| KR | 10-2015-0028935 A | 3/2015 |
| KR | 20150054797 A | 5/2015 |
| KR | 10-2015-0069346 A | 6/2015 |
| KR | 10-2015-0099750 A | 9/2015 |
| KR | 10-2015-0124000 A | 11/2015 |
| KR | 10-2015-0124637 A | 11/2015 |
| KR | 10-2015-0132873 A | 11/2015 |
| KR | 10-2015-0136579 A | 12/2015 |
| KR | 10-2016-0006633 A | 1/2016 |
| KR | 10-2016-0018332 A | 2/2016 |
| KR | 10-2016-0046046 A | 4/2016 |
| KR | 10-1627691 | 6/2016 |
| KR | 10-2016-0141359 | 12/2016 |
| KR | 10-2017-0023025 A | 3/2017 |
| KR | 20170032833 A | 3/2017 |
| KR | 20170049440 A | 5/2017 |
| KR | 10-2017-0104718 | 9/2017 |
| KR | 10-2017-0134264 A | 12/2017 |
| KR | 10-2018-0005533 A | 1/2018 |
| KR | 20180010132 A | 1/2018 |
| KR | 10-2018-0059286 A | 6/2018 |
| KR | 10-2018-0086126 A | 7/2018 |
| KR | 10-2018-0120569 A | 11/2018 |
| KR | 10-2018-0130329 A | 12/2018 |
| KR | 10-2019-0013527 A | 2/2019 |
| TW | 201100522 A1 | 1/2011 |
| WO | WO 2004/106311 A2 | 12/2004 |
| WO | WO 2010/126270 A1 | 11/2010 |
| WO | WO 2010/015306 A1 | 2/2012 |
| WO | WO 2012/086170 A1 | 6/2012 |
| WO | WO 2012/173073 A1 | 12/2012 |
| WO | WO 2014/104720 A1 | 7/2014 |
| WO | WO 2016/002864 A1 | 1/2016 |
| WO | WO 2016/121597 A1 | 8/2016 |
| WO | WO 2018/190522 A1 | 10/2018 |
| WO | WO 2018/199466 A1 | 11/2018 |

OTHER PUBLICATIONS

Tang, et al., Organic electroluminescent diodes, Appl. Phys. Lett., 51, 913 (1987).
Adachi, et al., Confinement of charge carriers and molecular excitons within 5-nm-thick emitter layer in organic electroluminescent devices with a double heterostructure, Appl. Phys. Lett., 57, 531 (1990).
Johansson, et al., Solid-State Amplified Spontaneous Emission in Some Spiro-Type Molecules; A New Concept for the Design of Solid-State lasting Molecules., Adv. Mater. 10 (1998) 1136.
Sakamoto, et al., Synthesis, Characterization and Electron-Transport Property of Perfluorinated Phenylene Dendrimers., J. Am. Chem. Soc., 2000, 122 (8), pp. 1832-1833.
Tao, et al., Sharp green electroluminescence from 1H-pyrozolo [3,4-b] quinoline-based light-emitting diodes, Appl. Phys. Lett. 77 (2000) 1575.
Yamaguchi, et al., Diphenylamino-Substituted 2,5-Diarylsiloles for Single-Layer Organic Electroluminesent Devices. Chem. Lett., 98(2001).
Berger, Ricarda, et al., "New symmetrically substituted 1,3,5-triazines as host compounds for channel-type inclusion formation," CrystEngComm, 2012, vol. 14, 3 pages.
Debnath, Pradip, et al., "A novel straightforward synthesis of 2,4,6-triaryl-1,3,5-triazines via copper-catalyzed cyclization of N-benzylbenzamidines," Tetrahedron Letters, 2014, vol. 55, 3 pages.
Ishi-I, Tsutomu, et al., "High Electron Drift Mobility in an Amorphous Film of 2,4,6,-Tris[4-(1-naphthyl)phenyl]-1,3,5-triazine," Chemistry Letters, 2004, vol. 33, No. 10, 2 pages.
Kotha, Sambasivarao, et al., "Synthesis of nano-sized C3-symmetric2,4,6-triphenyl-1,3,5-s-triazine and 1,3,5-triphenylbenzene derivatives via the trimerization followed by Suzuki-Miyaura cross-coupling or O-alkylation reactions and their biological evaluation," Indian Journal of Chemistry, Dec. 2009, vol. 48B, 5 pages.
Kwon, Jang Hyeok et al., "Preparation of phenanthroline derivatives for organic electric device," Sep. 18, 2017, XP002782646.
Lee, Dong Ryun, et al., "Design Strategy for 25% External Quantum Efficiency in Green and Blue Thermally Activated Delayed Fluorescent Devices," Advanced Materials, 2015, vol. 27, 7 pages.
Zeika, Olaf, et al., "Synthesis of Polynitroxides Based on Nucleophilic Aromatic Substitution," Organic Letters, 2010, vol. 12, No. 16, 4 pages.
Internet Material: 2009 Fall Assembly and Symposium. vol. 34, No. 2, 2009; Publication Date, Oct. 8, 2009-Oct. 9, 2009; Title: A novel conjugated polymer based on 4H-benzo[det]carbazole backbone for OLED, 1 page.
Swensen et al.; Blue phosphorescent organic light-emitting devices utilizing cesium-carbonate-doped 2,4,6-tris(2',4'-difluoro-[1, 1 '-biphenyl]-4-yl)-1,3,5-triazine; Journal of Photonics for Energy (2011 ), 1, 011008/1-011008/11 (Year: 2011).
EPO Extended Search Report dated Jul. 11, 2018, for corresponding European Patent Application No. 18175088.6 (8 pages).
EPO Extended Search Report dated Sep. 21, 2018, for corresponding European Patent Application No. 18178734.2 (11 pages).
Machine translation of JP 2003045662, translation generated Feb. 2020, 70 pages. (Year: 2020).
U.S. Office Action dated Apr. 1, 2021, issued in U.S. Appl. No. 16/250,946 (25 pages).
U.S. Final Office Action dated Jul. 16, 2021, issued in U.S. Appl. No. 16/250,946 (31 pages).
"fused pyridine derivatives," Heterocycles, vol. 57, 2002, 1 page.
Rahman, A.F.M. Motiur, et al., "Synthesis and Properties of Benzo[b]-1,10-phenanthrolines and Their Ruthenium(II) Complexes," Heteroatom Chemistry, vol. 18, No. 6, 2007, pp. 650-656.
Heterocycles, vol. 78, No. 6, 2009, 7 pages.
Jahng, Yurngdong, et al., "Synthesis and Properties of 2,2'-Di(heteroaryl)-9,9'-spirobifluorenes," Bulletin of the Chemical Society of Japan, vol. 83, No. 6, 2010, pp. 672-677.
U.S. Notice of Allowance from U.S. Appl. No. 15/867,357, dated Mar. 31, 2021, 10 pages.
U.S. Office Action from U.S. Appl. No. 14/198,372, dated Dec. 10, 2015, 7 pages.
U.S. Office Action from U.S. Appl. No. 14/290,950, dated Oct. 6, 2016, 7 pages.
U.S. Office Action from U.S. Appl. No. 15/867,357, dated Dec. 9, 2020, 12 pages.
U.S. Office Action from U.S. Appl. No. 15/867,357, dated Feb. 20, 2020, 8 pages.
U.S. Office Action from U.S. Appl. No. 15/867,357, dated Jun. 25, 2020, 9 pages.
U.S. Office Action from U.S. Appl. No. 15/867,357, dated Sep. 16, 2021, 9 pages.
U.S. Office Action from U.S. Appl. No. 15/913,162, dated Jun. 15, 2020, 9 pages.
U.S. Office Action from U.S. Appl. No. 15/913,162, dated Mar. 6, 2020, 9 pages.
Chinese Office Action dated Jan. 18, 2022, issued in Chinese Patent Application No. 201810652269.6 (9 pages).

(56) References Cited

OTHER PUBLICATIONS

U.S. Final Office Action dated Feb. 3, 2022, issued in U.S. Appl. No. 15/867,357 (9 pages).
Korean Notice of Allowance, for Patent Application No. 10-2017-0100434, dated Mar. 23, 2022, 6 pages.
Fink, Ralf et al., "Aromatic polyethers with 1,3,5-triazine units as hole-blocking/elecgtron-transport materials in LEDs," Proceedings of SPIE, vol. 3148, 1997, 9 pages.
Japanese Office Action dated Jun. 7, 2022, issued in corresponding Japanese Patent Application No. 2018-117229, 5 pages.
U.S. Notice of Allowance issued in U.S. Appl. No. 14/198,372, dated Apr. 13, 2016, 9 pages.
U.S. Notice of Allowance issued in U.S. Appl. No. 14/290,950, dated Mar. 9, 2017, 8 pages.
U.S. Notice of Allowance issued in U.S. Appl. No. 15/913,162, dated Aug. 12, 2020, 5 pages.
U.S. Advisory Action issued in U.S. Appl. No. 15/867,357, dated Aug. 17, 2020, 3 pages.
U.S. Notice of Allowance issued in U.S. Appl. No. 15/867,357, dated Apr. 4, 2022, 8 pages.
U.S. Notice of Allowance dated Aug. 29, 2022, issued in U.S. Appl. No. 15/867,357 (10 pages).
Office Action for U.S. Appl. No. 16/250,946 dated Nov. 25, 2022, 28 pages.
Office Action for U.S. Appl. No. 17/395,913 dated Jan. 20, 2023, 12 pages.

\* cited by examiner

| 190 |
|-----|
| 150 |
| 110 |

| 190 |
|-----|
| 150 |
| 110 |
| 210 |

| 220 |
|---|
| 190 |
| 150 |
| 110 |

| 220 |
|-----|
| 190 |
| 150 |
| 110 |
| 210 |

CONDENSED-CYCLIC COMPOUND AND ORGANIC LIGHT-EMITTING DEVICE INCLUDING THE SAME

CROSS-REFERENCE TO RELATED APPLICATION

Korean Patent Application No. 10-2017-0099082, filed on Aug. 4, 2017, in the Korean Intellectual Property Office, and entitled: "Condensed-Cyclic Compound and Organic Light-Emitting Device Including the Same," is incorporated by reference herein in its entirety.

BACKGROUND

1. Field

Embodiments relate to a condensed cyclic compound and an organic light-emitting device.

2. Description of the Related Art

Organic light-emitting devices are self-emission devices that produce full-color images, and also have wide viewing angles, high contrast ratios, short response times, and excellent characteristics in terms of luminance, driving voltage, and response speed, compared to other devices.

An example of such organic light-emitting devices may include a first electrode located on a substrate, and a hole transport region, an emission layer, an electron transport region, and a second electrode, which are sequentially located on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit from an excited state to a ground state, thereby generating light.

SUMMARY

Embodiments are directed to a condensed cyclic compound and an organic light-emitting device.

The embodiments may be realized by providing a condensed cyclic compound represented by Formula 1:

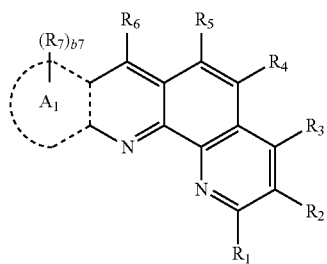

<Formula 1> wherein, in Formula 1, $A_1$ is a benzene ring or a naphthalene ring, $R_1$ to $R_7$ are each independently selected from a group represented by Formula 2, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_1$)($Q_2$)($Q_3$), —B($Q_1$)($Q_2$), —C(=O)($Q_1$), —N($Q_1$)($Q_2$), —P(=O)($Q_1$)($Q_2$), —P(=S)($Q_1$)($Q_2$), —S(=O)($Q_1$)($Q_2$), and —S(=O)$_2$($Q_1$)($Q_2$), provided that at least one of $R_1$ to $R_7$ is a group represented by Formula 2, $$*\text{-}(L_{21})_{a21}\text{-}(Ar_{21})_{b21}$$ <Formula 2> wherein, in Formulae 1 and 2, b7 is an integer of 1 to 6, and when b7 is 2, 3, 4, 5, or 6, the $R_7$(s) are identical to or different from each other, $L_{21}$ is a single bond, a substituted or unsubstituted $C_5$-$C_{60}$ carbocyclic group, or a substituted or unsubstituted $C_1$-$C_{60}$ heterocyclic group, a21 is an integer of 1 to 5, and when a21 is 2, 3, 4, or 5, the $L_{21}$(s) are identical to or different from each other, $Ar_{21}$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_1$)($Q_2$)($Q_3$), —B($Q_1$)($Q_2$), —C(=O)($Q_1$), —N($Q_1$)($Q_2$), —P(=O)($Q_1$)($Q_2$), —P(=S)($Q_1$)($Q_2$), —S(=O)($Q_1$)($Q_2$), and —S(=O)$_2$($Q_1$)($Q_2$), b21 is an integer of 1 to 8, and when b21 is 2, 3, 4, 5, 6, 7, or 8, the $Ar_{21}$(s) are identical to or different from each other, two selected from $L_{21}$ and $Q_1$ to $Q_3$ are separate or are linked to form a substituted or unsubstituted $C_5$-$C_{60}$ carbocyclic group or a substituted or unsubstituted $C_1$-$C_{60}$ heterocyclic group, at least one substituent of the substituted $C_5$-$C_{60}$ carbocyclic group, substituted $C_1$-$C_{60}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted $C_1$-$C_{60}$hetero aryloxy group, substituted monovalent non-aromatic condensed polycyclic group, or substituted monovalent non-aromatic condensed heteropolycyclic group is selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$); a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and * indicates a binding site to a neighboring atom.

The embodiments may be realized by providing an organic light-emitting device including a first electrode; a second electrode facing the first electrode; and an organic layer including an emission layer between the first electrode and the second electrode, wherein the organic layer includes the condensed cyclic compound according to an embodiment.

BRIEF DESCRIPTION OF THE DRAWINGS

Features will be apparent to those of skill in the art by describing in detail exemplary embodiments with reference to the attached drawings in which:

FIG. 1 illustrates a schematic view of an organic light-emitting device according to an embodiment;

FIG. 2 illustrates a schematic view of an organic light-emitting device according to an embodiment;

FIG. 3 illustrates a schematic view of an organic light-emitting device according to an embodiment; and FIG. 4 illustrates a schematic view of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. In addition, it will also be understood that when a layer is referred to as being "between" two layers, it can be the only layer between the two layers, or one or more intervening layers may also be present. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list. The term "or" is not an exclusive term, e.g., "A or B" would include A, B, or A and B.

As used herein, the singular forms "a," "an" and "the" are intended to include the plural forms as well, unless the context clearly indicates otherwise.

It will be further understood that the terms "includes," "including," "comprises," and/or "comprising" used herein specify the presence of stated features or components, but do not preclude the presence or addition of one or more other features or components.

It will be understood that when a layer, region, or component is referred to as being "on" or "onto" another layer, region, or component, it may be directly or indirectly formed on the other layer, region, or component. That is, for example, intervening layers, regions, or components may be present.

A condensed cyclic compound according to an embodiment may be represented by Formula 1 below.

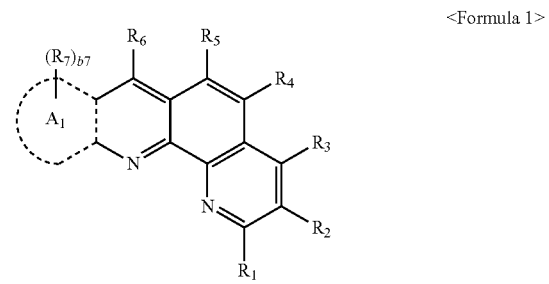

<Formula 1>

$A_1$ in Formula 1 may be, e.g., a benzene ring or a naphthalene ring.

$R_1$ to $R_7$ in Formula 1 may each independently be selected from or include, e.g., a group represented by Formula 2, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_1$)($Q_2$)($Q_3$), —B($Q_1$)($Q_2$), —C(=O)($Q_1$), —N($Q_1$)($Q_2$), —P(=O)($Q_1$)($Q_2$), —P(=S)($Q_1$)($Q_2$), —S(=O)($Q_1$)($Q_2$), and —S(=O)$_2$($Q_1$)($Q_2$).

In an implementation, at least one selected from $R_1$ to $R_7$ may be a group represented by Formula 2.

$$*-(L_{21})_{a21}-(Ar_{21})_{b21}. \qquad \text{<Formula 2>}$$

In an implementation, $R_1$ to $R_7$ may each independently be selected from or include, e.g., a group represented by Formula 2, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a phenanthrolinyl group, a triazinyl group, a dibenzofuranyl group, a dibenzothiophenyl group, a benzocarbazolyl group, and a dibenzocarbazolyl group.

In an implementation, $R_1$ to $R_7$ may each independently be selected from or include, e.g., a group represented by Formula 2, hydrogen, deuterium, —F, —Cl, —Br, —I, a hydroxyl group, a cyano group, a nitro group, an amidino group, a hydrazino group, a hydrazono group, a methyl group, an ethyl group, a propyl group, an iso-propyl group, an n-butyl group, an isobutyl group, a sec-butyl group, ter-butyl group, pentyl group, an iso-amyl group, a hexyl group, a phenyl group, a biphenyl group, a naphthyl group, a fluorenyl group, a phenanthrenyl group, an anthracenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a phenanthrolinyl group, a triazinyl group, a dibenzofuranyl group, and a dibenzothiophenyl group.

b7 in Formula 1 indicates the number of $R_7$(s). b7 may be, e.g., an integer of 1 to 6. When b7 is 2, 3, 4, 5, or 6, the $R_7$(s) may be identical to or different from each other.

$L_{21}$ in Formula 2 may be selected from or include, e.g., a single bond, a substituted or unsubstituted $C_5$-$C_{60}$ carbocyclic group, and a substituted or unsubstituted $C_1$-$C_{60}$ heterocyclic group.

In an implementation, $L_{21}$ may be selected from or include, e.g., a single bond, a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a phenalenylene group, a phenanthrenylene group, an anthracenylene group, a fluoranthenylene group, a triphenylenylene group, a pyrenylene group, a chrysenylene group, a naphthacenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, benzophenanthrolinylene group, a phenazinylene group, a benzimidazolylene group, a benzofuranylene group, a benzothiophenylene group, a benzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a benzophenanthrolinylene group, a phenazinylene group, a benzimidazolylene group, a benzofuranylene group, a benzothiophenylene group, a benzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a benzophenanthrolinyl group, a phenazinyl group, a benzimidazolyl group, a benzofuranyl group, a benzothiophenyl group, a benzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group.

In an implementation, $L_{21}$ may be selected from, e.g., single bond or a group represented by one of Formulae 3-1 to 3-35.

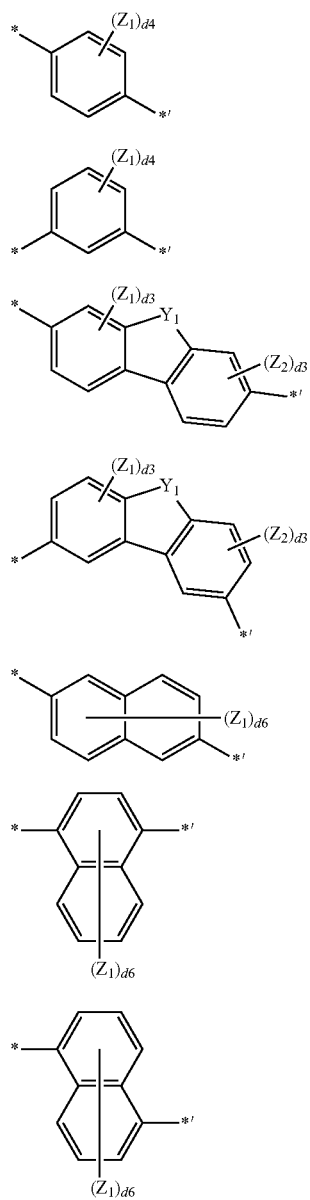
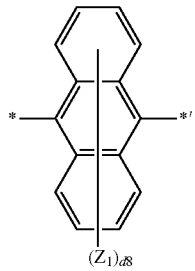
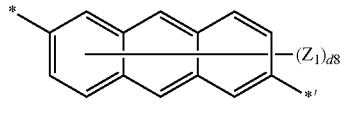
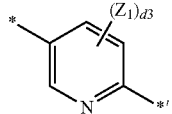
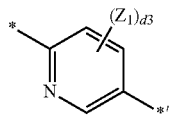
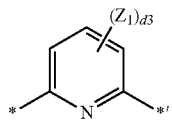
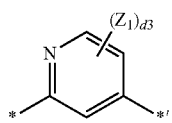
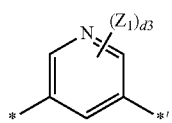
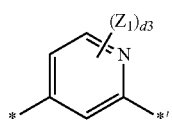
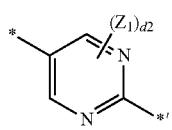
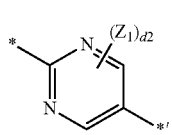

3-19 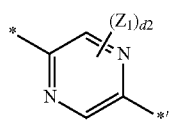
3-20 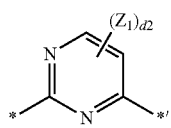
3-21 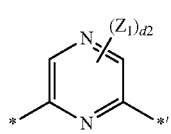
3-22 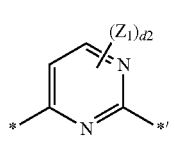
3-23 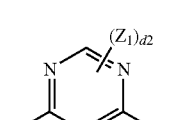
3-24 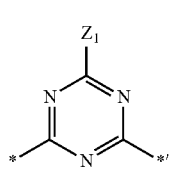
3-25 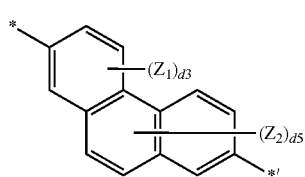
3-26 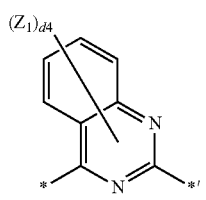
3-27 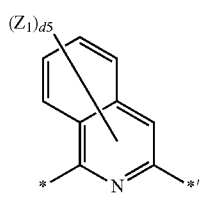
3-28 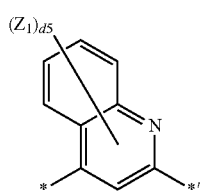
3-29 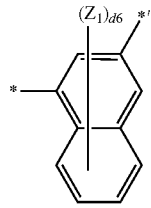
3-30 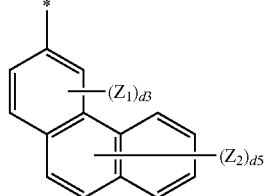
3-31 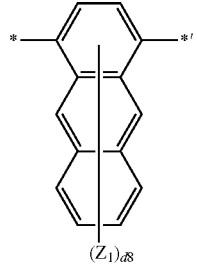
3-32 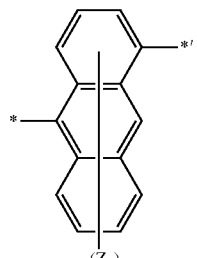
3-33 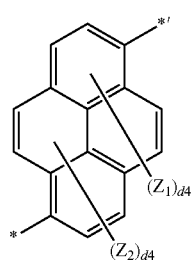
3-34 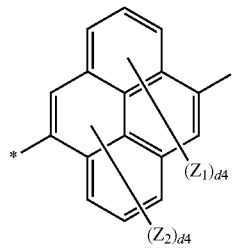

3-35

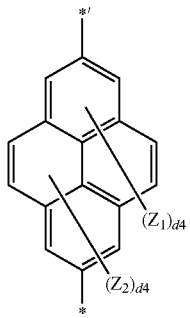

In Formula 3-1 to 3-35, $Y_1$ may be O, S, $C(Z_3)(Z_4)$, $N(Z_5)$, or $Si(Z_6)(Z_7)$, $Z_1$ to $Z_7$ may each independently be selected from or include, e.g., hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, d2 may be, e.g., an integer of 0 to 2, and when d2 is 2, the $Z_1$(s) may be identical to or different from each other, d3 may be, e.g., an integer of 0 to 3, and when d3 is 2 or 3, the $Z_1$(s) may be identical to or different from each other and the $Z_2$(s) may be identical to or different from each other, d4 may be, e.g., an integer of 0 to 4, and when d4 is 2, 3, or 4, the $Z_1$(s) may be identical to or different from each other and the $Z_2$(s) may be identical to or different from each other, d5 may be, e.g., an integer of 0 to 5, and when d5 is 2, 3, 4, or 5, the $Z_1$(s) may be identical to or different from each other and the $Z_2$(s) may be identical to or different from each other, d6 may be, e.g., an integer of 0 to 6, and when d6 is 2, 3, 4, 5, or 6, the $Z_1$(s) may be identical to or different from each other and the $Z_2$(s) may be identical to or different from each other, d8 may be, e.g., an integer of 0 to 8, and when d8 is 2, 3, 4, 5, 6, 7, or 8, the $Z_1$(s) may be identical to or different from each other, and

* and *' each indicate a binding site to a neighboring atom.

In an implementation, $L_{21}$ may be selected from, e.g., a single bond or a group represented by one of Formulae 4-1 to 4-8.

4-1

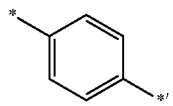

4-2

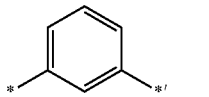

4-3

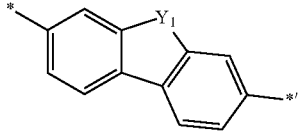

4-4

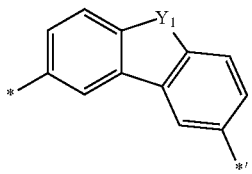

4-5

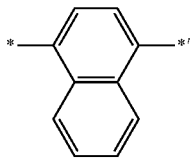

4-6

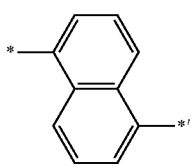

4-7

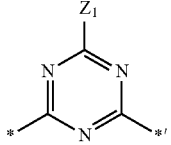

4-8

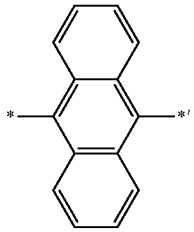

In Formulae 4-1 to 4-8, $Y_1$ may be O, S, $C(Z_3)(Z_4)$, $N(Z_5)$, or $Si(Z_6)(Z_7)$, $Z_1$ and $Z_3$ to $Z_7$ may each independently be selected from or include, e.g., hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, and a naphthyl group,

* and *' each indicate a binding site to a neighboring atom.

a21 in Formula 2 indicates the number of $L_{21}$(s). a21 may be, e.g., an integer of 1 to 5. When a21 is 2, 3, 4, or 5, the $L_{21}$(s) may be identical to or different from each other.

In an implementation, a21 may be, e.g., 1, 2, 3, or 4.

$Ar_{21}$ in Formula 2 may be selected from or include, e.g., a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_1$)($Q_2$)($Q_3$), —B($Q_1$)($Q_2$), —C(=O)($Q_1$), —N($Q_1$)($Q_2$), —P(=O)($Q_1$)($Q_2$), —P(=S)($Q_1$)($Q_2$), —S(=O)(Q)($Q_2$), and —S(=O)$_2$($Q_1$)($Q_2$).

In an implementation, $Ar_{21}$ may be selected from or include, e.g., a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and —P(=O)($Q_1$)($Q_2$).

In an implementation, $Ar_{21}$ may be selected from or include, e.g., a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a benzophenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzoxazolyl group, a dibenzofuranyl group, a dibenzothiophenyl group, and a benzocarbazolyl group;

a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a benzophenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzoxazolyl group, a dibenzofuranyl group, a dibenzothiophenyl group, and a benzocarbazolyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a $C_6$-$C_{20}$ aryl group, and a $C_2$-$C_{20}$ heteroaryl group, and —Si($Q_1$)($Q_2$)($Q_3$), —B($Q_1$)($Q_2$), —C(=O)($Q_1$), —N($Q_1$)($Q_2$), —P(=O)($Q_1$)($Q_2$), —P(=S)($Q_1$)($Q_2$), —S(=O)($Q_1$)($Q_2$), and —S(=O)$_2$($Q_1$)($Q_2$).

In an implementation, $Ar_{21}$ may be selected from, e.g., a group represented by one of Formulae 5-1 to 5-53 or —P(=O)($Q_1$)($Q_2$).

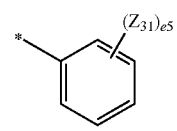

5-1

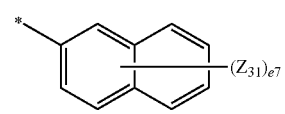

5-2

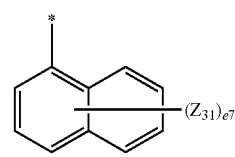

5-3

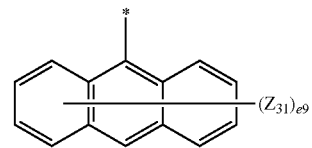

5-4

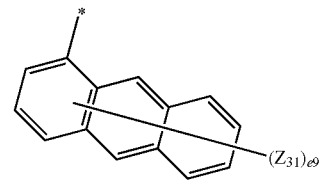

5-5

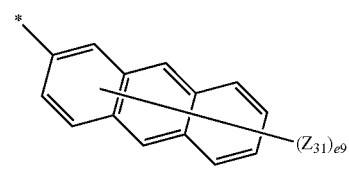

5-6

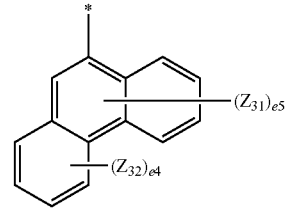

5-7

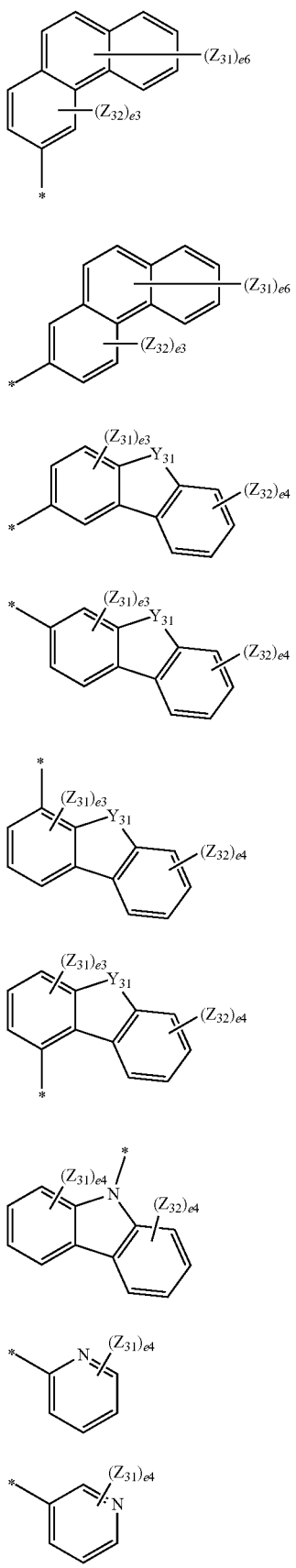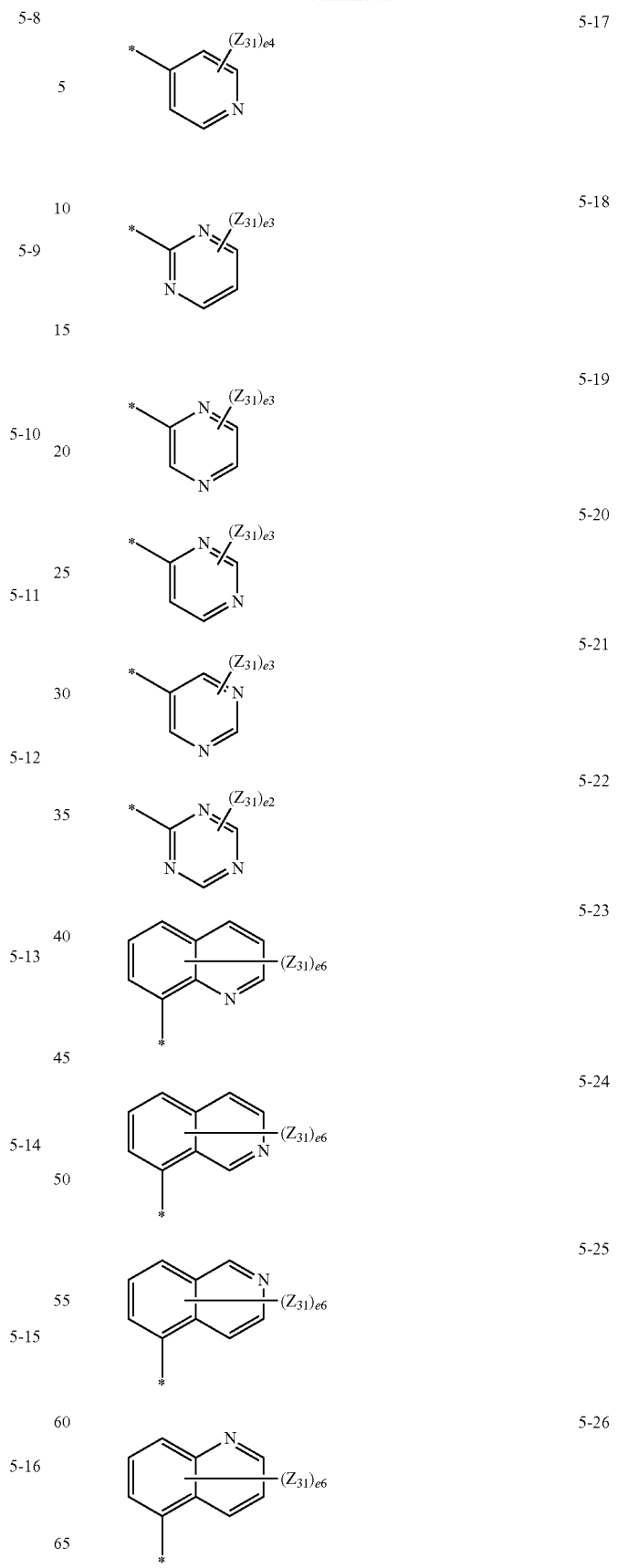

17
-continued
5-27
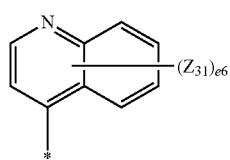
5-28
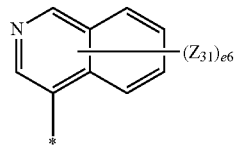
5-29
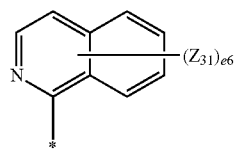
5-30
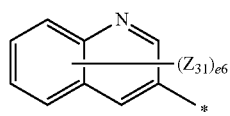
5-31
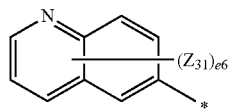
5-32
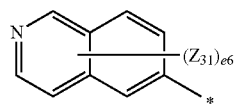
5-33
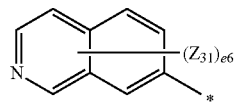
5-34
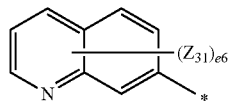
5-35
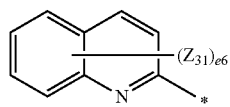
5-36
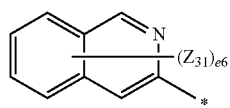
5-37
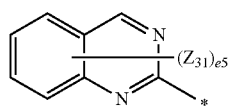
18
-continued
5-38
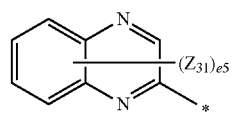
5-39
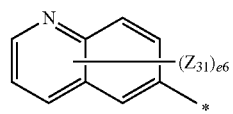
5-40
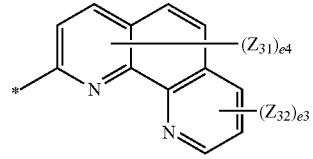
5-41
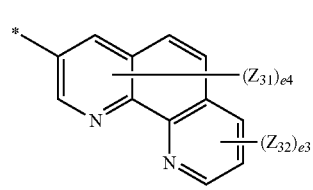
5-42
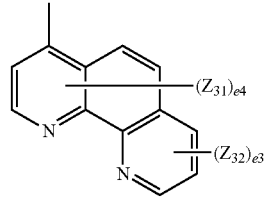
5-43
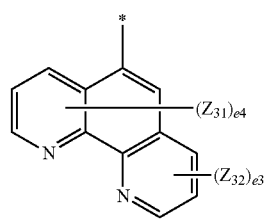
5-44
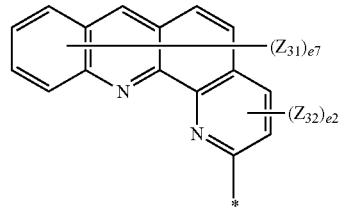
5-45
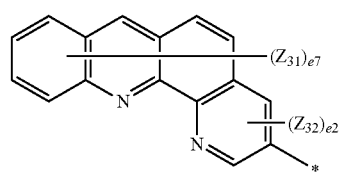

-continued 5-46
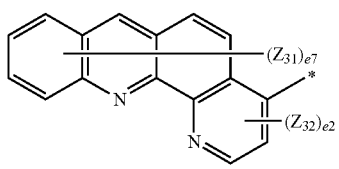

5-47
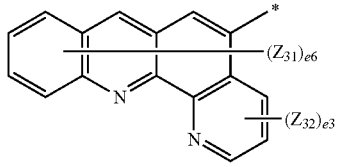

5-48
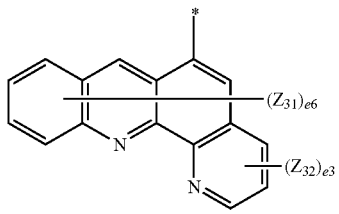

5-49
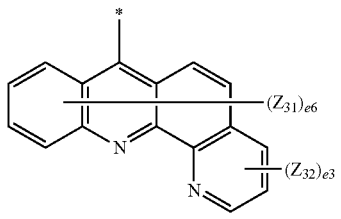

5-50
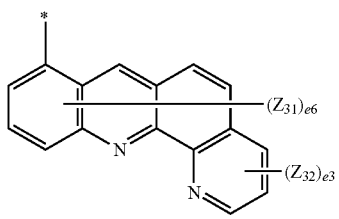

5-51
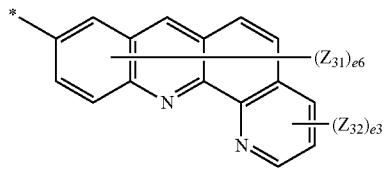

5-52
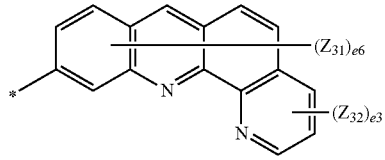

5-53
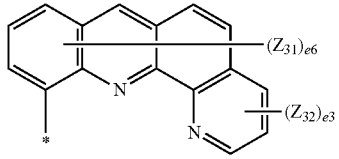

In Formulae 5-1 to 5-53,
$Y_{31}$ may be O, S, $C(Z_{33})(Z_{34})$, $N(Z_{35})$, $Si(Z_{36})(Z_{37})$, or $P(=O)(Z_{38})$, $Z_{31}$ to $Z_{38}$, $Q_1$, and $Q_2$ may each independently be selected from or include, e.g., hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzo-fluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a benzophenanthrolinyl group, a phenazinyl group, a triazinyl group, a dibenzofuranyl group, and a dibenzothiophenyl group, e2 may be an integer of 0 to 2, when e2 is 2, the $Z_{31}$(s) may be identical to or different from each other and $Z_{32}$(s) may be identical to or different from each other, e3 may be an integer of 0 to 3, and when e3 is 2 or 3, the $Z_{31}$(s) may be identical to or different from each other and $Z_{32}$(s) may be identical to or different from each other, e4 may be an integer of 0 to 4, and when e4 is 2, 3, or 4, the $Z_{31}$(s) may be identical to or different from each other and $Z_{32}$(s) may be identical to or different from each other, e5 may be an integer of 0 to 5, and when e5 is 2, 3, 4, or 5, the $Z_{31}$(s) may be identical to or different from each other, e6 may be an integer of 0 to 6, and when e6 is 2, 3, 4, 5, or 6, the $Z_{31}$(s) may be identical to or different from each other, e7 may be an integer of 0 to 7, and when e7 is 2, 3, 4, 5, 6, or 7, the $Z_{31}$(s) may be identical to or different from each other, e9 may be an integer of 0 to 9, and when e9 is 2, 3, 4, 5, 6, 7, 8, or 9, the $Z_{31}$(s) may be identical to or different from each other, and

* indicates a binding site to a neighboring atom.

In an implementation, $Ar_{21}$ may be selected from, e.g., a group represented by one of Formulae 5-1, 5-3, 5-11, 5-12, 5-22, and 5-40 to 5-53 or $P(=O)(Q_1)(Q_2)$.

In an implementation, $Ar_{21}$ may be, e.g., a group represented by one of Formulae 6-1 to 6-16.

6-1
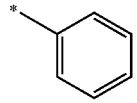

6-2
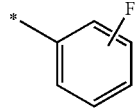

6-3
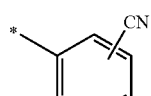

-continued 6-4
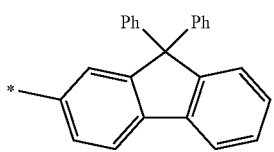

6-5
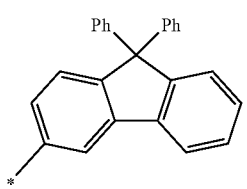

6-6
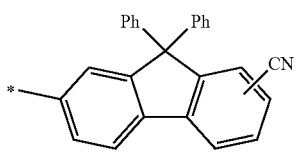

6-7
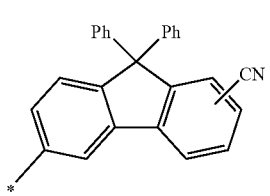

6-8
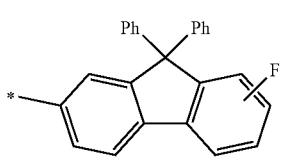

6-9
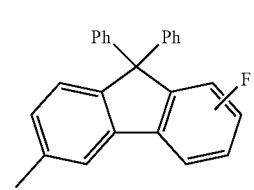

6-10
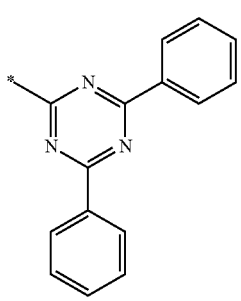

6-11
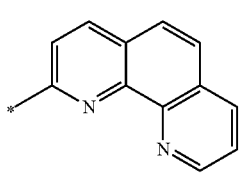

6-12
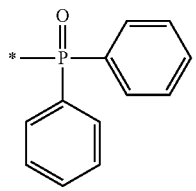

6-13
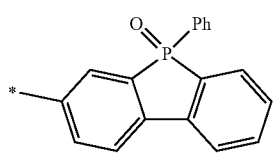

6-14
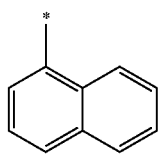

6-15
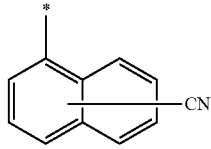

6-16
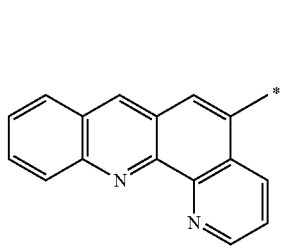

In Formulae 6-1 to 6-16, Ph indicates a phenyl group, and * indicates a binding site to a neighboring atom.

b21 in Formula 2 indicates the number of $Ar_{21}(s)$. b21 may be, e.g., an integer of 1 to 8. When b21 is 2, 3, 4, 5, 6, 7, or 8, the $Ar_{21}(s)$ may be identical to or different from each other.

In an implementation, two (e.g., adjacent ones) of $L_{21}$ and $Q_1$ to $Q_3$ in Formulae 1 and 2 may be separate or may optionally be linked to form a substituted or unsubstituted $C_5$-$C_{60}$ carbocyclic group or a substituted or unsubstituted $C_1$-$C_{60}$ heterocyclic group.

In an implementation, $L_{21}$ in Formula 2 may be selected from, e.g., a single bond and a group represented by one of Formulae 4-1 to 4-8, and $Ar_{21}$ in Formula 2 may be, e.g., a group represented by one of Formulae 6-1 to 6-16.

In an implementation, the condensed cyclic compound represented by Formula 1 may be represented by, e.g., one of Formulae 1-1 to 1-4.

<Formula 1-1>
<Formula 1-2>
<Formula 1-3>
<Formula 1-4>

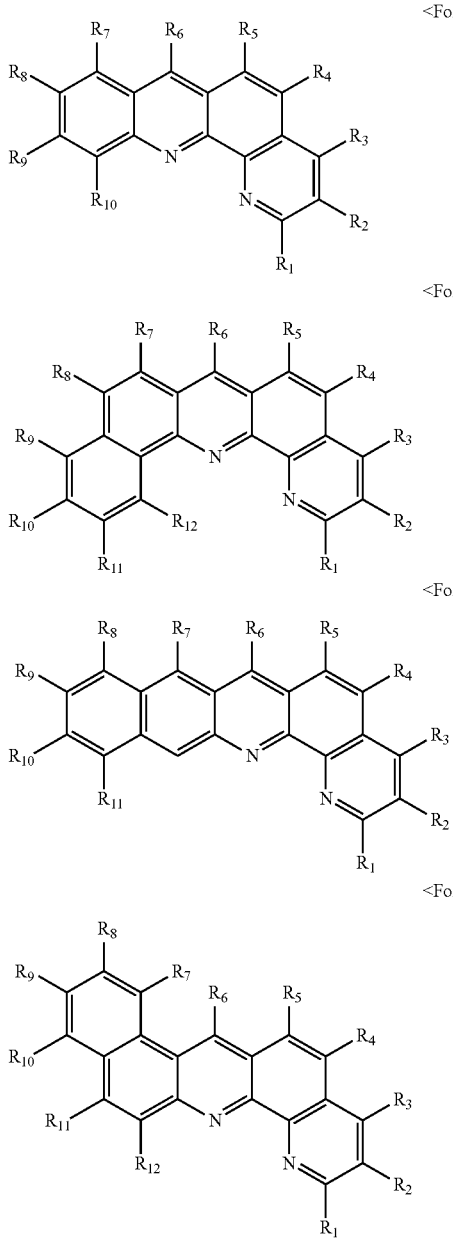

In Formulae 1-1 to 1-4, $R_1$ to $R_7$, $L_{21}$, $Ar_{21}$, a21, and b21 may be defined the same as those of Formulae 1 and 2, $R_8$ to $R_{12}$ may be defined the same as $R_1$ of Formula 1, at least one of $R_1$ to $R_{10}$ in Formula 1-1 may be a group represented by Formula 2, at least one of $R_1$ to $R_{12}$ in Formulae 1-2 to 1-4 may be a group represented by Formula 2, and

* indicates a binding site to a neighboring atom.

In an implementation, at least one of $R_1$, $R_2$, $R_4$, and $R_8$ in Formulae 1-1 and 1-2 may be a group represented by Formula 2.

In an implementation, $R_1$, $R_2$, $R_4$, or $R_8$ (e.g., only one of $R_1$, $R_2$, $R_4$, or $R_8$) in Formulae 1-1 and 1-2 may be a group represented by Formula 2.

In an implementation, at least one of $R_1$, $R_2$, $R_4$, and $R_5$ in Formulae 1-1 to 1-4 may be a group represented by Formula 2.

In an implementation, $R_1$, $R_2$, $R_4$, or $R_5$ in Formulae 1-1 to 1-4 may be a group represented by Formula 2.

In an implementation, at least one of $R_1$, $R_2$, $R_4$, $R_5$, and $R_7$ in Formula 1 may be a group represented by Formula 2.

In an implementation, $R_1$, $R_2$, $R_4$, $R_5$, or $R_7$ in Formula 1 may be a group represented by Formula 2.

In an implementation, $R_1$, $R_2$, $R_4$, $R_5$, or $R_7$ in Formula 1 may be a group represented by Formula 2, and the remaining ones of $R_1$ to $R_7$ may each independently be selected from or include hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a phenanthrolinyl group, a triazinyl group, a dibenzofuranyl group, a dibenzothiophenyl group, a benzocarbazolyl group, and a dibenzocarbazolyl group.

In an implementation, in Formula 1, $R_1$ may be a group represented by Formula 2, and $R_2$ to $R_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, and a naphthyl group; or $R_2$ may be a group represented by Formula 2, and $R_1$ and $R_3$ to $R_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, and a naphthyl group; or $R_4$ may be a group represented by Formula 2, and $R_1$ to $R_3$ and $R_5$ to $R_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, and a naphthyl group; or $R_5$ may be a group represented by Formula 2, and $R_1$ to $R_4$, $R_6$, and $R_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, and a naphthyl group; or $R_7$ may be a group represented by Formula 2, and $R_1$ to $R_6$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, and a naphthyl group.

In an implementation, $R_1$, $R_2$, $R_4$, $R_5$, or $R_7$ in Formula 1 may be a group represented by Formula 2, $L_{21}$ in Formula 2 may be selected from a single bond and a group represented by one of Formulae 4-1 to 4-8, and $Ar_{21}$ in Formula 2 may be a group represented by one of Formulae 6-1 to 6-16.

In an implementation, the condensed cyclic compound represented by Formula 1 may be, e.g., one of the following Compounds 1 to 118.

1
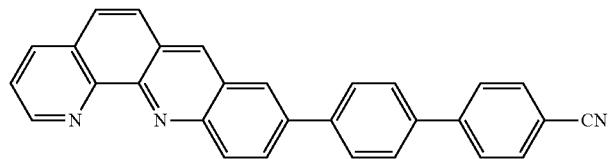
2
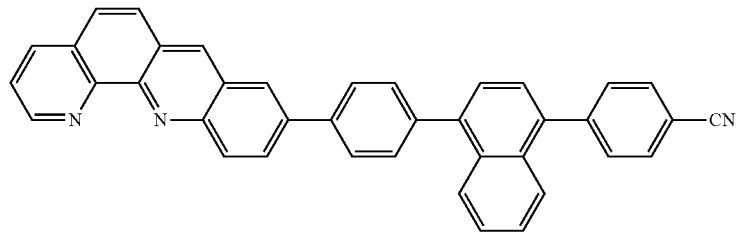
3
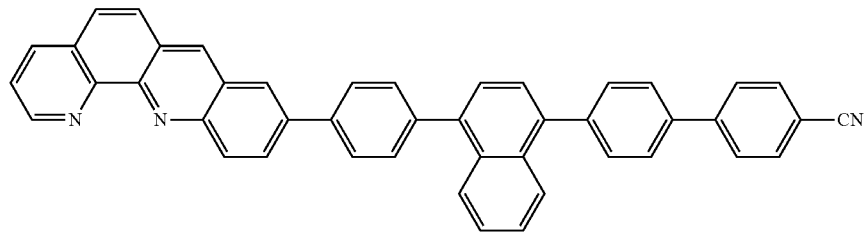
4
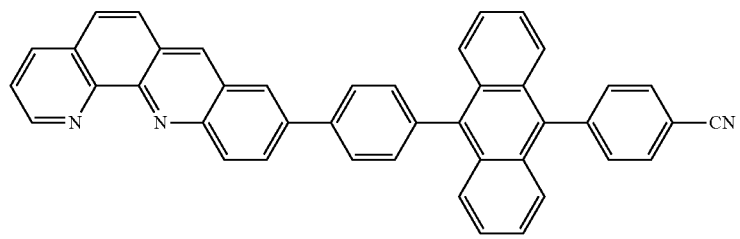
5
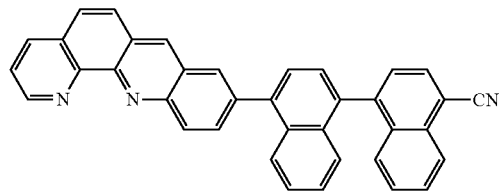
6
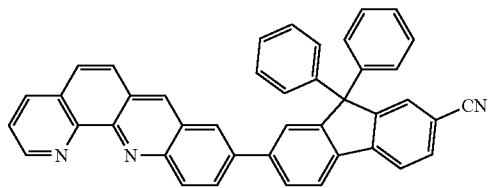
7
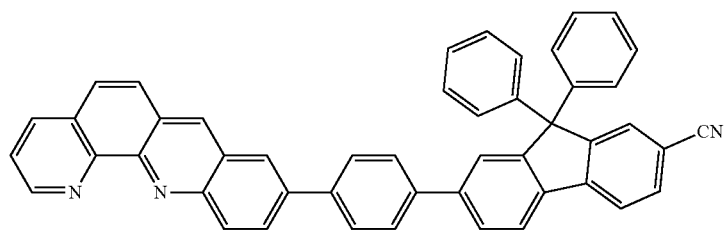

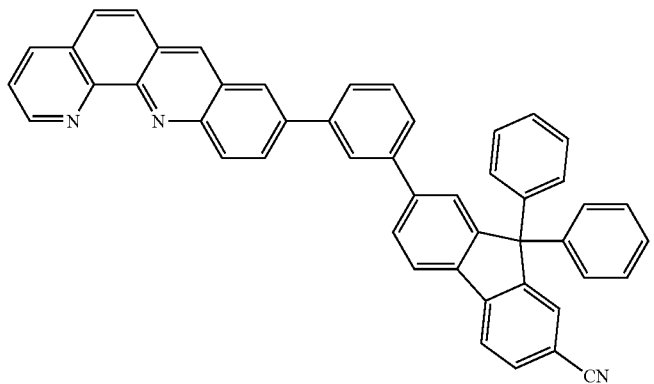
8
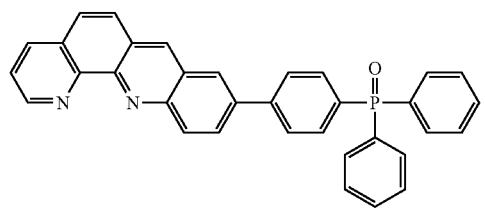
9
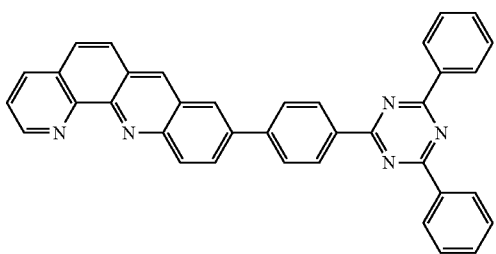
10
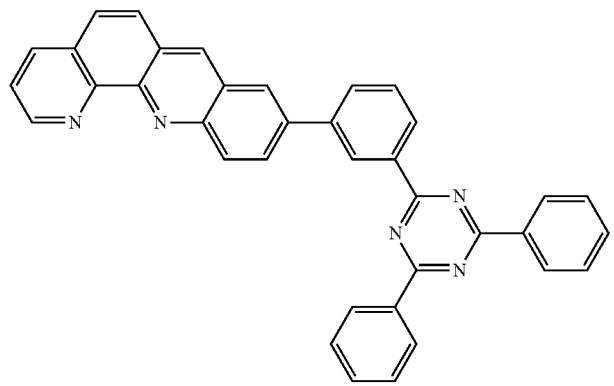
11
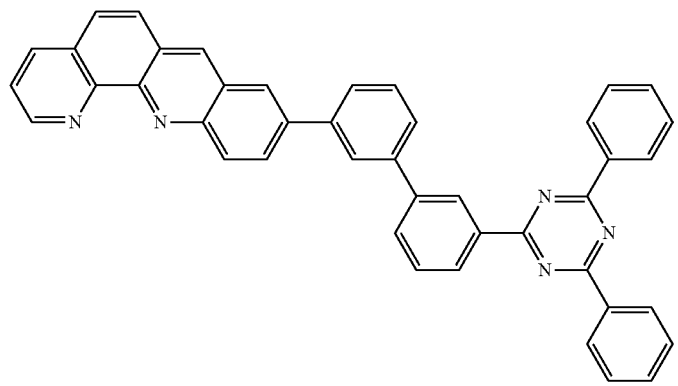
12

13
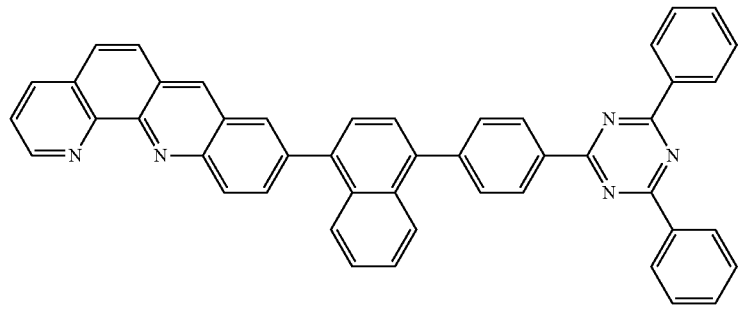
14
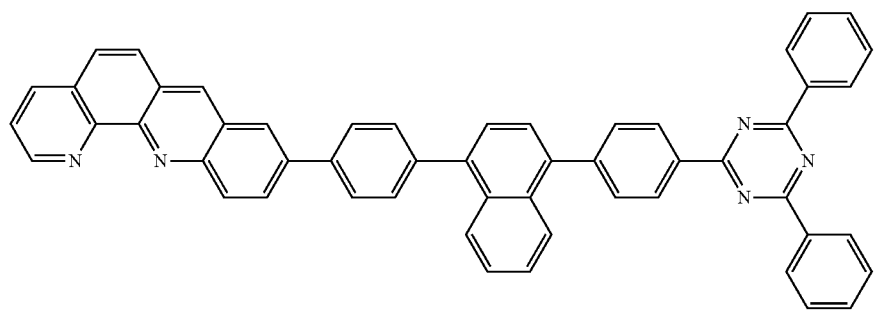
15
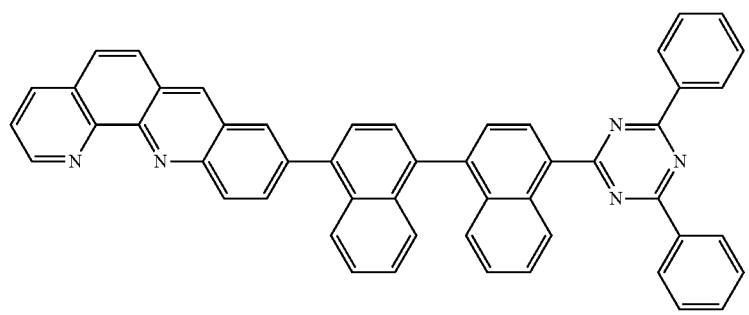
16
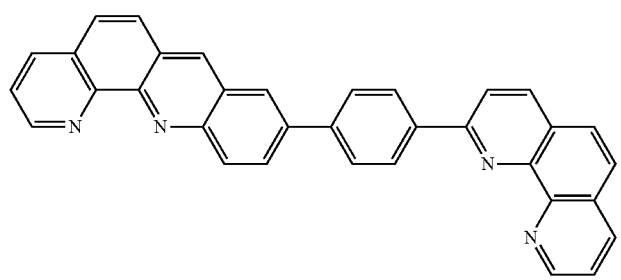
17
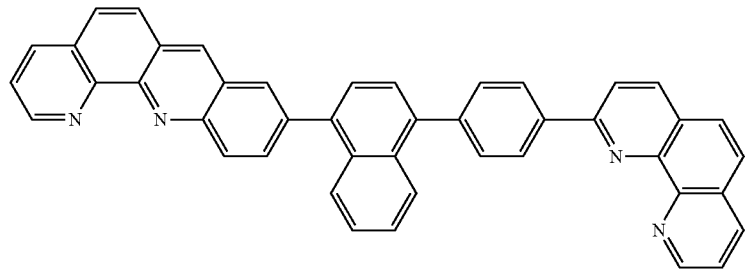

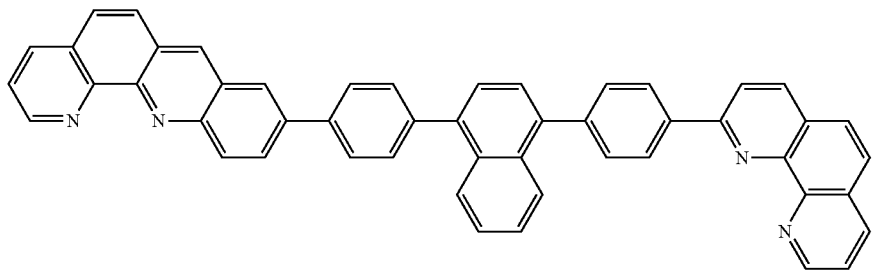
18
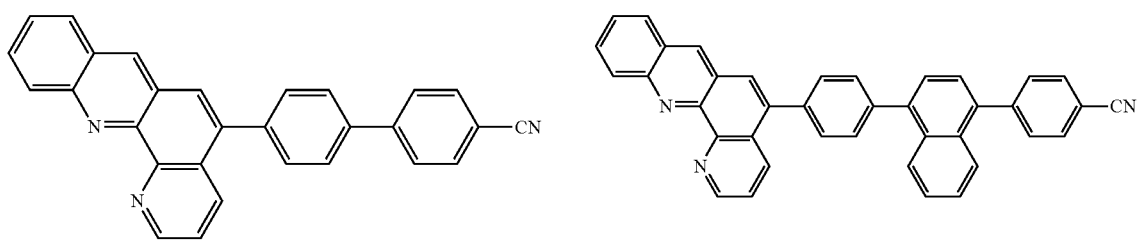
19  20
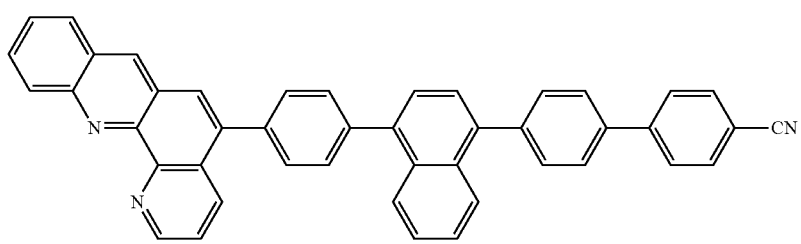
21
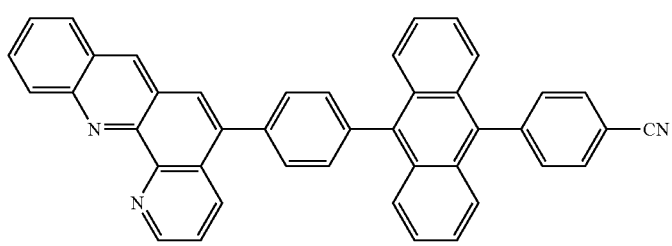
22
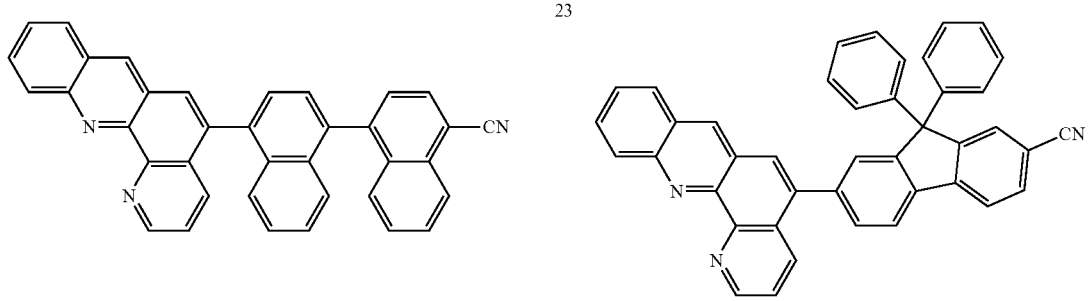
23  24
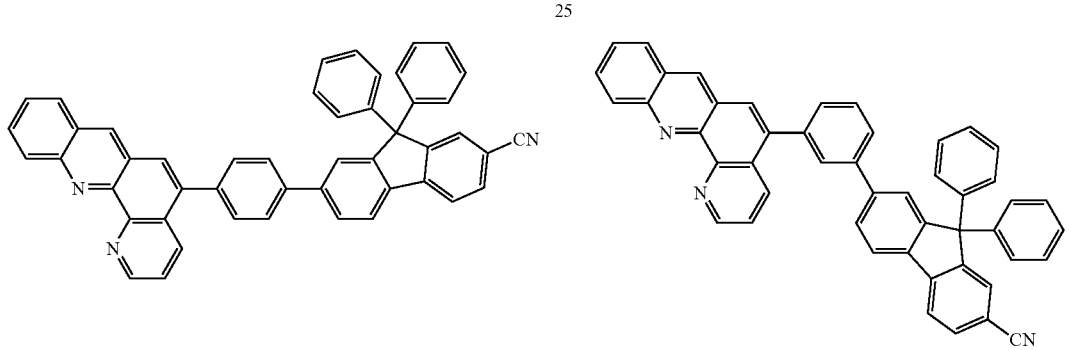
25  26

-continued
27
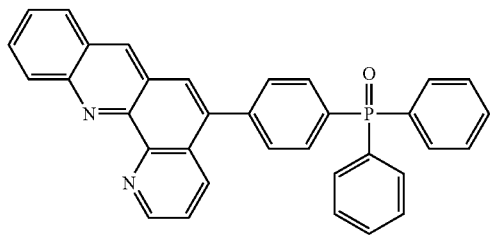
28
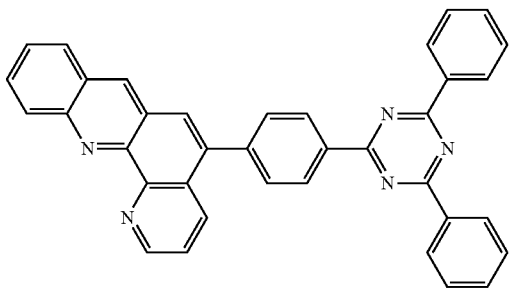
29
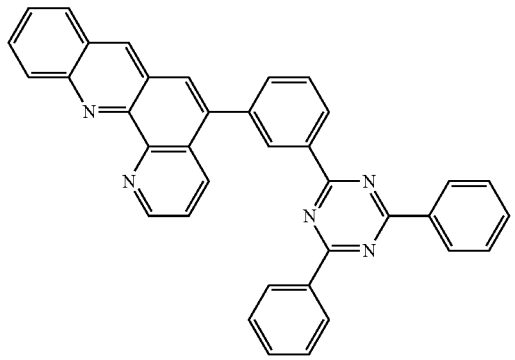
30
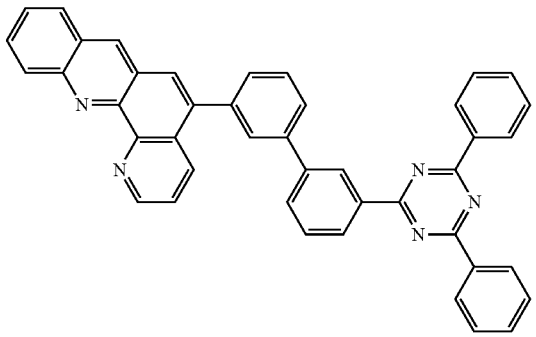
31
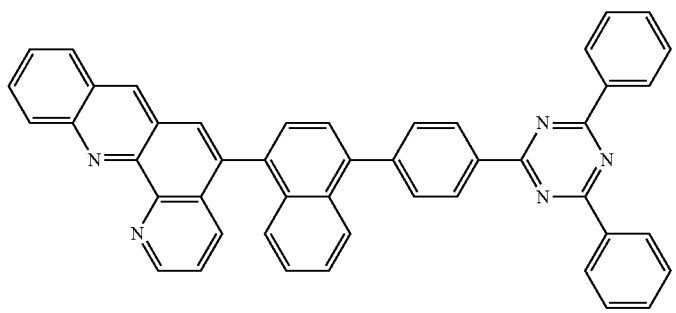
32
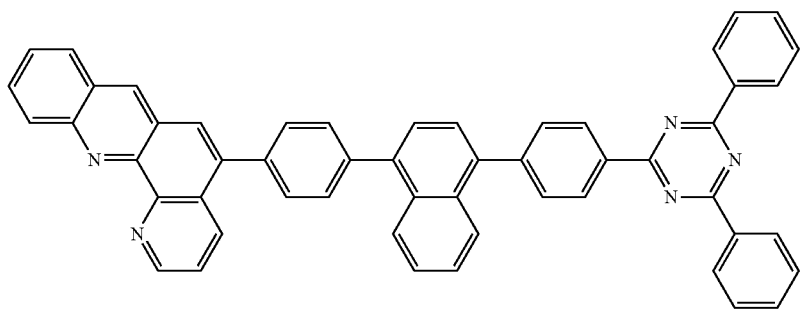
33
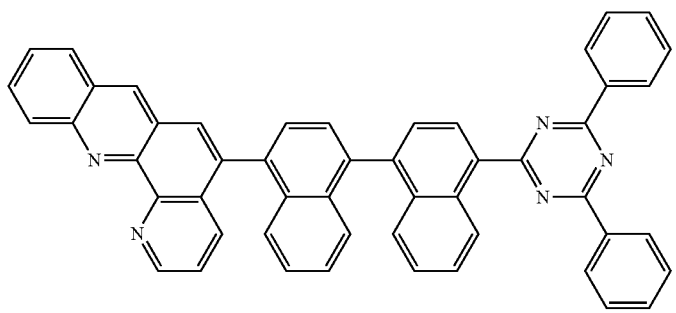

-continued
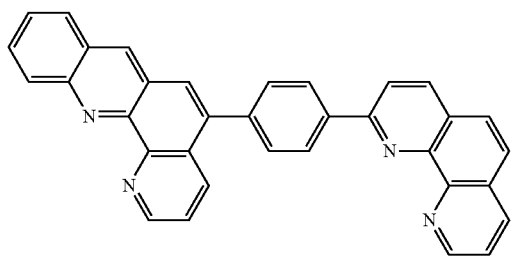
34
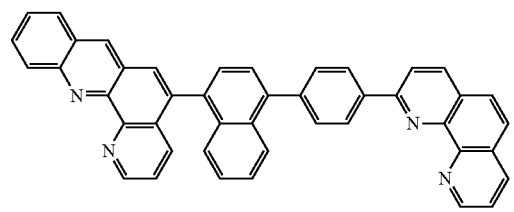
35
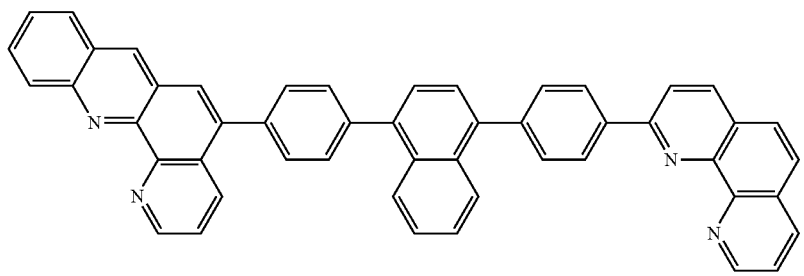
36
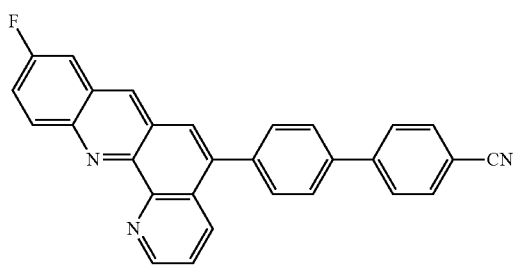
37
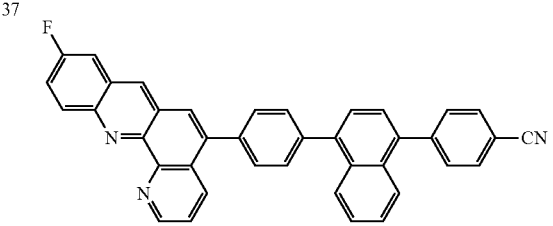
38
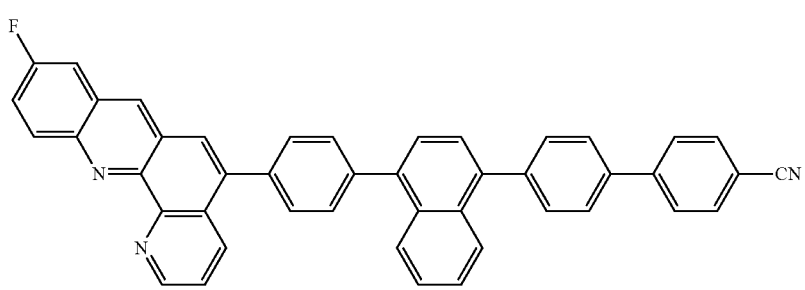
39
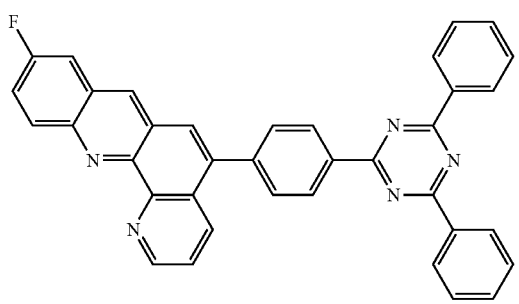
40
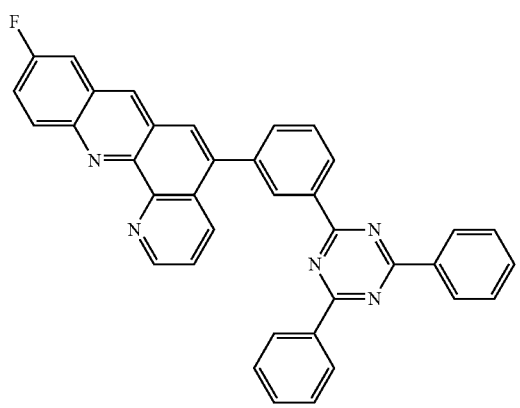
41

42
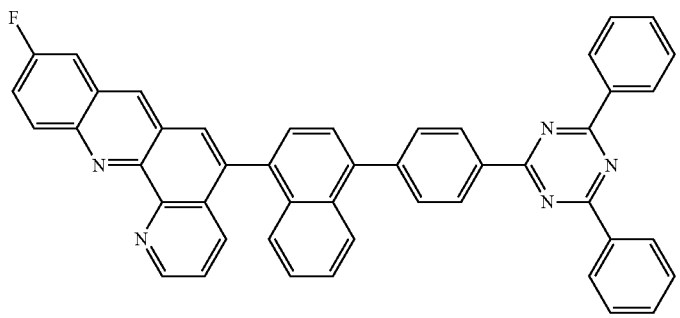
43
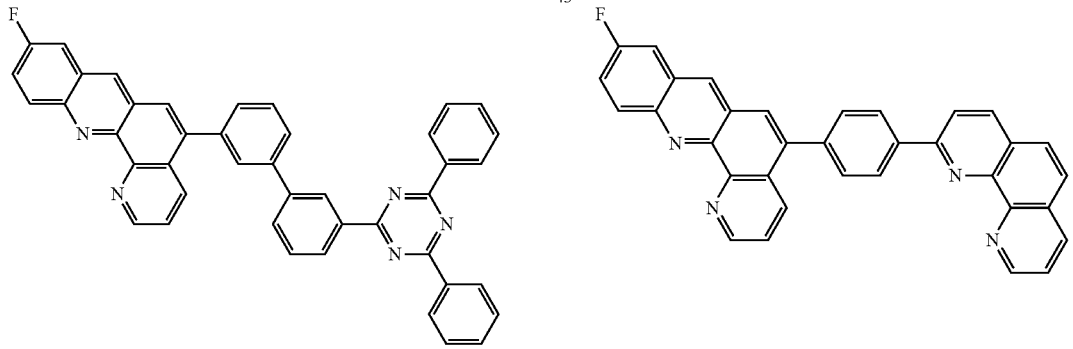
44
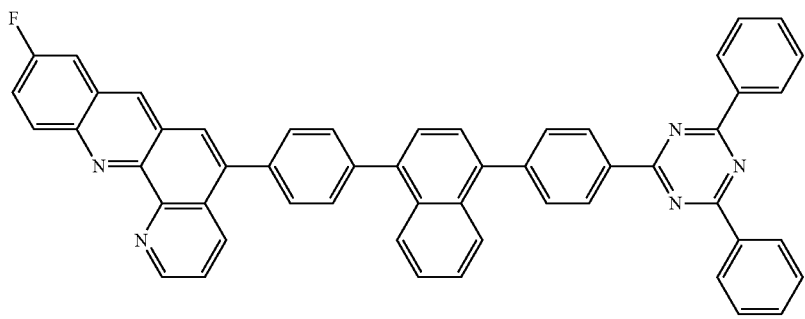
45
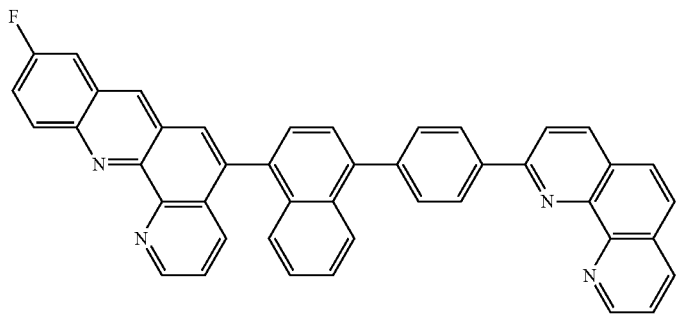
46
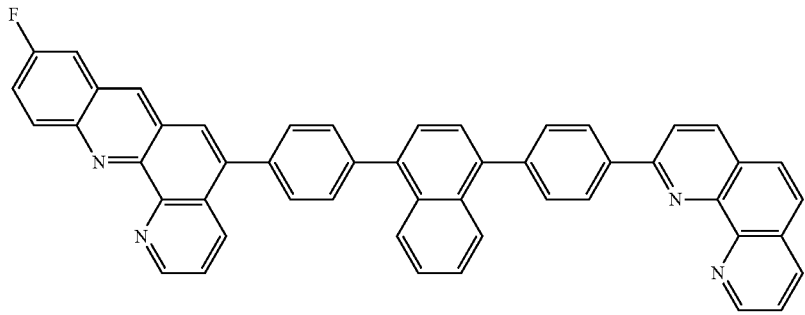
47

-continued
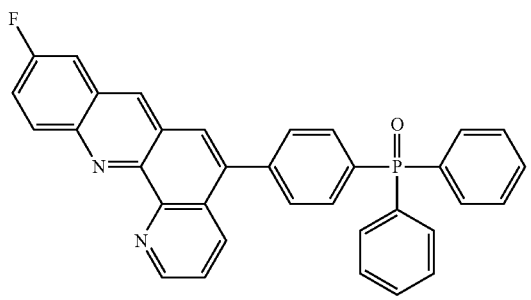
48
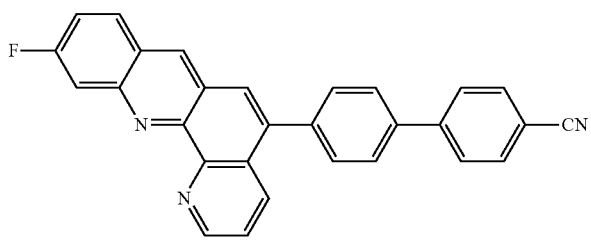
49
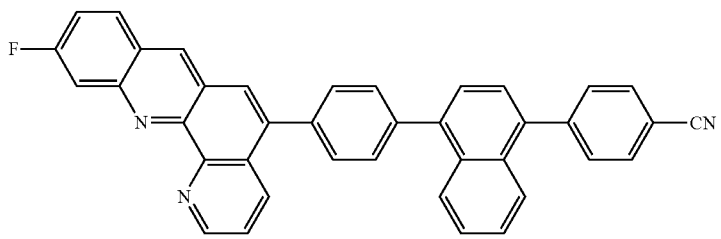
50
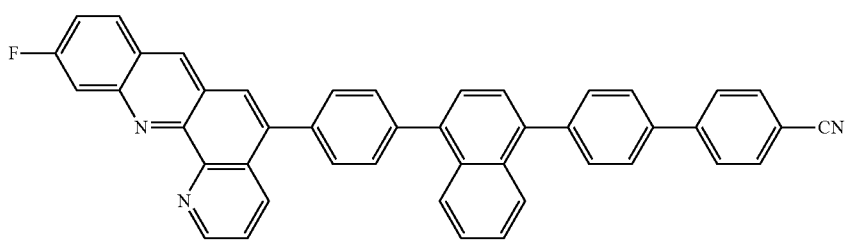
51
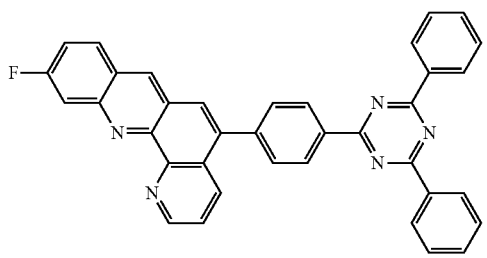
52
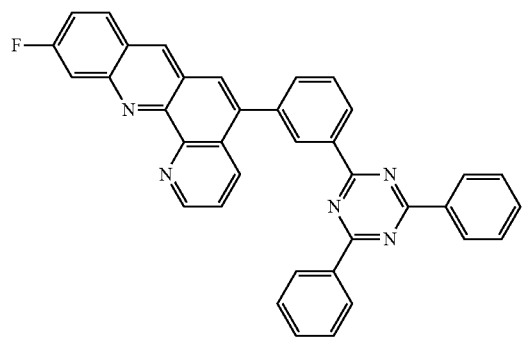
53

54
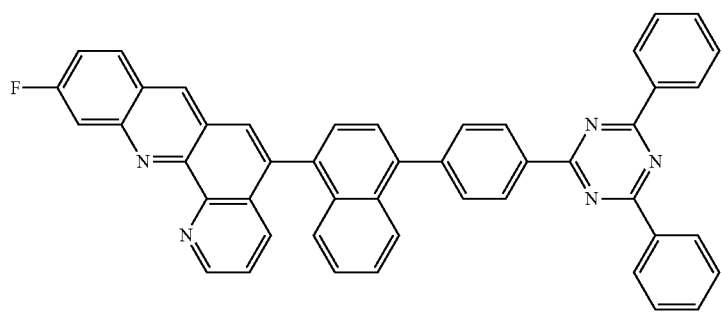
55
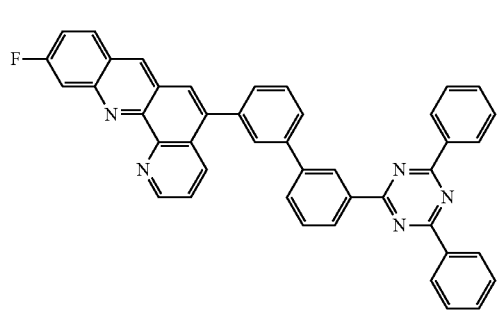
56
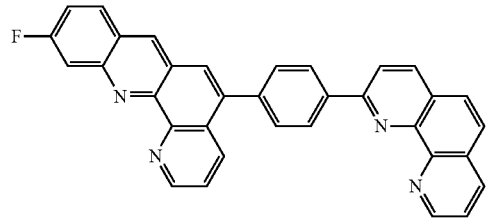
57
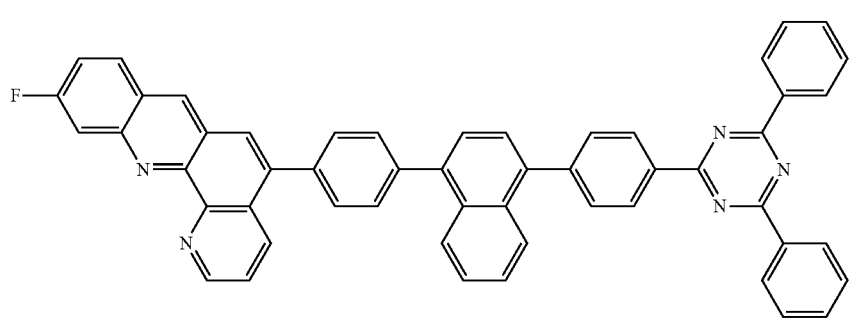
58
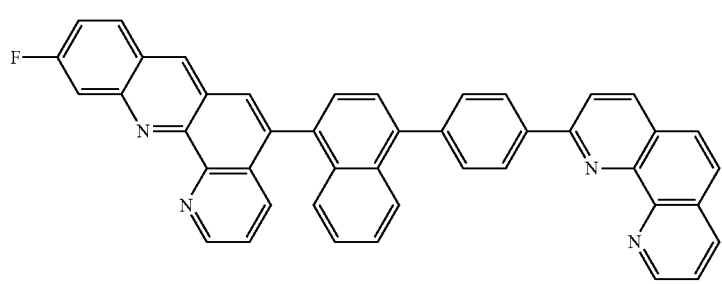
59
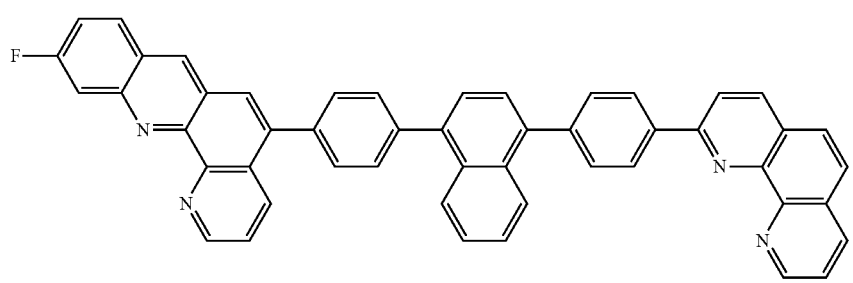

-continued
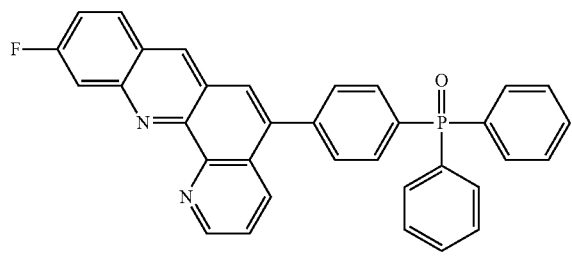
60
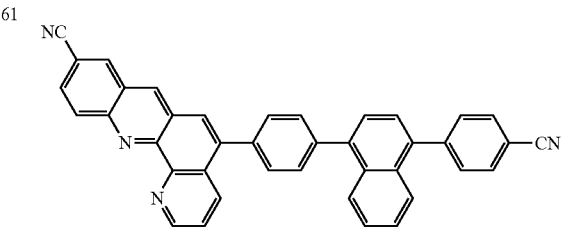
61   62
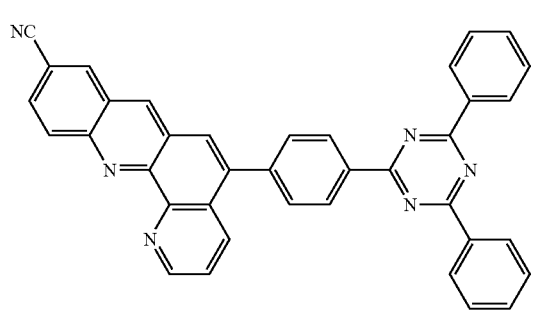
63
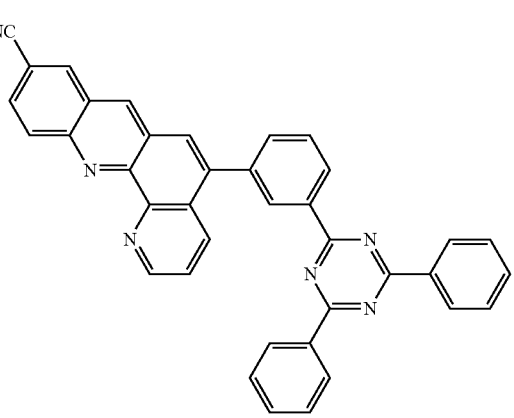
64   65
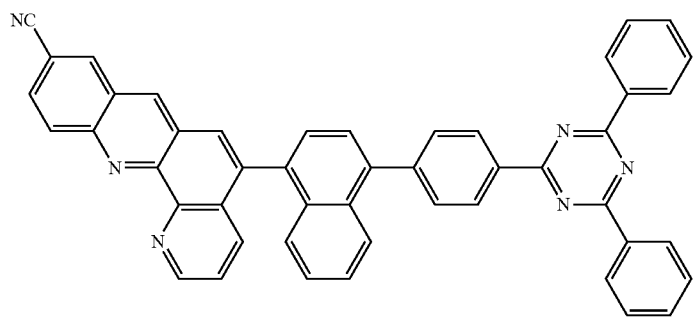
66

-continued
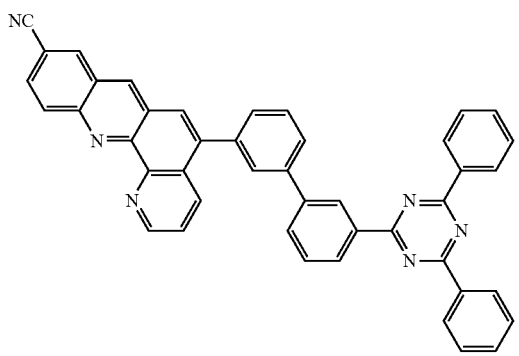
67
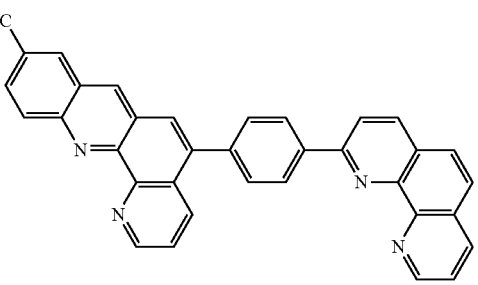
68
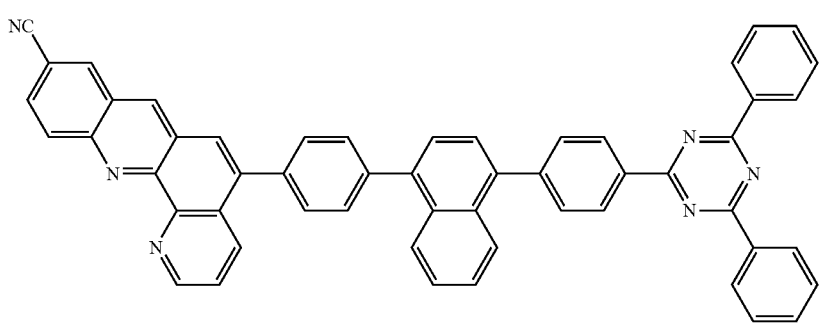
69
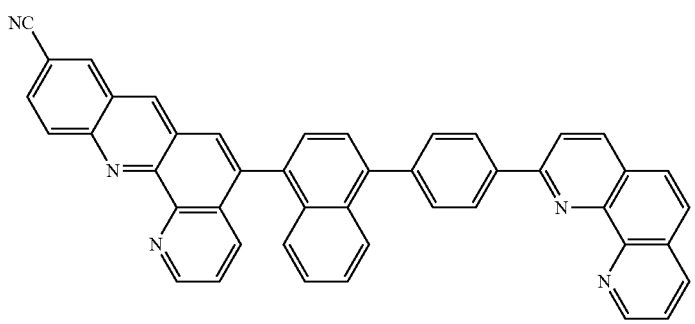
70
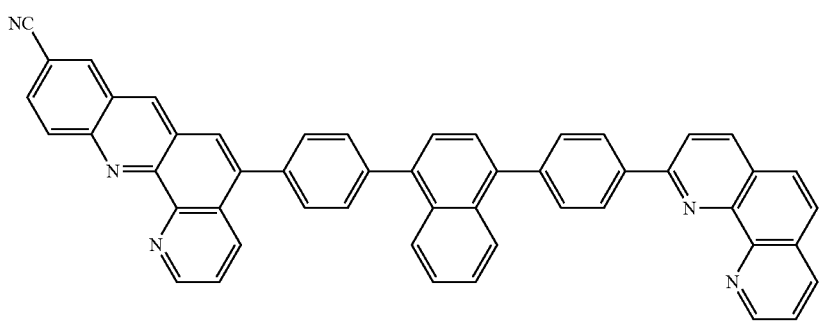
71
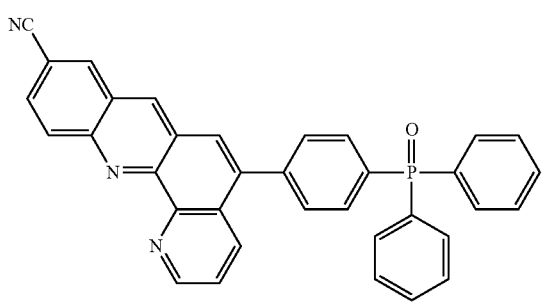
72

-continued
73
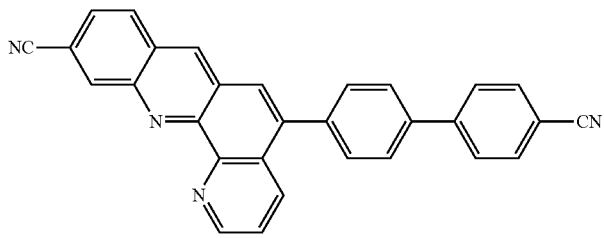
74
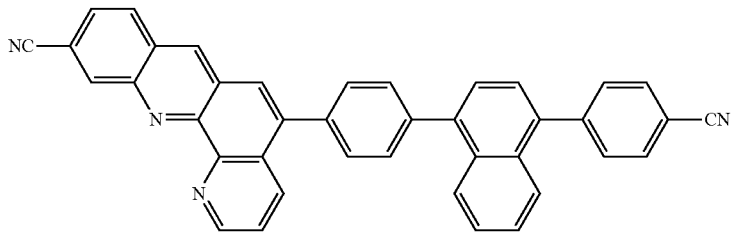
75
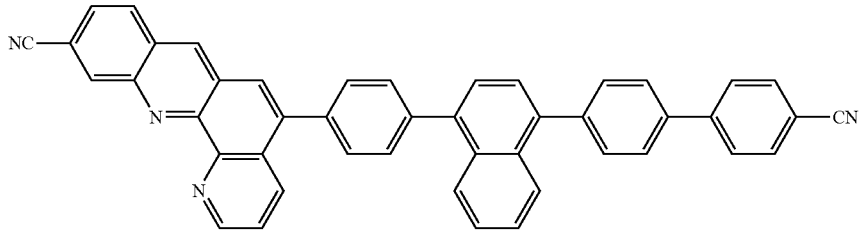
76
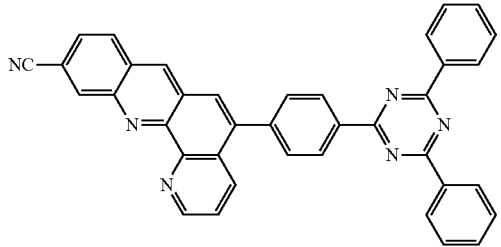
77
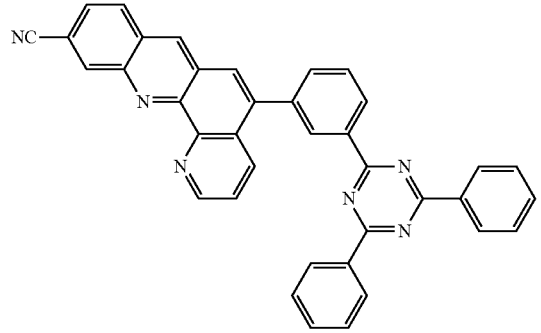
78
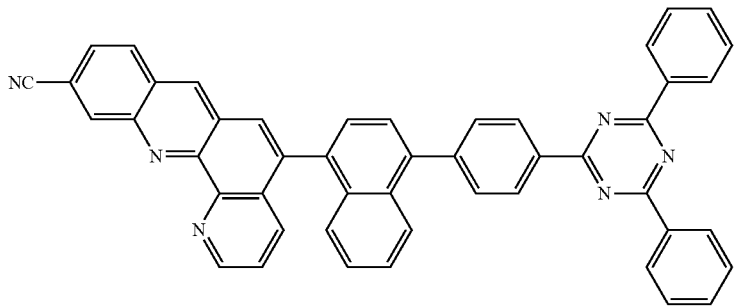

-continued
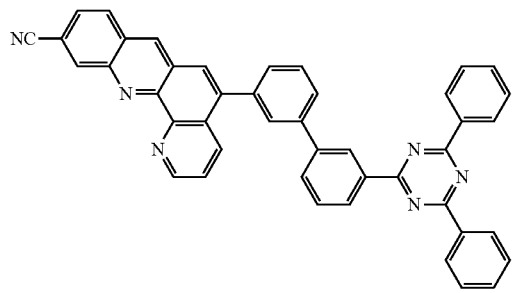
79
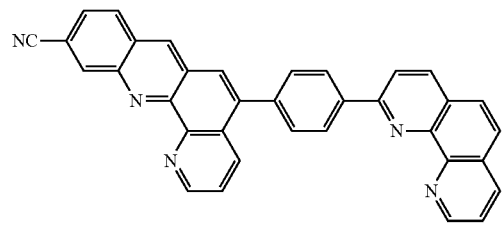
80
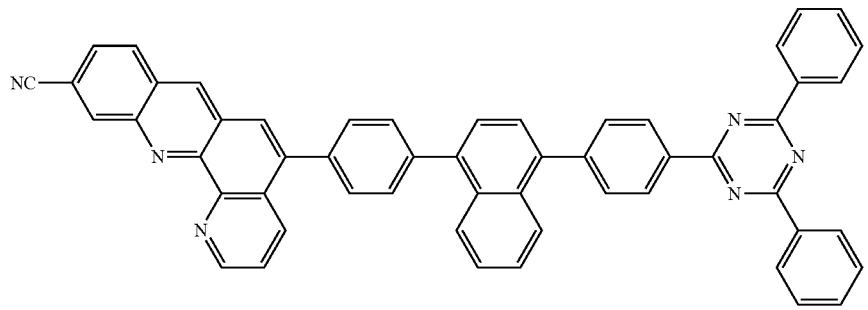
81
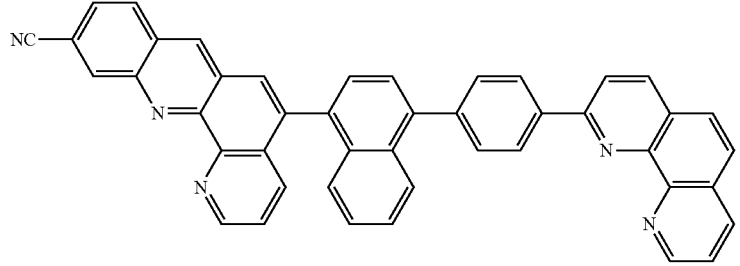
82
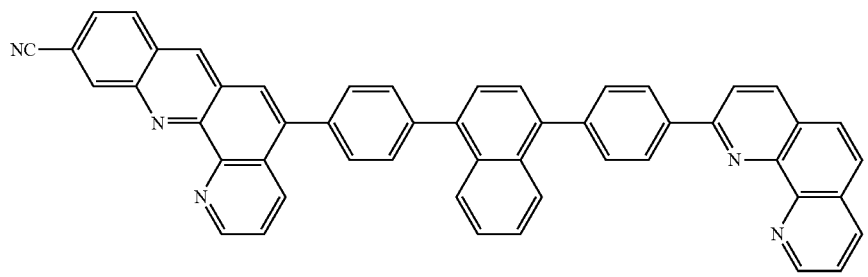
83
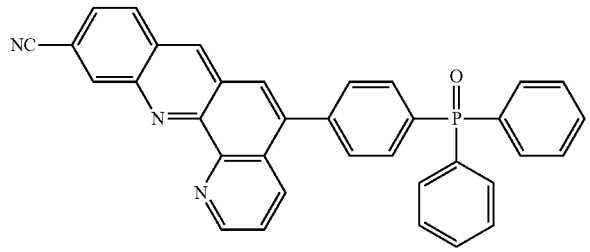
84

85
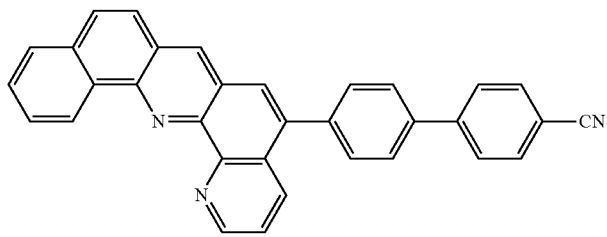
86
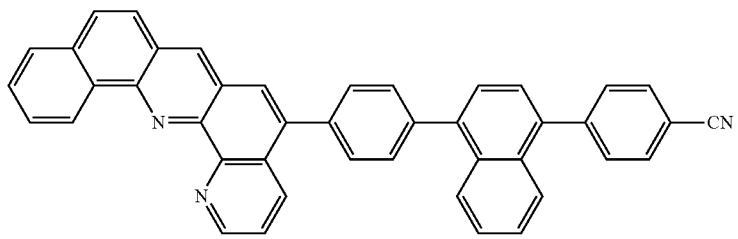
87
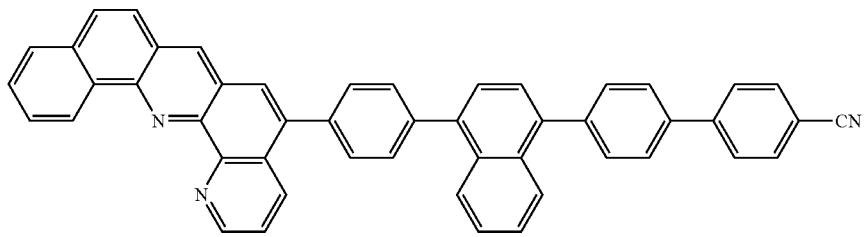
88
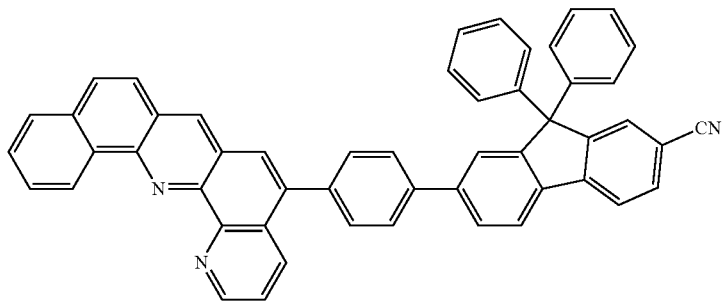
89
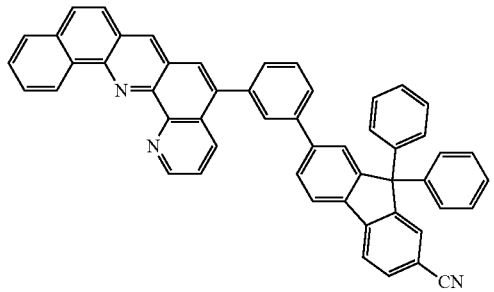
90
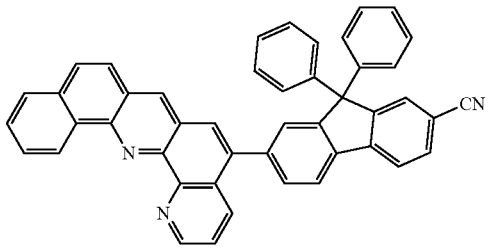
91
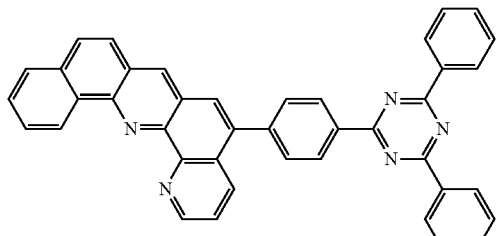
92
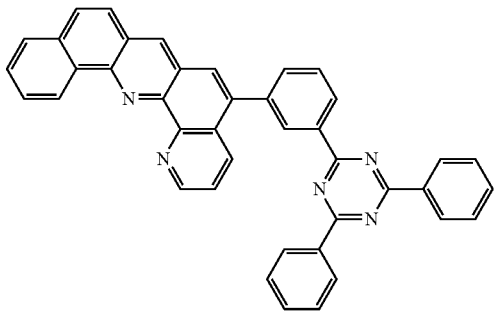

93
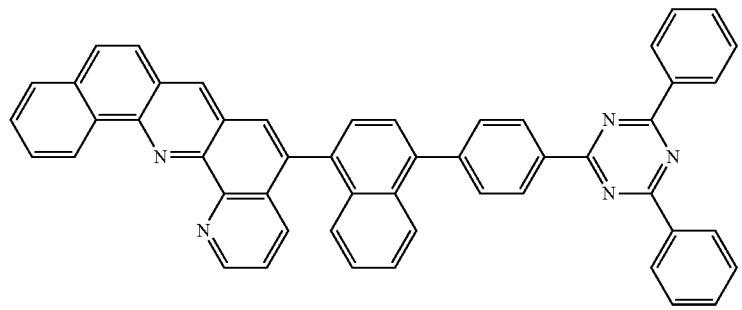
94
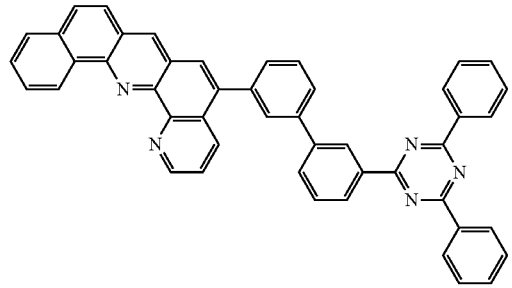
95
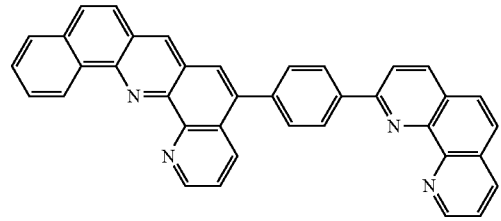
96
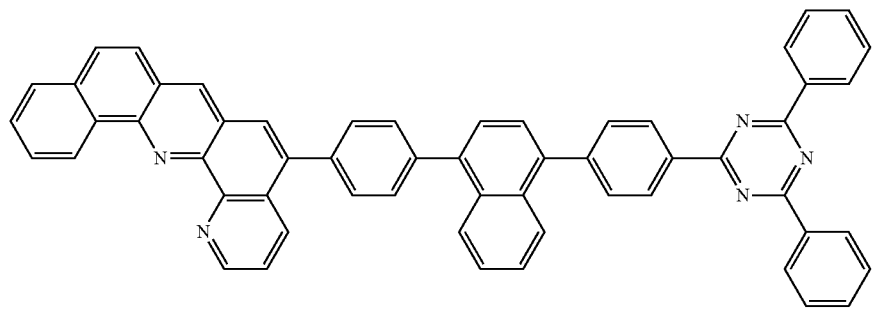
97
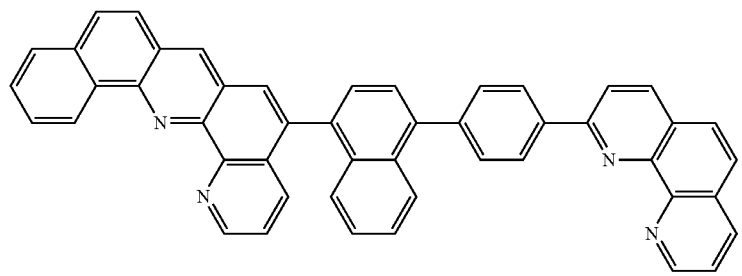
98
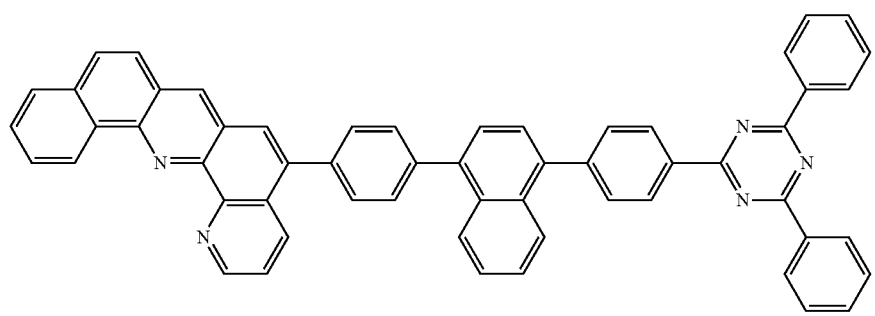

-continued
99
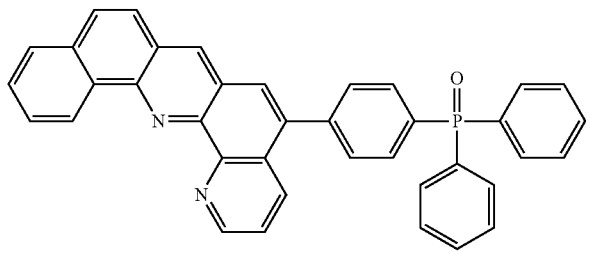
100
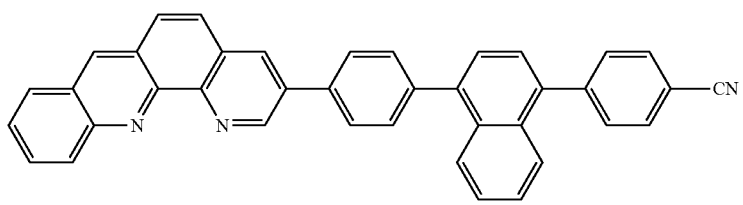
101
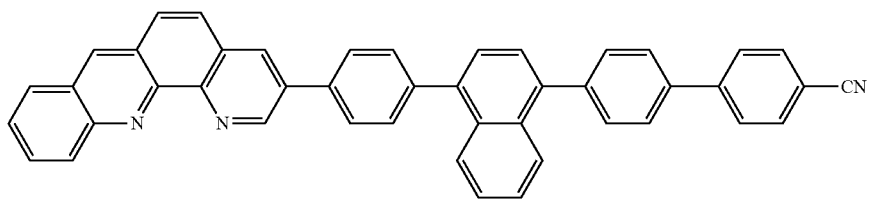
102
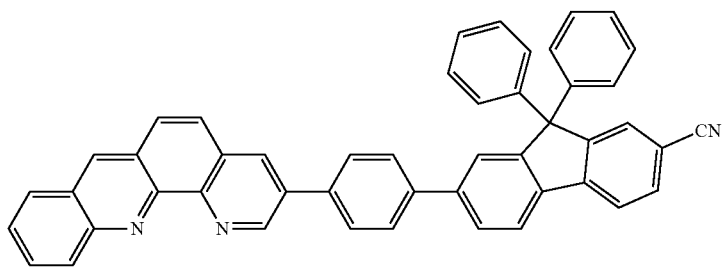
103
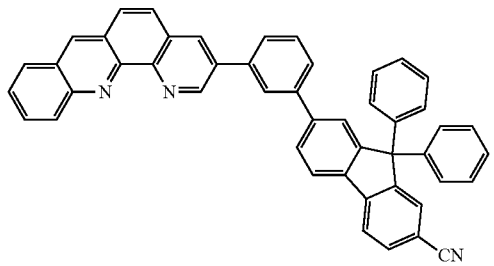
104
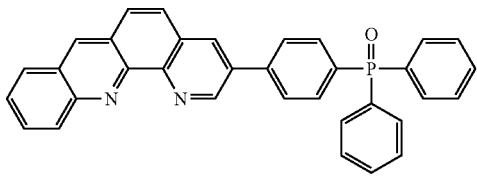
105
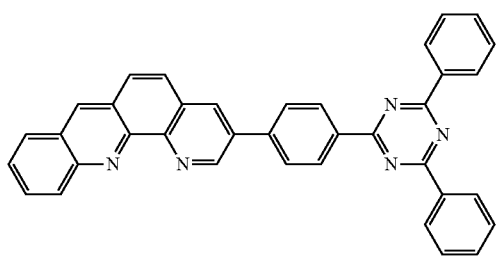
106
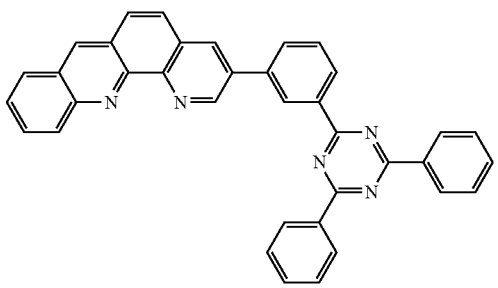

107
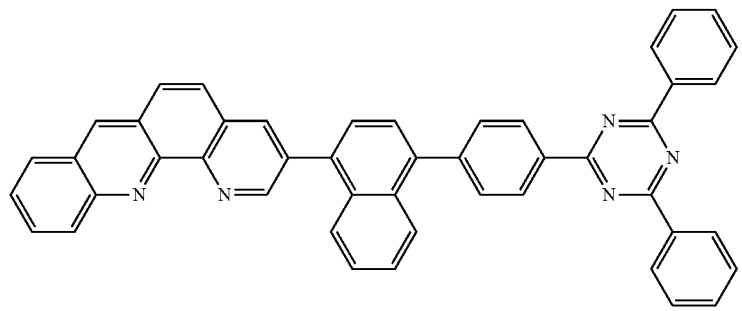
108
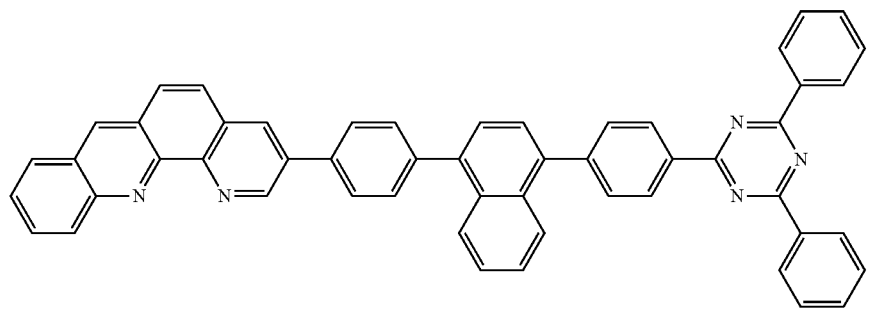
109
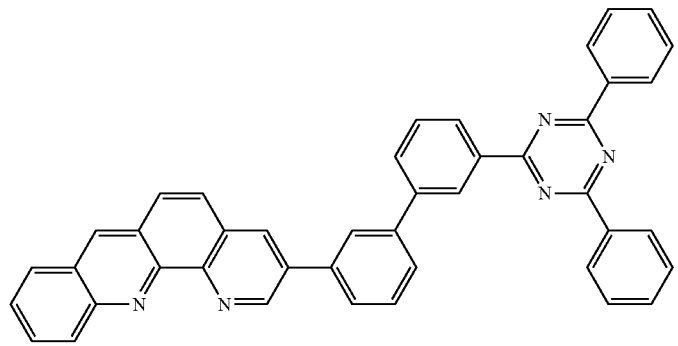
110
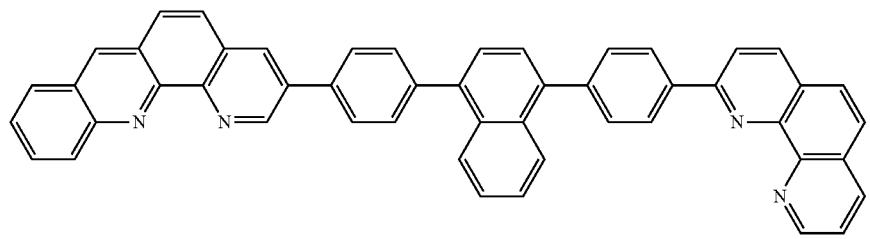
111
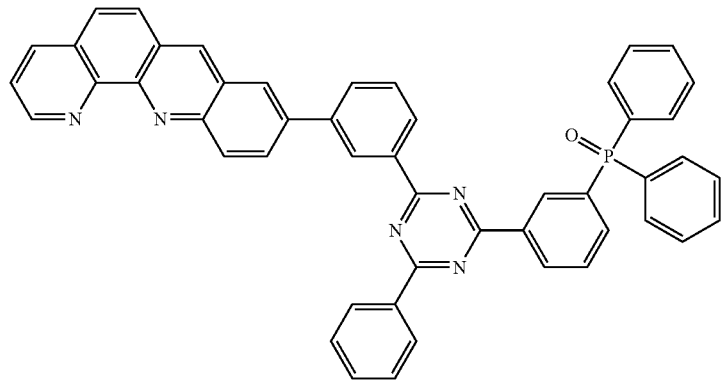

-continued
112
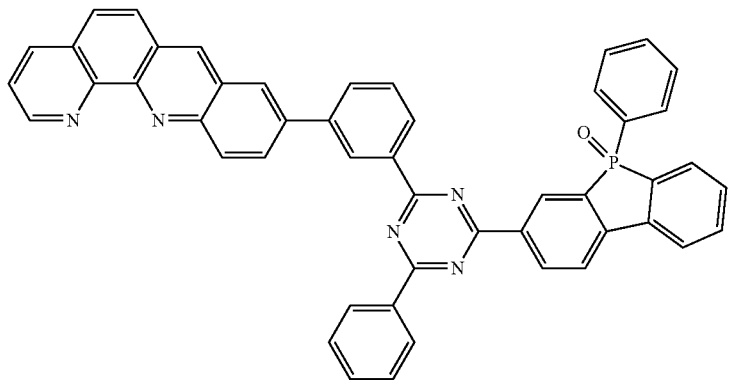
113
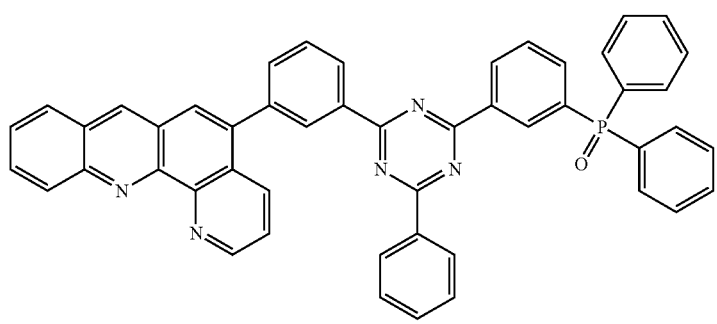
114
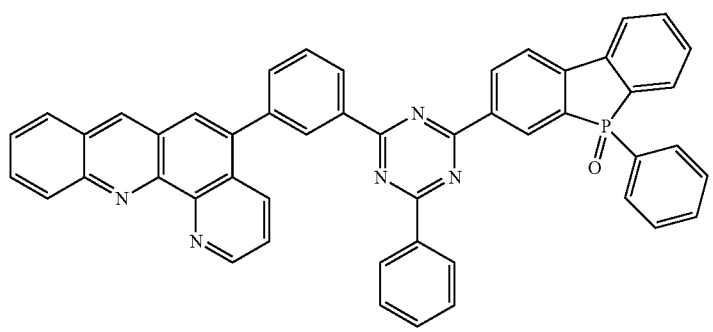
115
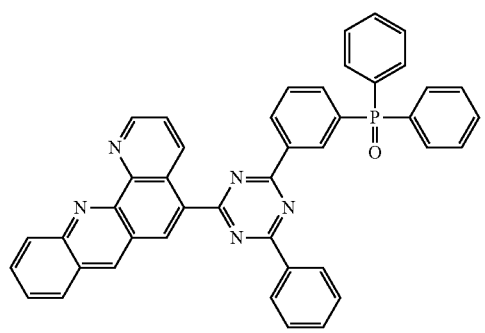
116
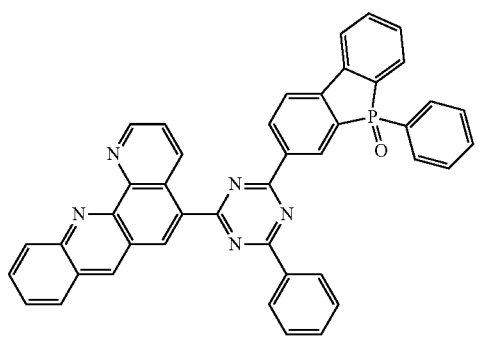

117 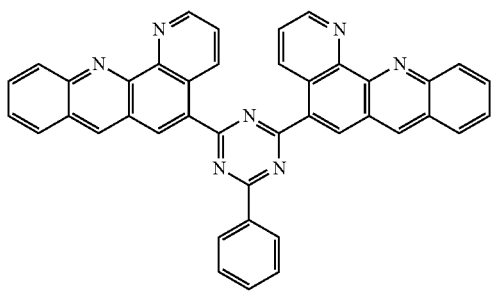

118 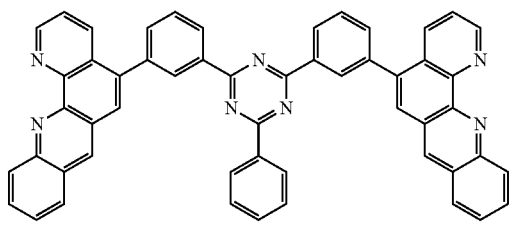

The condensed cyclic compound represented by Formula 1 may include a pi-conjugated system and may have a small intramolecular steric hindrance. Accordingly, the condensed cyclic compound may have enhanced intermolecular packing and high charge transport ability. Due to the intermolecular packing, the condensed cyclic compound may have high glass transition temperature ($T_g$) and melting point. In addition, in the condensed cyclic compound, two N atoms of the core represented by Formula 1 may be located in such positions favorable for coordinate bonding with an n-type dopant. Therefore, an organic light-emitting device including the condensed cyclic compound may have high durability during driving, low driving voltage, and high efficiency.

The structure represented by Formula 1 may have a long conjugate system length and hence a large pi-orbital overlap. The large pi-orbital overlap may result in an increase in the transfer integral and hence high hopping rate, which is suitable for charge-transport. A molecule having a linear rod shape may have a high mobility obtained by enhanced packing when forming a bulk film. Regarding the condensed cyclic compound represented by Formula 1, the core may have the rod shape. For example, the group represented by Formula 2 may be introduced into end parts of the core in a longitudinal direction of the core (e.g., $R_1$, $R_2$, $R_4$, and $R_7$ in Formula 1), and the steric hindrance between the core represented by Formula 1 and the group represented by Formula 2 may be reduced and the angle between the core represented by Formula 1 and the group represented by Formula 2 may be reduced to further expand the pi-conjugated system. Also, the entire molecule may have a rod shape in addition to the core structure represented by Formula 1, and the electron mobility may be increased.

Synthesis methods for the condensed cyclic compound represented by Formula 1 may be understood in view of the following examples.

At least one of the condensed cyclic compounds of Formula 1 may be used or included between a pair of electrodes of an organic light-emitting device. For example, the condensed cyclic compound may be included in at least one layer selected from a hole transport region, an electron transport region, and an emission layer. In an implementation, the condensed cyclic compound of Formula 1 may be used as a material for a capping layer located outside a pair of electrodes of an organic light-emitting device.

Another aspect provides an organic light-emitting device that includes: a first electrode; a second electrode facing the first electrode; and an organic layer that is located between the first electrode and the second electrode and includes an emission layer, wherein the organic layer includes at least one condensed cyclic compound represented by Formula 1.

The expression "(an organic layer) includes at least one condensed cyclic compound" used herein may include a case in which "(an organic layer) includes identical compounds represented by Formula 1" and a case in which "(an organic layer) includes two or more different condensed cyclic compounds."

In an implementation, the first electrode may be an anode, the second electrode may be a cathode, and the organic layer may further include a hole transport region between the first electrode and the emission layer and an electron transport region between the emission layer and the second electrode, and the hole transport region includes a hole injection layer, a hole transport layer, an emission auxiliary layer, an electron blocking layer, or any combination thereof, and the electron transport region includes a buffer layer, a hole blocking layer, an electron control layer, an electron transport layer, an electron injection layer, or any combination thereof.

In an implementation, the electron transport region may include the condensed cyclic compound represented by Formula 1.

In an implementation, the electron transport region may include at least one of an electron transport layer and an electron injection layer, and the at least one of the electron transport layer and the electron injection layer may include the condensed cyclic compound represented by Formula 1.

In an implementation, the emission layer may include the condensed cyclic compound represented by Formula 1.

In an implementation, the emission layer may consist of the condensed cyclic compound represented by Formula 1. In an implementation, the emission layer may further include a dopant. An amount of the dopant may be in a range of, e.g., about 0.1 parts by weight to about 50 parts by weight, based on 100 parts by weight of the the emission layer.

The dopant may be a phosphorescent dopant or a fluorescent dopant.

In an implementation, the hole transport region of the organic light-emitting device may include a p-dopant having a lowest unoccupied molecular orbital (LUMO) energy level of, e.g., less than −3.5 eV.

The emission layer of the organic light-emitting device may be a first color light emission layer, the organic light-emitting device may further include i) at least one second color light emission layer or ii) at least one second color light emission layer and at least one third color light emission layer, between the first electrode and the second electrode, a maximum emission wavelength of the first color light-emitting emission layer, a maximum emission wavelength of the second color light-emitting emission layer, and a maximum emission wavelength of the third color light-emitting emission layer are identical to or different from each other, and the first color light and the second color light may be emitted in the form of mixed light, or the first color light, the second color light, and the third color light may be emitted in the form of mixed light.

The organic light-emitting device may further include at least one selected from a first capping layer located in a pathway along which light generated in an emission layer proceeds toward the outside through the first electrode and a second capping layer located in a pathway along which light generated in an emission layer proceeds toward the outside through the second electrode, and the at least one selected from the first capping layer and the second capping layer may include the condensed cyclic compound represented by Formula 1.

For example, the organic light-emitting device may have i) a stacked structure including a first electrode, an organic layer, a second electrode, and a second capping layer which are sequentially stacked in this stated order, ii) a stacked structure including a first capping layer, a first electrode, an organic layer, and a second electrode which are sequentially stacked in this stated order, or iii) a stacked structure including a first capping layer, a first electrode, an organic layer, a second electrode, and a second capping layer which are sequentially stacked in this stated order, and at least one selected from the first capping layer and the second capping layer may include the condensed cyclic compound.

The term "organic layer" used herein refers to a single layer and/or a plurality of layers located between the first electrode and the second electrode of an organic light-emitting device. A material included in the "organic layer" is not limited to an organic material.

Figure 1:
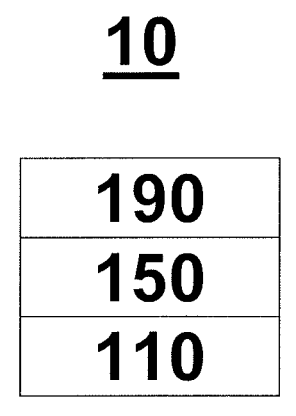

FIG. 1 illustrates a schematic view of an organic light-emitting device 10 according to an embodiment. The organic light-emitting device 10 may include a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

In an implementation, a substrate may be additionally located under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide (SnO$_2$), zinc oxide (ZnO), and any combinations thereof. When the first electrode 110 is a semi-transmissive electrode or a reflective electrode, as a material for forming the first electrode 110, magnesium (Mg), silver (Ag), aluminum (Al), aluminum-lithium (Al—Li), calcium (Ca), magnesium-indium (Mg—In), magnesium-silver (Mg—Ag), or any combination thereof may be used.

The first electrode 110 may have a single-layered structure, or a multi-layered structure including two or more layers. For example, the first electrode 110 may have a three-layered structure of ITO/Ag/ITO.

The organic layer 150 is located on the first electrode 110. The organic layer 150 may include an emission layer.

The organic layer 150 may further include a hole transport region between the first electrode 110 and the emission layer, and an electron transport region between the emission layer and the second electrode 190.

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer (HIL), a hole transport layer (HTL), an emission auxiliary layer, and an electron blocking layer (EBL).

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order.

The hole transport region may include at least one selected from m-MTDATA, TDATA, 2-TNATA, NPB (NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

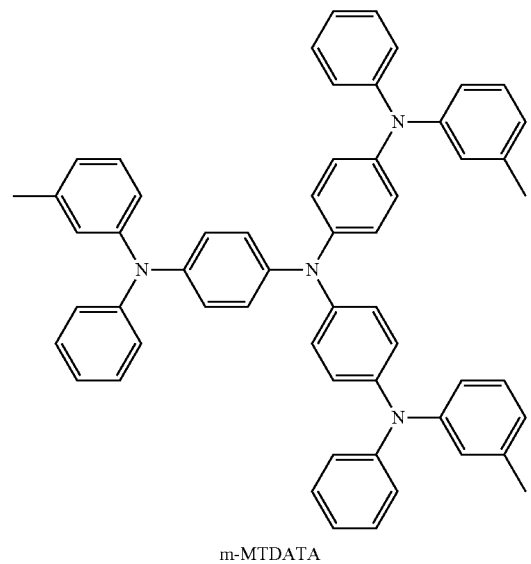

m-MTDATA

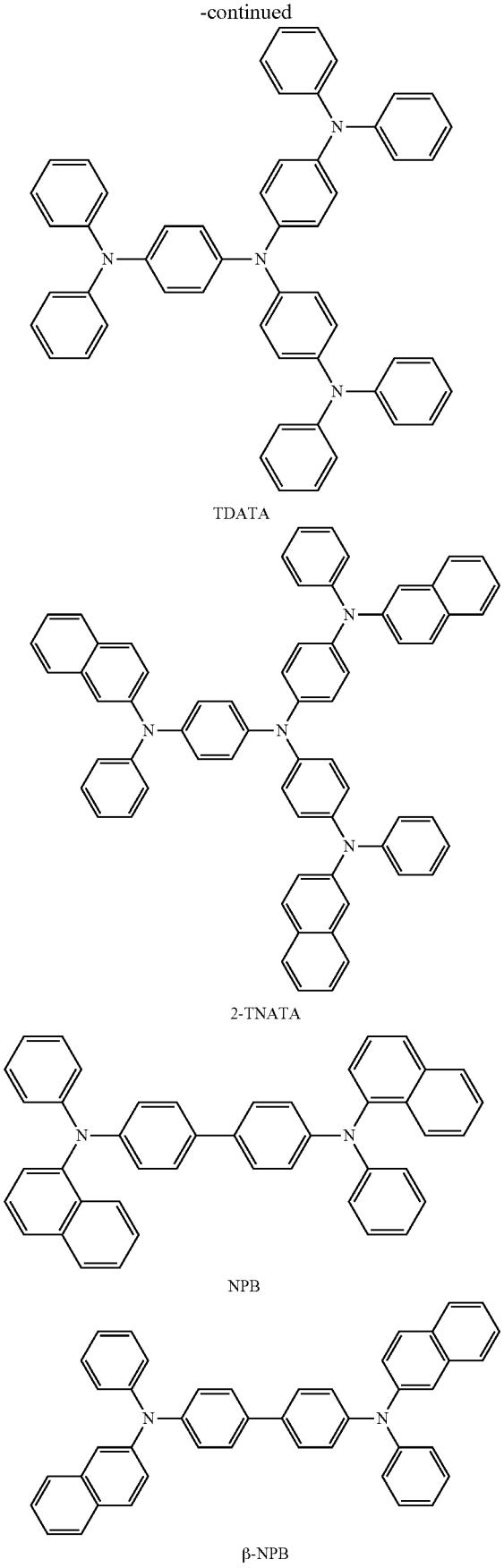
TDATA
2-TNATA
NPB
β-NPB
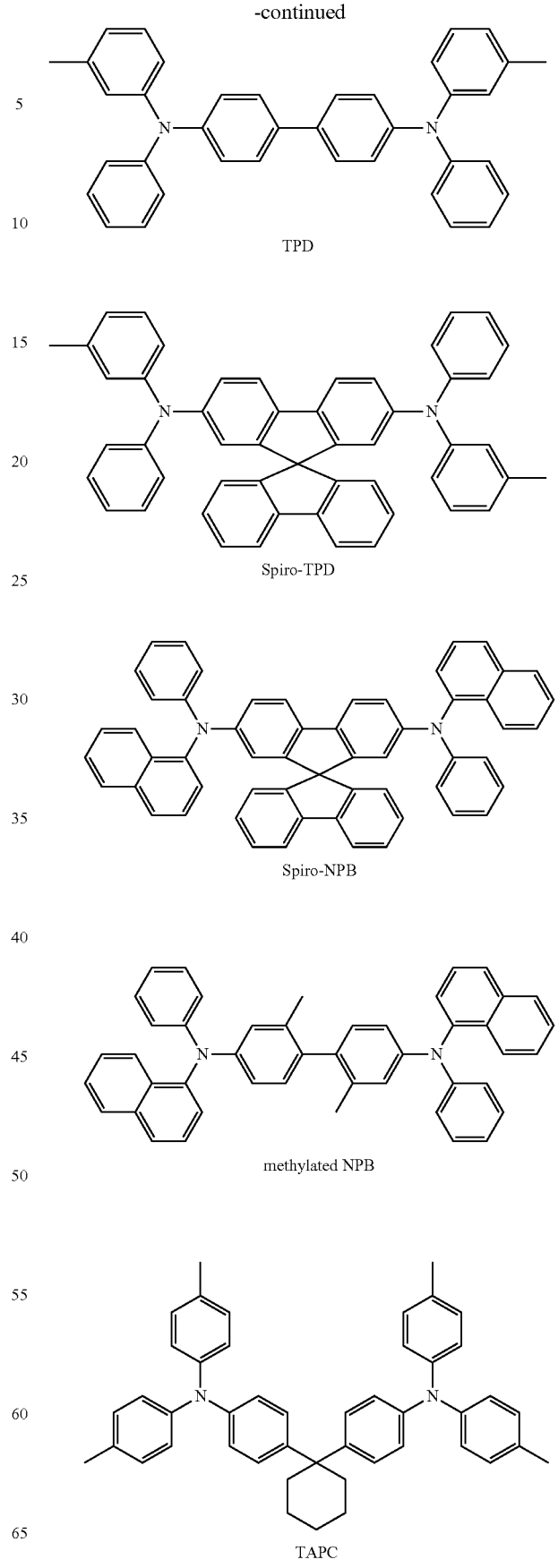
TPD
Spiro-TPD
Spiro-NPB
methylated NPB
TAPC

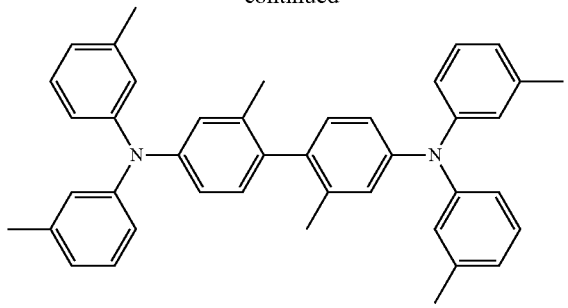

HMTPD

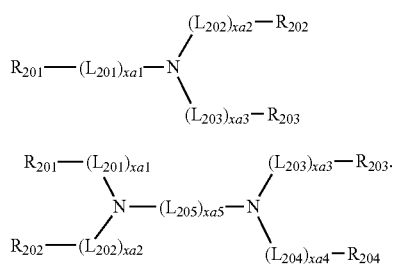

<Formula 201>

<Formula 202>

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer of 0 to 3, xa5 may be an integer of 1 to 10, and $R_{201}$ to $R_{204}$ and $Q_{20}1$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one embodiment, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one or more embodiments, regarding Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$) and —N($Q_{31}$)($Q_{32}$);

wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ are the same as described above.

In one or more embodiments, at least one selected from $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group In one or more embodiments, in Formula 202, i) $R_{201}$ and $R_{202}$ may be linked via a single bond, and/or ii) $R_{203}$ and $R_{204}$ may be linked via a single bond.

In one or more embodiments, at least one selected from $R_{201}$ to $R_{204}$ in Formula 202 may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group.

The compound represented by Formula 201 may be represented by Formula 201A:

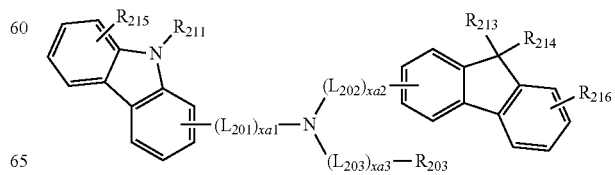

<Formula 201A>

In one embodiment, the compound represented by Formula 201 may be represented by Formula 201A(1) below:

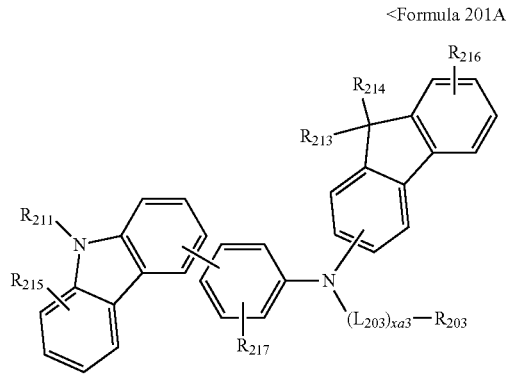

<Formula 201A(1)>

In one embodiment, the compound represented by Formula 201 may be represented by Formula 201A-1 below:

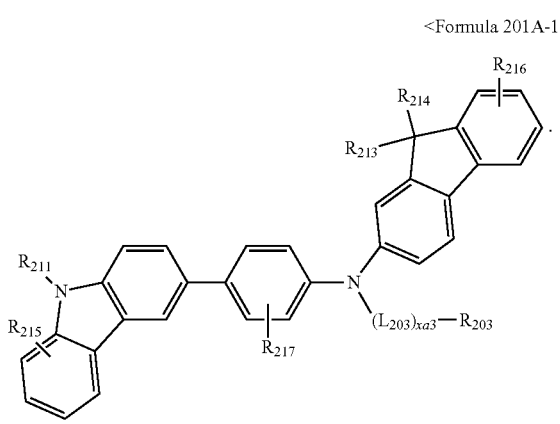

<Formula 201A-1>

In one embodiment, the compound represented by Formula 202 may be represented by Formula 202A:

In one embodiment, the compound represented by Formula 202 may be represented by Formula 202A-1:

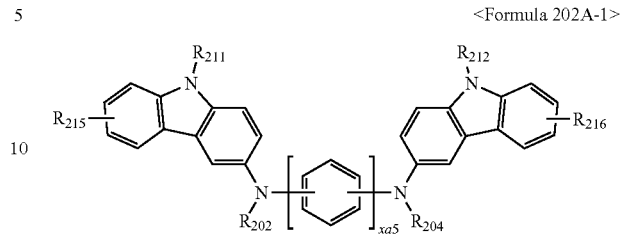

<Formula 202A-1>

In Formulae 201A, 201A(1), 201A-1, 202A, and 202A-1, $L_{201}$ to $L_{203}$, xa1 to xa3, xa5, and $R_{202}$ to $R_{204}$ may be the same as described above, $R_{211}$ and $R_{212}$ are the same as described in connection with $R_{203}$, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39:

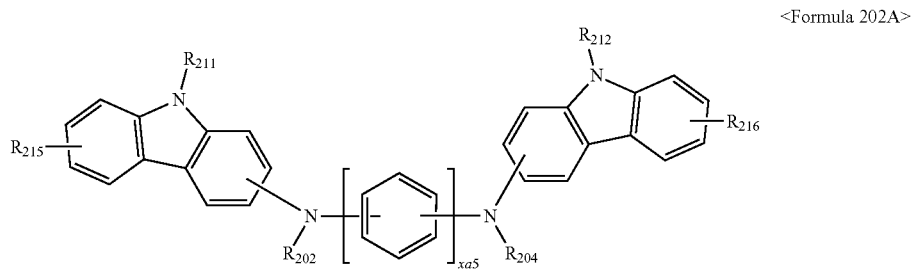

<Formula 202A>

73 HT1
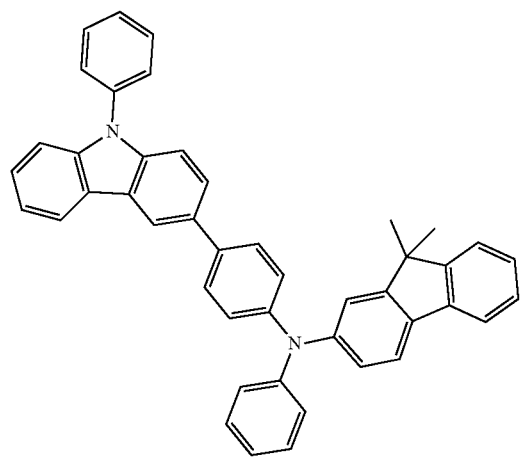
74 HT2
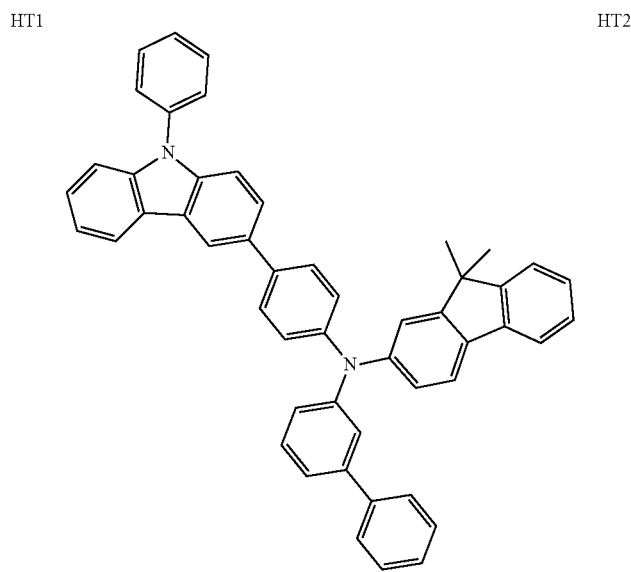
HT3
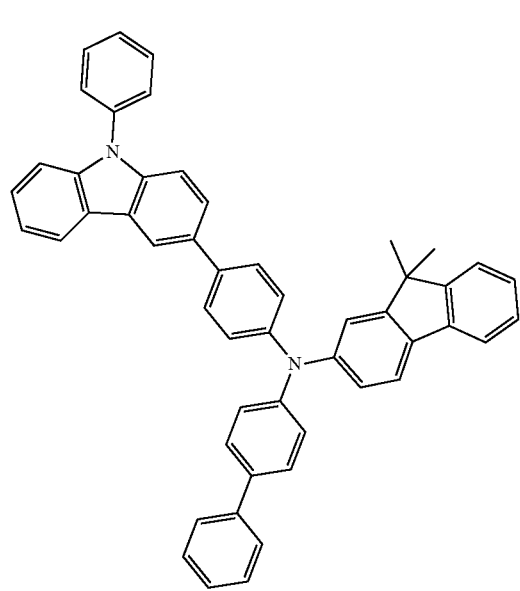
HT4
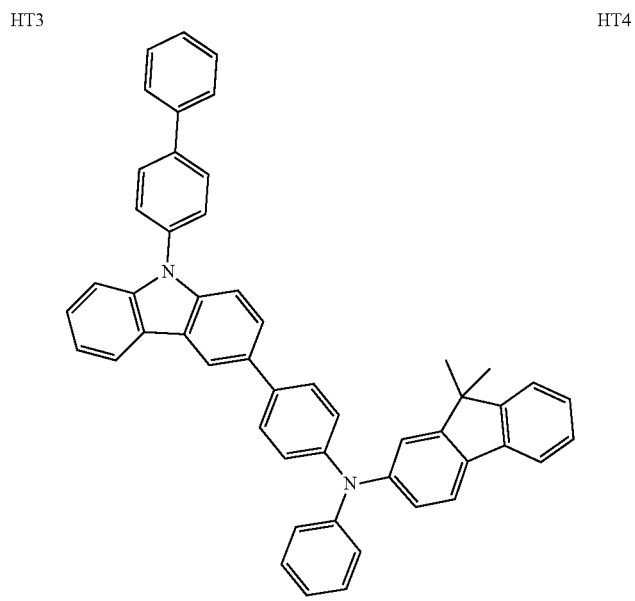

-continued
HT5
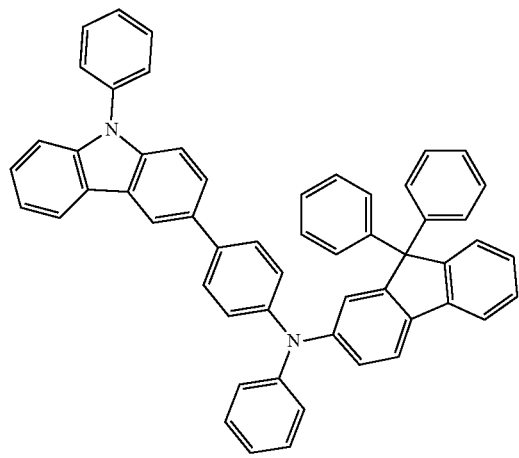
HT6
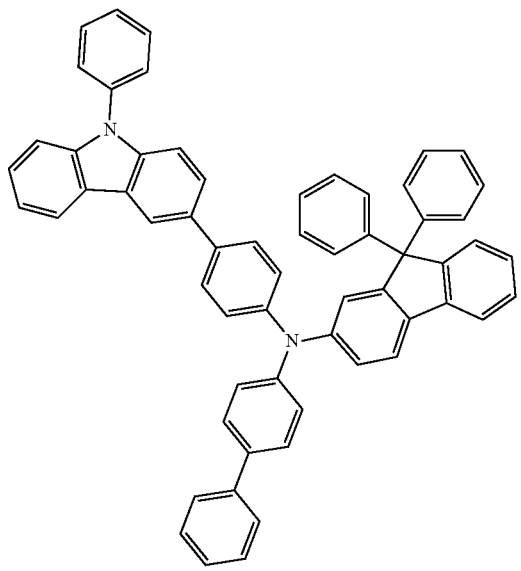
HT7
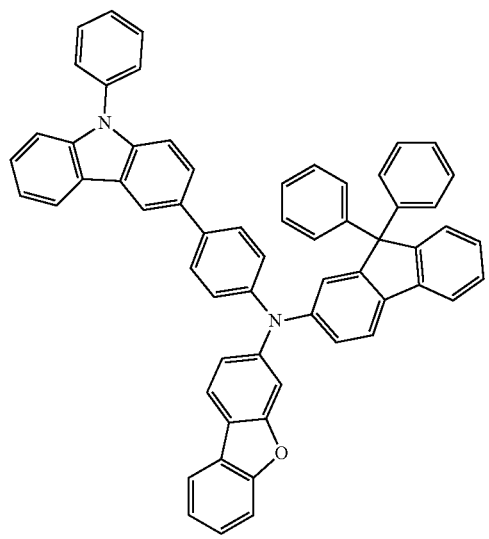
HT8
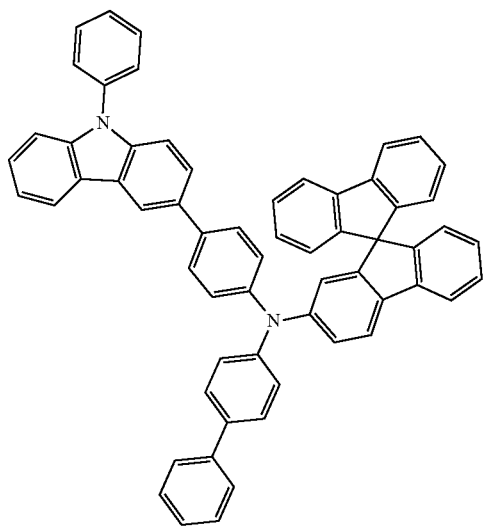
HT9
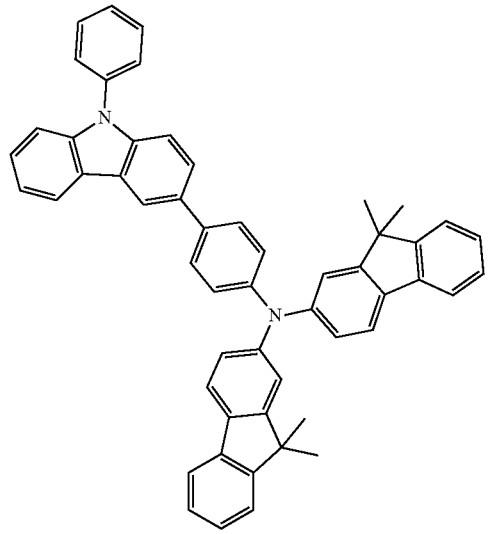
HT10
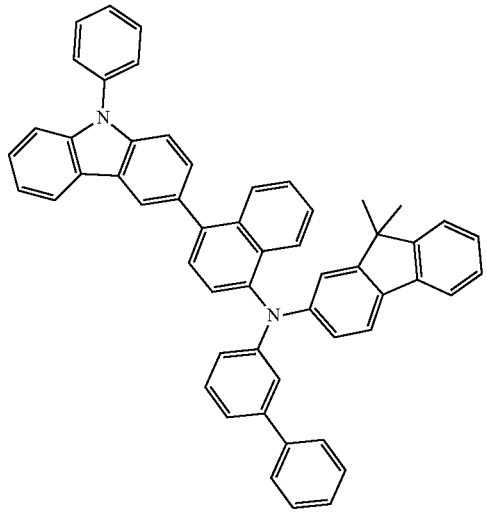

-continued
HT11
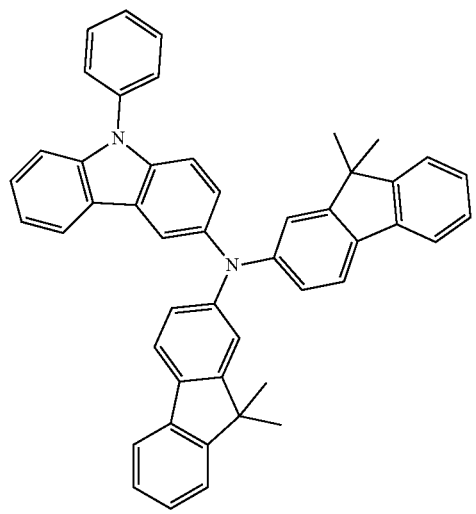
HT12
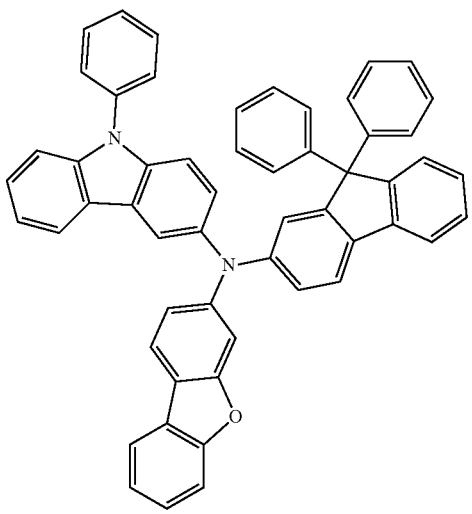
HT13
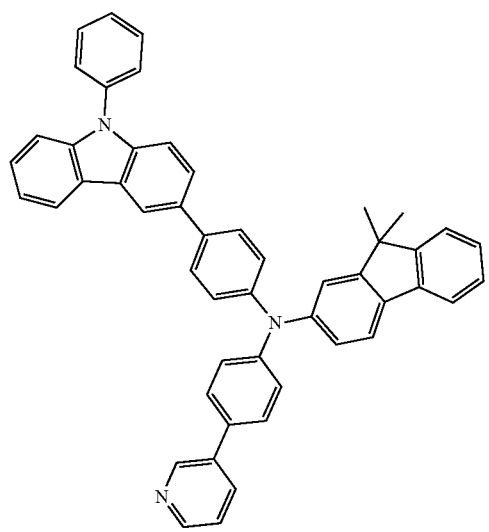
HT14
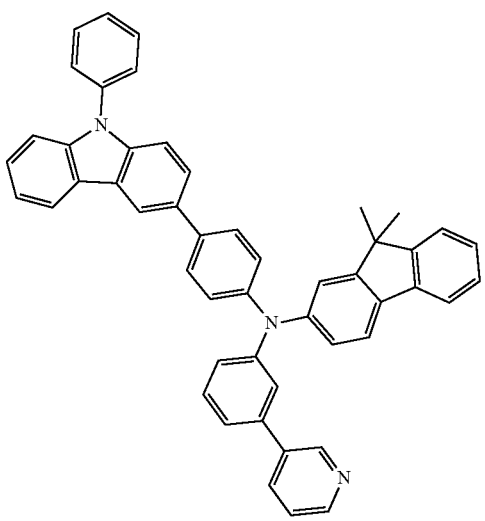
HT15
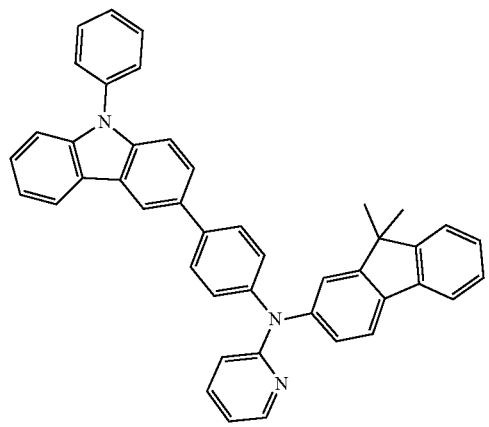
HT16
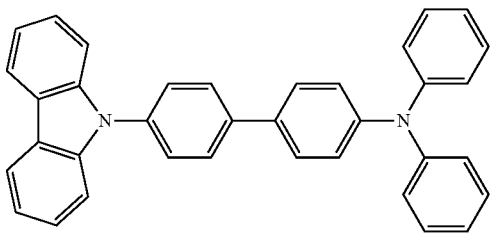

-continued
HT17
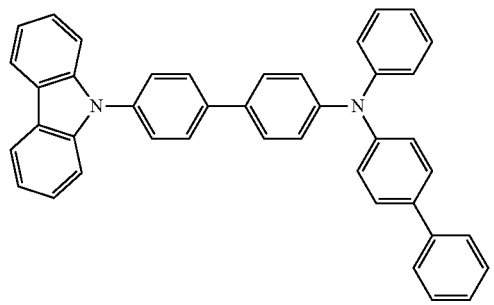
HT18
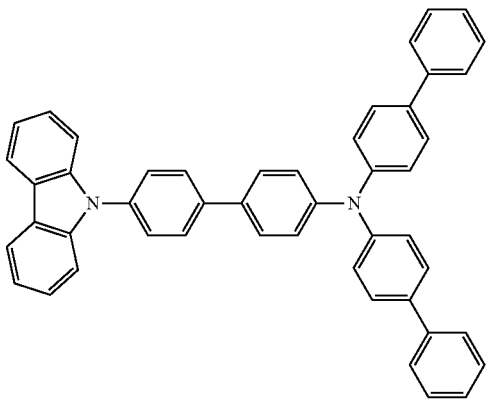
HT19
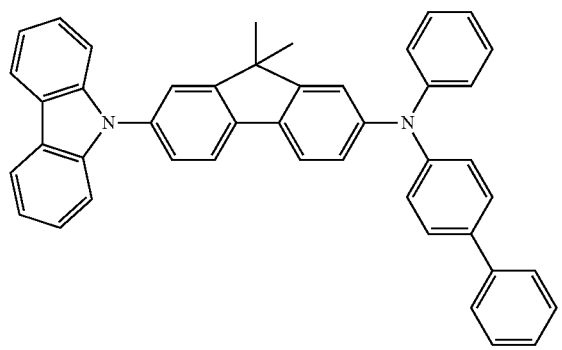
HT20
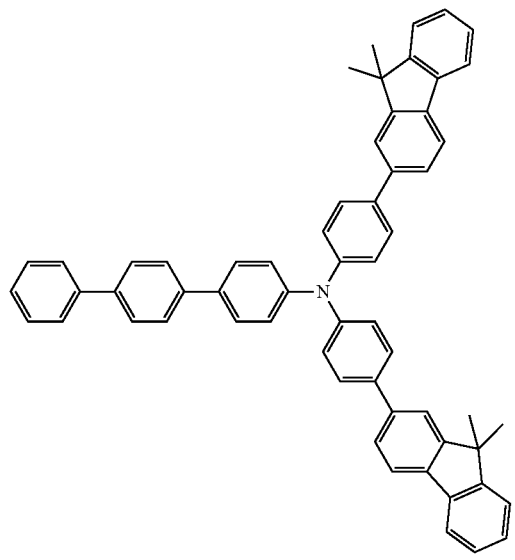
HT21
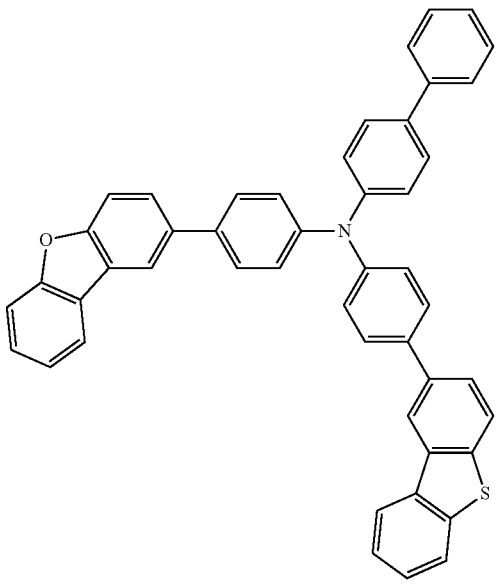

HT22
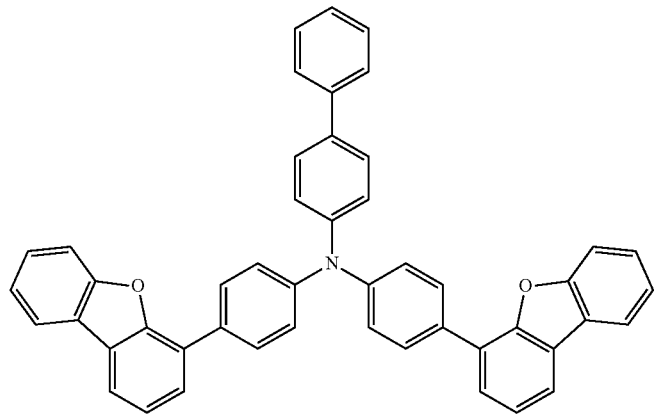
HT23
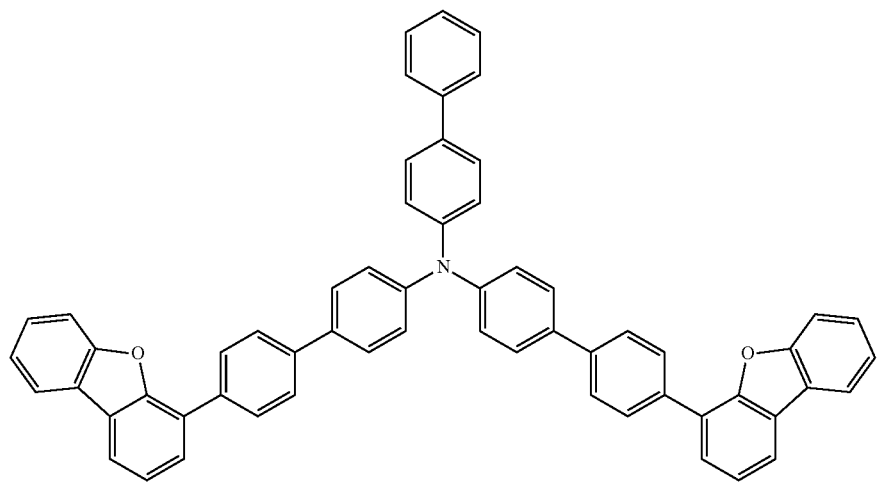
HT24
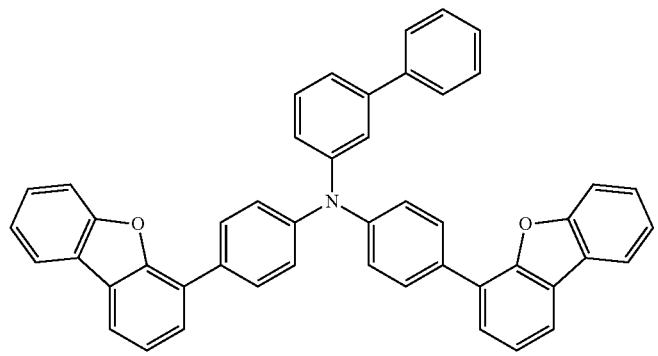

-continued
HT25
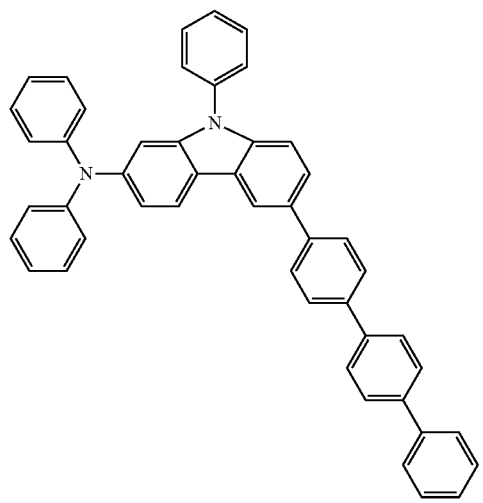
HT26
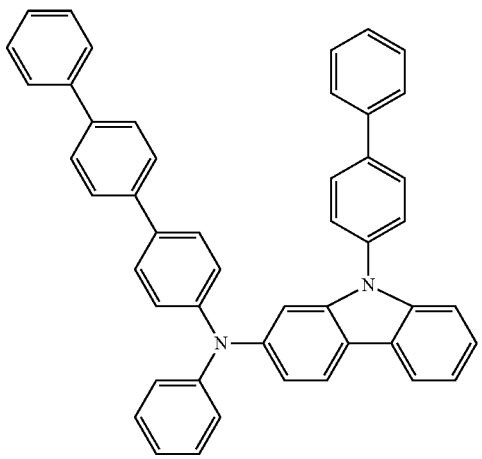
HT27
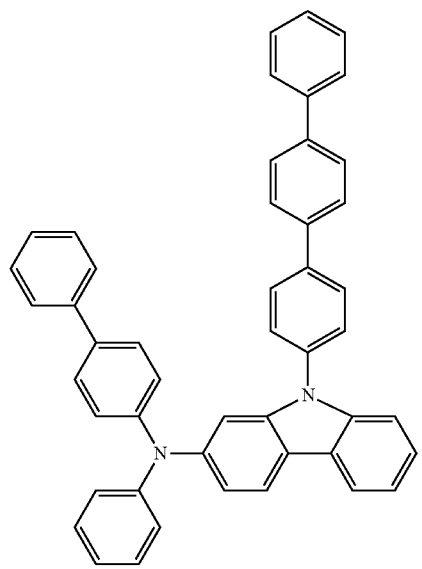
HT28
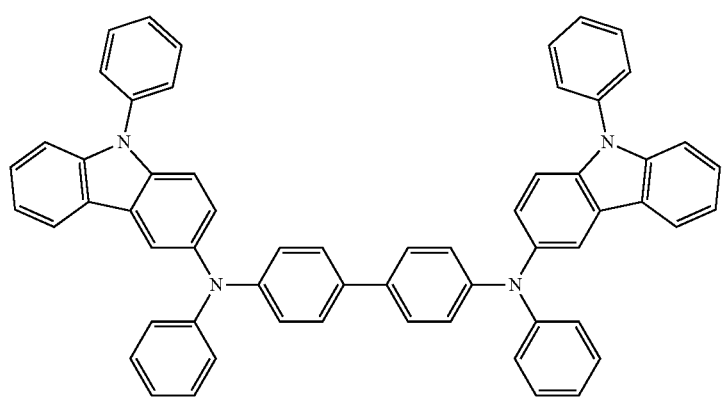

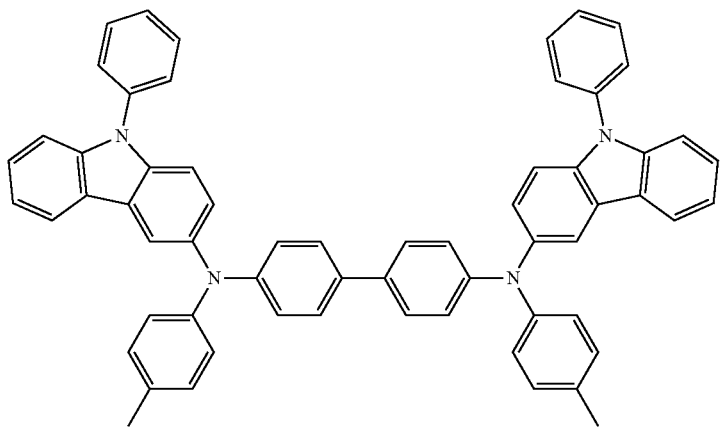
HT29
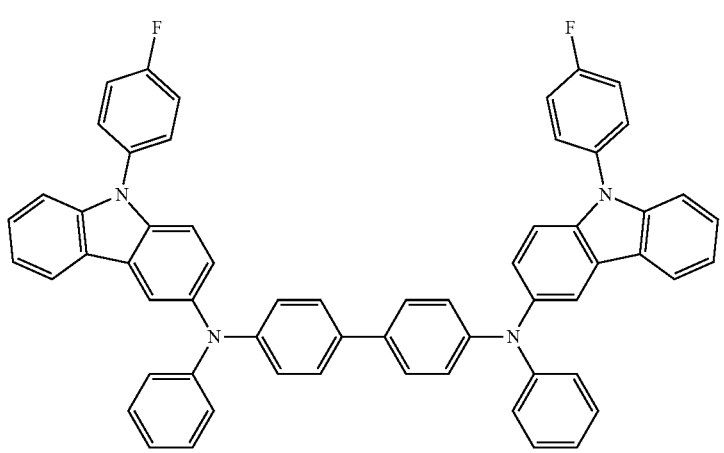
HT30
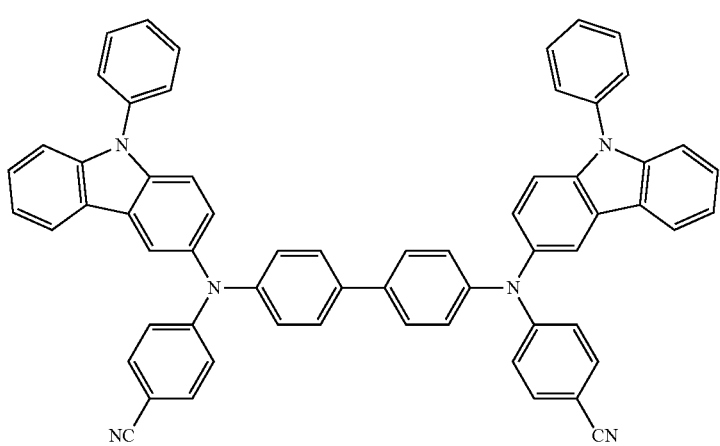
HT31

-continued
HT32
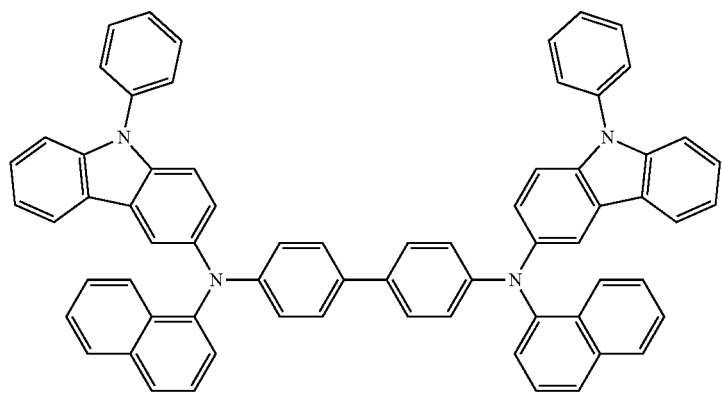
HT33
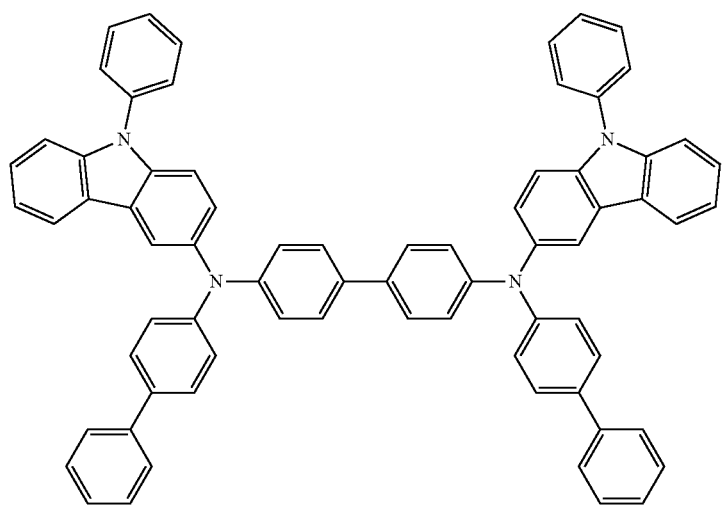
HT34
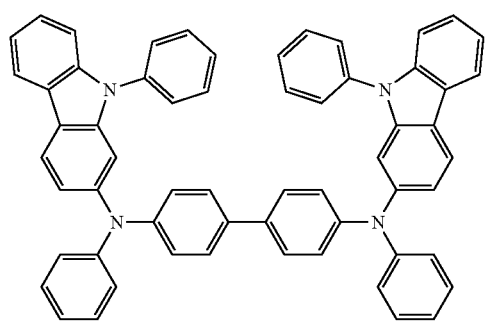
HT35
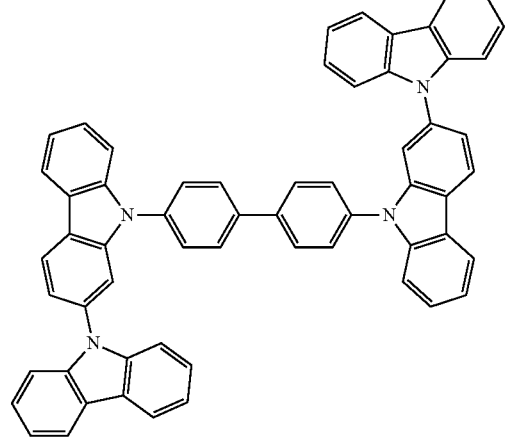

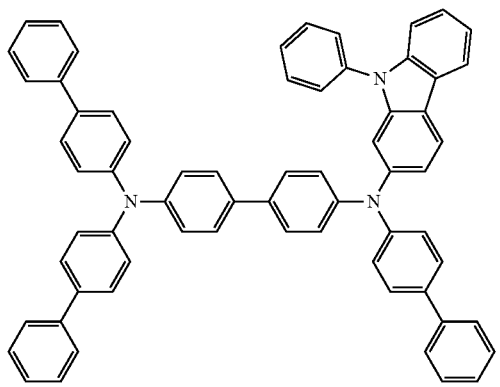

HT36

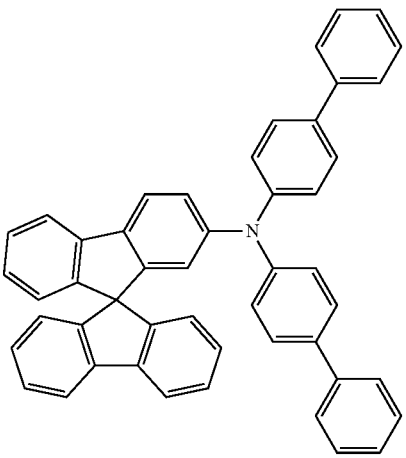

HT37

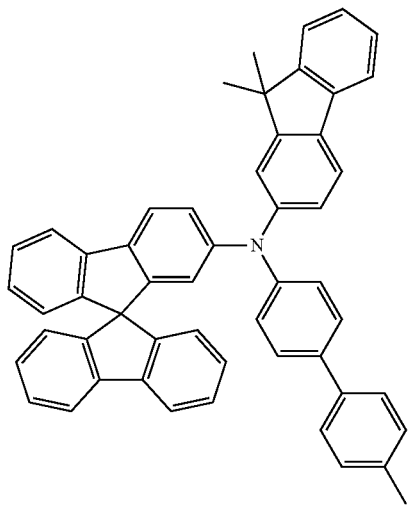

HT38

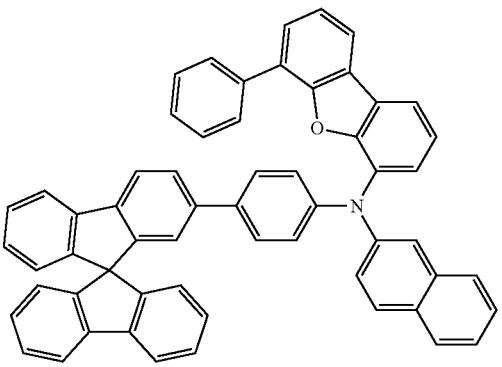

HT39

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å.

When the thicknesses of the hole transport region, the hole injection layer and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, a lowest unoccupied molecular orbital (LUMO) energy level of the p-dopant may be −3.5 eV or less.

The p-dopant may include at least one selected from a quinone derivative, a metal oxide, and a cyano group-containing compound.

For example, the p-dopant may include at least one selected from a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221 below:

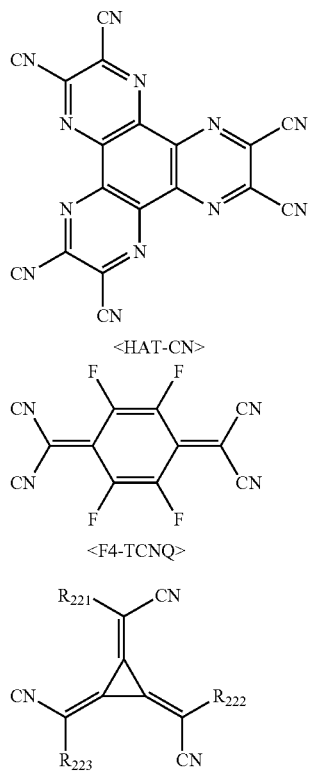

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one selected from $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

An amount of the dopant in the emission layer may be, in general, in a range of about 0.01 parts by weight to about 15 parts by weight based on 100 parts by weight of the host.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

The host may include the condensed cyclic compound represented by Formula 1.

In one or more embodiments, the host may include a compound represented by Formula 301 below.

$[Ar_{301}]_{xb11}$-$[(L_{301})_{xb1}$-$R_{301}]_{xb21}$ <Formula 301>

In Formula 301, $Ar_{301}$ may be a substituted or unsubstituted $C_5$-$C_{60}$ carbocyclic group, or a substituted or unsubstituted $C_1$-$C_{60}$ heterocyclic group, xb11 may be 1, 2, or 3; and $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer of 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer of 1 to 5, $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group.

In one embodiment, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$);

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xb11 in Formula 301 is two or more, two or more $Ar_{301}$(s) may be linked via a single bond.

In one or more embodiments, the compound represented by Formula 301 may be represented by Formula 301-1 or 301-2:

xb22 and xb23 may each independently be 0, 1, or 2, $L_{301}$, xb1, $R_{301}$, and $Q_{31}$ to $Q_{33}$ are the same as described above, $L_{302}$ to $L_{304}$ may each independently be the same as described in connection with $L_{301}$, Xb2 to xb4 may each independently be the same as described in connection with xb1, $R_{302}$ to $R_{304}$ may each independently be the same as described in connection with $R_{301}$.

For example, $L_{301}$ to $L_{304}$ in Formulae 301, 301-1 and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofura-

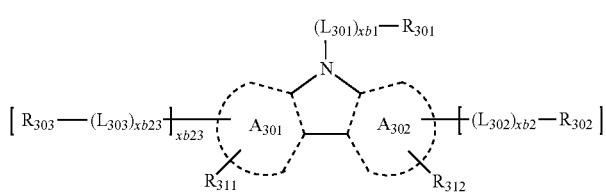

<Formula 301-1>

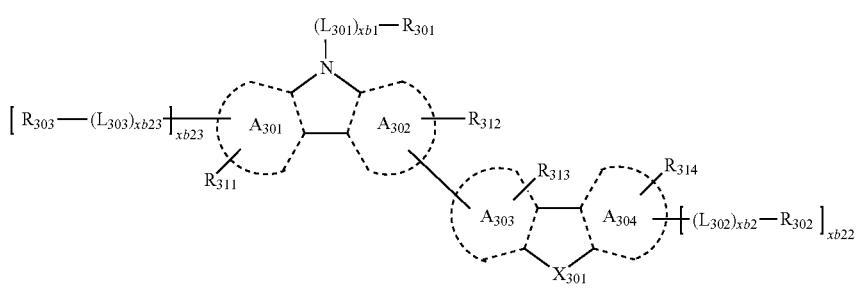

<Formula 301-2>

In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), nylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may be the same as described above.

In one embodiment, $R_{301}$ to $R_{304}$ in Formulae 301, 301-1 and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$);

Q$_{31}$ to Q$_{33}$ may be the same as described above.

In one or more embodiments, the host may include an alkaline earth metal complex. For example, the host may be selected from a Be complex (for example, Compound H55), a Mg complex, and a Zn complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55:

H1

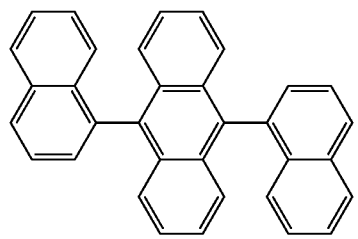

H2

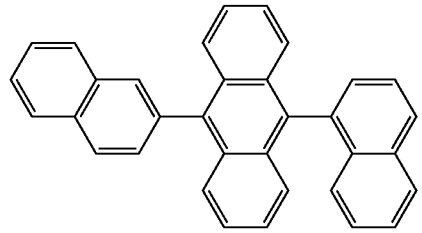

H3

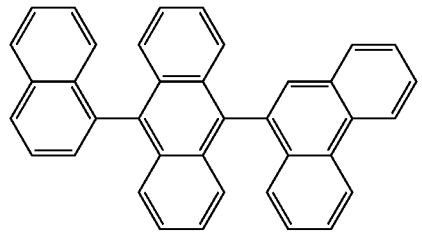

H4

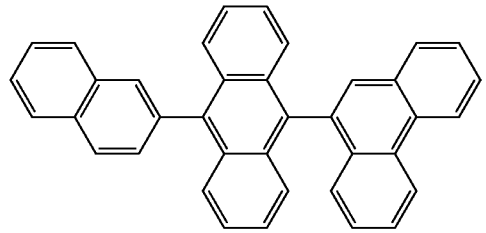

H5

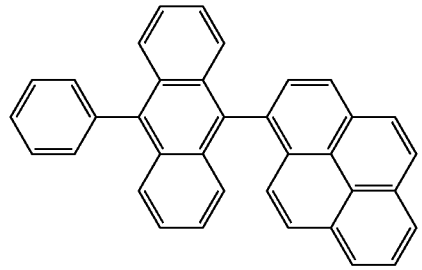

H6

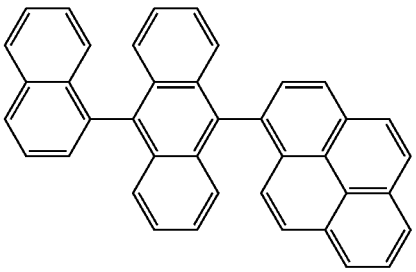

H7

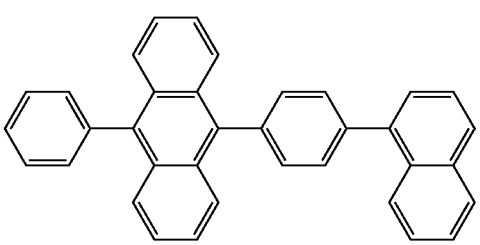

H8

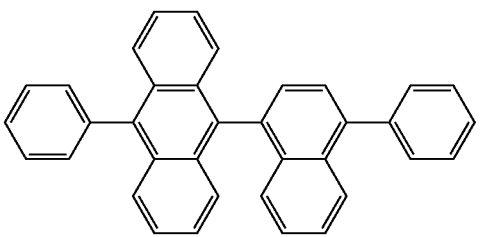

H9

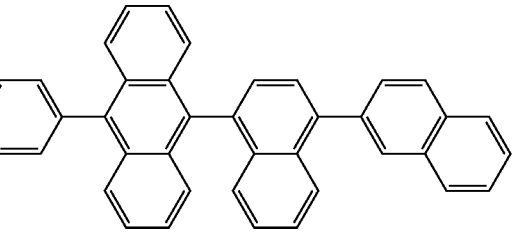

H10

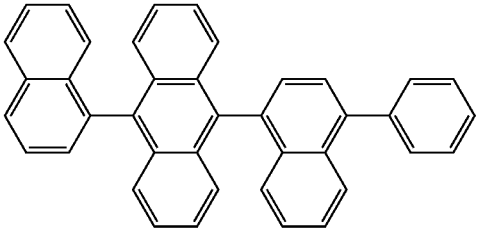

H11

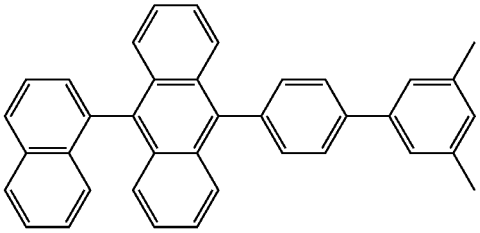

H12
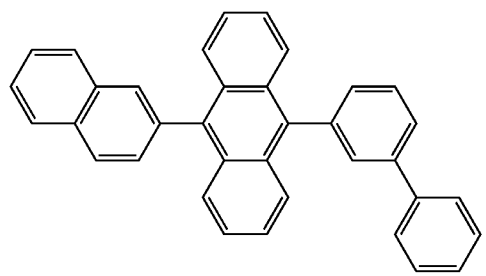
H13
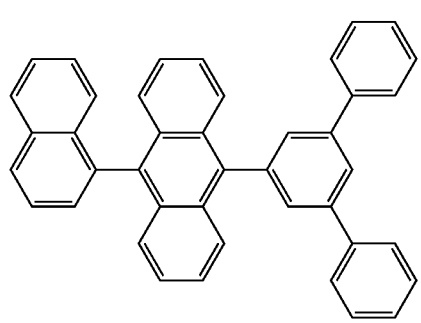
H14
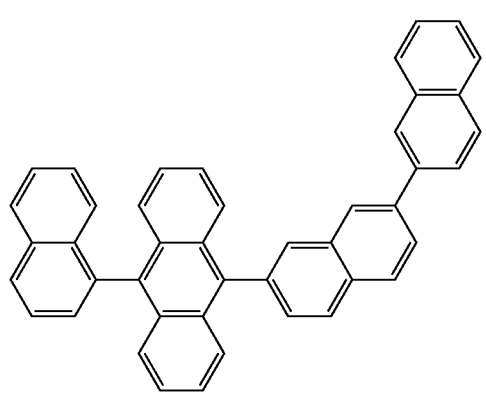
H15
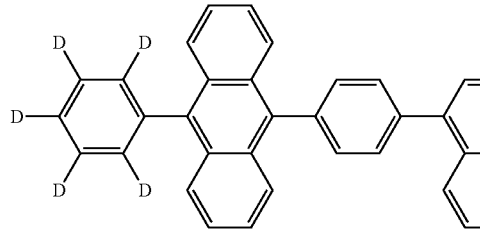
H16
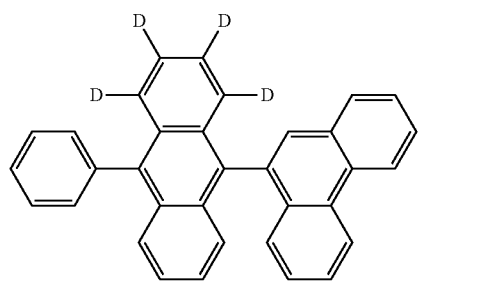
H17
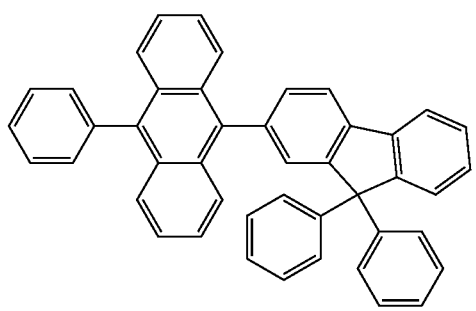
H18
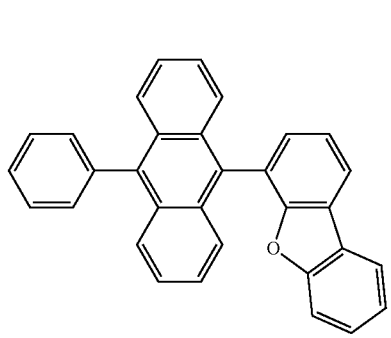
H19
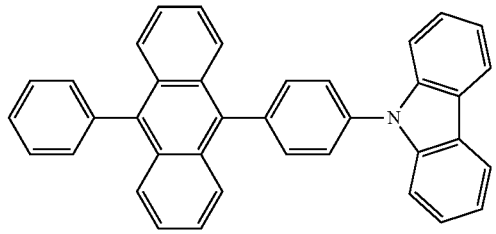
H20
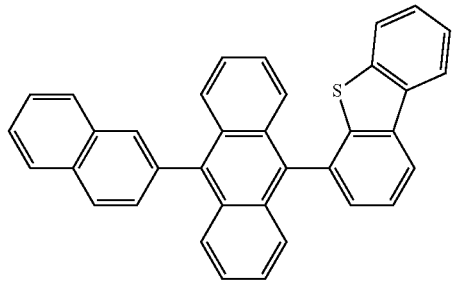
H21
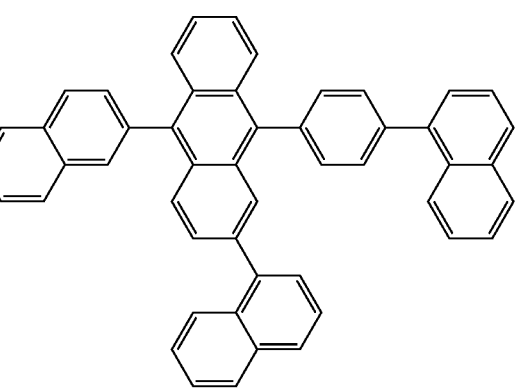

101 -continued
H22
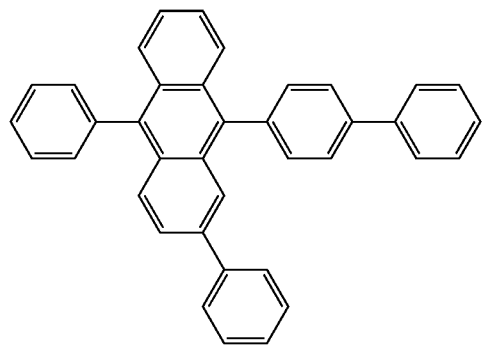
H23
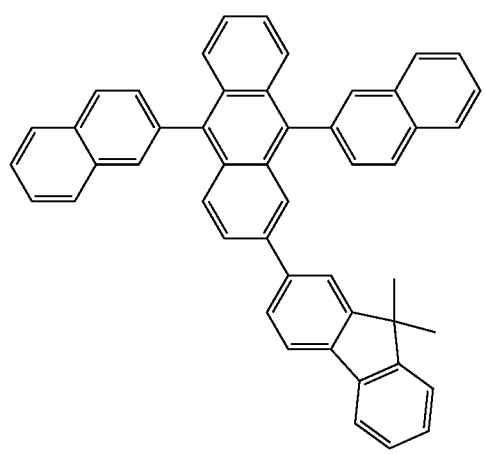
H24
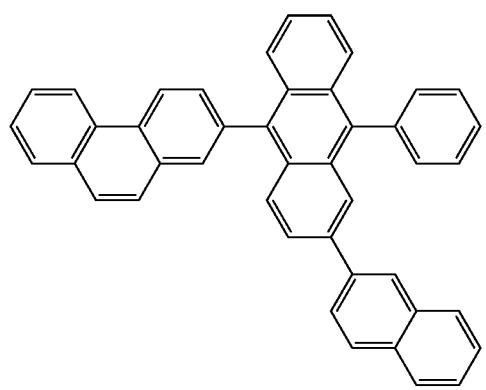
102 -continued
H25
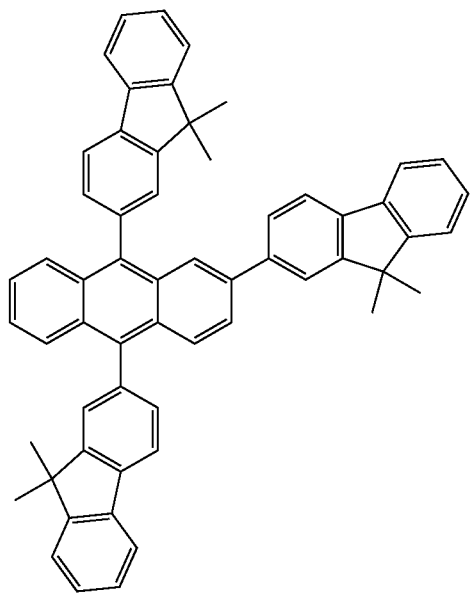
H26
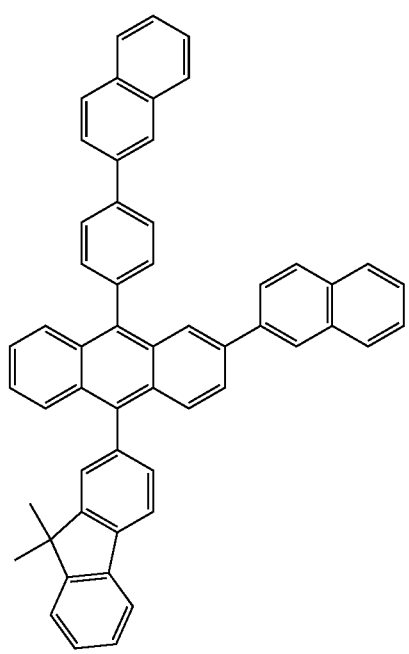

H27
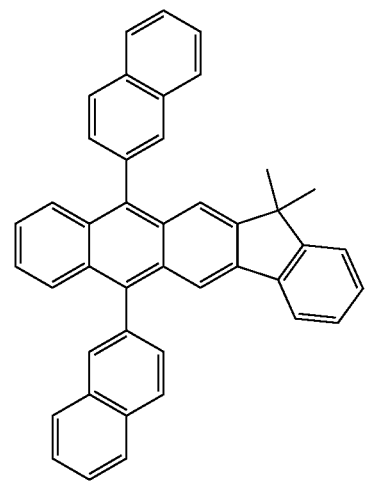
H28
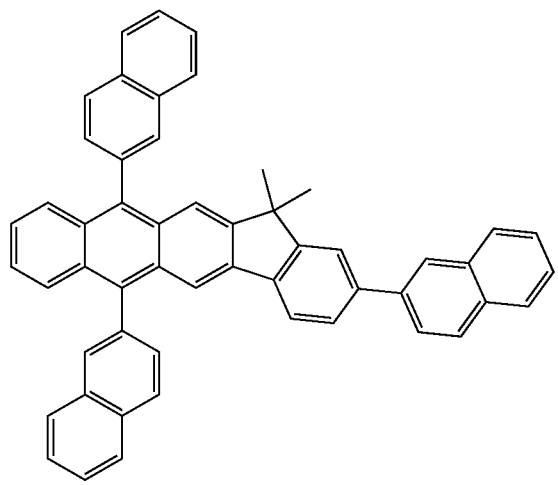
H29
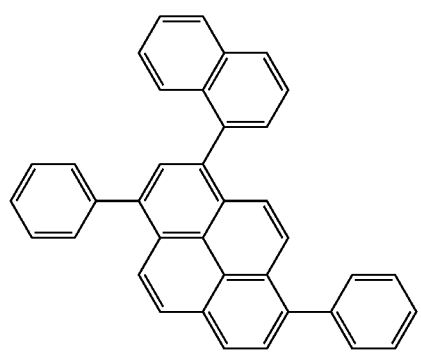
H30
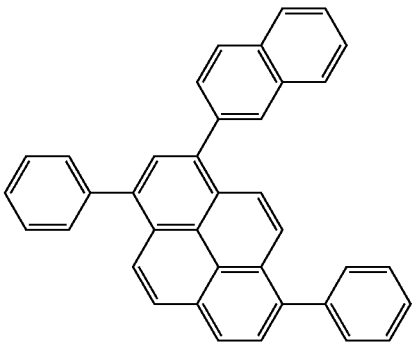
H31
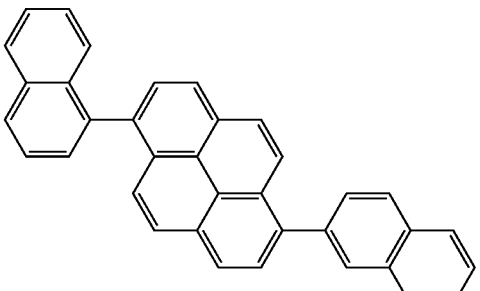
H32
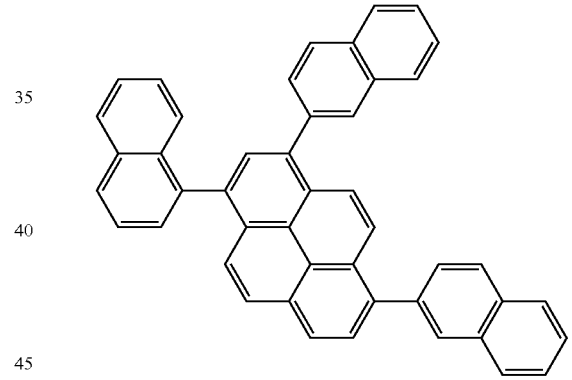
H33
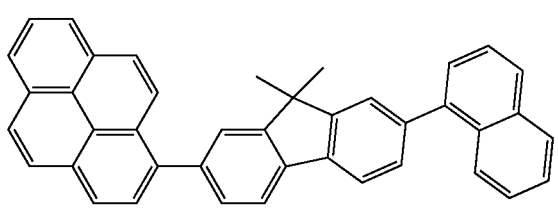
H34
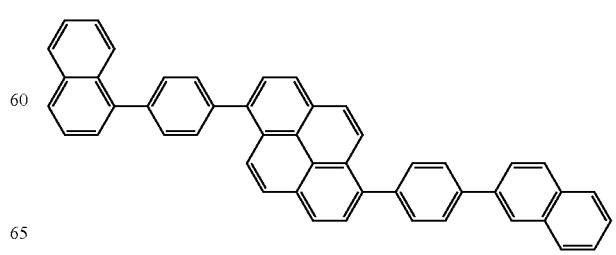

H35
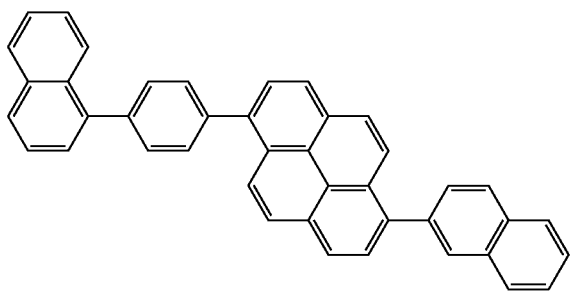
H36
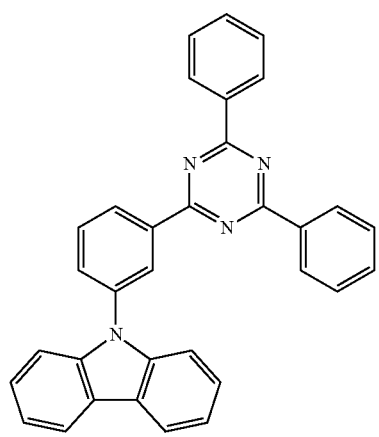
H37
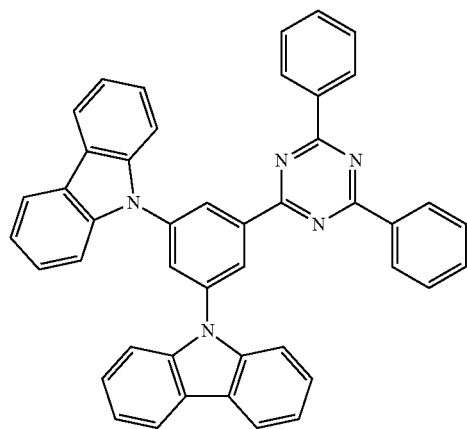
H38
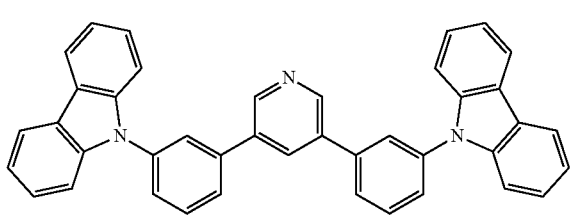
H39
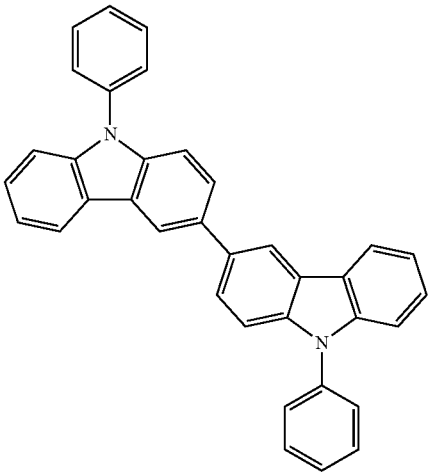
H40
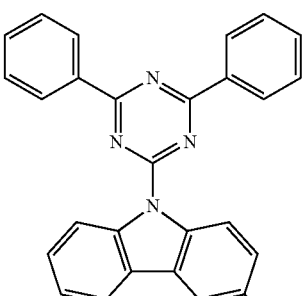
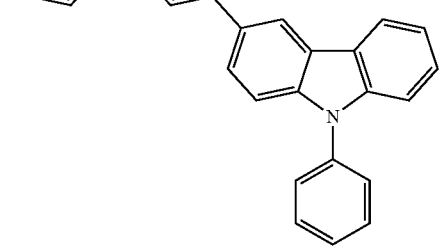
H41
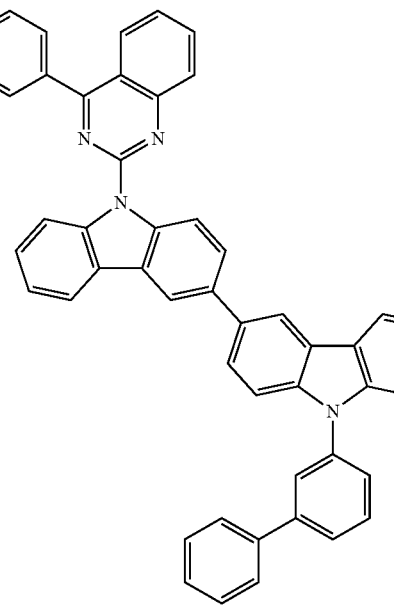

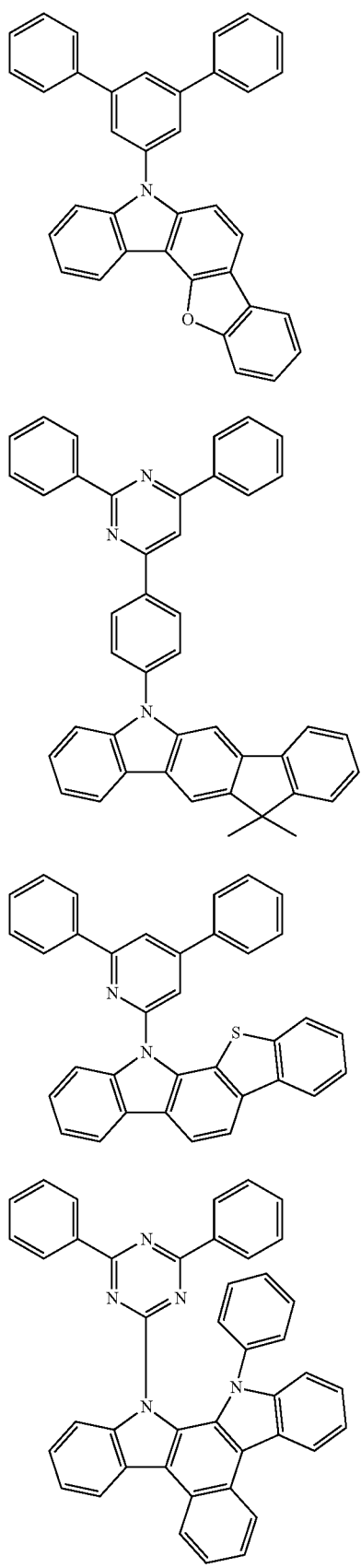
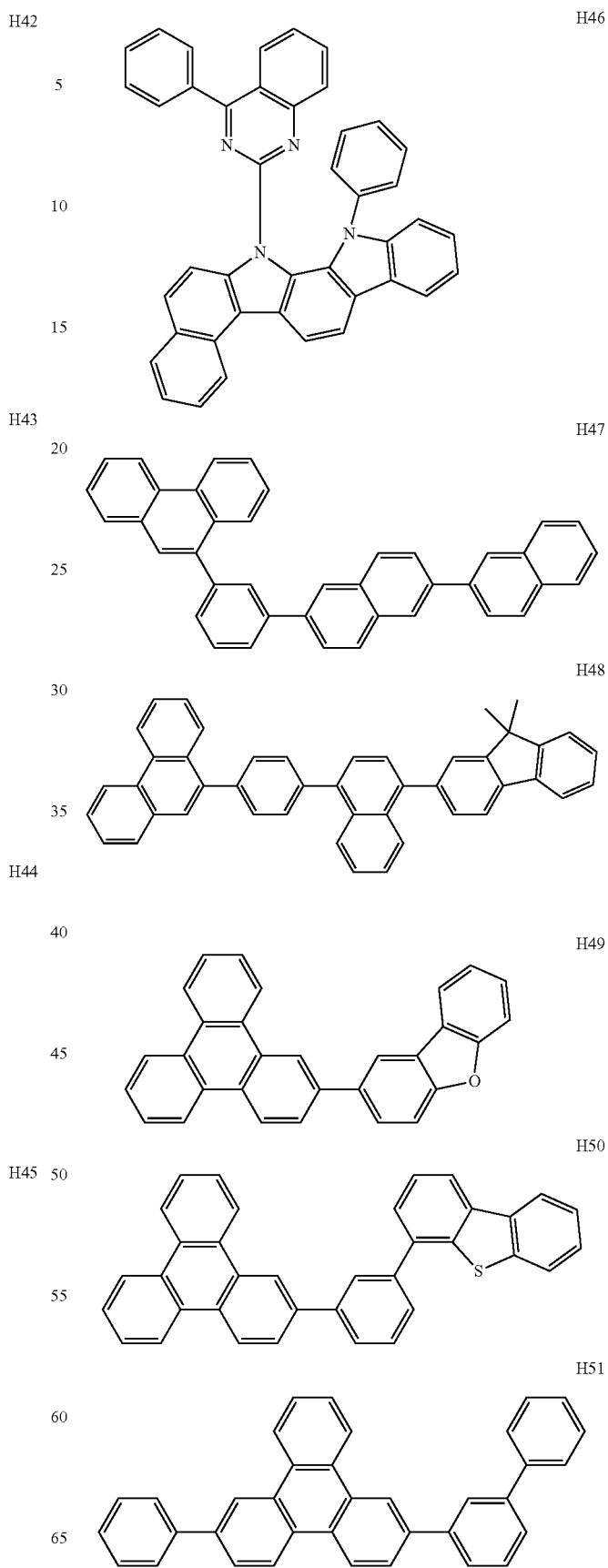

-continued

H52
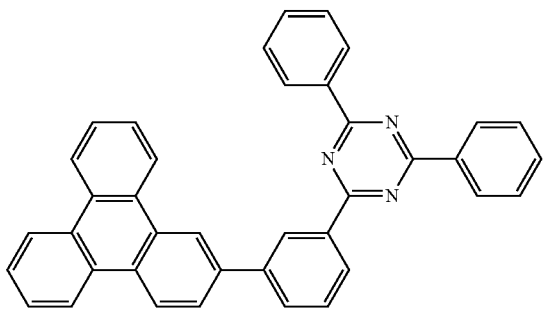

H53
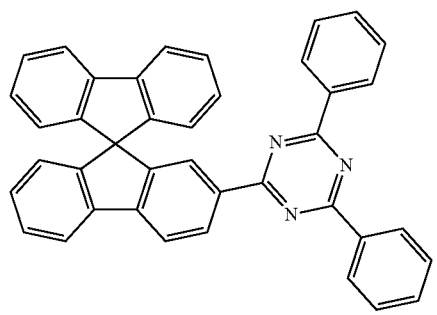

H54
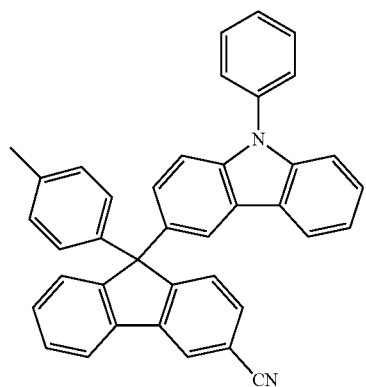

H55
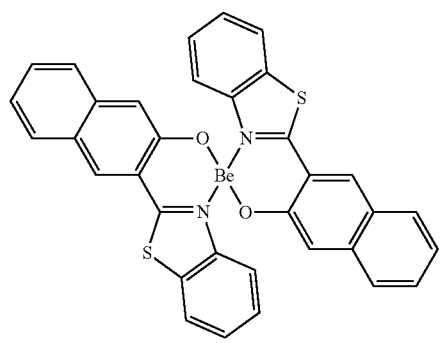

The phosphorescent dopant may include an organometallic complex represented by Formula 401 below:

$$M(L_{401})_{xc1}(L_{402})_{xc2}$$ <Formula 401>

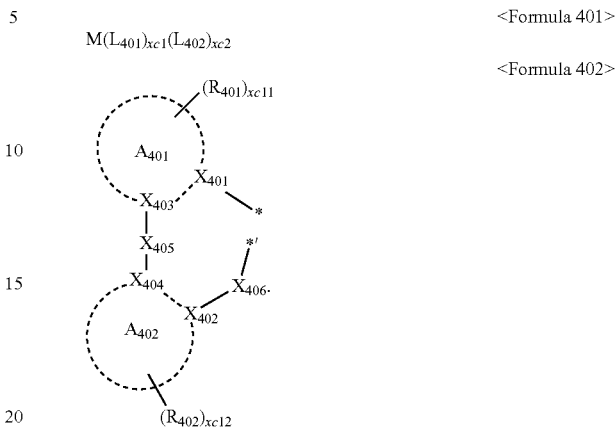

<Formula 402>

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer of 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*, *—C($Q_{411}$)=*, or *'=C($Q_{411}$)=*, $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer of 0 to 10, and

* and *' in Formula 402 each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ is nitrogen and $X_{402}$ is carbon, or ii) each of $X_{401}$ and $X_{402}$ may be nitrogen.

In one or more embodiments, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group.

In one or more embodiments, when xc1 in Formula 401 is two or more, two $A_{401}$(s) in two or more $L_{401}$(s) may optionally be linked via $X_{407}$, which is a linking group, or two $A_{402}$(s) in two or more $L_{401}$(s) may optionally be linked via $X_{408}$, which is a linking group (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group).

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine, or phosphite).

In one or more embodiments, the phosphorescent dopant may be selected from, for example, Compounds PD1 to PD25:

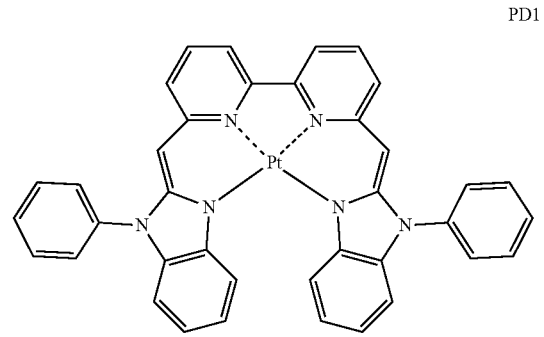

PD1

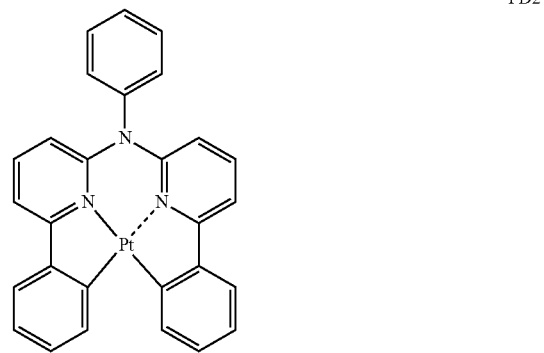

PD2

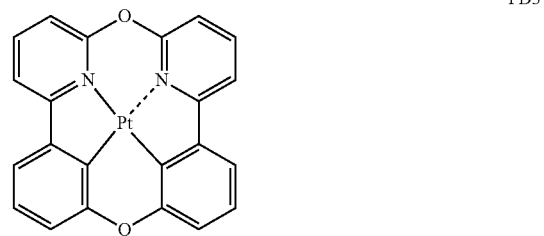

PD3

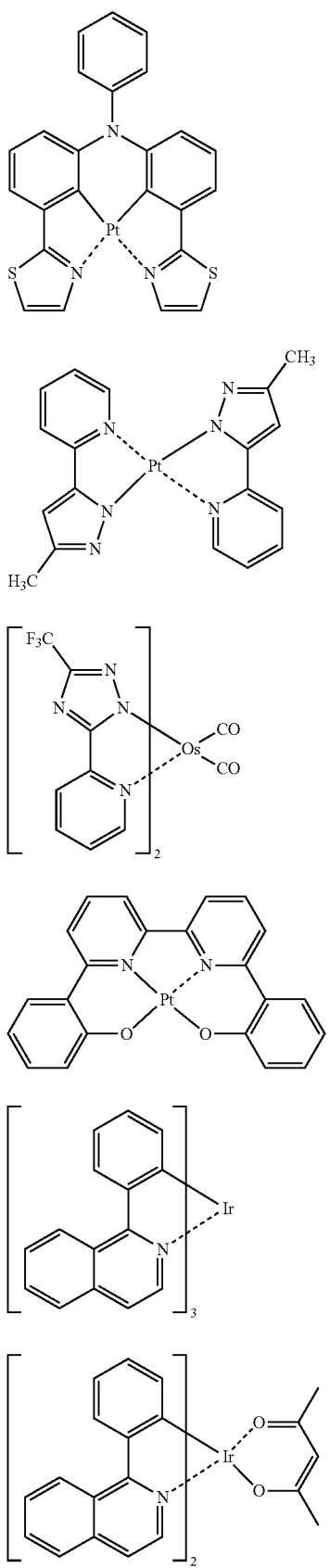

PD15 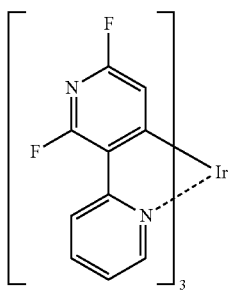
PD16 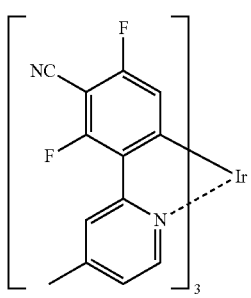
PD17 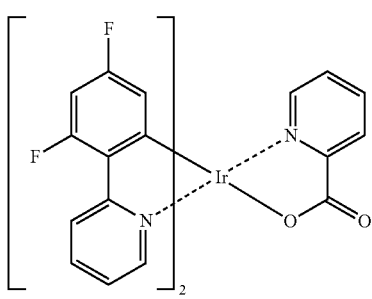
PD18 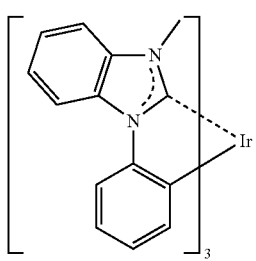
PD19 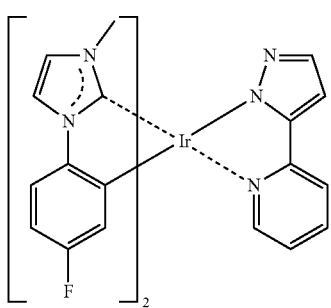
PD20 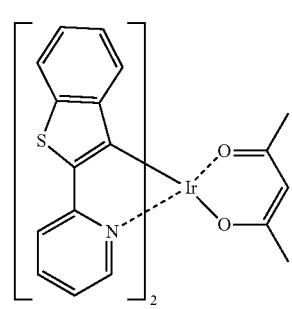
PD21 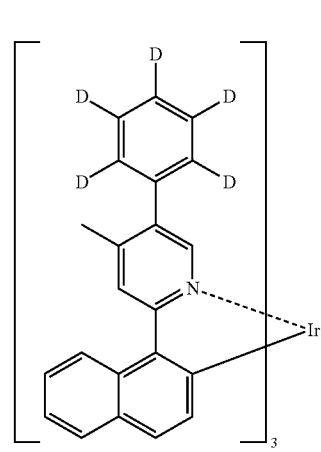
PD22 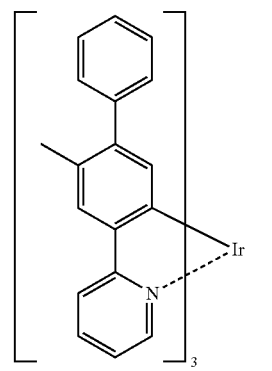
PD23 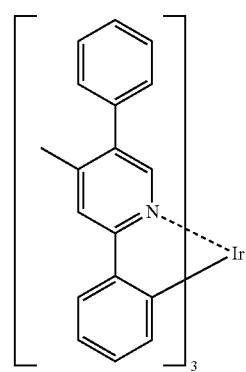

PD24

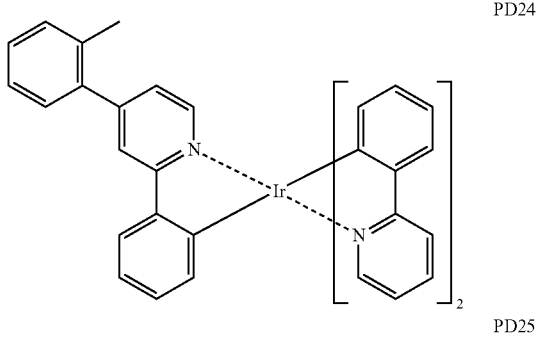

PD25

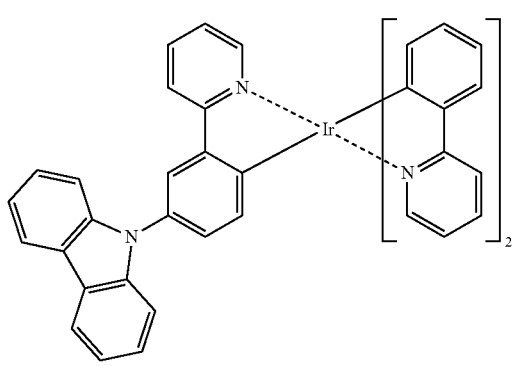

The fluorescent dopant may include an arylamine compound or a styrylamine compound.

The fluorescent dopant may include a compound represented by Formula 501 below.

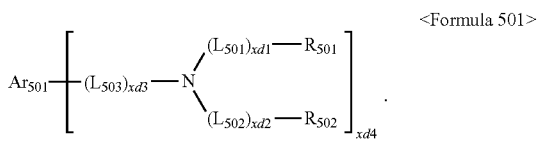

<Formula 501>

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3;

$R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, xd4 may be an integer of 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$);

wherein $Q_{31}$ to $Q_{33}$ may each be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2.

For example, the fluorescent dopant may be selected from Compounds FD1 to FD22:

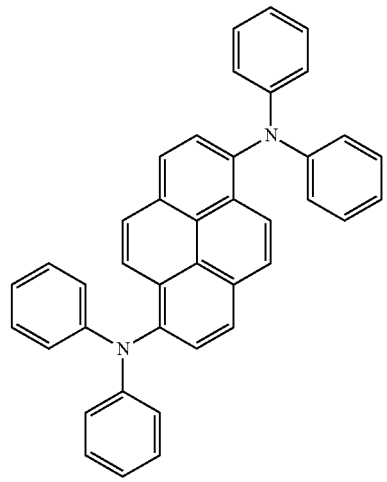

FD1

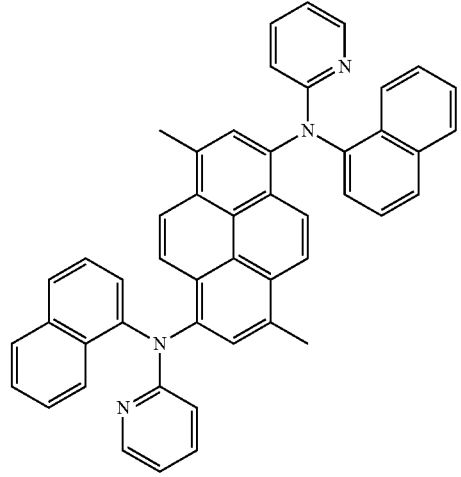

FD2

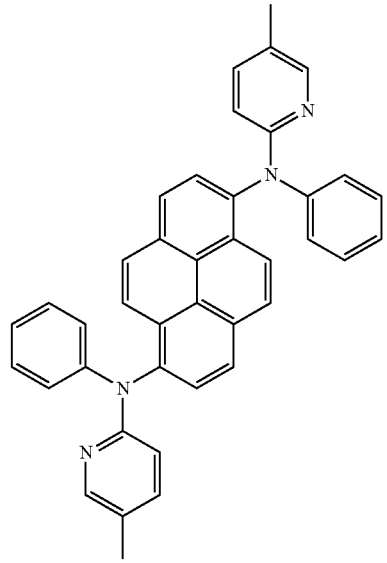

FD3

FD4
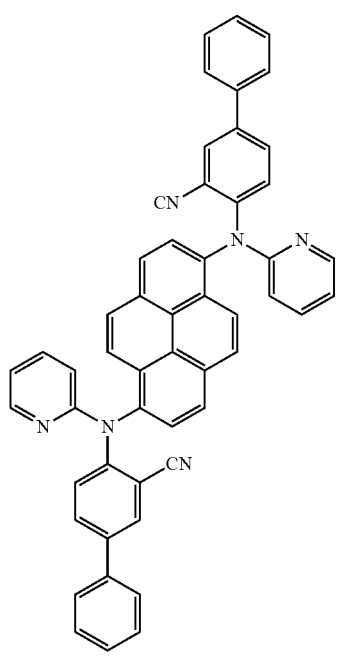
FD7
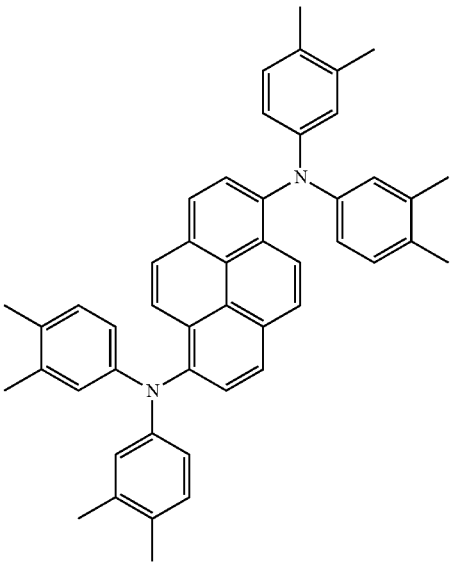
FD5
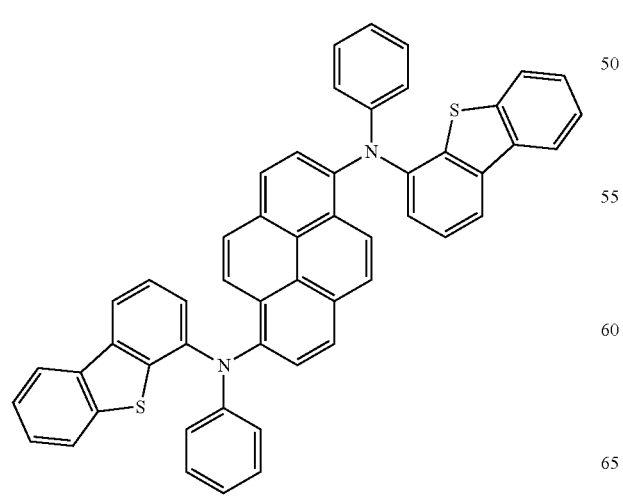
FD8
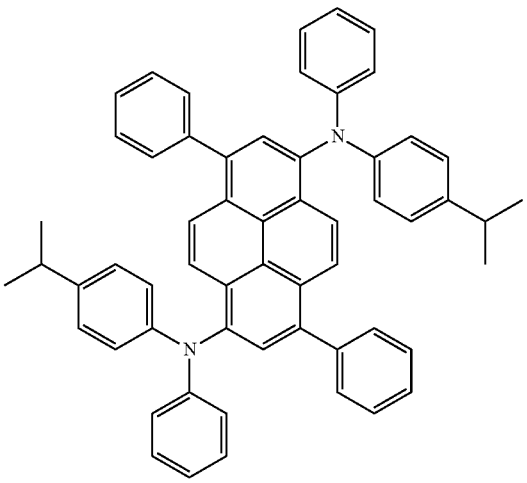
FD6
FD9
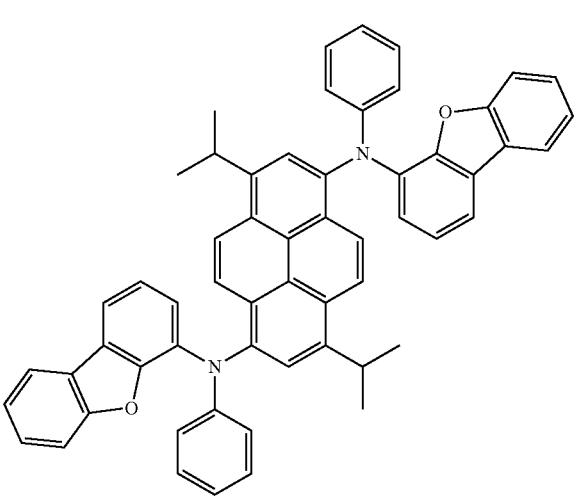

FD10
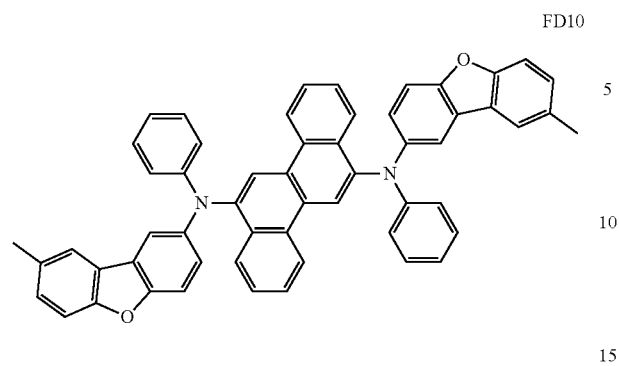
FD15
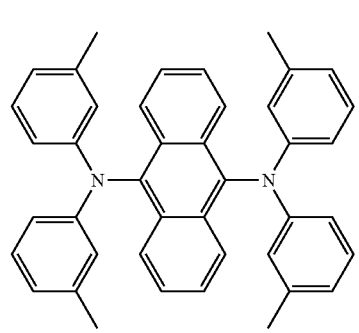
FD11
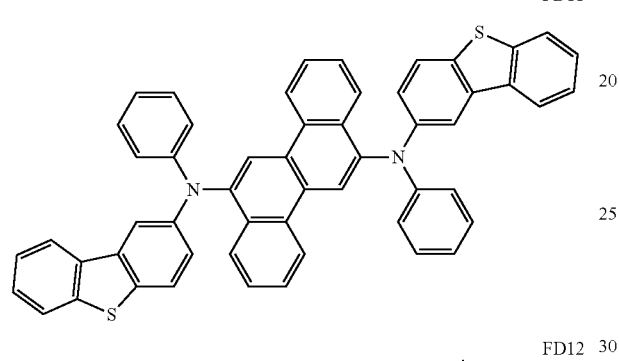
FD16
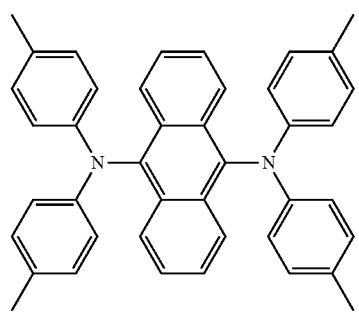
FD12
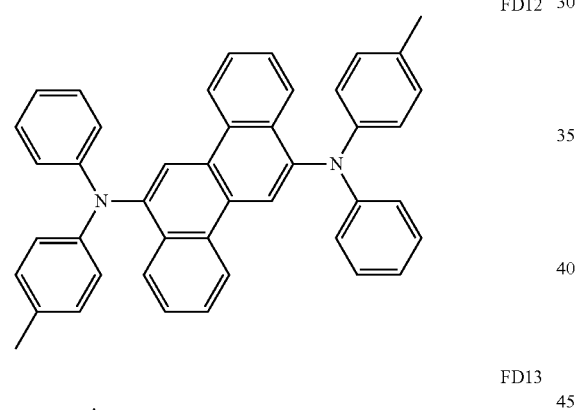
FD17
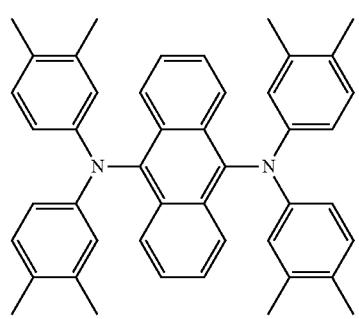
FD13
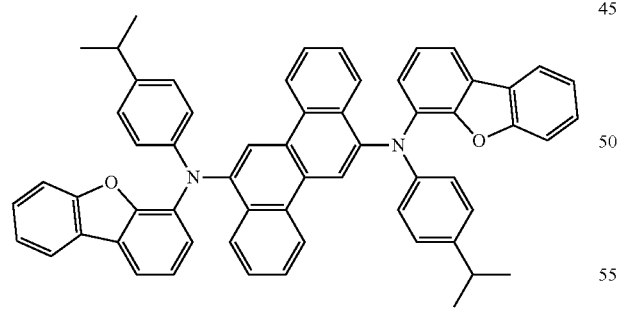
FD18
FD14
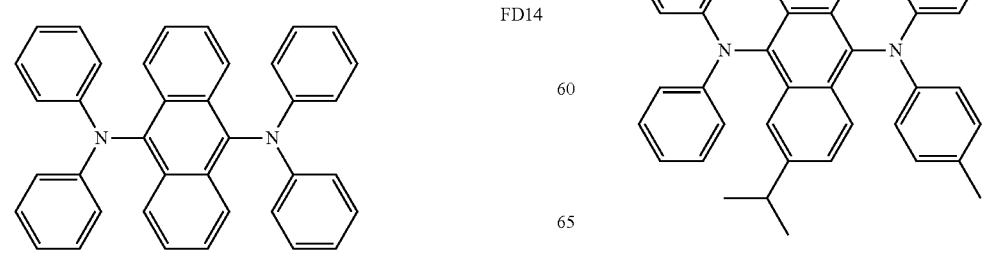

FD19
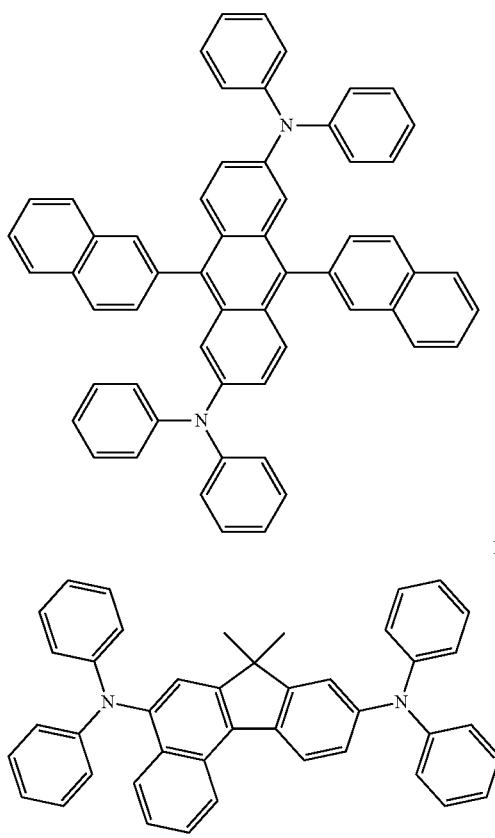
FD20
FD21
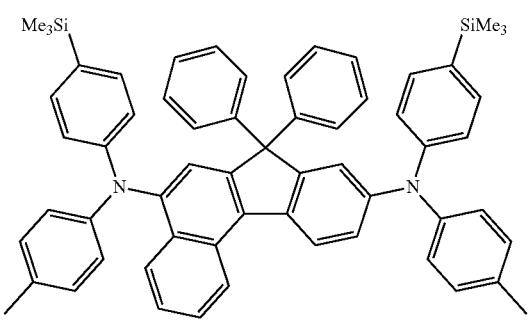
FD22
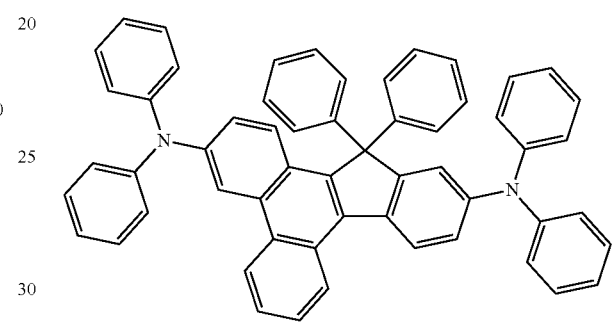
In one or more embodiments, the fluorescent dopant may be selected from the following compounds.
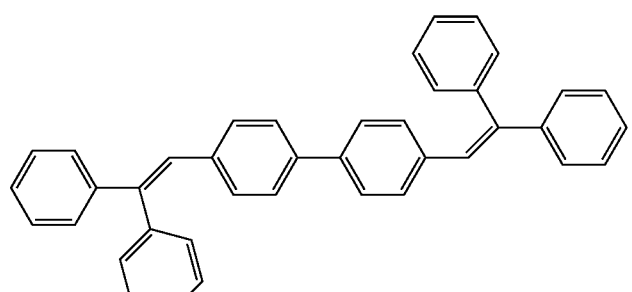
DPVBi
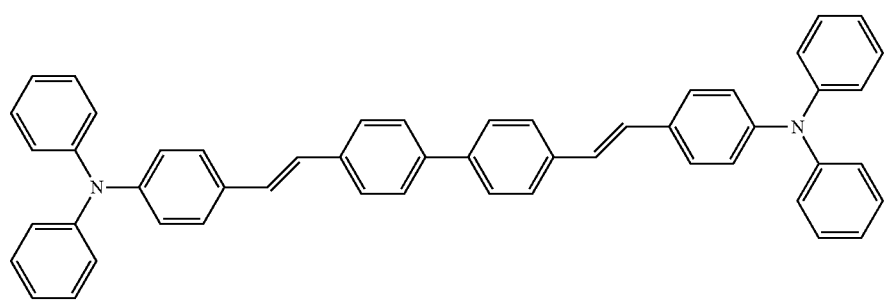
DPAVBi

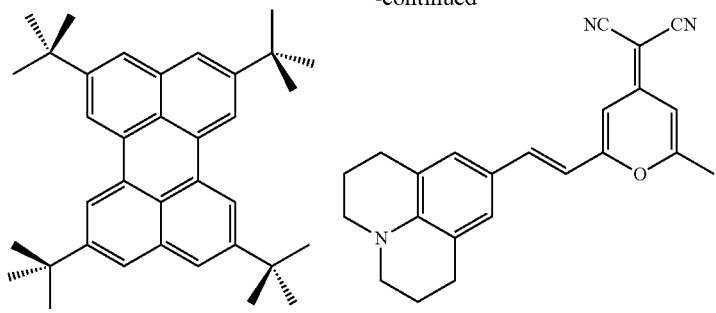

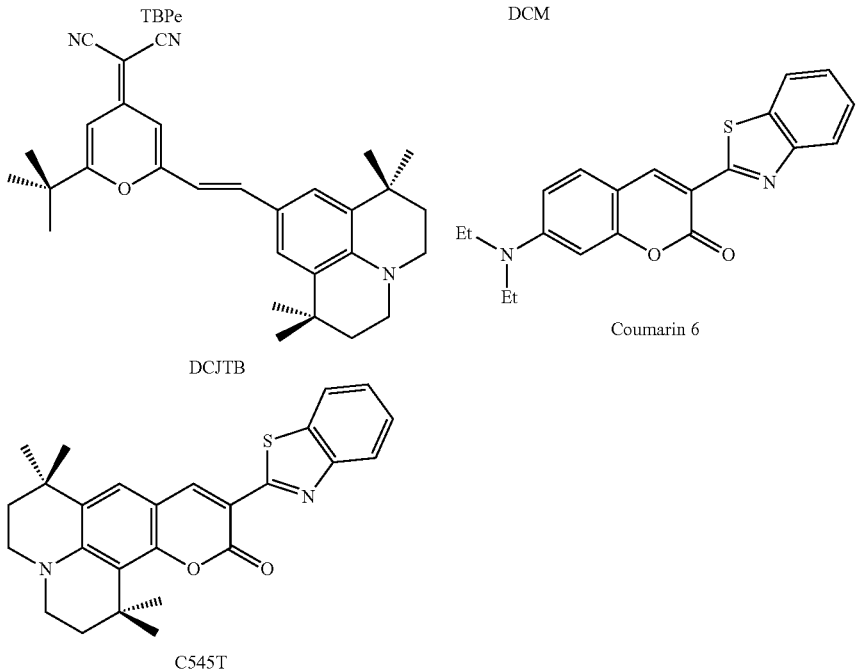

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer.

The electron transport region may include the condensed cyclic compound represented by Formula 1.

In one or more embodiments, the electron transport region (for example, a buffer layer, a hole blocking layer, an electron control layer, or an electron transport layer in the electron transport region) may further include a metal-free compound containing at least one π electron-depleted nitrogen-containing ring.

The "π electron-depleted nitrogen-containing ring" indicates a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole.

For example, the electron transport region may include a compound represented by Formula 601:

$[Ar_{601}]_{xe11}-[(L_{601})_{xe1}-R_{601}]_{xe21}$.     <Formula 601>

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer of 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_{601})(Q_{602})(Q_{603})$, $-C(=O)(Q_{601})$, $-S(=O)_2(Q_{601})$, and $-P(=O)(Q_{601})(Q_{602})$, $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer of 1 to 5.

In one embodiment, at least one of $Ar_{601}$(s) in the number of xe11 and $R_{601}$(s) in the number of xe21 may include the π electron-depleted nitrogen-containing ring.

In one embodiment, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, $-Si(Q_{31})(Q_{32})(Q_{33})$, $-S(=O)_2(Q_{31})$, and $-P(=O)(Q_{31})(Q_{32})$;

wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more $Ar_{601}$(s) may be linked via a single bond.

In one or more embodiments, $Ar_{601}$ in Formula 601 may be an anthracene group.

In one or more embodiments, a compound represented by Formula 601 may be represented by Formula 601-1:

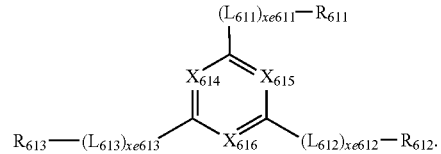

<Formula 601-1>

In Formula 601-1, $X_{614}$ may be N or $C(R_{614})$, $X_{615}$ may be N or $C(R_{615})$, $X_{616}$ may be N or $C(R_{616})$, at least one selected from $X_{614}$ to $X_{616}$ may be N, $L_{611}$ to $L_{613}$ are the same as described in connection with $L_{601}$, xe611 to xe613 are the same as described in connection with xe1, $R_{611}$ to $R_{613}$ are the same as described in connection with $R_{601}$, $R_{614}$ to $R_{616}$ may each independently be selected from hydrogen, deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formulae 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), wherein Q$_{601}$ and Q$_{602}$ are the same as described above.

The electron transport region may include at least one compound selected from Compounds ET1 to ET36:

ET1

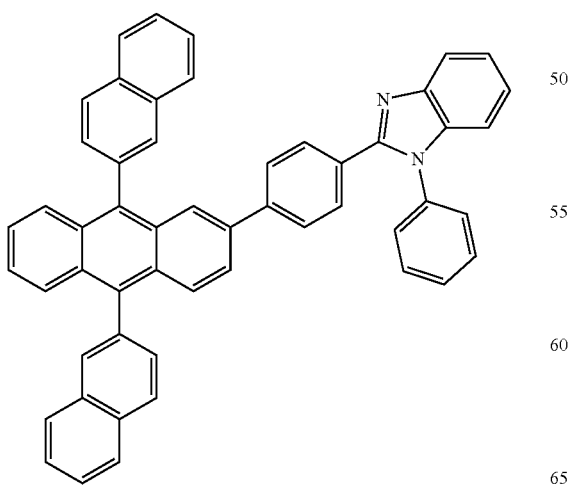

ET2

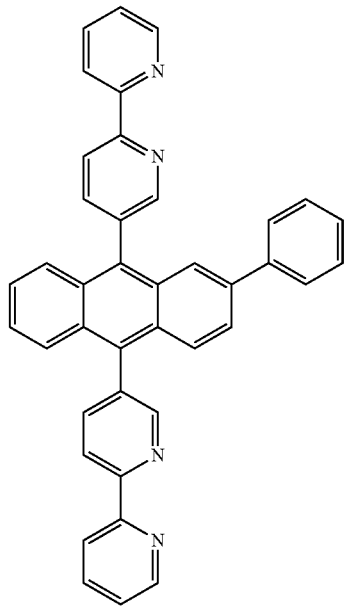

ET3

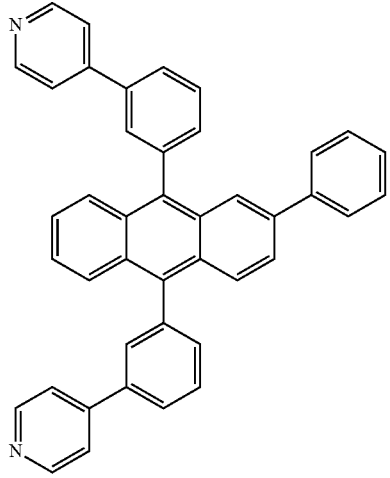

ET4

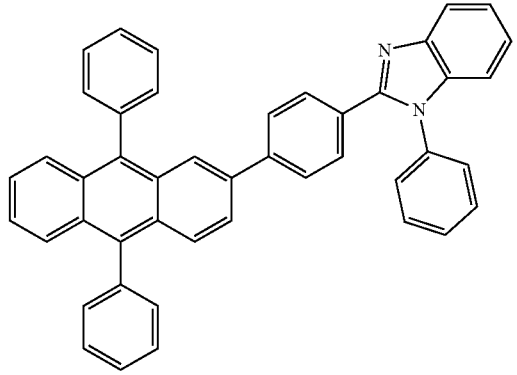

ET5
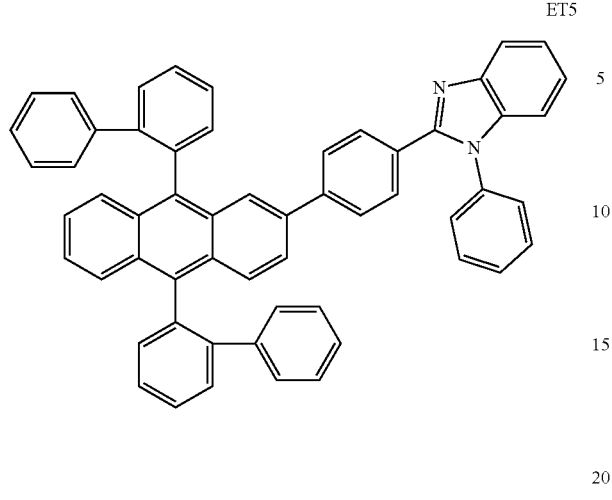
ET6
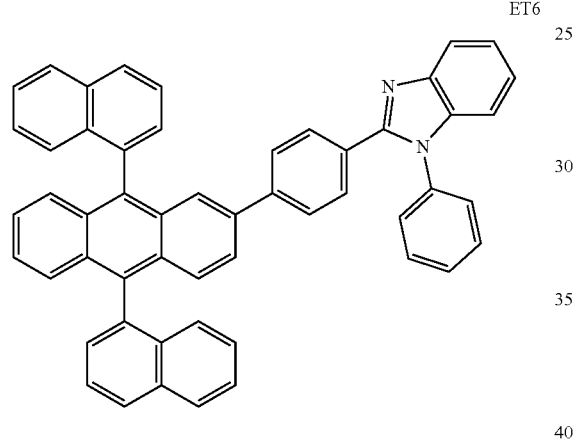
ET7
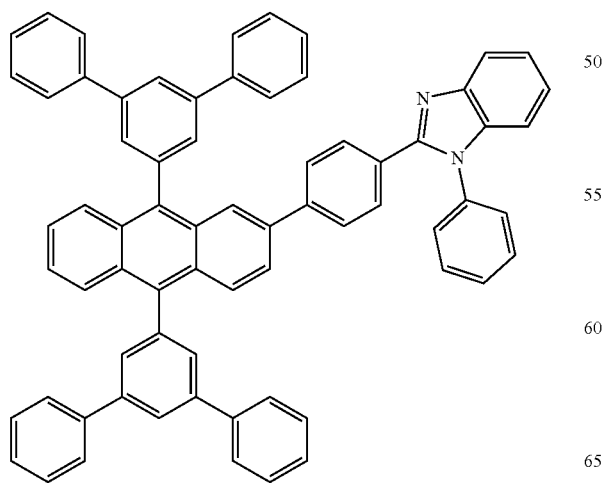
ET8
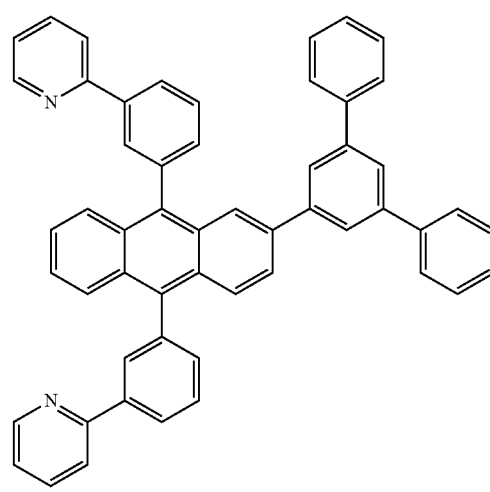
ET9
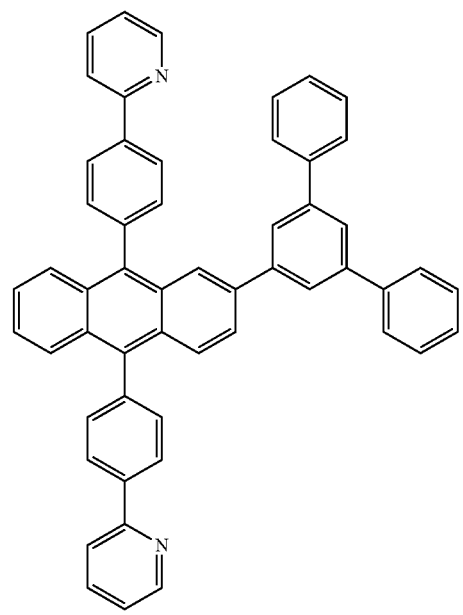

137
-continued
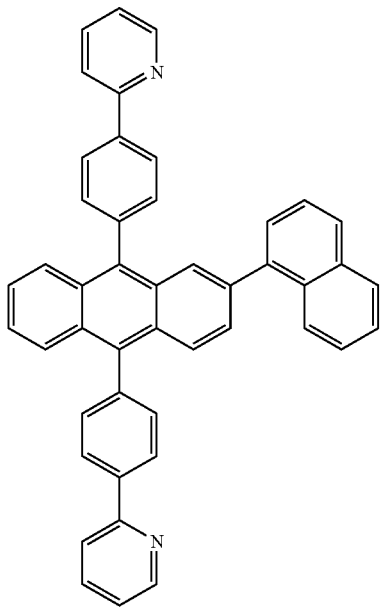
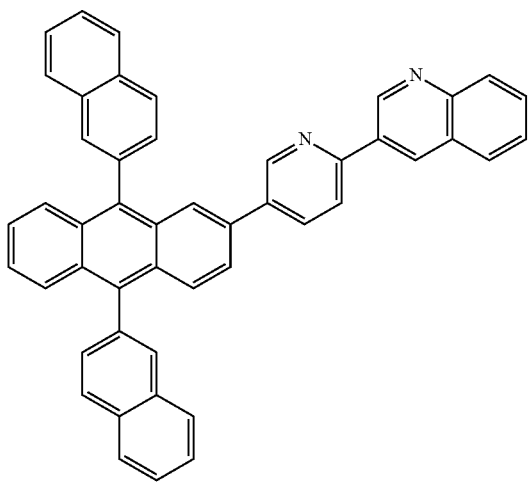
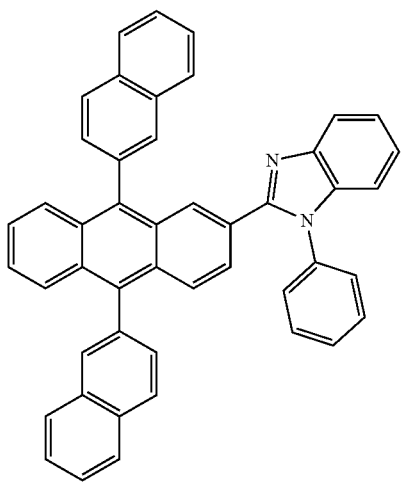
138
-continued
ET10
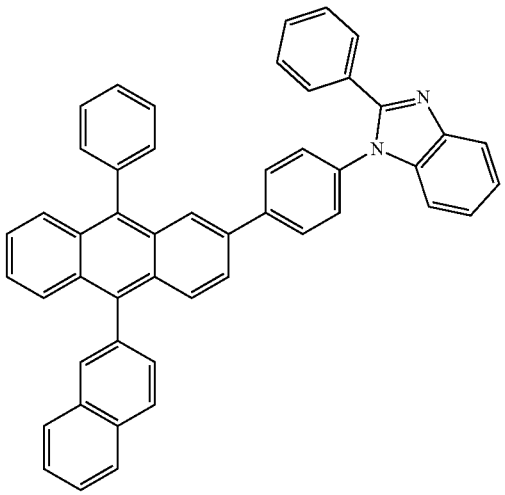
ET11
ET13
ET14
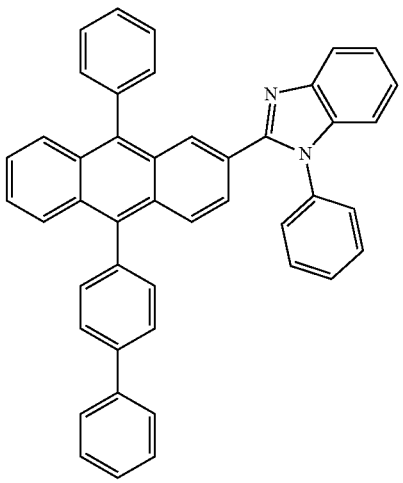
ET12
ET15
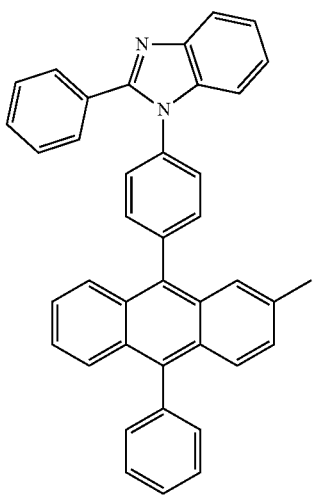

ET16
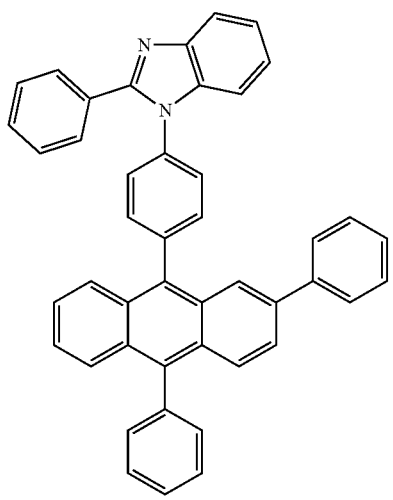
ET17
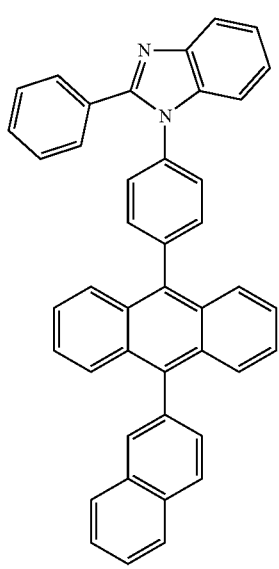
ET18
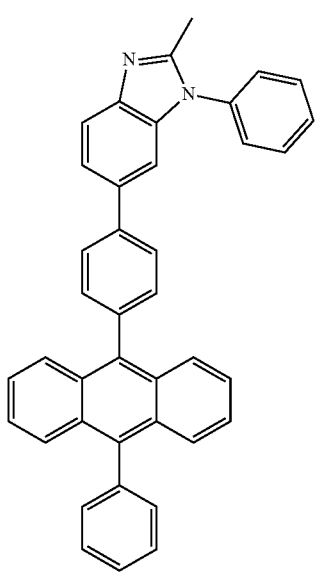
ET19
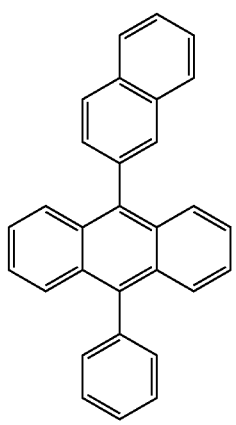
ET20
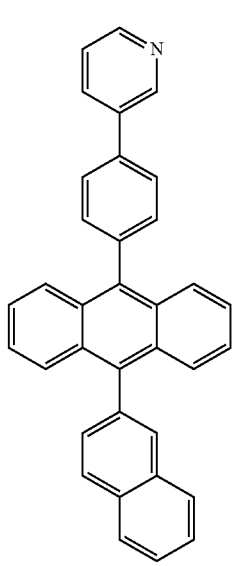
ET21
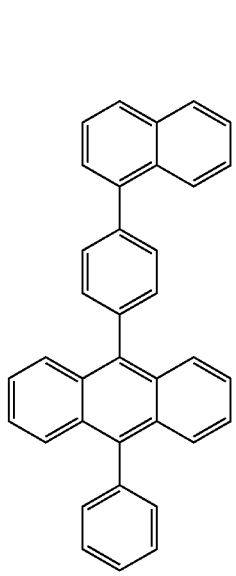

ET22
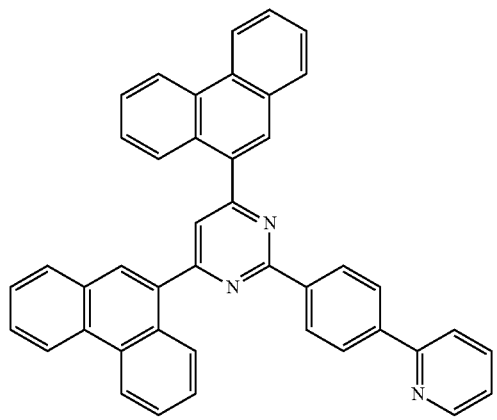
ET23
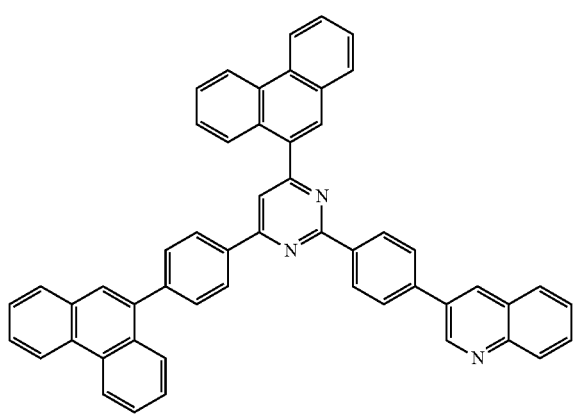
ET24
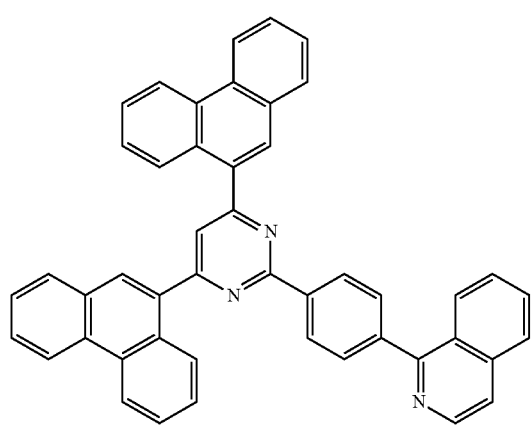
ET25
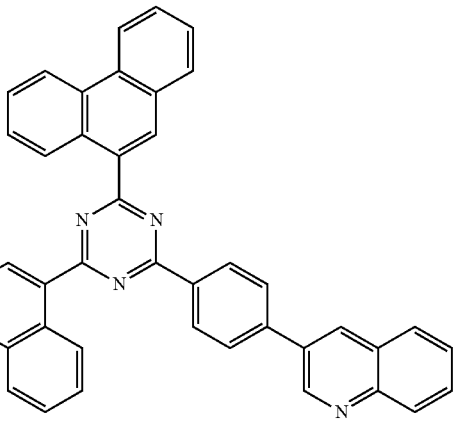
ET26
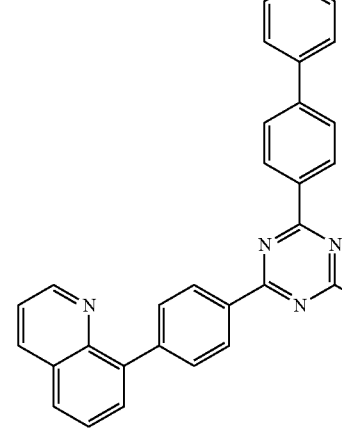
ET27
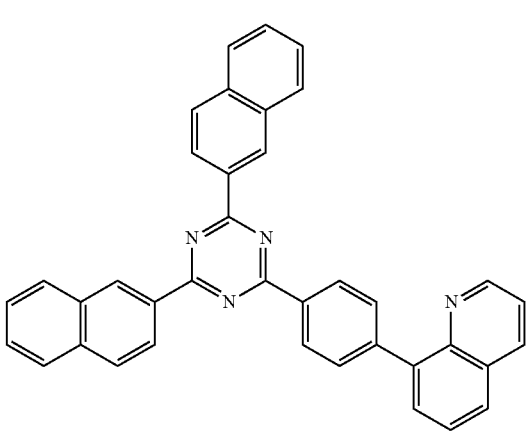

ET28
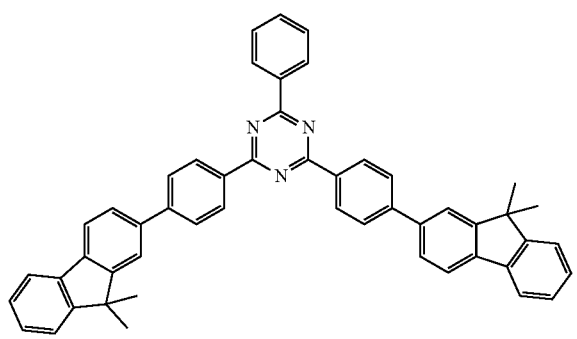
ET29
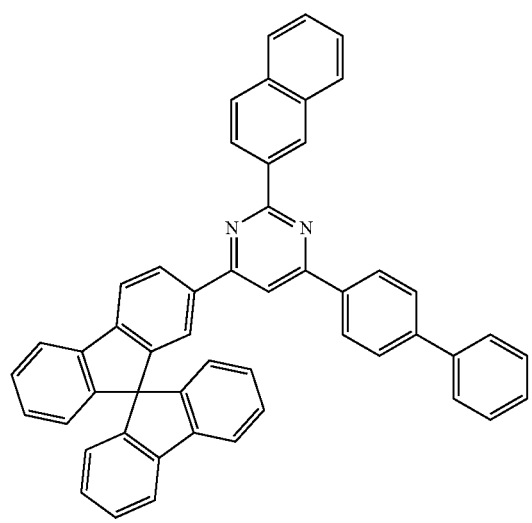
ET30
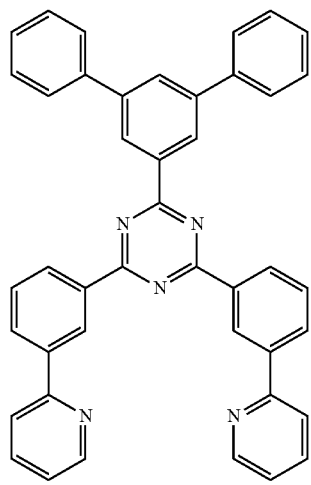
ET31
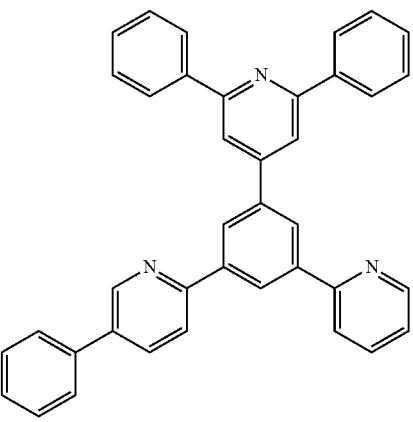
ET32
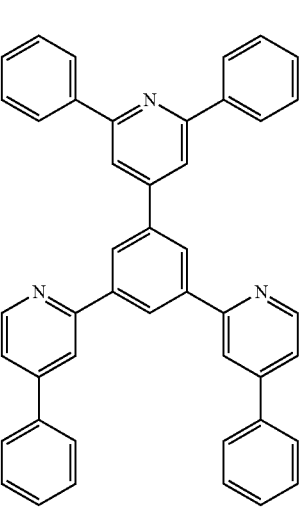
ET33
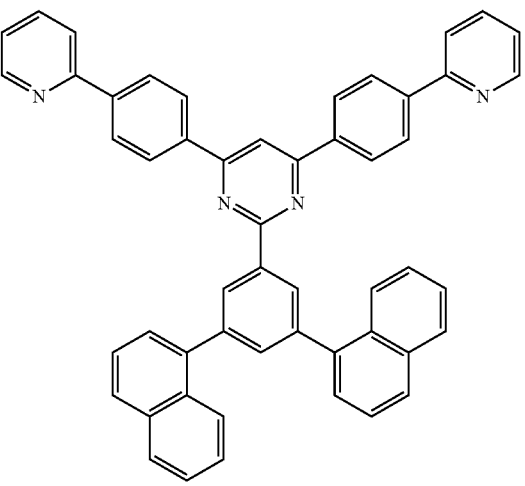

ET34

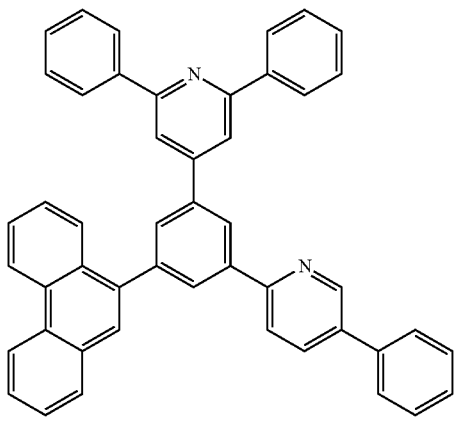

ET35

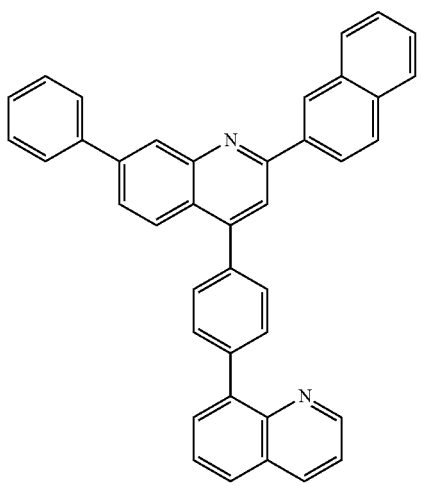

ET36

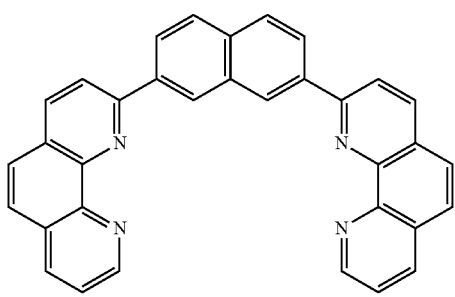

In one or more embodiments, the electron transport region may include at least one selected from 2,9-dimethyl-4,7-diphenyl-1,10-phenanthroline (BCP), 4,7-dphenyl-1,10-phenanthroline (Bphen), Alq3, BAlq, 3-(biphenyl-4-yl)-5-(4-tert-butylphenyl)-4-phenyl-4H-1,2,4-triazole (TAZ), and NTAZ.

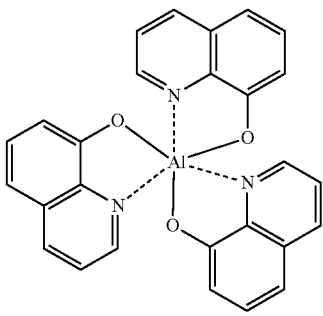

Alq₃

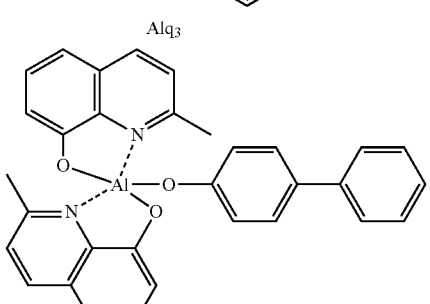

BAlq

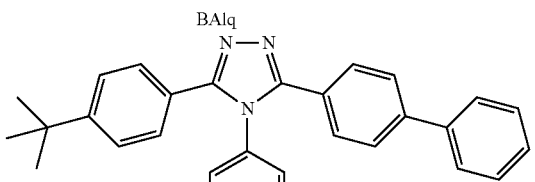

TAZ

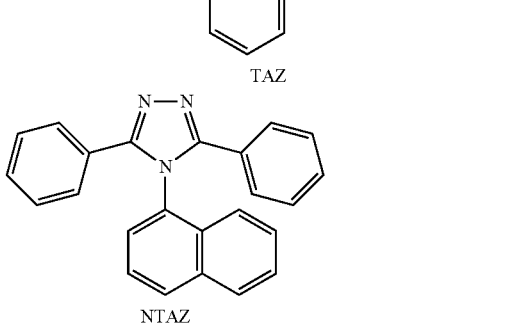

NTAZ

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene.

For example, the metal-containing material may include a Li complex. The Li complex may include, for example, Compound ET-D1 (lithium quinolate, LiQ) or ET-D2.

ET-D1

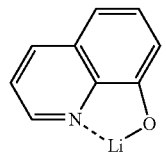

ET-D2

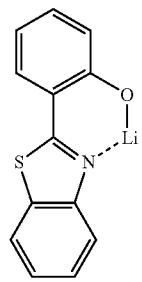

The electron transport region may include an electron injection layer that facilitates the injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In one embodiment, the alkali metal compound may be selected from LiF, $Li_2O$, NaF, Li, NaI, CsI, and KI.

The alkaline earth-metal compound may be selected from alkaline earth-metal oxides, such as BaO, SrO, CaO, $Ba_xSr_{1-x}O$ (0<x<1), $Ba_xCa_{1-x}O$ (0<x<1). In one embodiment, the alkaline earth-metal compound may be selected from BaO, SrO, and CaO.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazol, hydroxy phenylpyridine, hydroxy phenylbenzimidazole, hydroxy phenylbenzothiazole, bipyridine, phenanthroline, and cyclopentadiene.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 190 may be located on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Si), magnesium (Mg), aluminum (Al), aluminum-lithium (Al—Li), calcium (Ca), magnesium-indium (Mg—In), magnesium-silver (Mg—Ag), ITO, and IZO. The second electrode 190 may be a transmissive electrode, a semi-transmissive electrode, or a reflective electrode.

The second electrode 190 may have a single-layered structure, or a multi-layered structure including two or more layers.

Figure 2:
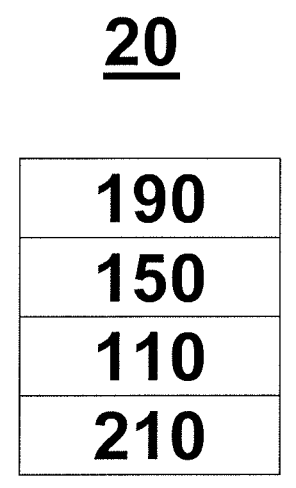
Figure 3:
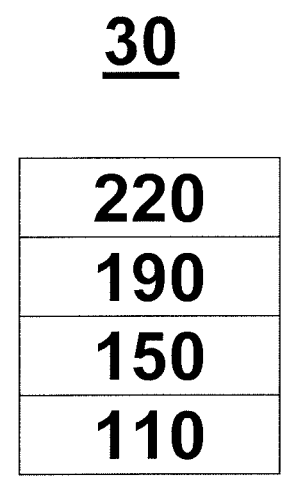
Figure 4:
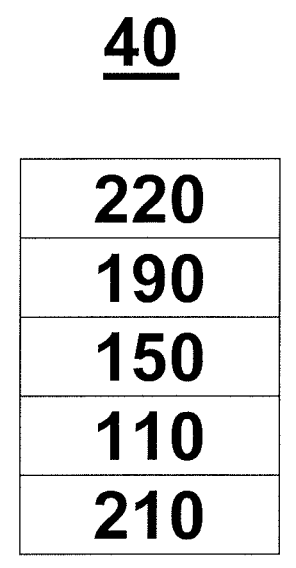

An organic light-emitting device 20 of FIG. 2 includes a first capping layer 210, a first electrode 110, an organic layer 150, and a second electrode 190, sequentially stacked in this stated order, an organic light-emitting device 30 of FIG. 3 includes a first electrode 110, an organic layer 150, a second electrode 190, and a second capping layer 220, sequentially stacked in this stated order, and an organic light-emitting device 40 of FIG. 4 includes a first capping layer 210, a first electrode 110, an organic layer 150, a second electrode 190, and a second capping layer 220, sequentially stacked in this stated order.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110 and the first capping layer 210 toward the outside, wherein the first electrode 110 may be a semi-transmissive electrode or a transmissive electrode. In the organic layer 150 of each of the organic light-emitting devices 30 and 40, light generated in an emission layer may pass through the second electrode 190 and the second capping layer 220 toward the outside, wherein the second electrode 190 may be a semi-transmissive electrode or a transmissive electrode.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5.

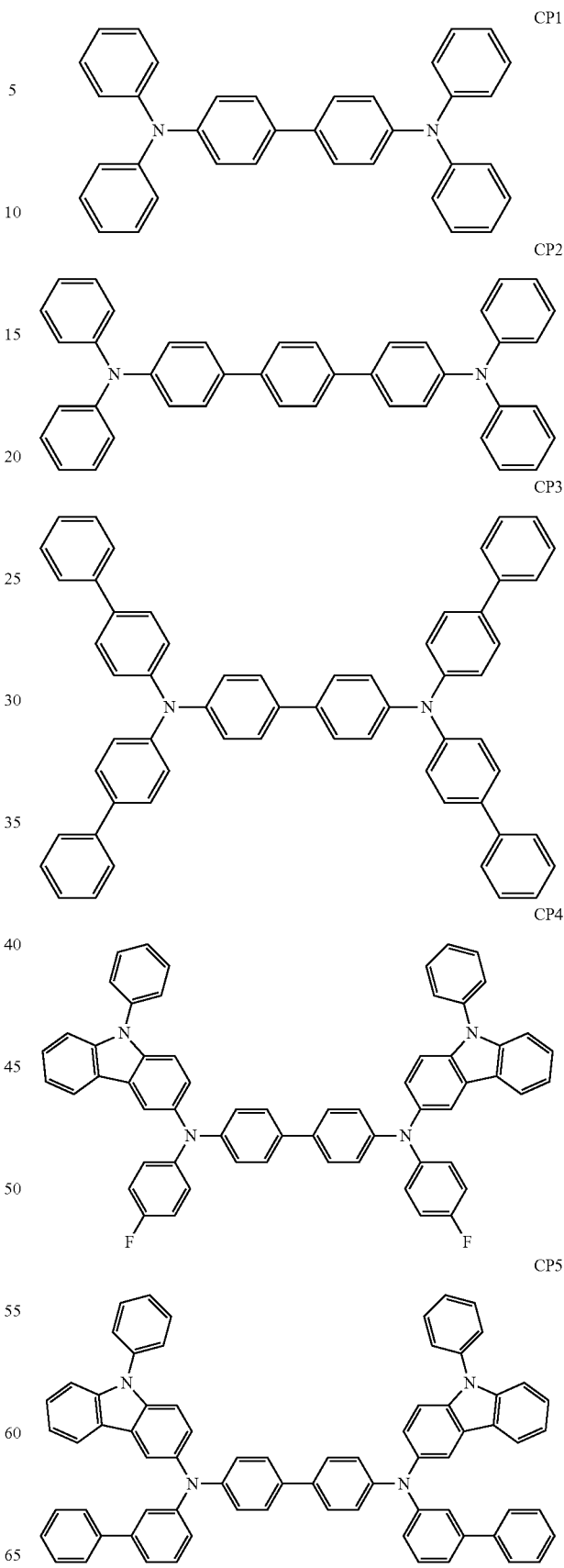

Hereinbefore, the organic light-emitting device according to an embodiment has been described in connection with FIGS. 1-4.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, for example, the vacuum deposition may be performed at a deposition temperature of about 100 to about 500° C., at a vacuum degree of about 10-8 to about 10-3 torr, and at a deposition rate of about 0.01 to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2000 rpm to about 5000 rpm and at a heat treatment temperature of about 80° C. to 200° C. by taking into account a material to be included in a layer to be formed, and the structure of a layer to be formed.

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. A $C_1$-$C_{60}$ alkylene group used herein refers to a divalent group having the same structure as that of the $C_1$-$C_{60}$ alkyl group.

The term "$C_2$-$C_{60}$ alkenyl group" as used herein refers to a hydrocarbon group having the same structure as that of the $C_2$-$C_{60}$ alkyl group, except for at least one carbon-carbon double bond in the middle or at the terminus of the $C_2$-$C_{60}$ alkyl group, and examples thereof include an ethenyl group, a propenyl group, and a butenyl group. A $C_2$-$C_{60}$ alkenylene group used herein refers to a divalent group having the same structure as that of the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as that of the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as that of the $C_3$-$C_{10}$ cycloalkyl group.

The term "$C_1$-$C_{10}$ heterocycloalkyl group" as used herein refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Examples of the $C_1$-$C_{10}$ heterocycloalkenyl group may include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, Si, P, and S as a ring-forming atom, in addition to 1 to 60 carbon atoms. The term "$C_1$-$C_{60}$ heteroarylene group" as used herein refers to a divalent group having a heterocyclic aromatic system that has at least one heteroatom selected from N, O, Si, P, and S as a ring-forming atom, in addition to 1 to 60 carbon atoms. Examples of the $C_6$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_6$-$C_{60}$ heteroaryl group and the $C_6$-$C_{60}$ heteroarylene group each include two or more rings, the rings may be fused to each other.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed with each other, only carbon atoms as ring-forming atoms, and no aromaticity in its entire molecular structure. A detailed example of the monovalent non-aromatic condensed polycyclic group is a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom selected from N, O, Si, P, and S, other than carbon atoms, as a ring-forming atom, and no aromaticity in its entire molecular structure. An example of the monovalent non-aromatic condensed heteropolycyclic group is a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$);

wherein $Q_{11}$ to $Q_{13}$, $Q_{21}$ to $Q_{23}$ and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph", as used herein, may refer to a phenyl group; the term "Me", as used herein, may refer to a methyl group; the term "Et", as used herein, may refer to an ethyl group; the terms "ter-Bu" or "But", as used herein, may refer to a tert-butyl group; and the term "OMe" as used herein may refer to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The "terphenyl group" used herein refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

Hereinafter, a compound according to embodiments and an organic light-emitting device according to embodiments will be described in detail with reference to Synthesis Examples and Examples. The wording "B was used instead of A" used in describing Synthesis Examples refers to that an identical molar equivalent of B was used in place of A.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis Example

Synthesis Example 1: Synthesis of Compound 3

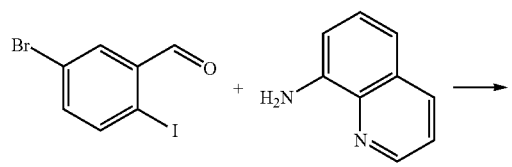

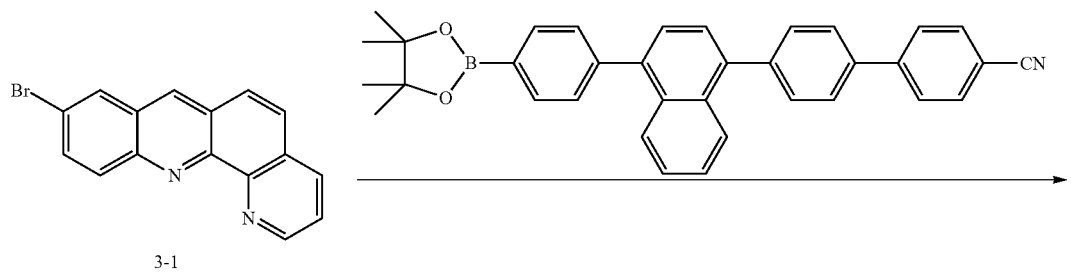

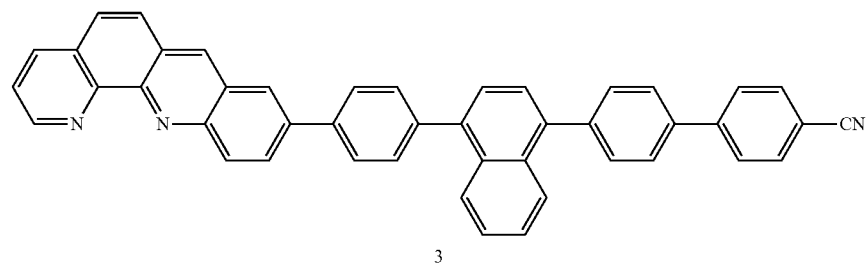

Synthesis of Intermediate 3-1

3.11 g (10 mmol) of 5-bromo-2-iodobenzaldehyde, 1.44 g (10 mmol) of 8-aminoquinoline, 0.23 g (0.25 mmol) of Pd$_2$(dba)$_3$, 0.28 g (0.5 mmol) of dppf, and 2.76 g (20 mmol) of K$_2$CO$_3$ were dissolved in 250 mL of toluene, and then, the mixture was stirred at a temperature of 80° C. for 24 hours. The reaction solution was cooled to ambient temperature, immediately filtered through silica, and the filtrate was dried under reduced pressure. Then, 2.66 g (20 mmol) of AlCl$_3$ was added thereto and dissolved in 300 mL of toluene, followed by stirring at 80° C. for 24 hours. The reaction solution was cooled to ambient temperature, and then subjected to an extraction process three times by using 60 mL of water and 60 mL of diethyl ether. An organic layer obtained therefrom was dried by using magnesium sulfate and the residual obtained by evaporating a solvent therefrom was separation-purified by silica gel column chromatography to obtain 1.23 g (yield: 40%) of Intermediate 3-1. The obtained compound was identified by LC-MS.

C16H9BrN2: M+1 309.16

Synthesis of Compound 3

3.09 g (10 mmol) of Intermediate 3-1, 5.07 g (10 mmol) of 4'-(4-(4-(4,4,5,5-tetramethyl-1,3,2-dioxaborolan-2-yl) phenyl)naphthalen-1-yl)-[1,1'-biphenyl]-4-carbonitrile, 0.58 g (0.5 mmol) of Pd(PPh$_3$)$_4$, and 4.15 g (30.0 mmol) of K$_2$CO$_3$ were dissolved in a mixed solution including 180 mL of THF/H$_2$O (2/1), and then, the mixture was stirred at a temperature of 80° C. for 16 hours. The reaction solution was cooled to ambient temperature, and then, subjected to an extraction process three times by using 60 mL of water and 60 mL of diethyl ether. An organic layer obtained therefrom was dried by using magnesium sulfate and the residual obtained by evaporating a solvent therefrom was separation-purified by silica gel column chromatography to obtain 3.65 g (yield 60%) of Compound 3. The obtained compound was confirmed by LC-MS and $^1$H NMR.

C45H27N3: M+1 609.72

Synthesis Example 2: Synthesis of Compound 11

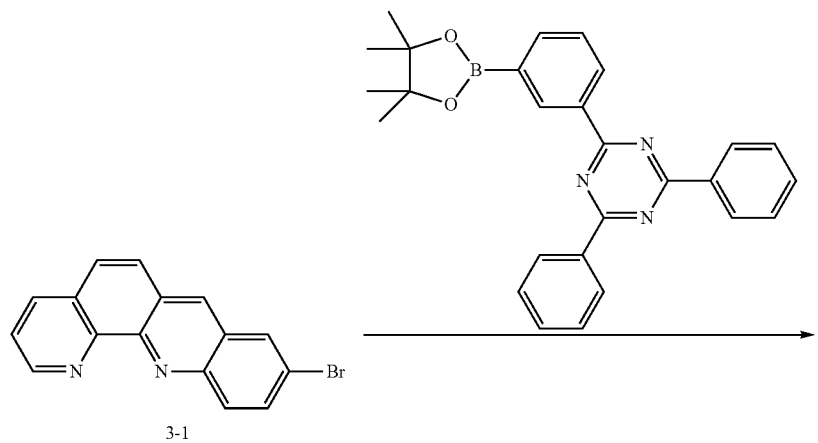

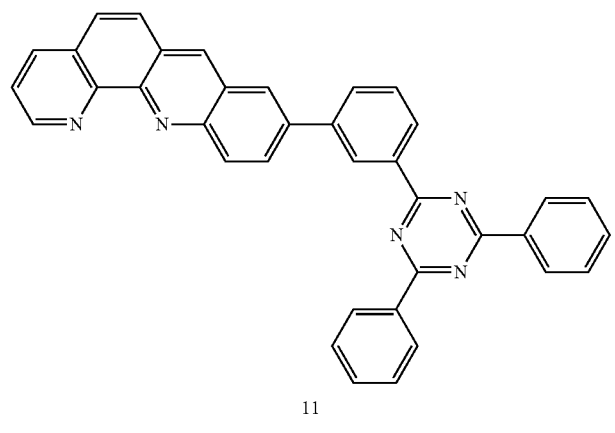

Synthesis of Compound 11

3.49 g (yield 65%) of Compound 11 was obtained in the same manner as used to synthesize Compound 3, except that 2,4-diphenyl-6-(3-(4,4,5,5-tetramethyl-1,3,2-dioxaborolan-2-yl)phenyl)-1,3,5-triazine was used instead of 4'-(4-(4,4,5,5-tetramethyl-1,3,2-dioxaborolan-2-yl)phenyl)naphthalen-1-yl)-[1,1'-biphenyl]-4-carbonitrile. The obtained compound was confirmed by LC-MS and $^1$H NMR.

C37H23N5: M+1 537.61

Synthesis Example 3: Synthesis of Compound 13

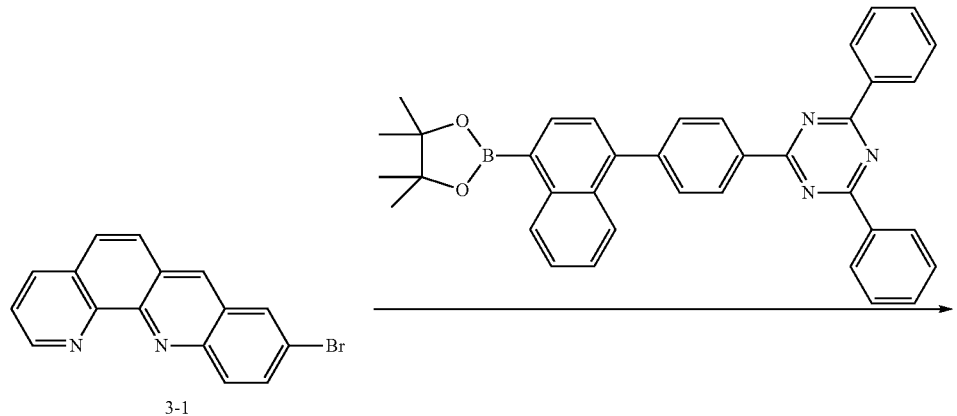

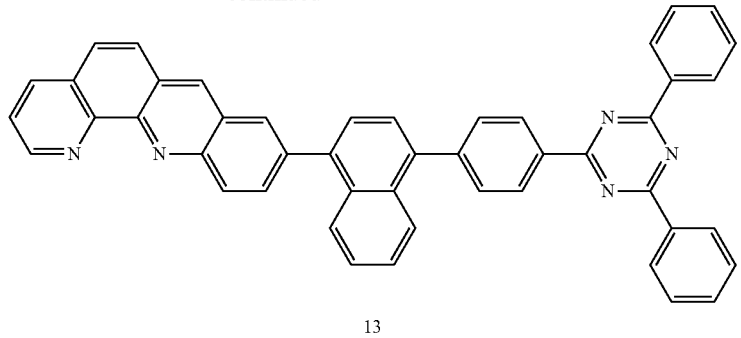

13

Synthesis of Compound 13

5.3 g (yield 80%) of Compound 13 was obtained in the same manner as used to synthesize Compound 3, except that 2,4-diphenyl-6-(4-(4-(4,4,5,5-tetramethyl-1,3,2-dioxaborolan-2-yl)naphthalen-1-yl)phenyl)-1,3,5-triazine was used instead of 4'-(4-(4-(4,4,5,5-tetramethyl-1,3,2-dioxaborolan-2-yl)phenyl)naphthalen-1-yl)-[1,1'-biphenyl]-4-carbonitrile. The obtained compound was confirmed by LC-MS and $^1$H NMR.

$C_{47}H_{29}N_5$: M+1 663.76

Synthesis Example 4: Synthesis of Compound 21

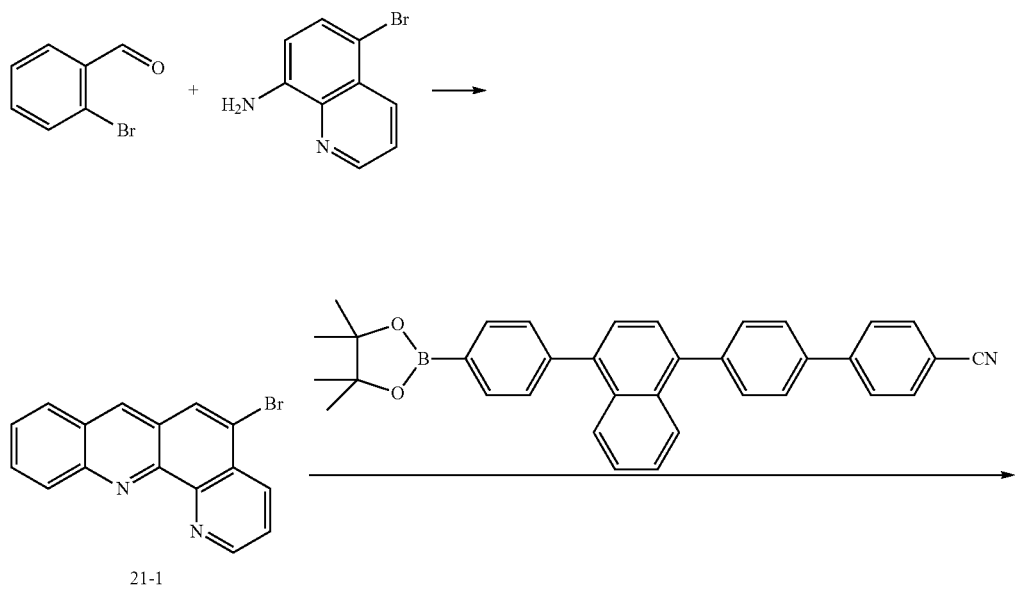

21-1

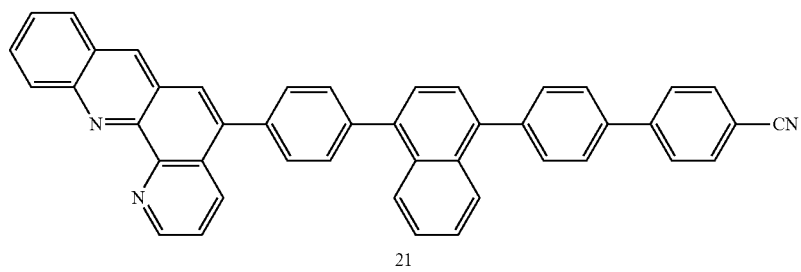

21

Synthesis of Intermediate 21-1

1.39 g (yield 45%) of Intermediate 21-1 was obtained in the same manner as used to synthesize Intermediate 3-1, except that 2-bromobenzaldehyde was used instead of 5-bromo-2-iodobenzaldehyde and 5-bromo-8-aminoquinoline was used instead of 8-aminoquinoline. The obtained compound was identified by LC-MS.

C16H9BrN2: M+1 309.15

Synthesis of Compound 21

4.58 g (yield 75%) of Compound 21 was obtained in the same manner as used to synthesize Compound 3, except that Intermediate 21-1 was used instead of Intermediate 3-1.

The obtained compound was confirmed by LC-MS and $^1$H NMR.

C45H27N3: M+1 609.71

Synthesis Example 5: Synthesis of Compound 33

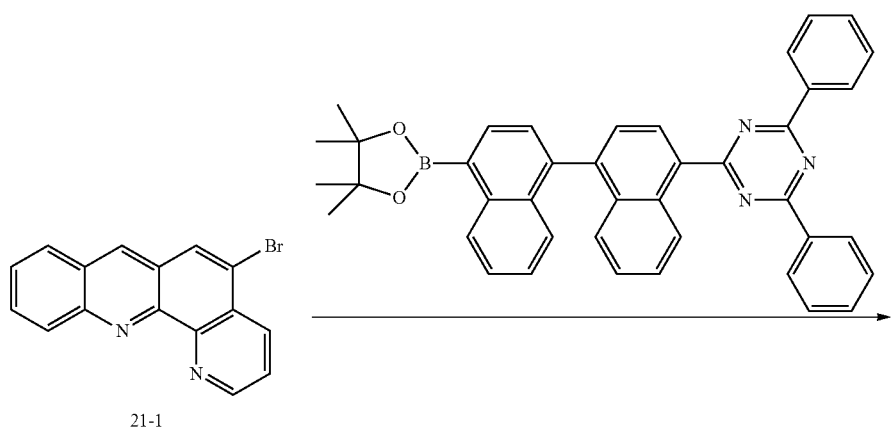

21-1

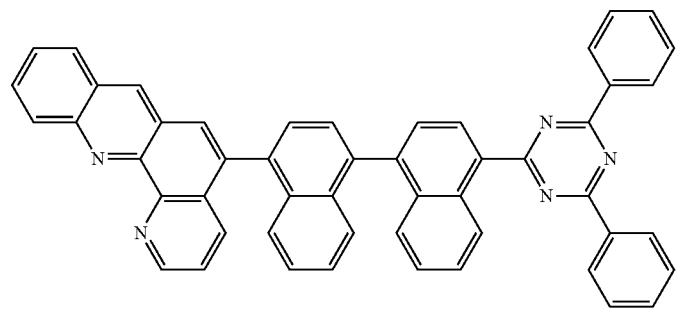

33

Synthesis of Compound 33

5.0 g (yield 70%) of Compound 33 was obtained in the same manner as used to synthesize Compound 3, except that Intermediate 21-1 was used instead of Intermediate 3-1 and 2,4-diphenyl-6-(4'-(4,4,5,5-tetramethyl-1,3,2-dioxaborolan-2-yl)-[1,1'-binaphthalen]-4-yl)-1,3,5-triazine was used instead of 4'-(4-(4-(4,4,5,5-tetramethyl-1,3,2-dioxaborolan-2-yl)phenyl)naphthalen-1-yl)-[1,1'-biphenyl]-4-carbonitrile. The obtained compound was confirmed by LC-MS and $^1$H NMR.

C51H31N5: M+1 713.8

Synthesis Example 6: Synthesis of Compound 34

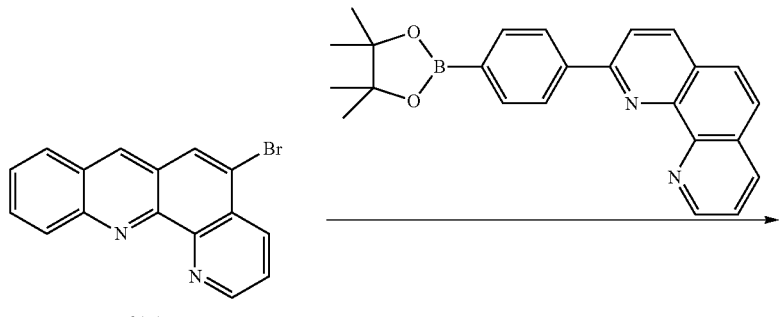

21-1

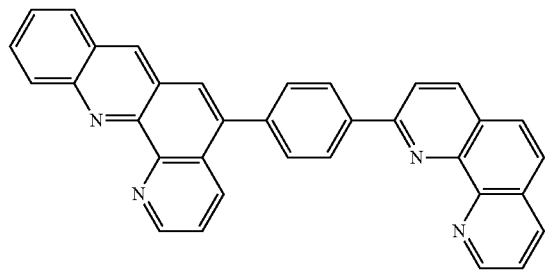

34

Synthesis of Compound 34

2.42 g (yield 50%) of Compound 34 was obtained in the same manner as used to synthesize Compound 3, except that Intermediate 21-1 was used instead of Intermediate 3-1, and 2-(4-(4,4,5,5-tetramethyl-1,3,2-dioxaborolan-2-yl)phenyl)-1,10-phenanthroline was used instead of 4'-(4-(4-(4,4,5,5-tetramethyl-1,3,2-dioxaborolan-2-yl)phenyl)naphthalen-1-yl)-[1,1'-biphenyl]-4-carbonitrile. The obtained compound was confirmed by LC-MS and $^1$H NMR.

C34H20N4: M+1 484.57

Synthesis Example 7: Synthesis of Compound 66

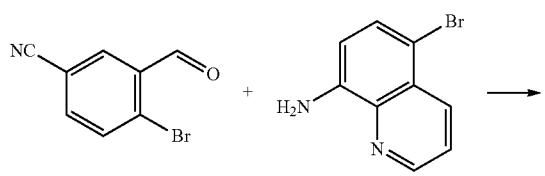

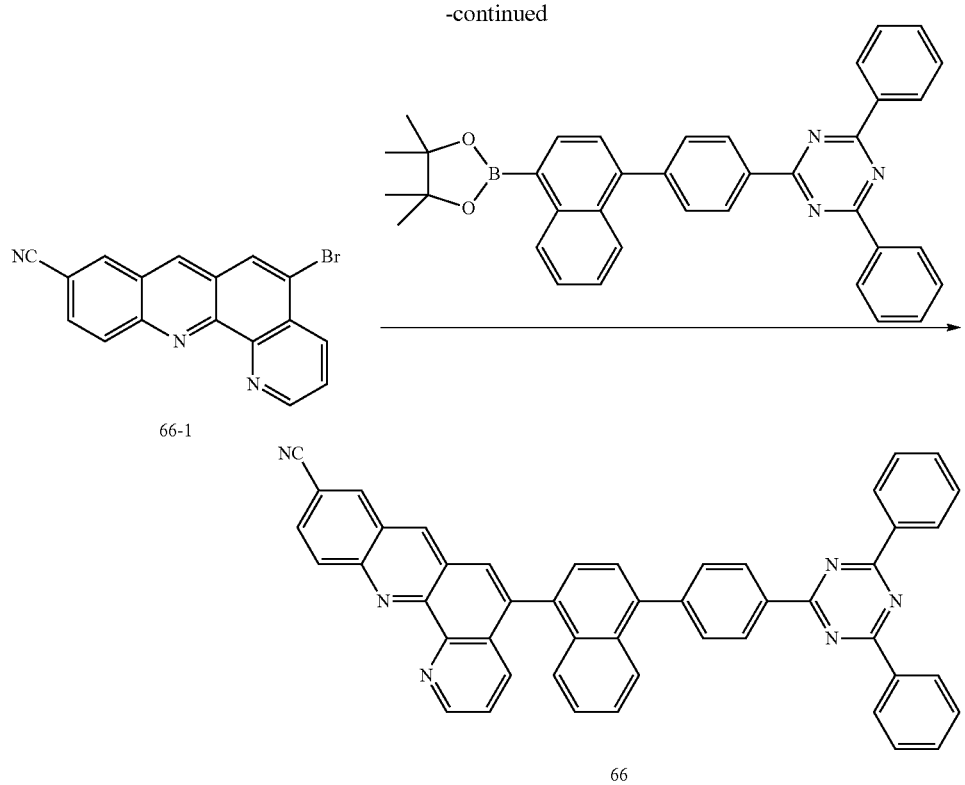

66-1

66

Synthesis of Intermediate 66-1

0.93 g (yield 30%) of Intermediate 66-1 was obtained in the same manner as used to synthesize Intermediate 3-1, except that 4-bromo-3-formylbenzonitrile was used instead of 5-bromo-2-iodobenzaldehyde, and 5-bromo-8-aminoquinoline was used instead of 8-aminoquinoline. The obtained compound was identified by LC-MS.

C16H9BrN2: M+1 309.16

Synthesis of Compound 66

4.48 g (yield 65%) of Compound 66 was obtained in the same manner as used to synthesize Compound 3, except that Intermediate 66-1 was used instead of Intermediate 3-1, and 2,4-diphenyl-6-(4-(4-(4,4,5,5-tetramethyl-1,3,2-dioxaborolan-2-yl)naphthalen-1-yl)phenyl)-1,3,5-triazine was used instead of 4'-(4-(4-(4,4,5,5-tetramethyl-1,3,2-dioxaborolan-2-yl)phenyl)naphthalen-1-yl)-[1,1'-biphenyl]-4-carbonitrile. The obtained compound was confirmed by LC-MS and $^1$H NMR.

C48H28N6: M+1 688.76

Synthesis Example 8: Synthesis of Compound 99

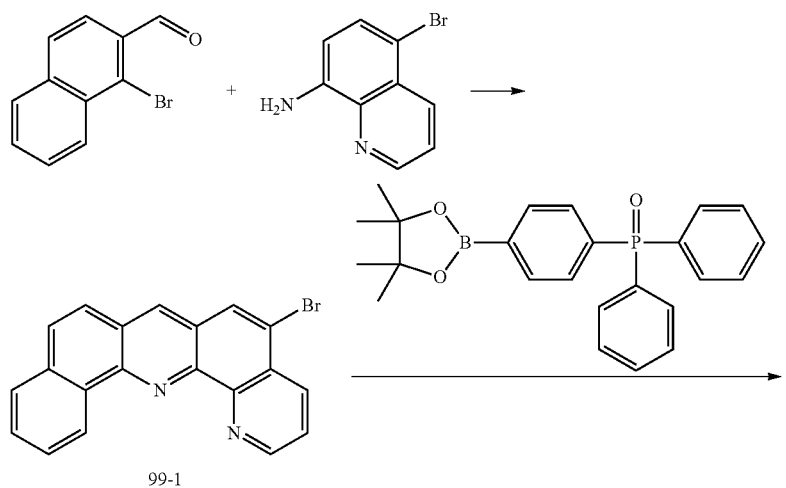

99-1

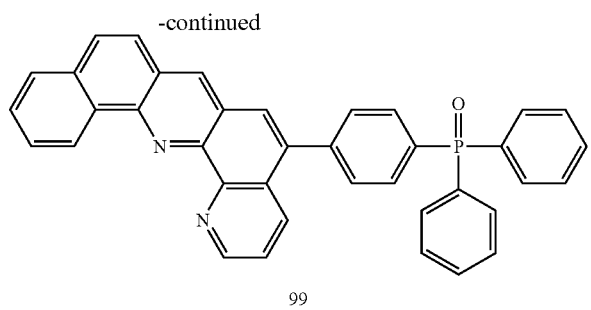

99

Synthesis of Intermediate 99-1

1.43 g (yield 40%) of Intermediate 99-1 was obtained in the same manner as used to synthesize Intermediate 3-1, except that 1-bromo-2-naphthaldehyde was used instead of 5-bromo-2-iodobenzaldehyde and 5-bromo-8-aminoquinoline was used instead of 8-aminoquinoline. The obtained compound was identified by LC-MS.

C20H11BrN2: M+1 359.21

Synthesis of Compound 99

4.28 g (yield 77%) of Compound 99 was obtained in the same manner as used to synthesize Compound 3, except that Intermediate 99-1 was used instead of Intermediate 3-1, and diphenyl(4-(4,4,5,5-tetramethyl-1,3,2-dioxaborolan-2-yl)phenyl)phosphine oxide was used instead of 4'-(4-(4-(4,4,5,5-tetramethyl-1,3,2-dioxaborolan-2-yl)phenyl)naphthalen-1-yl)-[1,1'-biphenyl]-4-carbonitrile. The obtained compound was confirmed by LC-MS and $^1$H NMR.

C38H25N2OP: M+1 556.58

Synthesis Example 9: Synthesis of Compound 105

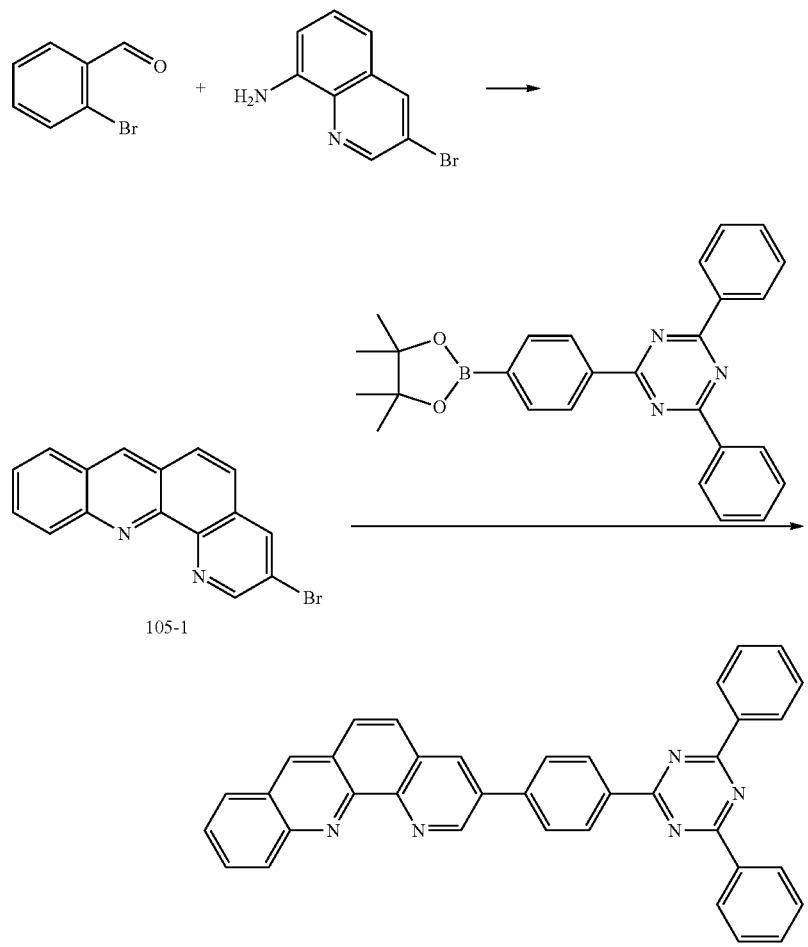

105

Synthesis of Intermediate 105-1

1.23 g (yield 40%) of Intermediate 105-1 was obtained in the same manner as used to synthesize Intermediate 3-1, except that 2-bromobenzaldehyde was used instead of 5-bromo-2-iodobenzaldehyde, and 3-bromoquinolin-8-amine was used instead of 8-aminoquinoline. The obtained compound was identified by LC-MS.

C16H9BrN2: M+1 309.15

Synthesis of Compound 105

2.95 g (yield 55%) of Compound 105 was obtained in the same manner as used to synthesize Compound 3, except that Intermediate 105-1 was used instead of Intermediate 3-1, and 2,4-diphenyl-6-(4-(4,4,5,5-tetramethyl-1,3,2-dioxaborolan-2-yl)phenyl)-1,3,5-triazine was used instead of 4'-(4-(4,4,5,5-tetramethyl-1,3,2-dioxaborolan-2-yl)phenyl)naphthalen-1-yl)-[1,1'-biphenyl]-4-carbonitrile. The obtained compound was confirmed by LC-MS and $^1$H NMR.

C37H23N5: M+1 537.64

$^1$H NMR and LC-MS of the compounds synthesized according to Synthesis Examples 1 to 9 are shown in Table 1. Methods of synthesizing compounds other than the compound shown in Table 1 may be understandable by referring to the synthesis paths and source materials described above.

EXAMPLES

Example 1

A substrate with an anode including the structure of ITO/Ag/ITO (70/1000/70A) deposited thereon was cut to a size of 50 mm×50 mm×0.5 mm, and then, the result was sonicated with isopropyl alcohol and pure water, each for 5 minutes. Then, the result was cleaned by exposure to ultraviolet rays and ozone for 30 minutes. The resultant substrate was provided on a vacuum deposition apparatus.

Compound 301 (N-([1,1'-biphenyl]-4-yl)-9,9-dimethyl-N-(4-(9-phenyl-9H-carbazol-3-yl)phenyl)-9H-fluoren-2-amine) and F4-TCNQ were vacuum-codeposited on the resultant substrate at a weight ratio of 98:2 to form a hole injection layer having a thickness of 100 Å, and then, Compound 301 was vacuum-deposited on the hole injection layer to form a first hole transport layer having a thickness of 1,200 Å, and N,N-di([1,1'-biphenyl]-4-yl)-4'-(9H-carbazol-9-yl)-[1,1'-biphenyl]-4-amine (Compound HA) was vacuum-deposited on the first hole transport layer to form a second hole transport layer having a thickness of 100 Å. 9,10-di-naphthalene-2-yl-anthracene (ADN), which is a blue fluorescent host, and N,N,N',N'-tetraphenyl-pyrene-1,6-diamine (TPD), which is a blue fluorescent dopant, were co-deposited at a weight ratio 98:2 on the second hole transport layer to form an emission layer having a thickness of 300 Å. Subsequently, Compound 3 and LiQ were codeposited at a weight ratio of 5:5 on the emission layer to form an electron transport layer having a thickness of 300 Å. LiF was deposited on the electron transport layer to form an electron injection layer having a thickness of 10 Å, and then, Mg and Ag were vacuum-deposited thereon at a weight ratio

TABLE 1

| Compound | $^1$H NMR (CDCl$_3$, 400 MHz) | MS/FAB found | MS/FAB calc. |
|---|---|---|---|
| 3 | 9.22-9.20 (m, 1H), 9.01-8.99 (m, 1H), 8.86-8.84 (m, 1H) 8.70-8.68 (m, 2H), 8.55-8.78 (m, 9H), 8.45-8.43 (m, 2H) 8.28-8.34 (m, 3H), 8.20-8.18 (m, 1H), 7.97-8.07 (m, 3H) 7.76-7.90 (m, 2H), 7.46-7.44 (m, 2H) | 609.72 | 609.73 |
| 11 | 9.23-9.20 (m, 1H), 8.79-8.75 (m, 1H), 8.65-8.72 (m, 2H) 8.59-8.55 (m, 1H), 8.51-8.57 (m, 2H), 8.35-8.32 (m, 1H) 8.18-8.33 (m, 8H), 7.85-8.05 (m, 7H) | 537.61 | 537.63 |
| 13 | 9.21-9.18 (m, 1H), 8.80-8.85 (m, 3H), 8.71-8.67 (m, 1H) 8.57-8.69 (m, 4H), 8.42-8.51 (m, 5H), 8.40-8.38 (m, 1H) 8.19-8.27 (m, 4H), 8.04-8.14 (m, 3H), 7.89-8.03 (m, 3H) 7.74-7.70 (m, 4H) | 663.76 | 663.78 |
| 21 | 9.30-9.28 (m, 1H), 9.22-9.20 (m, 1H), 8.98-8.95 (m, 1H) 8.84-8.81 (m, 1H), 8.62-8.73 (m, 4H), 8.60-8.58 (m, 2H) 8.49-8.60 (m, 4H), 8.45-8.41 (m, 2H), 8.18-8.34 (m, 3H) 8.00-8.08 (m, 3H), 7.76-7.91 (m, 3H), 7.46-7.43 (m, 2H) | 609.71 | 609.73 |
| 33 | 7.75-7.87 (m, 5H), 7.95-8.06 (m, 3H), 8.08-8.18 (m, 3H) 8.26-8.24 (m, 1H), 8.32-8.43 (m, 6H), 8.45-8.53 (m, 2H) 8.56-8.54 (m, 1H), 8.64-8.71 (m, 2H), 8.74-8.72 (m, 1H) 8.80-8.87 (m, 2H), 8.90-8.88 (m, 1H), 9.05-9.03 (m, 1H) 9.16-9.14 (m, 1H), 9.22-9.20 (m, 1H), 9.29-9.27 (m, 1H) | 713.8 | 713.84 |
| 34 | 7.97-7.97 (m, 1H), 8.03-8.24 (m, 4H), 8.26-8.33 (m, 3H) 8.37-8.35 (m, 1H), 8.45-8.41 (m, 1H), 8.52-8.48 (m, 1H) 8.62-8.72 (m, 5H), 8.76-8.74 (m, 1H), 8.73-8.81 (m, 2H) 9.22-9.20 (m, 1H) | 484.57 | 484.56 |
| 66 | 7.69-7.65 (m, 4H), 7.94-8.04 (m, 2H), 8.05-8.27 (m, 7H) 8.34-8.30 (m, 1H), 8.46-8.44 (m, 4H), 8.62-8.68 (m, 2H) 8.71-8.68 (m, 1H), 8.80-8.87 (m, 5H), 9.23-9.20 (m, 1H) 9.36-9.33 (m, 1H) | 688.76 | 688.79 |
| 99 | 7.26-7.37 (m, 8H), 7.45-7.42 (m, 2H), 7.95-8.05 (m, 4H) 8.09-8.23 (m, 4H), 8.43-8.55 (m, 2H), 8.64-8.62 (m, 1H) 8.68-8.78 (m, 2H), 8.89-8.85 (m, 1H), 9.52-9.50 (m, 1H) | 556.58 | 556.6 |
| 105 | 7.68-7.64 (m, 4H), 7.95-8.16 (m, 4H), 8.26-8.22 (m, 1H) 8.21-8.19 (m, 1H), 8.32-8.42 (m, 7H), 8.63-8.60 (m, 1H) 8.70-8.65 (m, 1H), 8.75-8.87 (m, 3H), 9.49-9.44 (m, 1H) | 537.64 | 537.63 | of 90:10 to form a cathode having a thickness of 120 Å, thereby completing the manufacture of an organic light-emitting device.

Examples 2 to 9

Organic light-emitting devices were manufactured in the same manner as in Example 1, except that, in forming the electron transport layer, Compounds shown in Table 2 were used instead of Compound 3.

Comparative Example 1

An organic light-emitting device was manufactured in the same manner as in Example 1, except that, in forming the electron transport layer, 2-(4-(9,10-di(naphthalen-2-yl)anthracen-2-yl)phenyl)-1-phenyl-1H-benzo [d]imidazole (Compound A) was used instead of Compound 3.

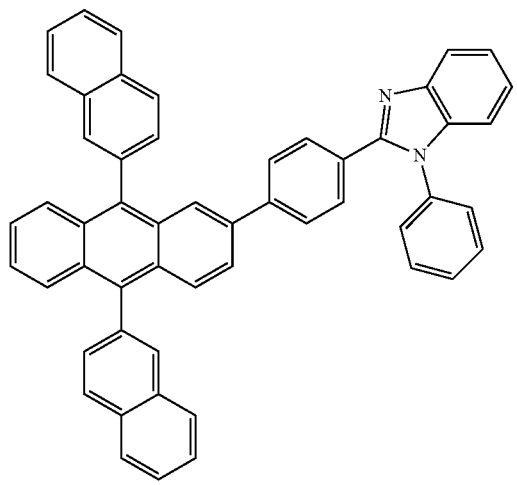

Comparative Example 2

An organic light-emitting device was manufactured in the same manner as in Example 1, except that, in forming the electron transport layer, Compound B was used instead of Compound 3.

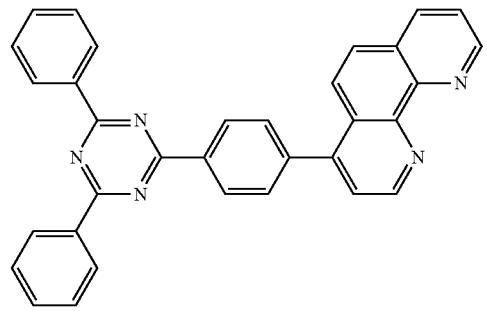

Comparative Example 3

An organic light-emitting device was manufactured in the same manner as in Example 1, except that, in forming the electron transport layer, Compound C was used instead of Compound 3.

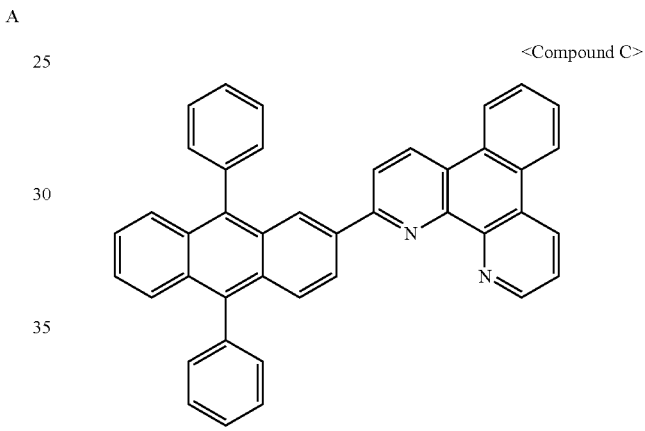

Regarding the organic light-emitting devices, performance (driving voltage, luminance, efficiency, and color coordinates) at a current density of 10 mA/cm$^2$ and a time (T97) that passed until the initial luminance decreased by 97% at a current density of 1.0 mA/cm$^2$ was measured, and results thereof are shown in Table 2.

Color coordinates: Power was supplied by using a current-voltmeter (Kethley SMU 236) and measured by using a luminance meter PR650.

Efficiency: Power was supplied by using a current-voltmeter (Kethley SMU 236) and measured by using a luminance meter PR650.

TABLE 2

| | Material | Driving voltage (V) | Current density (mA/cm$^2$) | Efficiency (cd/A) | Color coordinate CIE(x, y) | T97 lifespan (@1.0 mA/cm$^2$) |
|---|---|---|---|---|---|---|
| Example 1 | Compound 3 | 3.84 | 10 | 5.3 | 0.140, 0.055 | 155 |
| Example 2 | Compound 11 | 3.65 | 10 | 5.72 | 0.141, 0.056 | 121 |
| Example 3 | Compound 13 | 3.73 | 10 | 5.44 | 0.141, 0.055 | 162 |
| Example 4 | Compound 21 | 3.80 | 10 | 5.28 | 0.140, 0.057 | 128 |
| Example 5 | Compound 33 | 3.91 | 10 | 5.60 | 0.142, 0.058 | 148 |
| Example 6 | Compound 34 | 3.82 | 10 | 5.34 | 0.141, 0.054 | 139 |
| Example 7 | Compound 66 | 3.77 | 10 | 5.22 | 0.141, 0.056 | 145 |
| Example 8 | Compound 99 | 4.1 | 10 | 5.28 | 0.141, 0.056 | 142 |
| Example 9 | Compound 105 | 3.78 | 10 | 5.33 | 0.141, 0.055 | 131 |
| Comparative Example 1 | Compound A | 4.8 | 10 | 4.48 | 0.141, 0.054 | 77 |

TABLE 2-continued

| Material | | Driving voltage (V) | Current density (mA/cm$^2$) | Efficiency (cd/A) | Color coordinate CIE(x, y) | T97 lifespan (@1.0 mA/cm$^2$) |
|---|---|---|---|---|---|---|
| Comparative Example 2 | Compound B | 4.2 | 10 | 4.85 | 0.141, 0.054 | 105 |
| Comparative Example 3 | Compound C | 4.5 | 10 | 4.60 | 0.141, 0.056 | 98 |

Referring to Table 2, it may be seen that the organic light-emitting devices of Examples 1 to 9 had lower driving voltage, higher efficiency, and a longer T97 lifespan than the organic light-emitting devices of Comparative Examples 1 to 3.

An organic light-emitting device including the condensed cyclic compound according to an embodiment may have a low driving voltage, high efficiency, long lifespan, and high maximum quantum efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A condensed cyclic compound represented by Formula 1:

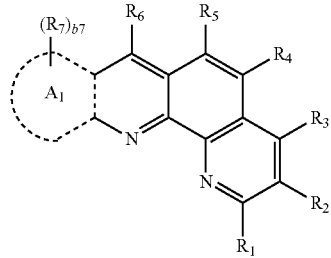

<Formula 1> wherein, in Formula 1, $A_1$ is a benzene ring or a naphthalene ring, $R_1$ to $R_7$ are each independently selected from a group represented by Formula 2, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a phenanthrolinyl group, a triazinyl group, a dibenzofuranyl group, a dibenzothiophenyl group, a benzocarbazolyl group, and a dibenzocarbazolyl group, provided that at least one selected from the group consisting of $R_2$, $R_4$, $R_5$, and $R_7$ is a group represented by Formula 2, and $R_4$ and $R_5$ are each independently not an unsubstituted naphthyl group or a phenyl group substituted with a $C_1$-$C_{60}$ alkoxy group, $$*-(L_{21})_{a21}-(Ar_{21})_{b21}$$ <Formula 2> wherein, in Formulae 1 and 2, b7 is an integer of 1 to 6, and when b7 is 2, 3, 4, 5, or 6, the $R_7$(s) are identical to or different from each other, $L_{21}$ is selected from a single bond, a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a benzophenanthrolinylene group, a phenazinylene group, a benzimidazolylene group, a benzofuranylene group, a benzothiophenylene group, a benzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a benzophenanthrolinylene group, a phenazinylene group, a benzimidazolylene group, a benzofuranylene group, a benzothiophenylene group, a benzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a phthalazinyl group, naphthyridinyl group, a quinoxalinyl group, a quinazolinyl group, a cinnolinyl group, a carbazolyl group, a phenanthridinyl group, an acridinyl group, a phenanthrolinyl group, a benzophenanthrolinyl group, a phenazinyl group, a benzimidazolyl group, a benzofuranyl group, a benzothiophenyl group, a benzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group;

a21 is an integer of 1 to 5, and when a21 is 2, 3, 4, or 5, the $L_{21}$(s) are identical to or different from each other, $Ar_{21}$ is selected from:

a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a benzophenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzoxazolyl group, a dibenzofuranyl group, a dibenzothiophenyl group, and a benzocarbazolyl group;

a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a benzophenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzoxazolyl group, a dibenzofuranyl group, a dibenzothiophenyl group, and a benzocarbazolyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a naphthyridinyl group, a quinoxalinyl group, a quinazolinyl group, a carbazolyl group, a phenanthridinyl group, an acridinyl group, a phenanthrolinyl group, a benzophenanthrolinyl group, a phenazinyl group, a triazinyl group, a dibenzofuranyl group, and a dibenzothiophenyl group;

—Si(Q$_1$)(Q$_2$)(Q$_3$), —B(Q$_1$)(Q$_2$), —C(=O)(Q$_1$), —N(Q$_1$)(Q$_2$), —P(=O)(Q$_1$)(Q$_2$), —P(=S)(Q$_1$)(Q$_2$), —S(=O)(Q$_1$)(Q$_2$), and —S(=O)$_2$(Q$_1$)(Q$_2$), in which Q$_1$ to Q$_3$ are each independently selected from hydrogen, deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_1$-C$_{60}$ heteroaryl group, a monovalent non-aromatic condensed polycyclic group, a monovalent non-aromatic condensed heteropolycyclic group, a biphenyl group, and a terphenyl group; and a group represented by Formula 6-13, wherein Ph indicates a phenyl group and * indicates a binding site to a neighboring atom:

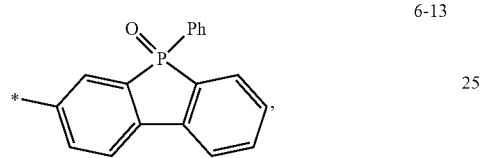

6-13 provided that when at least one selected from R$_2$, R$_4$, and R5 is a group represented by Formula 2, then L$_{21}$ is not an anthracenylene group, and Ar$_{21}$ is not an anthracenyl group, and when at least one selected from R$_4$ and R$_5$ is a group represented by Formula 2, then Ar$_{21}$ is not an unsubstituted naphthyl group or a phenyl group substituted with a C$_1$-C$_{60}$ alkoxy group, b21 is an integer of 1 to 8, and when b21 is 2, 3, 4, 5, 6, 7, or 8, the Ar$_{21}$(s) are identical to or different from each other, two selected from L$_{21}$ and Q$_1$ to Q$_3$ are separate or are linked to form a substituted or unsubstituted C$_5$-C$_{60}$ carbocyclic group or a substituted or unsubstituted C$_1$-C$_{60}$ heterocyclic group, at least one substituent of the substituted C$_5$-C$_{60}$ carbocyclic group, substituted C$_1$-C$_{60}$ heterocyclic group, substituted C$_1$-C$_{60}$ alkyl group, substituted C$_2$-C$_{60}$ alkenyl group, substituted C$_2$-C$_{60}$ alkynyl group, substituted C$_1$-C$_{60}$ alkoxy group, substituted C$_3$-C$_{10}$ cycloalkyl group, substituted C$_1$-C$_{10}$ heterocycloalkyl group, substituted C$_3$-C$_{10}$ cycloalkenyl group, substituted C$_1$-C$_{10}$ heterocycloalkenyl group, substituted C$_6$-C$_{60}$ aryl group, substituted C$_6$-C$_{60}$ aryloxy group, substituted C$_6$-C$_{60}$ arylthio group, substituted C$_1$-C$_{60}$ heteroaryl group, substituted C$_1$-C$_{60}$ hetero aryloxy group, substituted monovalent non-aromatic condensed polycyclic group, or substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, and a C$_1$-C$_{60}$ alkoxy group;

a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from deuterium, —F, —Cl, —Br, —I, a hydroxyl group, a cyano group, a nitro group, an amidino group, a hydrazino group, a hydrazono group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{11}$)(Q$_{12}$), —B(Q$_{11}$)(Q$_{12}$), —C(=O)(Q$_{11}$), —S(=O)$_2$(Q$_{11}$), and —P(=O)(Q$_{11}$)(Q$_{12}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{21}$)(Q$_{22}$), —B(Q$_{21}$)(Q$_{22}$), —C(=O)(Q$_{21}$), —S(=O)$_2$(Q$_{21}$), and —P(=O)(Q$_{21}$)(Q$_{22}$); and —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$), Q$_1$ to Q$_3$, Q$_{11}$ to Q$_{13}$, Q$_{21}$ to Q$_{23}$, and Q$_{31}$ to Q$_{33}$ are each independently selected from hydrogen, deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_1$-C$_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

2. The condensed cyclic compound as claimed in claim 1, wherein L$_{21}$ in Formula 2 is a single bond or a group represented by one of Formulae 3-1 to 3-35:

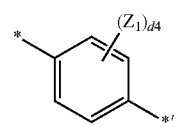

3-1

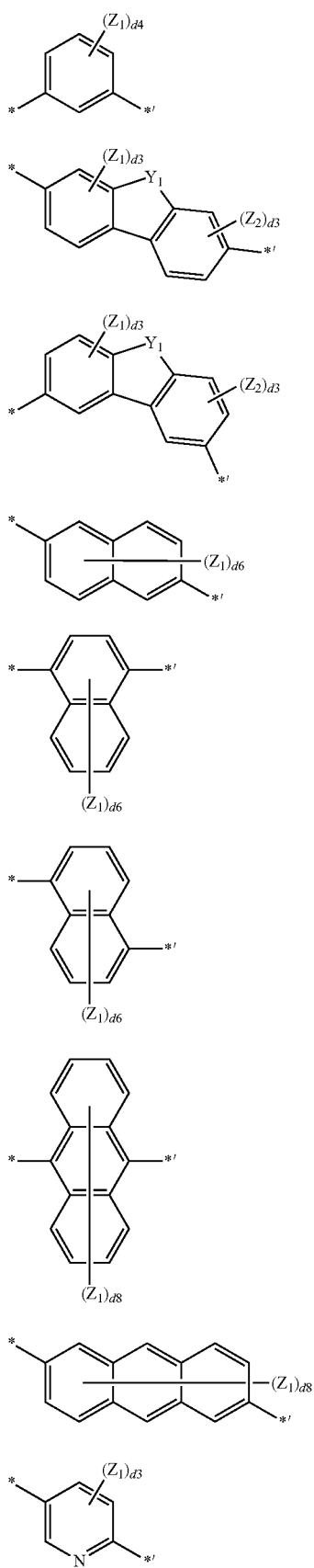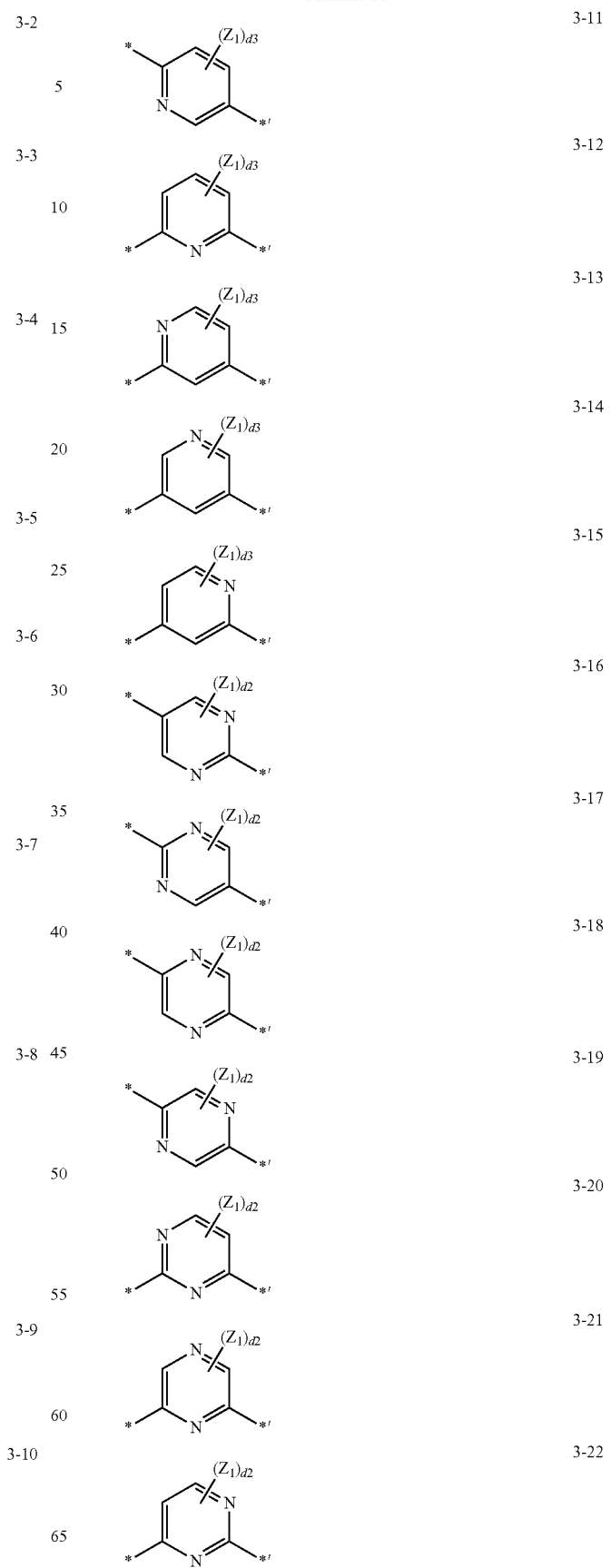

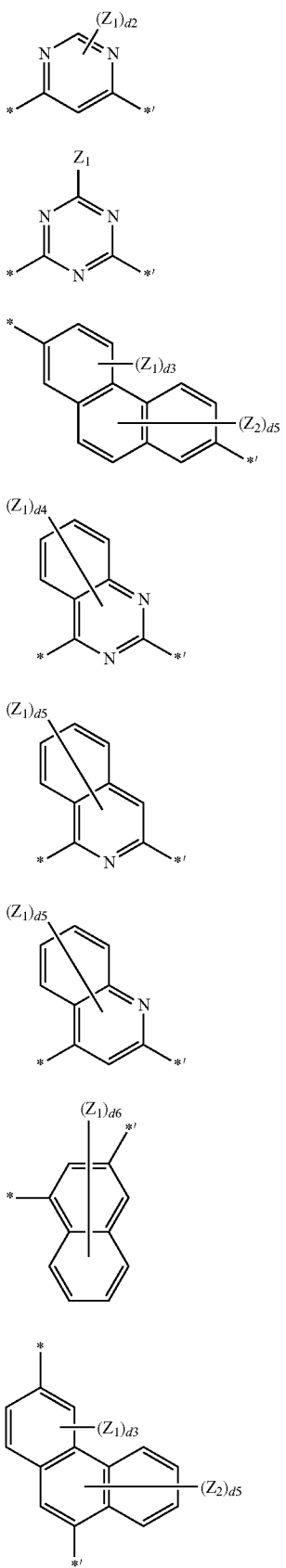

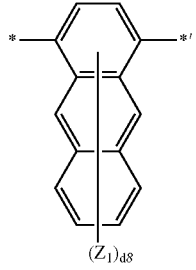

3-23

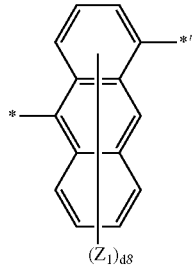

3-24

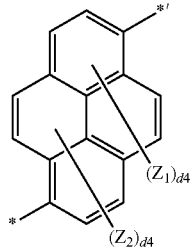

3-25

3-26

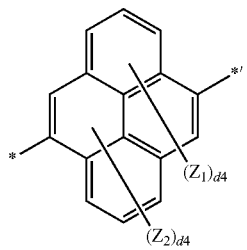

3-27

3-28

3-29

3-30

3-31

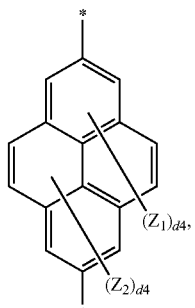

3-32

3-33

3-34

3-35 wherein, in Formulae 3-1 to 3-35, $Y_1$ is O, S, $C(Z_3)(Z_4)$, or $N(Z_5)$, $Z_1$ to $Z_5$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a triazinyl group, a dibenzofuranyl group, and a dibenzothiophenyl group, d2 is an integer of 0 to 2, and when d2 is 2, the $Z_1$(s) are identical to or different from each other, d3 is an integer of 0 to 3, and when d3 is 2 or 3, the $Z_1$(s) are identical to or different from each other and the $Z_2$(s) are identical to or different from each other, d4 is an integer of 0 to 4, and when d4 is 2, 3, or 4, the $Z_1$(s) are identical to or different from each other and the $Z_2$(s) are identical to or different from each other, d5 is an integer of 0 to 5, and when d5 is 2, 3, 4, or 5, the $Z_1$(s) are identical to or different from each other and the $Z_2$(s) are identical to or different from each other, d6 is an integer of 0 to 6, and when d6 is 2, 3, 4, 5, or 6, the $Z_1$(s) are identical to or different from each other and the $Z_2$(s) are identical to or different from each other, d8 is an integer of 0 to 8, and when d8 is 2, 3, 4, 5, 6, 7, or 8, the $Z_1$(s) are identical to or different from each other, and

* and *' each indicate a binding site to a neighboring atom.

3. The condensed cyclic compound as claimed in claim 1, wherein $L_{21}$ in Formula 2 is a single bond or a group represented by one of Formulae 4-1 to 4-8:

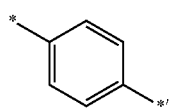
4-1

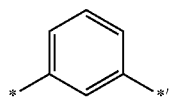
4-2

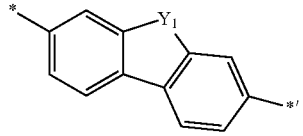
4-3

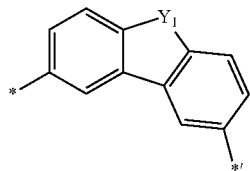
4-4

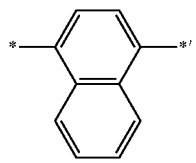
4-5

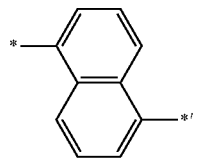
4-6

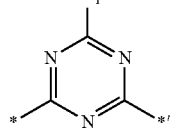
4-7

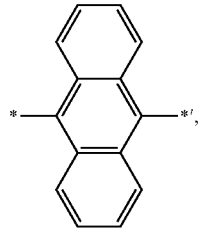
4-8 wherein, in Formulae 4-1 to 4-8, $Y_1$ is O, S, C($Z_3$)($Z_4$), or N($Z_5$), $Z_1$ and $Z_3$ to $Z_5$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, and a naphthyl group, and

* and *' each indicates a binding site to a neighboring atom.

4. The condensed cyclic compound as claimed in claim 1, wherein $Ar_{21}$ in Formula 2 is —P(═O)($Q_1$)($Q_2$) or a group represented by one of Formulae 5-1 to 5-53:

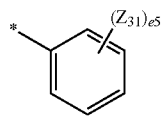
5-1

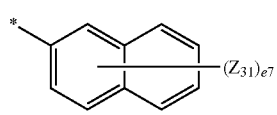
5-2

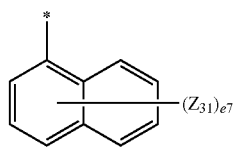
5-3

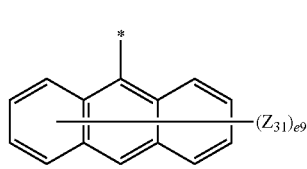
5-4

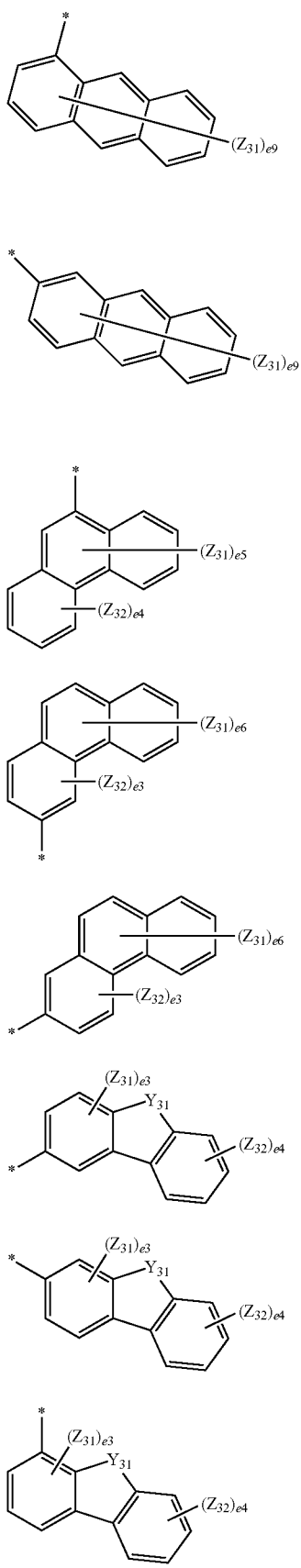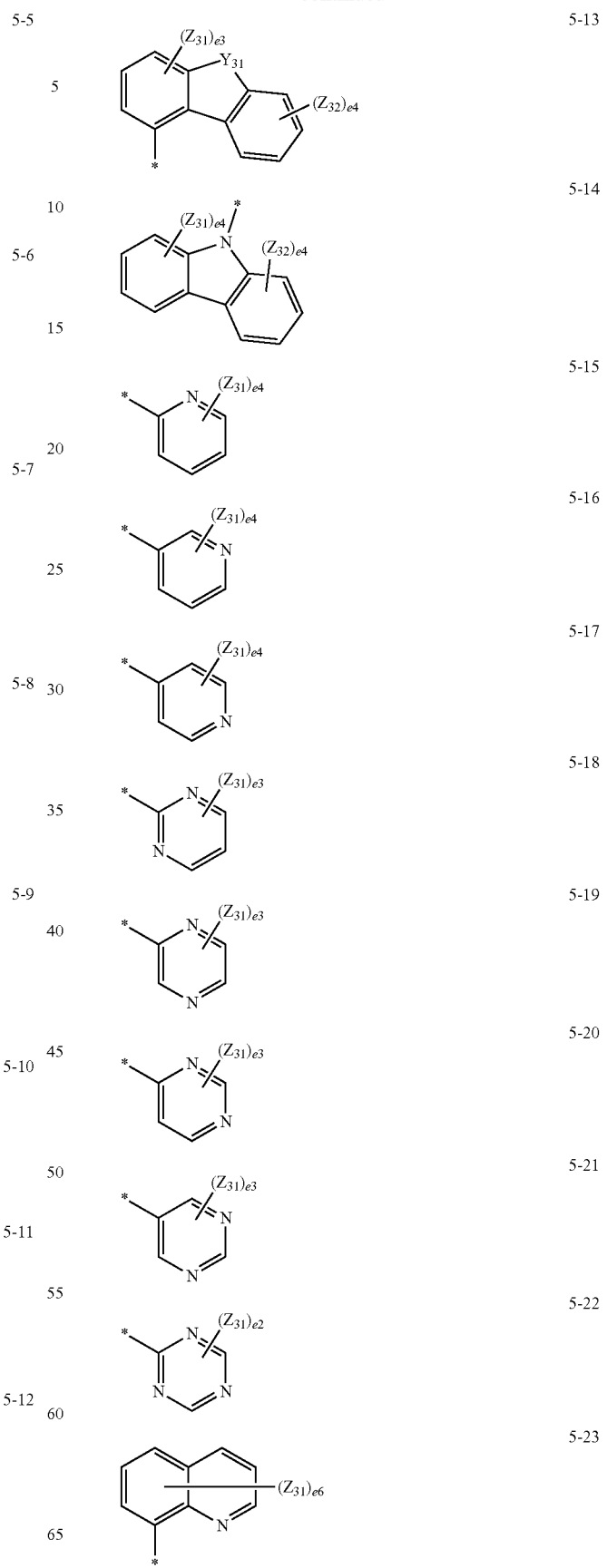

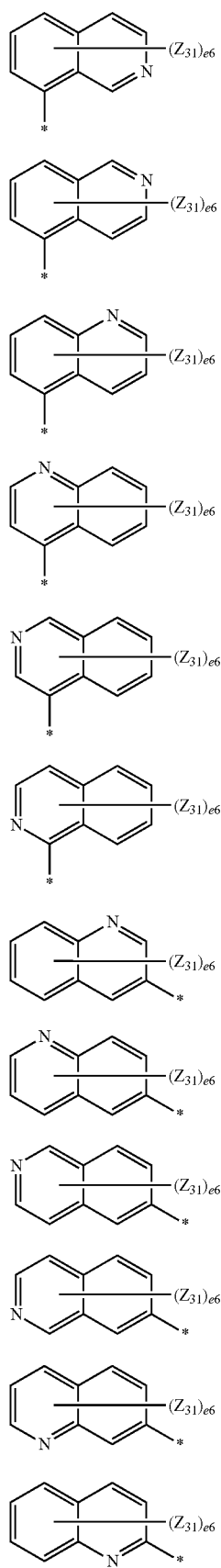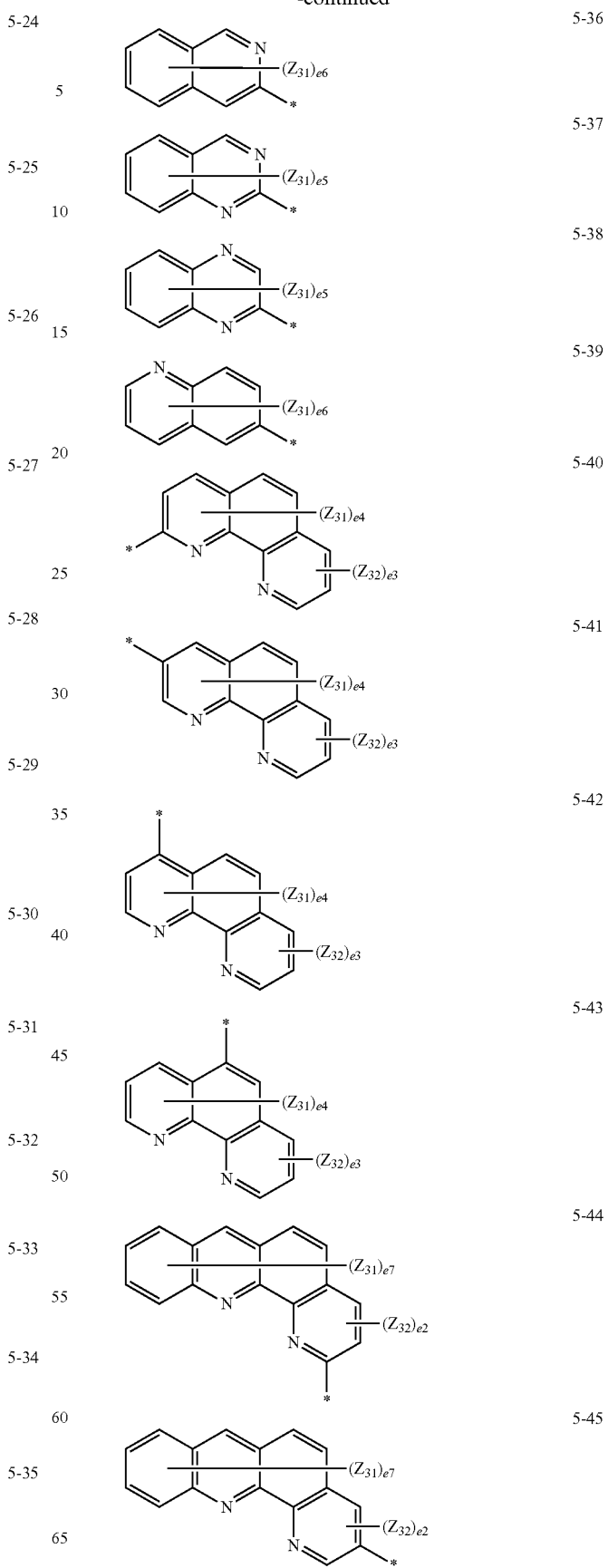

-continued

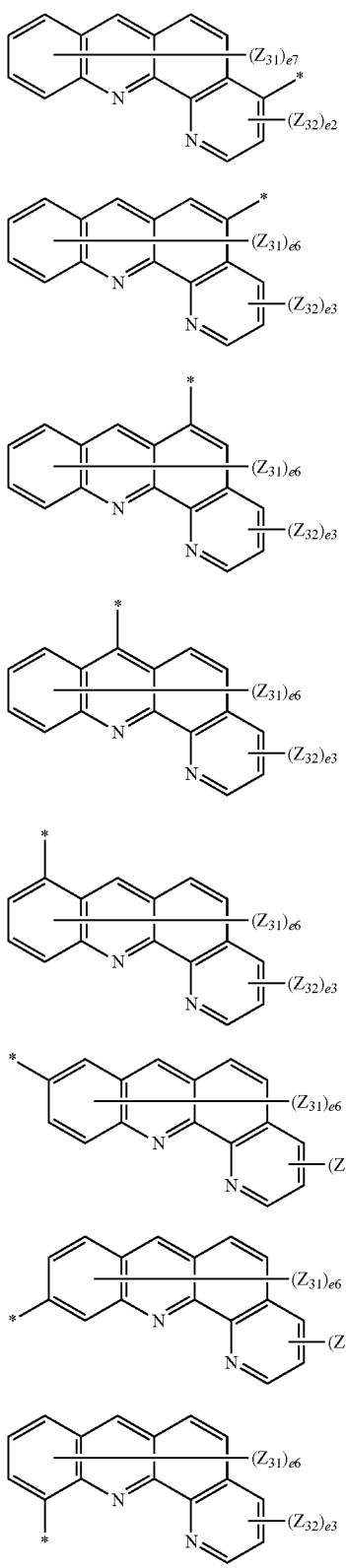

wherein, in Formulae 5-1 to 5-53,
Y$_{31}$ is O, S, C(Z$_{33}$)(Z$_{34}$), or N(Z$_{35}$),
Z$_{31}$ to Z$_{35}$, Q$_1$, and Q$_2$ are each independently selected from hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrazinyl group, a pyrimidinyl group, a quinolinyl group, an isoquinolinyl group, a naphthyridinyl group, a quinoxalinyl group, a quinazolinyl group, a carbazolyl group, a phenanthridinyl group, an acridinyl group, a phenanthrolinyl group, a benzophenanthrolinyl group, a phenazinyl group, a triazinyl group, a dibenzofuranyl group, and a dibenzothiophenyl group, e2 is an integer of 0 to 2, and when e2 is 2, the Z$_{31}$(s) are identical to or different from each other and Z$_{32}$(s) are identical to or different from each other, e3 is an integer of 0 to 3, and when e3 is 2 or 3, the Z$_{31}$(s) are identical to or different from each other and the Z$_{32}$(s) are identical to or different from each other, e4 is an integer of 0 to 4, and when e4 is 2, 3, or 4, the Z$_{31}$(s) are identical to or different from each other and the Z$_{32}$(s) are identical to or different from each other, e5 is an integer of 0 to 5, and when e5 is 2, 3, 4, or 5, the Z$_{31}$(s) are identical to or different from each other, e6 is an integer of 0 to 6, and when e6 is 2, 3, 4, 5, or 6, the Z$_{31}$(s) are identical to or different from each other, e7 is an integer of 0 to 7, and when e7 is 2, 3, 4, 5, 6, or 7, the Z$_{31}$(s) are identical to or different from each other, e9 is an integer of 0 to 9, and when e9 is 2, 3, 4, 5, 6, 7, 8, or 9, the Z$_{31}$(s) are identical to or different from each other, and

* indicates a binding site to a neighboring atom.

5. The condensed cyclic compound as claimed in claim 1, wherein Ar$_{21}$ in Formula 2 is a group represented by one of Formulae 6-1 to 6-16:

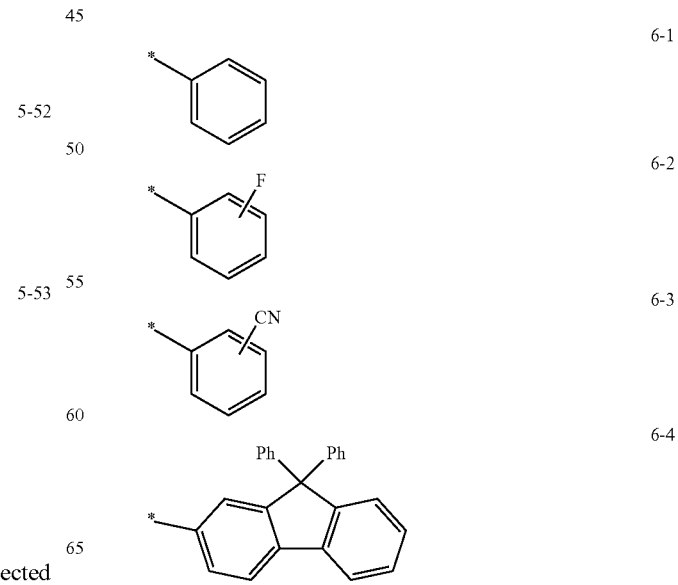

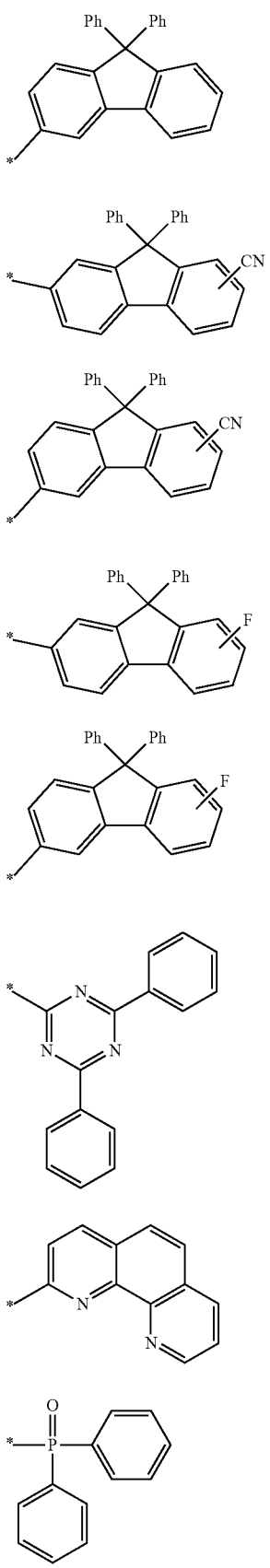
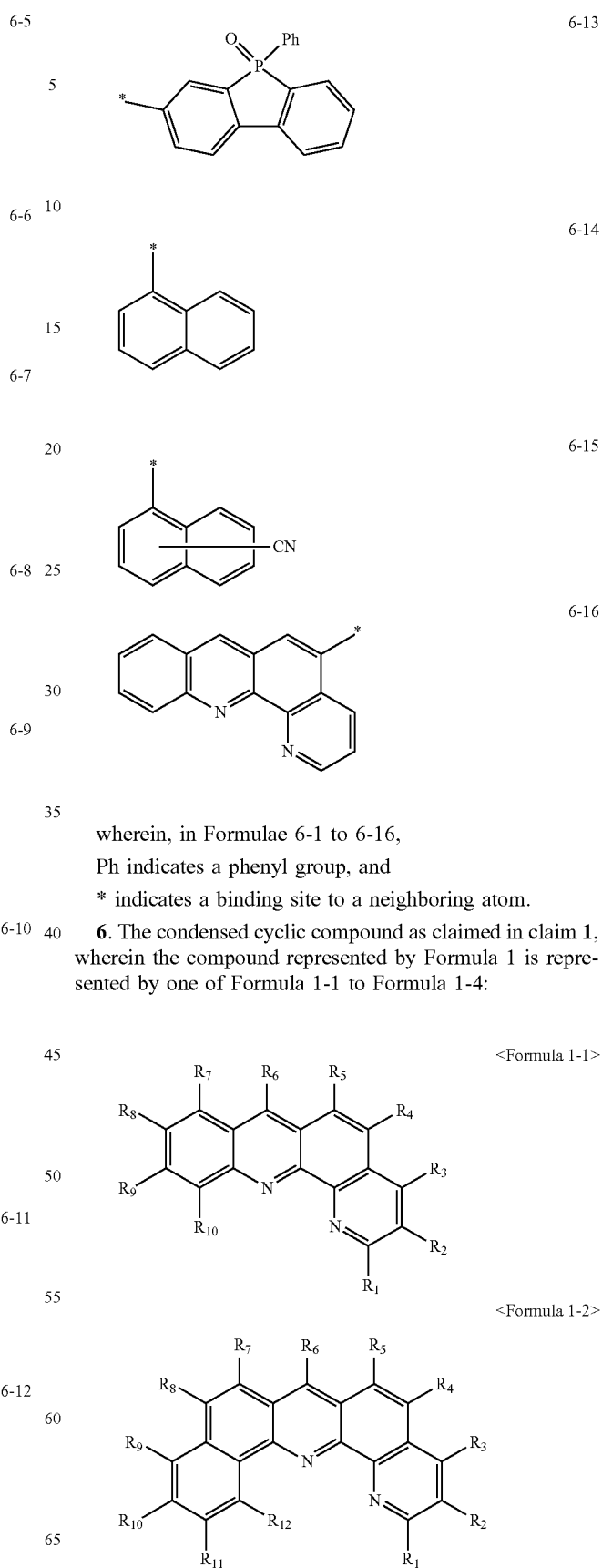
wherein, in Formulae 6-1 to 6-16,
Ph indicates a phenyl group, and
* indicates a binding site to a neighboring atom.
6. The condensed cyclic compound as claimed in claim 1, wherein the compound represented by Formula 1 is represented by one of Formula 1-1 to Formula 1-4:

<Formula 1-3>

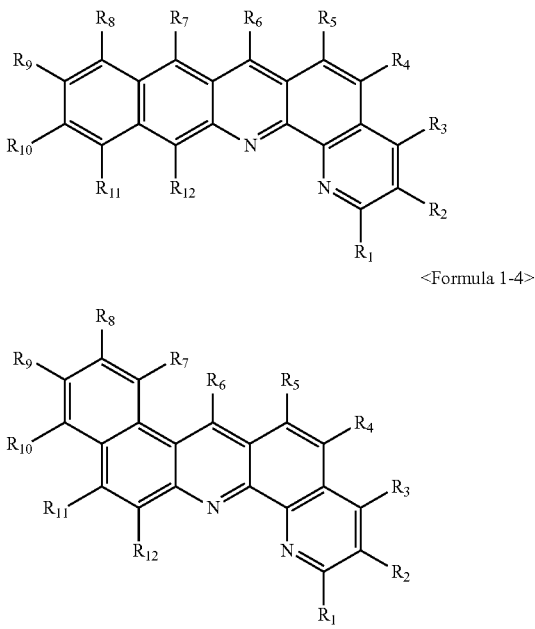

<Formula 1-4>

*-(L$_{21}$)$^{a21}$-(Ar$_{21}$)$_{b21}$,  <Formula 2> wherein, in Formulae 1-1 to 1-4 and 2,
R$_1$ to R$_7$, L$_{21}$, Ar$_{21}$, a21, and b21 are defined the same as those of Formulae 1 and 2,
R$_8$ to R$_{12}$ are defined the same as R$_1$ of Formula 1,
at least one of R$_1$ to R$_{10}$ in Formula 1-1 is a group represented by Formula 2,
at least one of R$_1$ to R$_{12}$ in Formulae 1-2 to 1-4 is a group represented by Formula 2, and

* indicates a binding site to a neighboring atom.

7. The condensed cyclic compound as claimed in claim 1, wherein R$_2$, R$_4$, R$_5$, or R$_7$ in Formula 1 is a group represented by Formula 2.

8. The condensed cyclic compound as claimed in claim 1, wherein
  i) R$_2$ is a group represented by Formula 2, and R$_1$ and R$_3$ to R$_7$ are each independently selected from hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, and a naphthyl group; or
  ii) R$_4$ is a group represented by Formula 2, and R$_1$ to R$_3$ and R$_5$ to R$_7$ are each independently selected from hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, and a naphthyl group; or
  iii) R$_5$ is a group represented by Formula 2, and R$_1$ to R$_4$, R$_6$, and R$_7$ are each independently selected from hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, and a naphthyl group; or
  iv) R$_7$ is a group represented by Formula 2, and R$_1$ to R$_6$ are each independently selected from hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, and a naphthyl group.

9. The condensed cyclic compound as claimed in claim 1, wherein the condensed cyclic compound is one of the following Compounds 1 to 21 and 23 to 118:

1

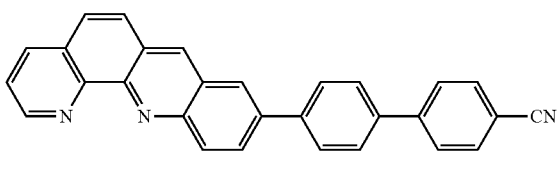

2

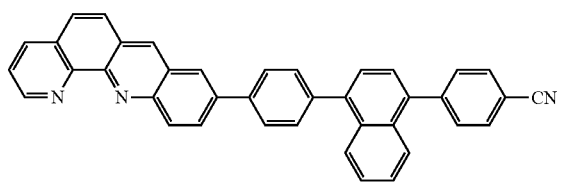

3

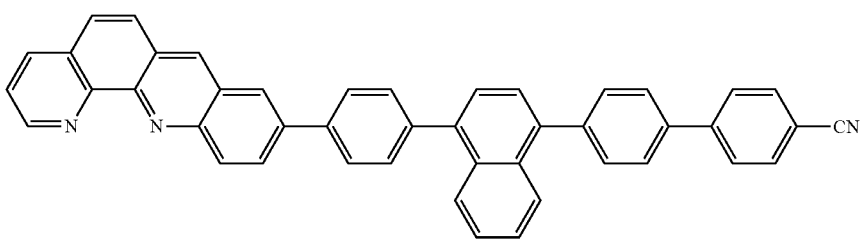

-continued
4
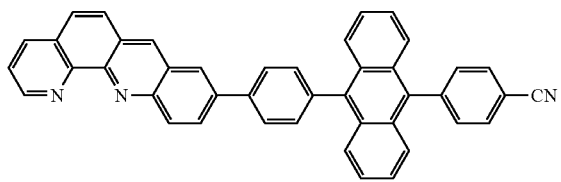
5
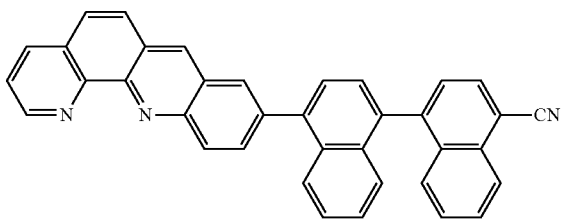
6
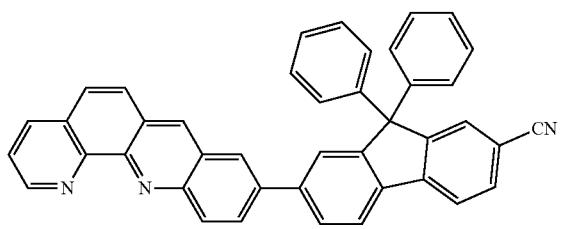
7
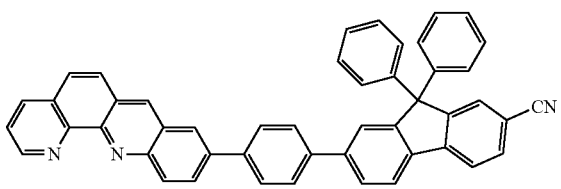
8
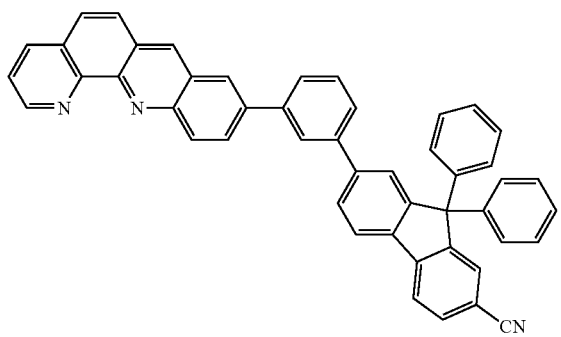
9
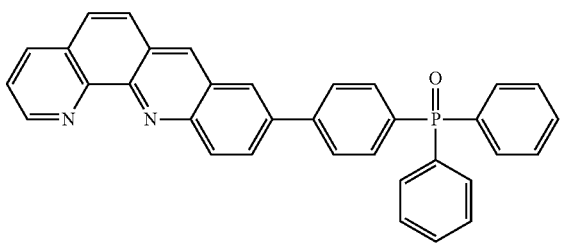
10
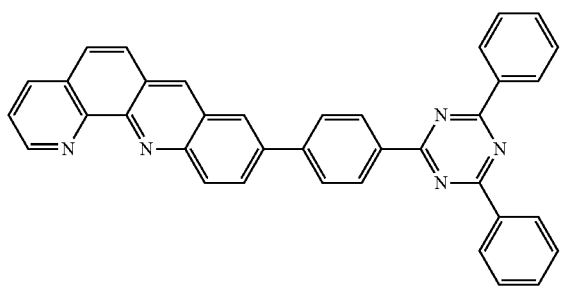
11
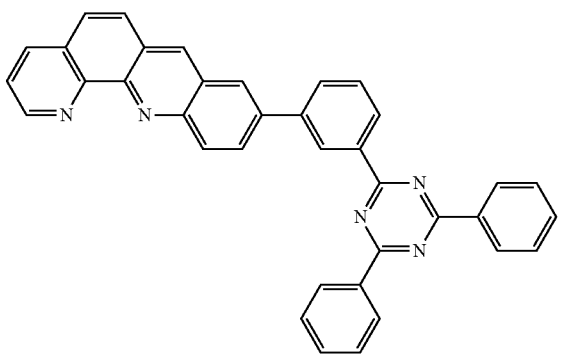
12
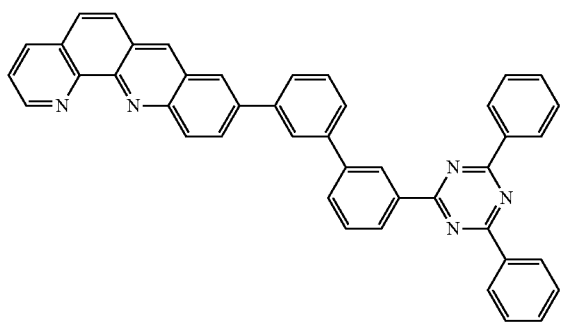
13
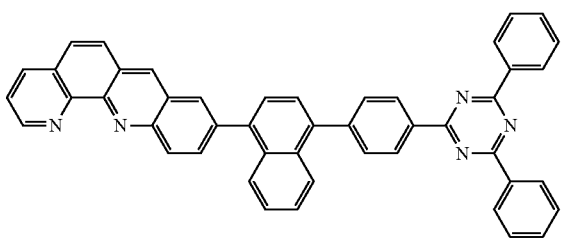

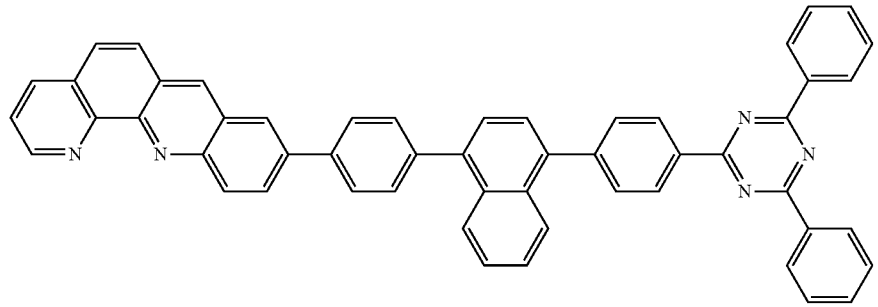
14
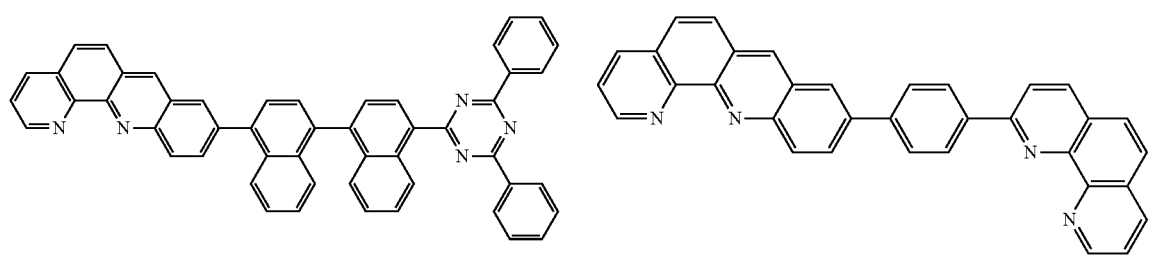
15
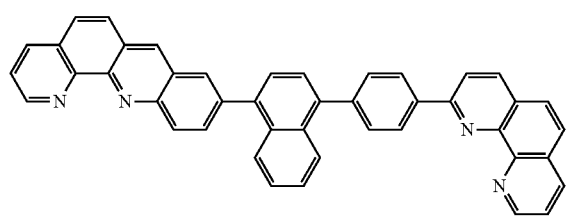
16
17
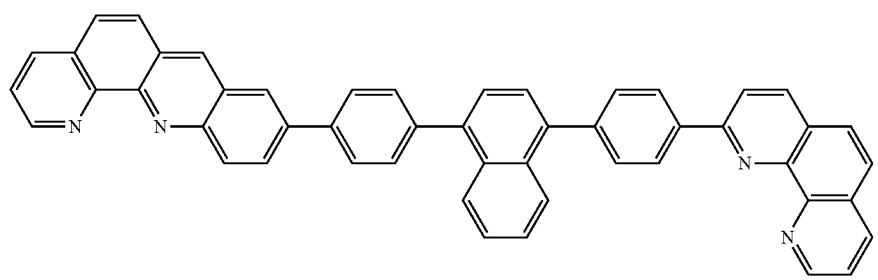
18
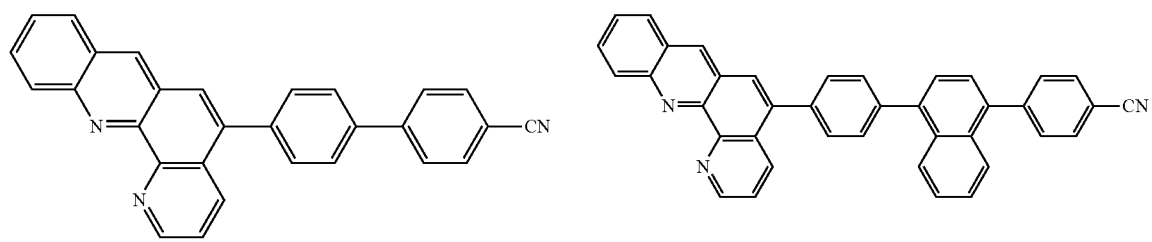
19
20
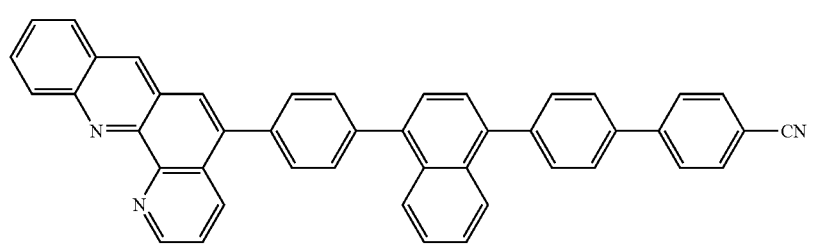
21

-continued
22
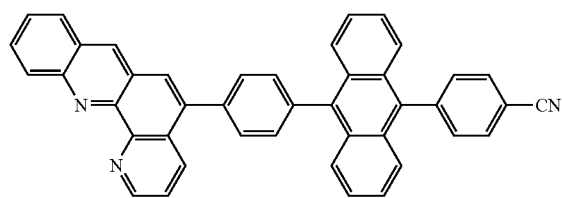
23
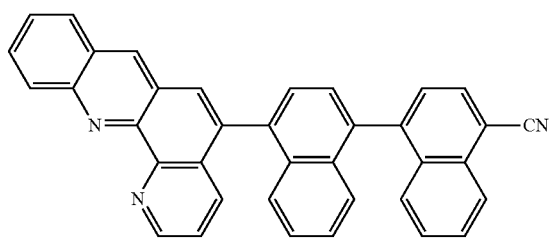
24
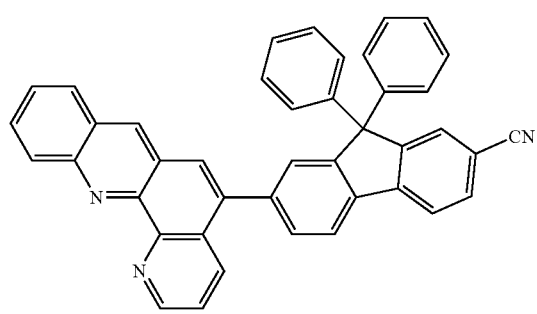
25
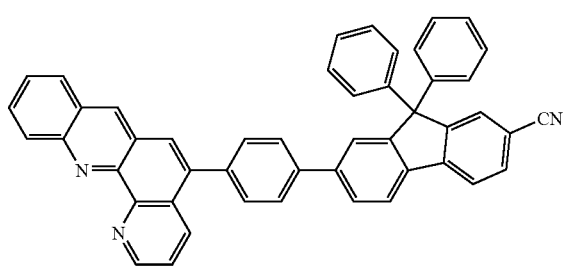
26
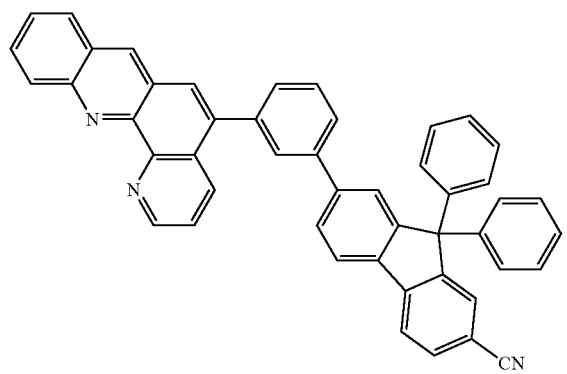
27
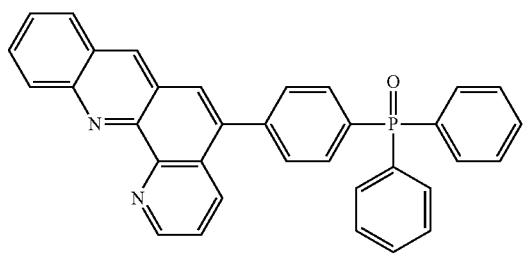
28
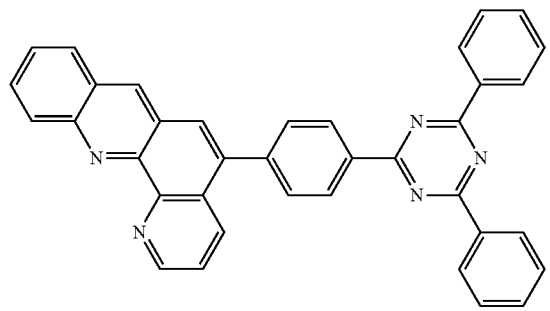
29
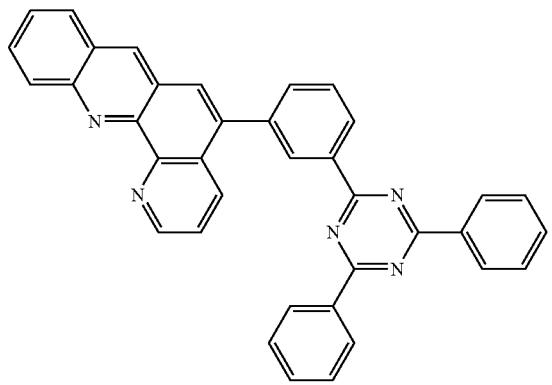

-continued
30
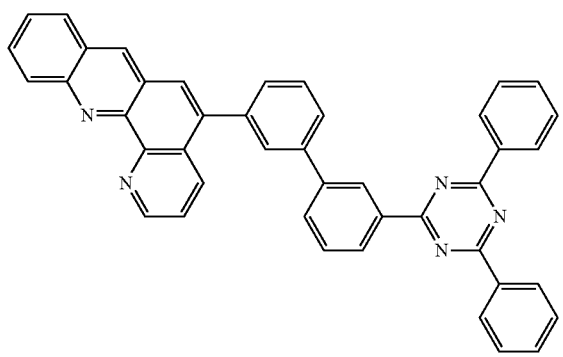
31
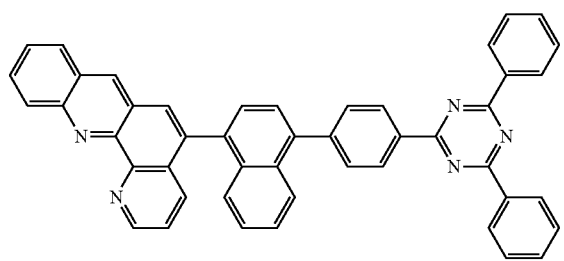
32
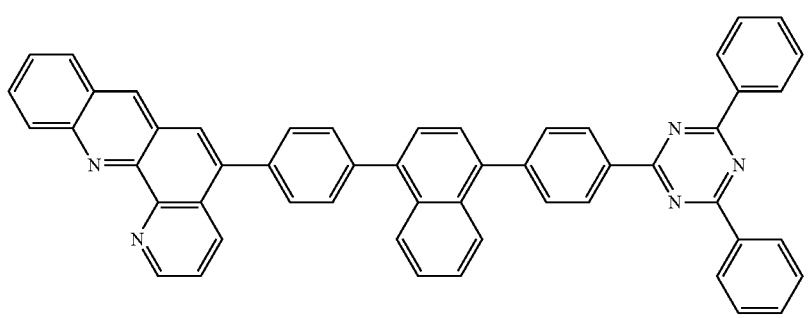
33
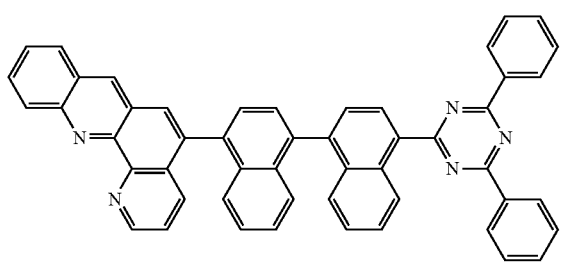
34
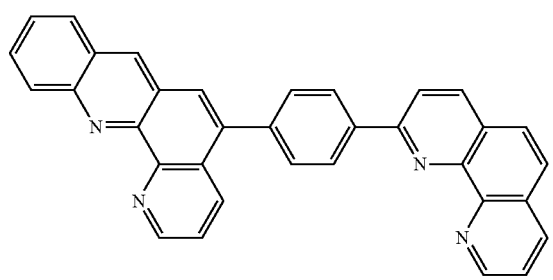
35
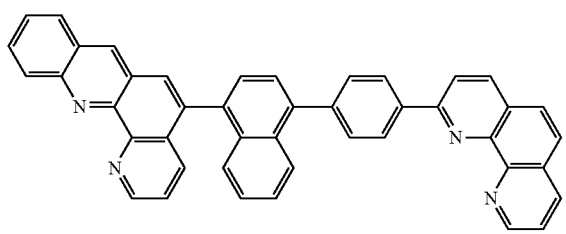
36
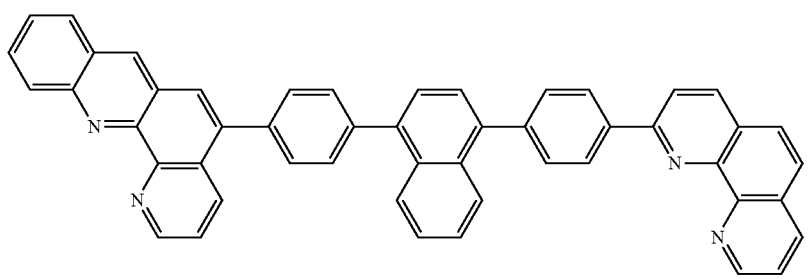

-continued
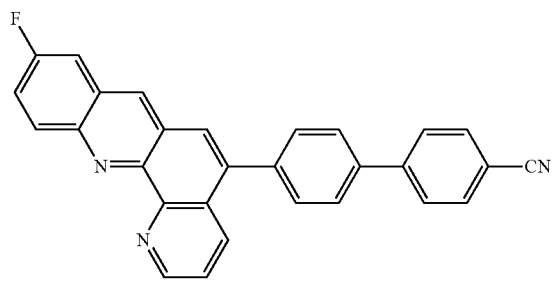
37
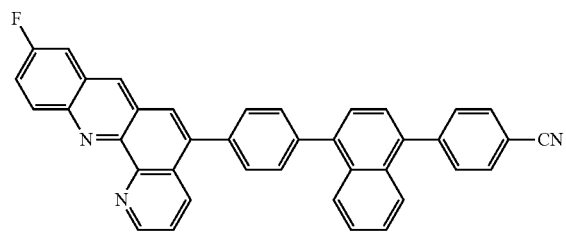
38
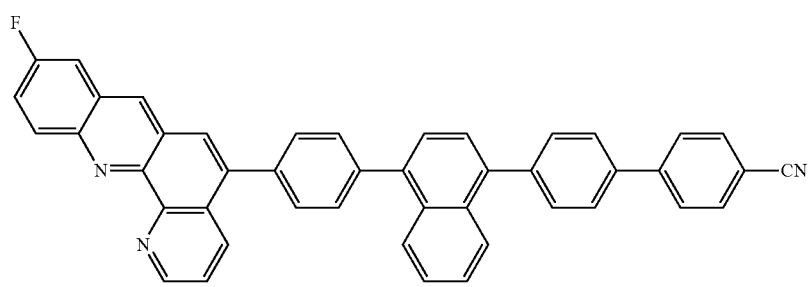
39
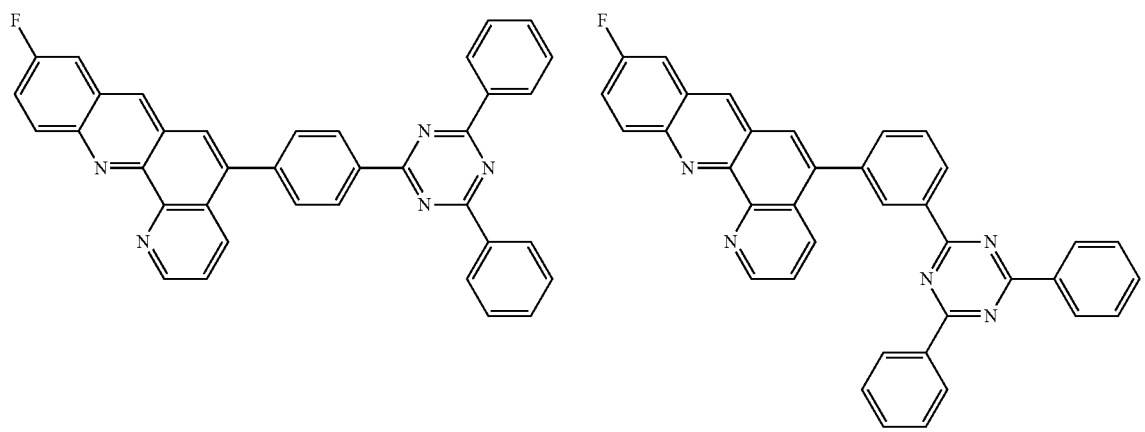
40 41
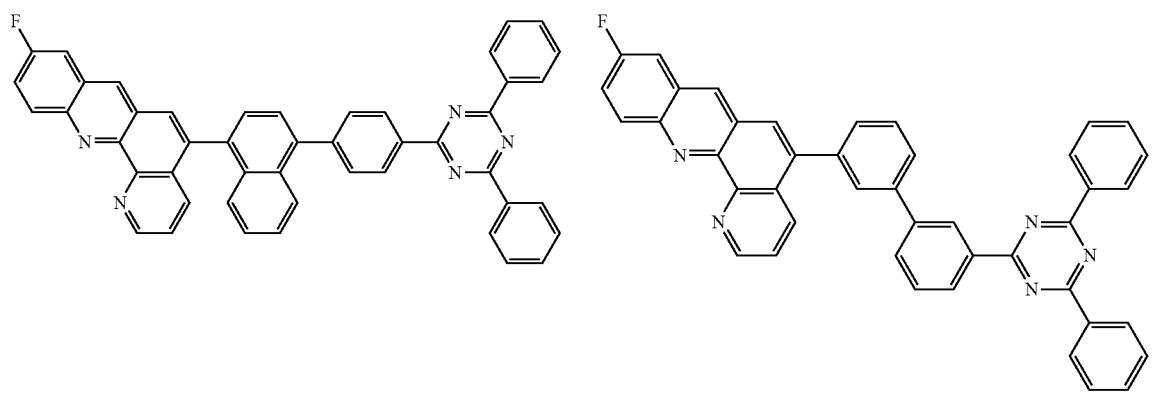
42 43

44
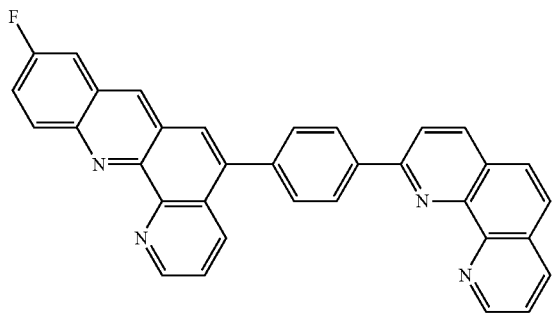
45
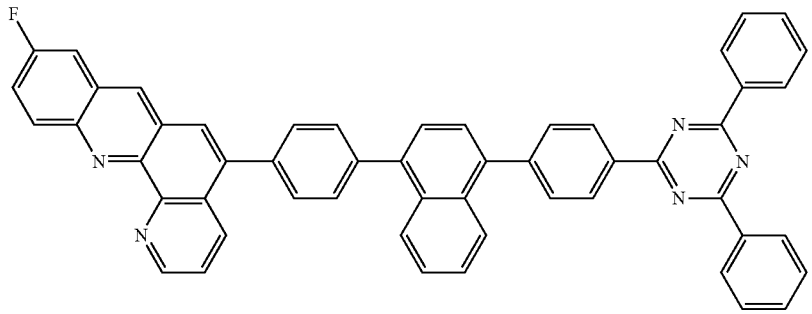
46
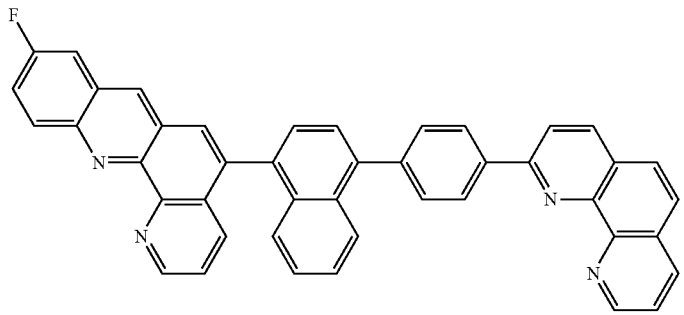
47
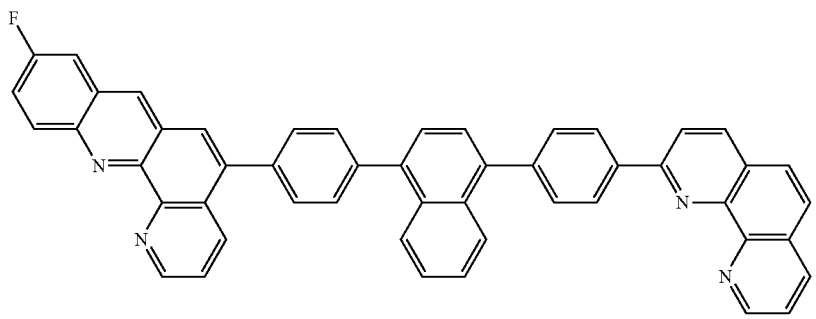
48
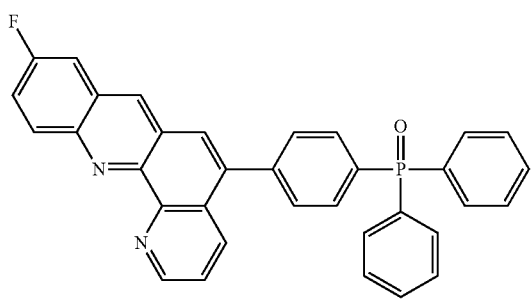
49
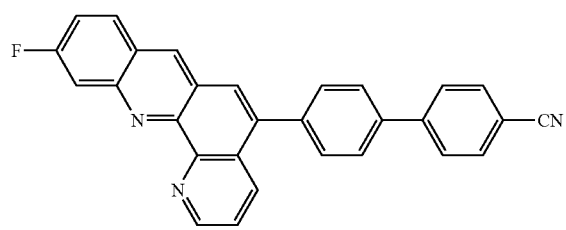

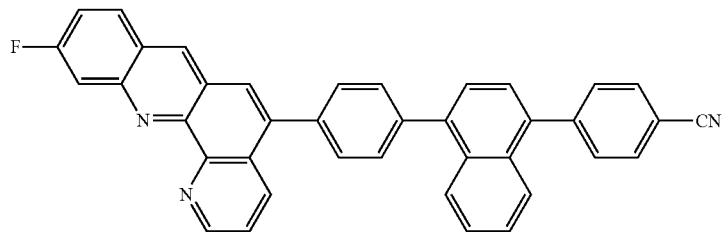
50
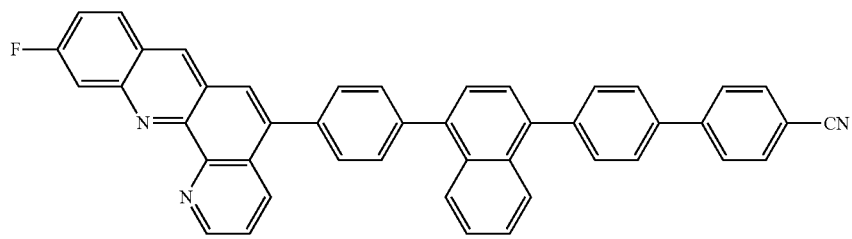
51
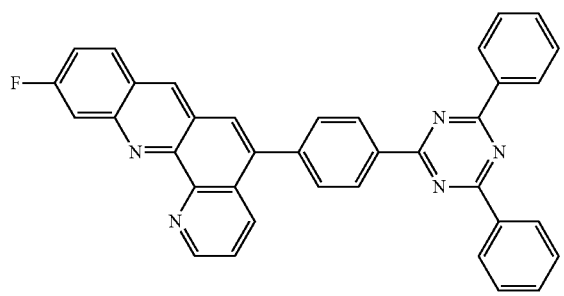
52
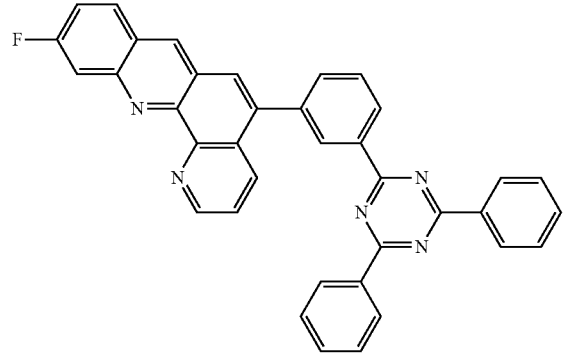
53
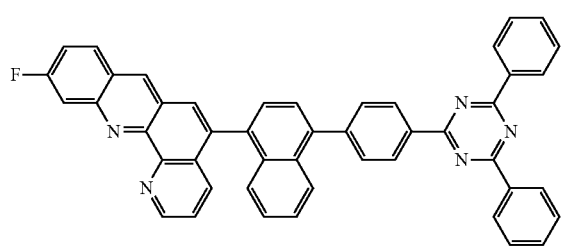
54
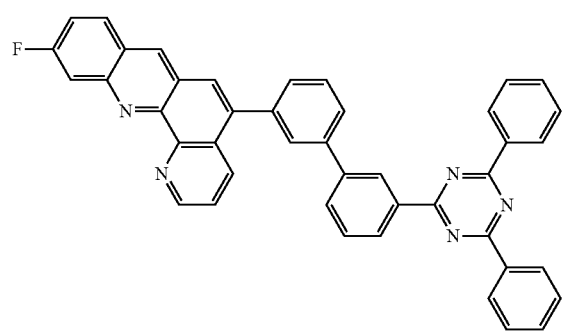
55
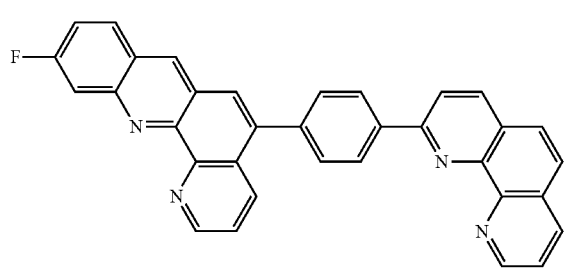
56

57
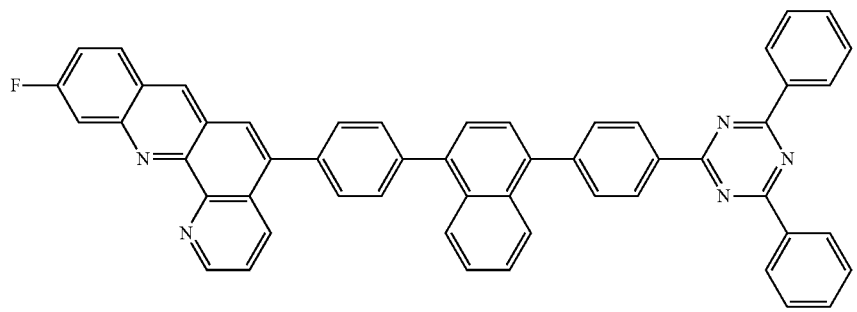
58
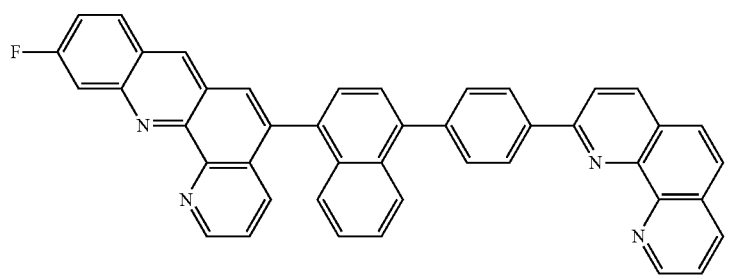
59
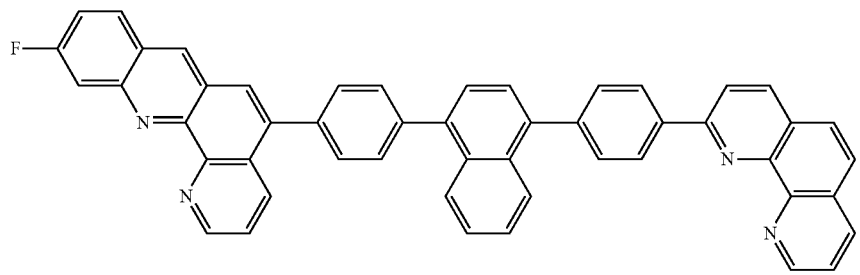
60 61
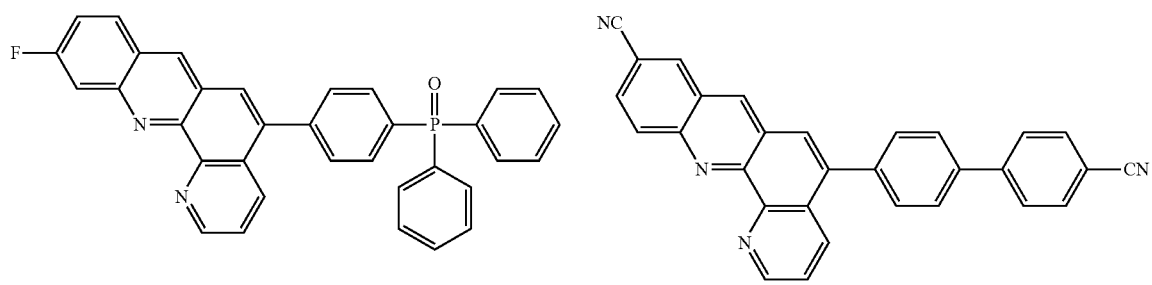
62
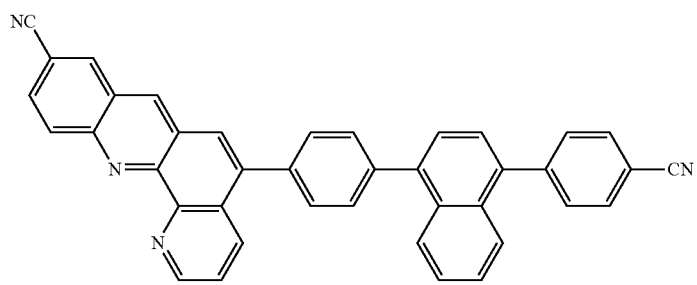

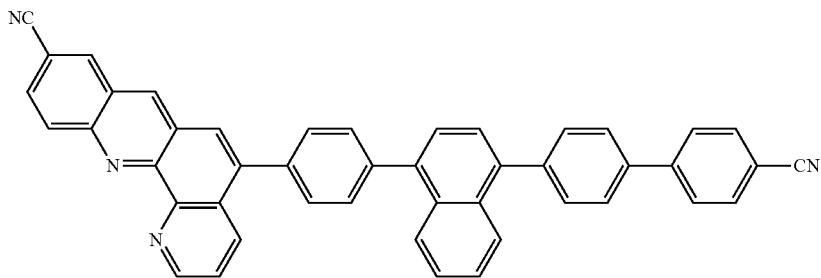
63
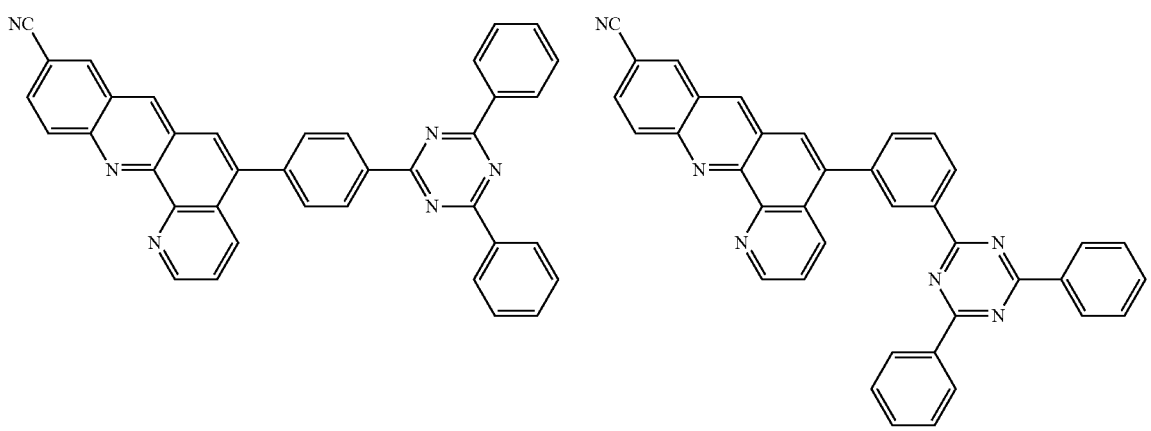
64
65
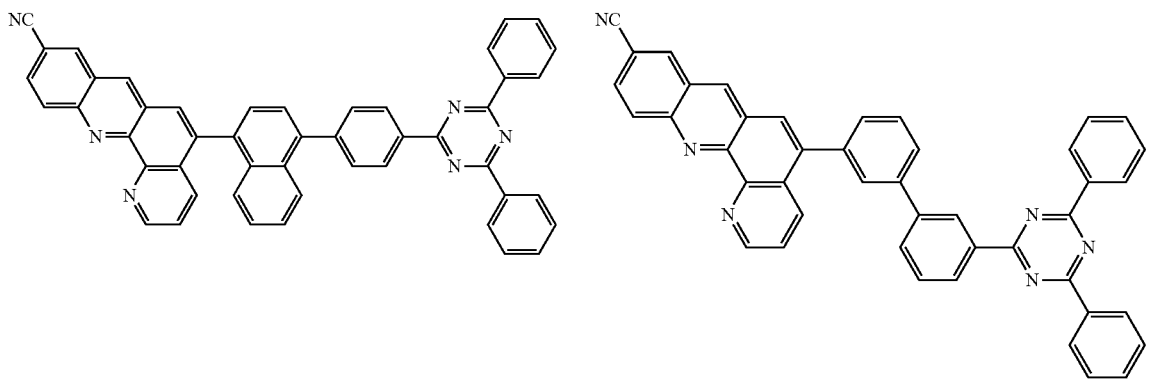
66
67
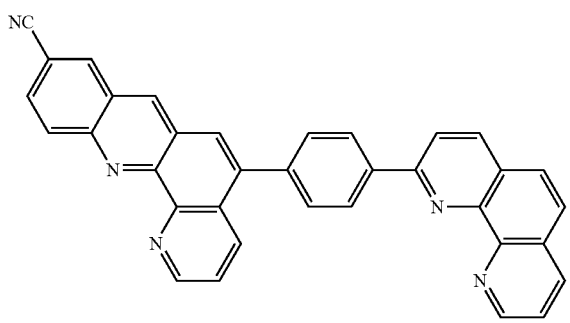
68

-continued
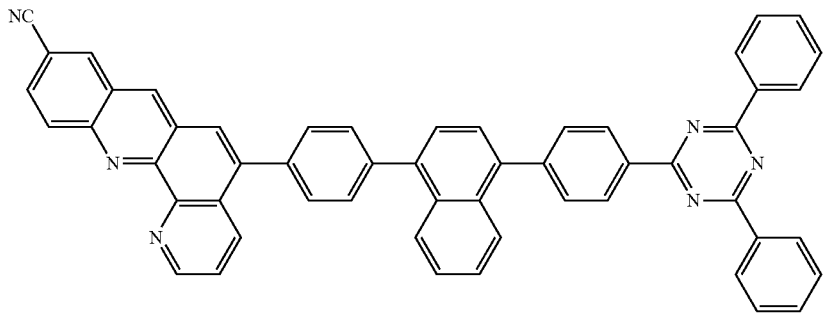
69
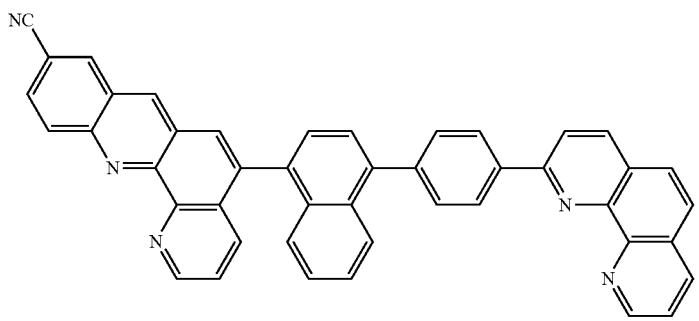
70
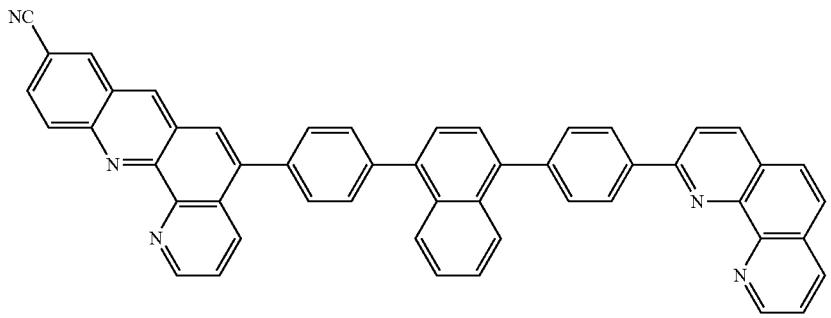
71
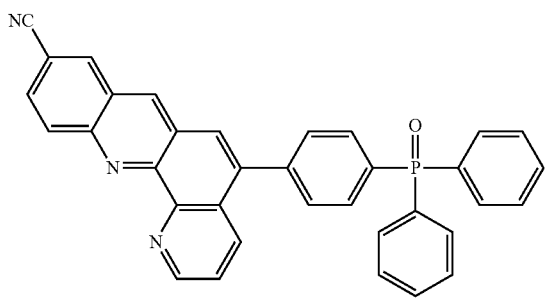
72
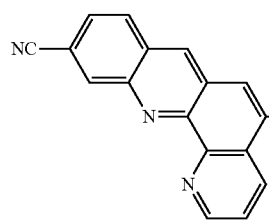
73
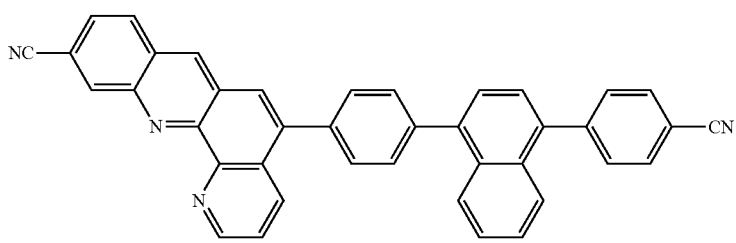
74

75
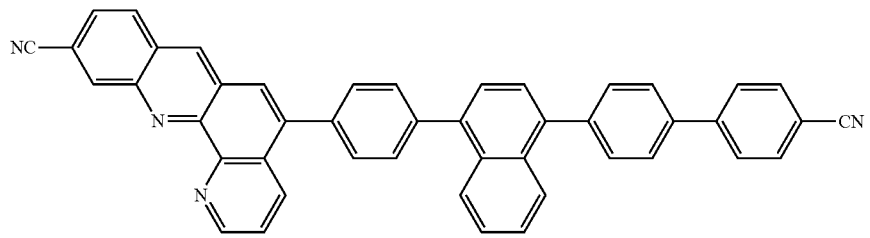
76
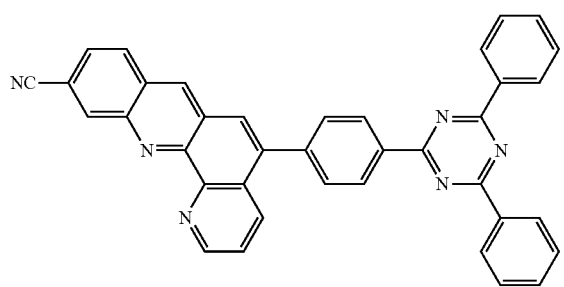
77
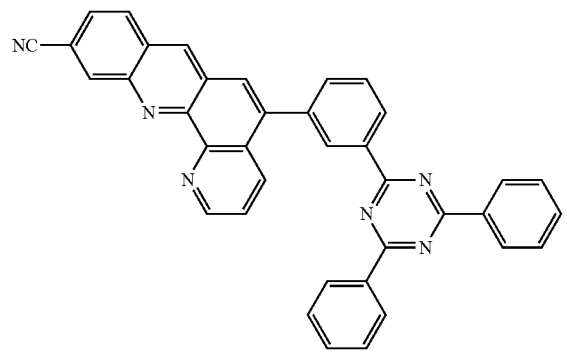
78
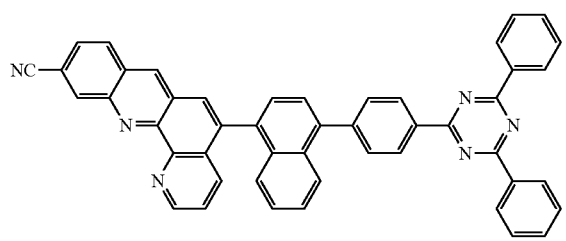
79
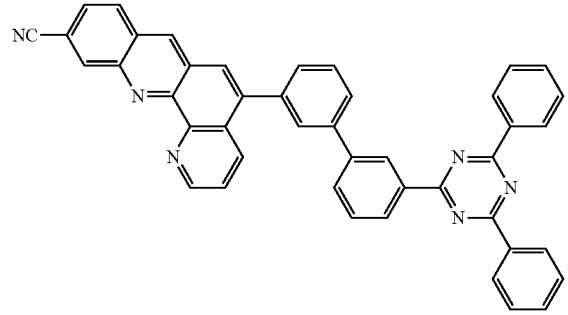
80
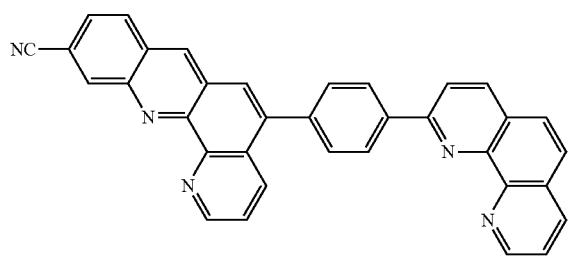
81
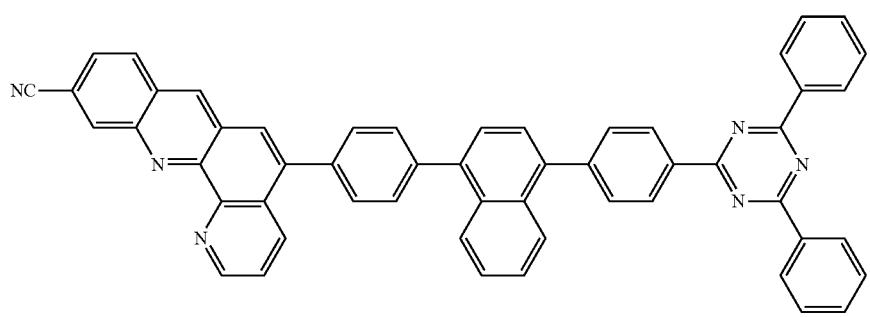

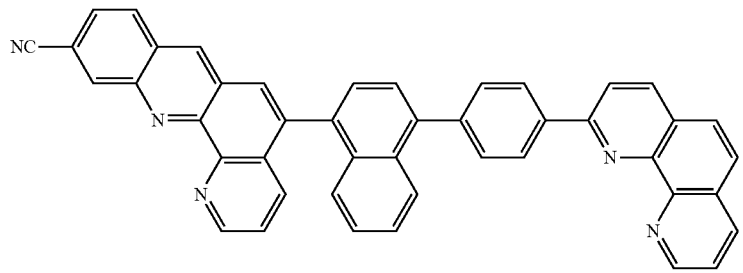
82
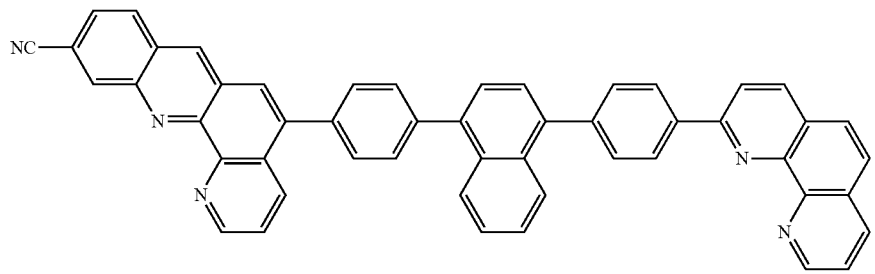
83
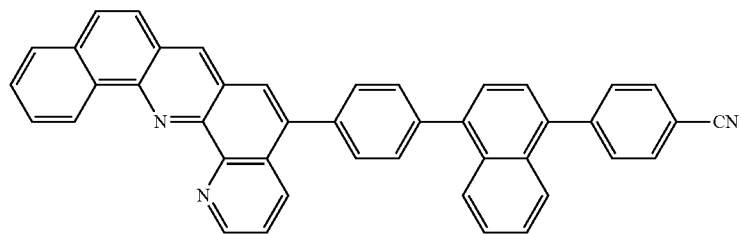
84
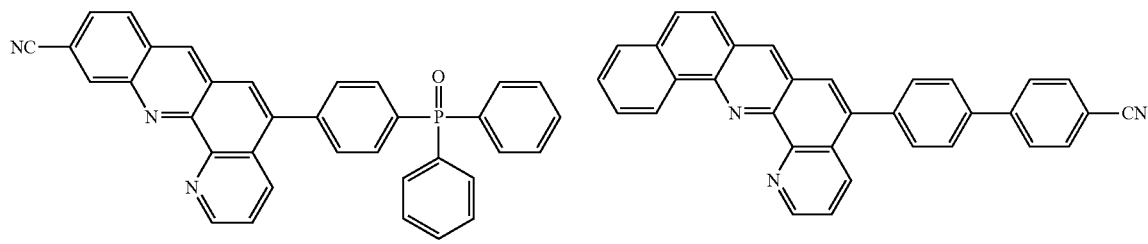
85
86
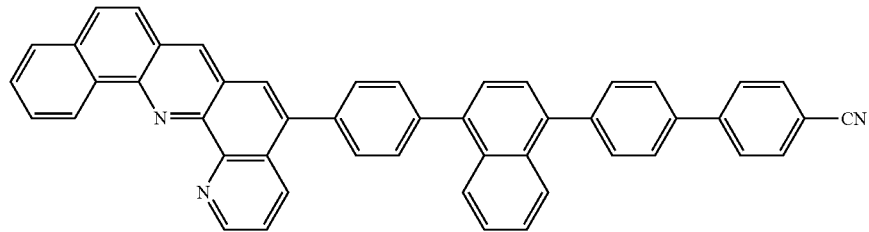
87

-continued
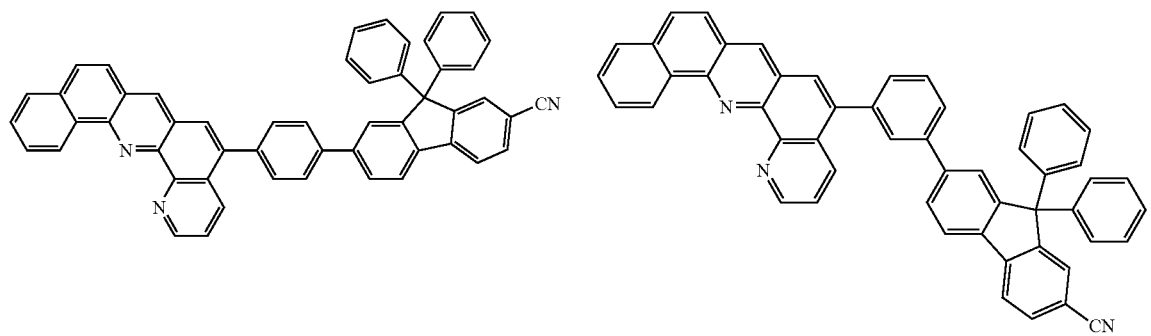
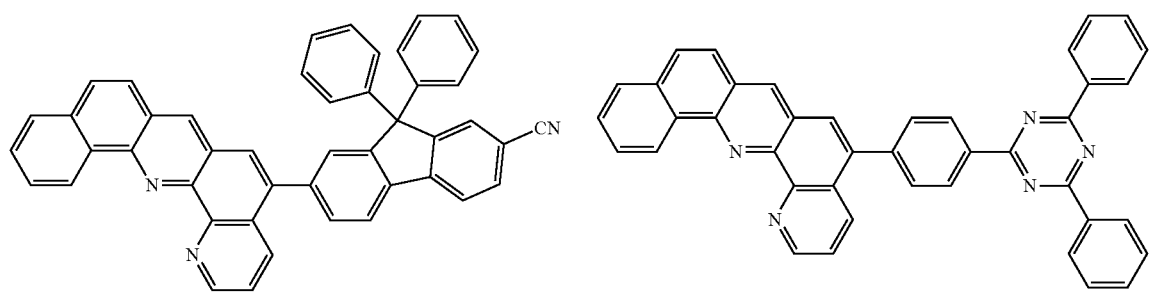
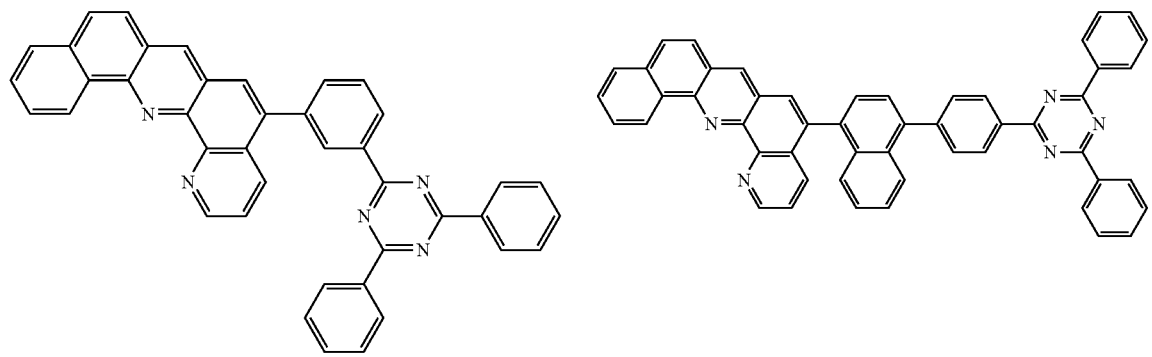
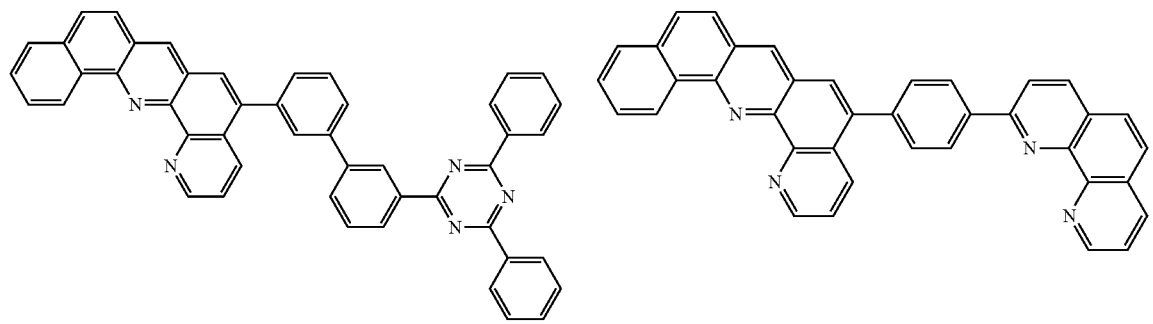

96
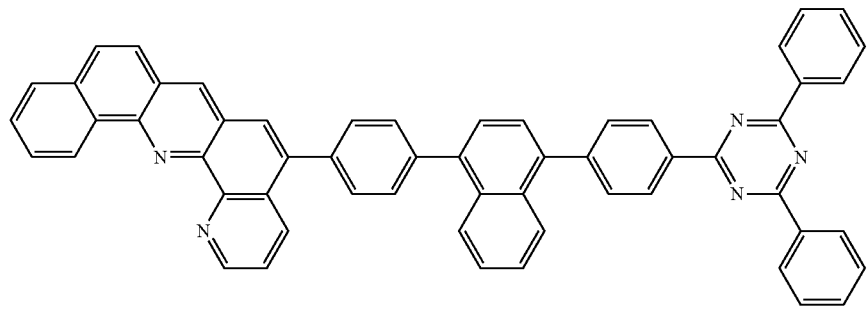
97
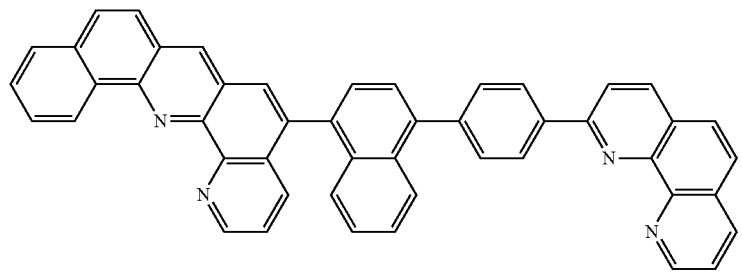
98
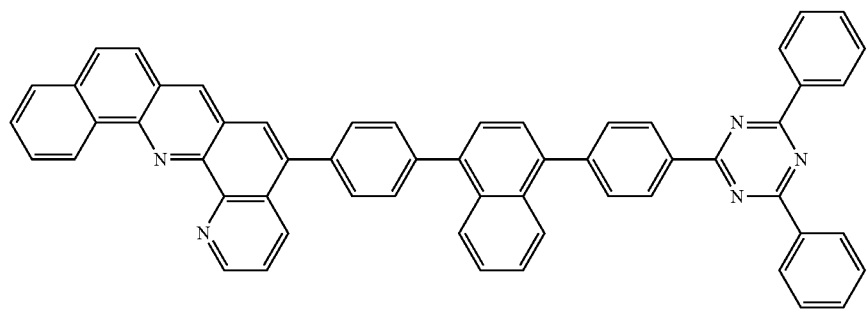
99 100
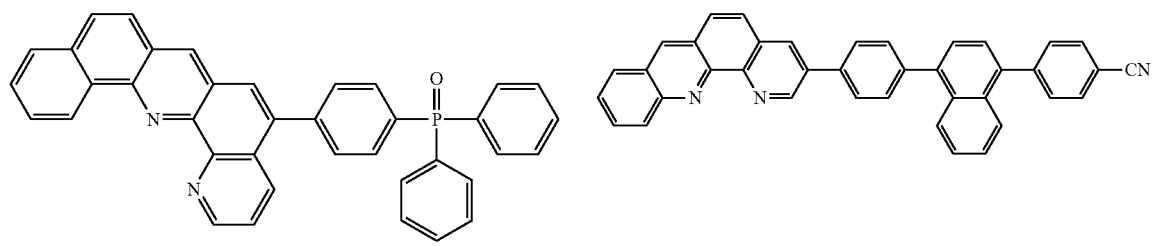
101
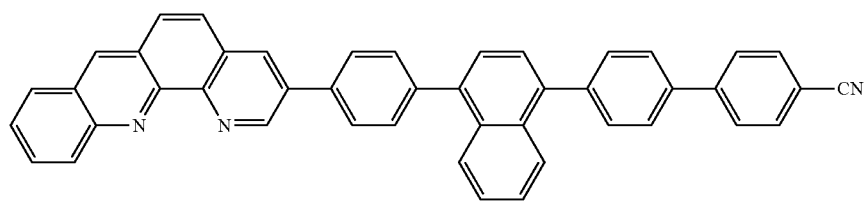

-continued
102
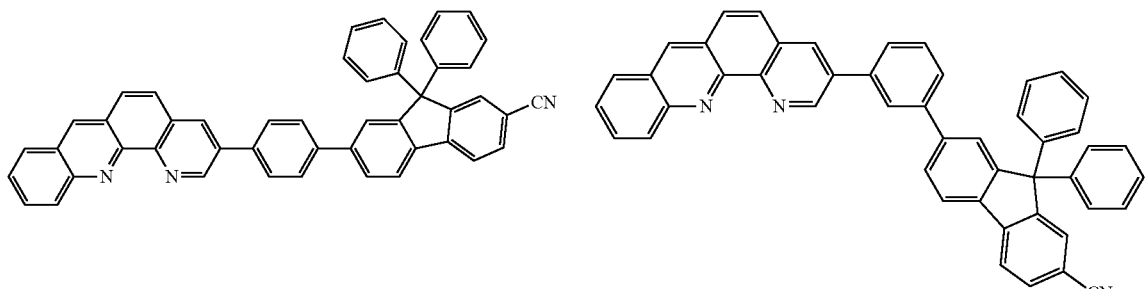
103
104
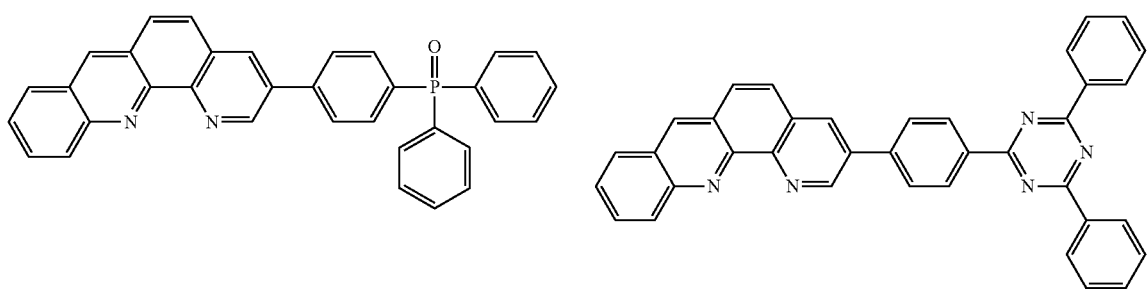
105
106
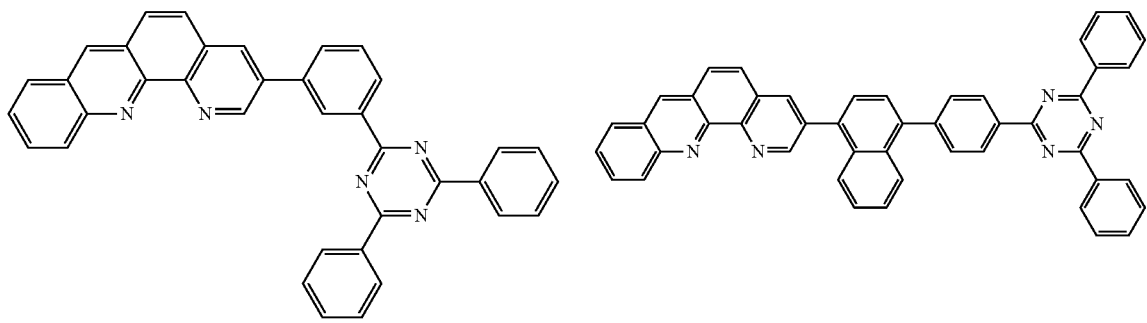
107
108
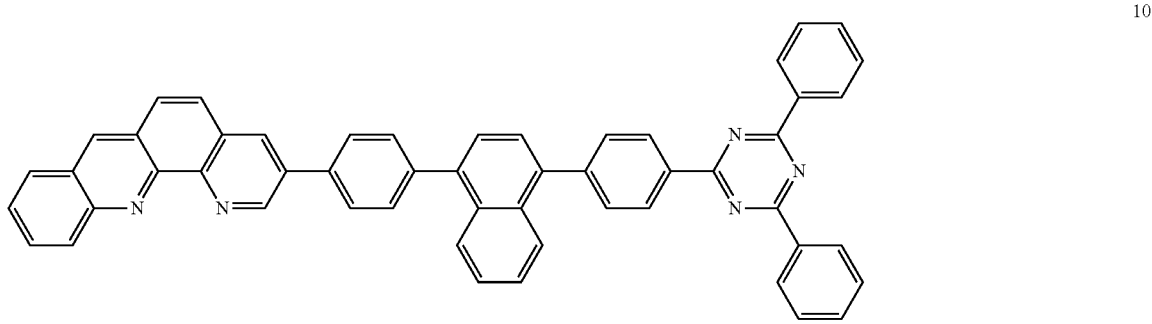
109
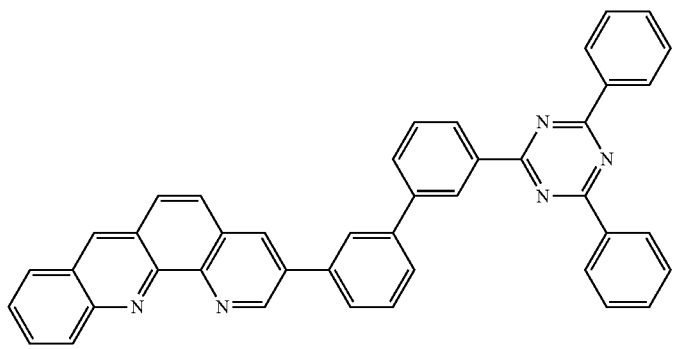

-continued
110
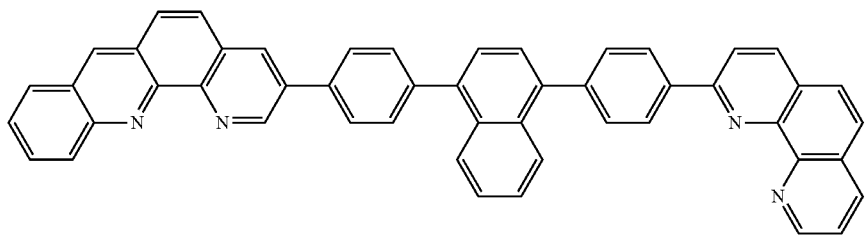
111
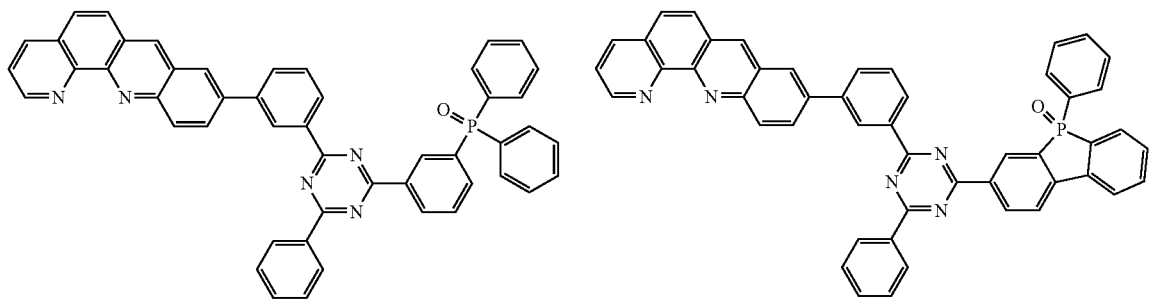
112
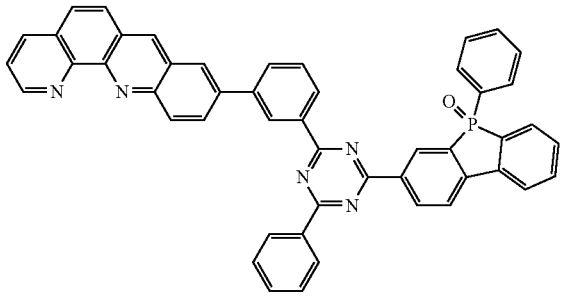
113 114
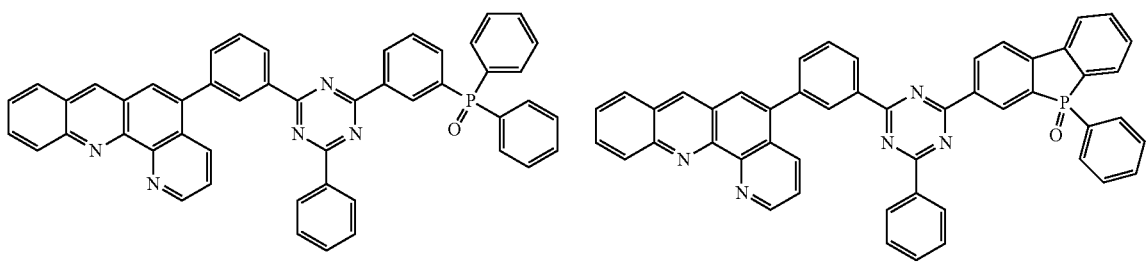
115 116
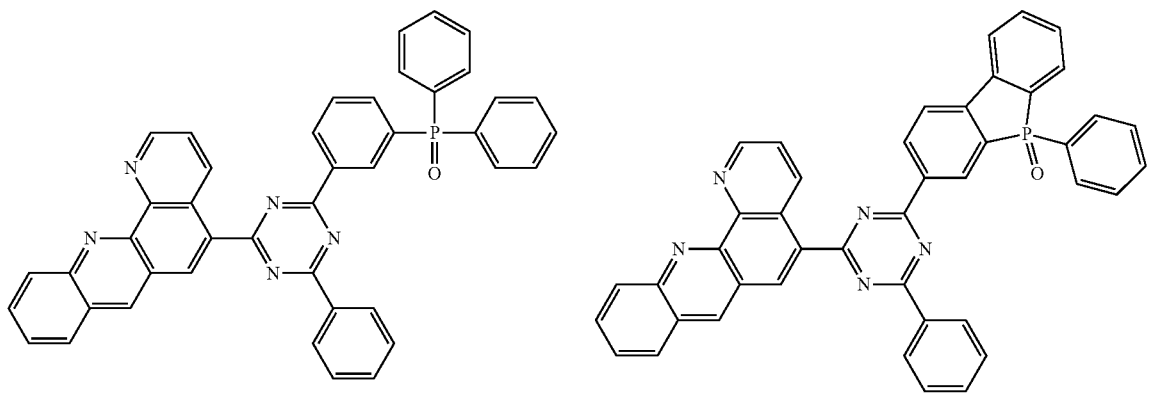
117 118
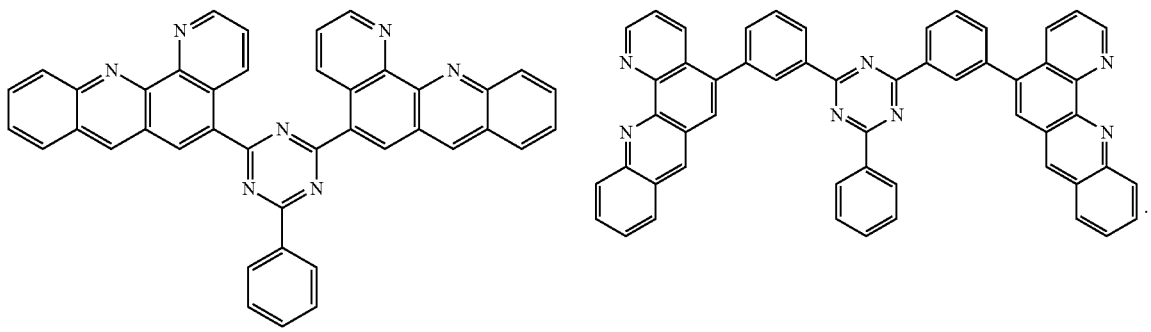

10. An organic light-emitting device, comprising:
a first electrode;
a second electrode facing the first electrode; and
an organic layer between the first electrode and the second electrode, the organic layer including an emission layer,
wherein the organic layer includes the condensed cyclic compound as claimed in claim 1.

11. The organic light-emitting device as claimed in claim 10, wherein:
the first electrode is an anode,
the second electrode is a cathode, and
the organic layer further includes a hole transport region between the first electrode and the emission layer and an electron transport region between the emission layer and the second electrode,
the hole transport region includes a hole injection layer, a hole transport layer, an emission auxiliary layer, an electron blocking layer, or any combination thereof, and
the electron transport region includes a hole blocking layer, an electron transport layer, an electron injection layer, or any combination thereof.

12. The organic light-emitting device as claimed in claim 11, wherein the electron transport region includes the condensed cyclic compound.

13. The organic light-emitting device as claimed in claim 11, wherein:
the electron transport region includes at least one of an electron transport layer and an electron injection layer, and
the at least one of the electron transport layer and the electron injection layer includes the condensed cyclic compound.

14. The organic light-emitting device as claimed in claim 10, wherein the emission layer includes the condensed cyclic compound.

15. The organic light-emitting device as claimed in claim 14, wherein:
the emission layer consists of the condensed cyclic compound; or
the emission layer further includes a dopant, and the dopant is included in an amount of about 0.1 parts by weight to about 50 parts by weight, based on 100 parts by weight of the emission layer.

16. The organic light-emitting device as claimed in claim 15, wherein the dopant is a phosphorescent dopant or a fluorescent dopant.

17. The organic light-emitting device as claimed in claim 11, wherein the hole transport region includes a p-dopant that has a lowest unoccupied molecular orbital (LUMO) energy level of less than ~3.5 eV.

* * * * *